United States Patent
Pastor Fernández et al.

(10) Patent No.: US 9,808,466 B2
(45) Date of Patent: *Nov. 7, 2017

(54) MACROCYCLIC COMPOUNDS AS PROTEIN KINASE INHIBITORS

(71) Applicant: Fundación Centro Nacional de Investigaciones Oncologicas Carlos III, Madrid (ES)

(72) Inventors: Joaquín Pastor Fernández, Madrid (ES); Rosa María Álvarez Escobar, Madrid (ES); Rosario Concepción Riesco Fagundo, Madrid (ES); Ana Belén García García, Madrid (ES); Antonio Rodríguez Hergueta, Madrid (ES); Jose Ignacio Martín Hernando, Madrid (ES); Carmen Blanco Aparicio, Madrid (ES); David Álvaro Cebrián Muñoz, Madrid (ES)

(73) Assignee: Fundación Centro Nacional de Investigaciones Oncologicas Carlos III

( * ) Notice: Subject to any disclaimer, the term of this patent is extended or adjusted under 35 U.S.C. 154(b) by 0 days.

This patent is subject to a terminal disclaimer.

(21) Appl. No.: 15/006,755

(22) Filed: Jan. 26, 2016

(65) Prior Publication Data

US 2016/0296528 A1    Oct. 13, 2016

Related U.S. Application Data

(63) Continuation of application No. 14/118,009, filed as application No. PCT/GB2012/051134 on May 18, 2012, now Pat. No. 9,284,334.

(30) Foreign Application Priority Data

May 19, 2011  (EP) .................................. 11382158
Mar. 9, 2012  (EP) .................................. 12275024

(51) Int. Cl.

| | |
|---|---|
| A61K 45/06 | (2006.01) |
| A61K 31/5383 | (2006.01) |
| C07D 513/16 | (2006.01) |
| C07D 513/22 | (2006.01) |
| C07D 515/22 | (2006.01) |
| A61K 31/4375 | (2006.01) |
| A61K 31/439 | (2006.01) |
| A61K 31/4745 | (2006.01) |
| A61K 31/5025 | (2006.01) |
| A61K 31/519 | (2006.01) |

(52) U.S. Cl.
CPC ........ *A61K 31/5383* (2013.01); *A61K 31/439* (2013.01); *A61K 31/4375* (2013.01); *A61K 31/4745* (2013.01); *A61K 31/5025* (2013.01); *A61K 31/519* (2013.01); *A61K 45/06* (2013.01); *C07D 513/16* (2013.01); *C07D 513/22* (2013.01); *C07D 515/22* (2013.01)

(58) Field of Classification Search
CPC ....................................................... A61K 45/06
See application file for complete search history.

(56) References Cited

U.S. PATENT DOCUMENTS

| | | |
|---|---|---|
| 4,814,470 A | 3/1989 | Colin et al. |
| 5,438,072 A | 8/1995 | Bobee et al. |
| (Continued) | | |

FOREIGN PATENT DOCUMENTS

| | | |
|---|---|---|
| AU | 2003250212 | 4/2004 |
| CN | 1202161 A | 12/1998 |
| (Continued) | | |

OTHER PUBLICATIONS

Hirsch, et al, In Antiviral Agents Chapter 12, pp. 431-466 in Fields Virology, Third Edition 1996.
Mikkers H. et al., "Mice Deficient for All PIM Kinases Display Reduced Body Size and Impaired Responses to Hematopoietic Growth Factors," Molecular and Cellular Biology, vol. 24, 6104-6115, 2004.
Mochizuki T. et al., "Physical and Functional Interactions between Pim-1 Kinase and Cdc25A phosphate: Implications for the Pim-1-Mediated Activation of the c-Myc Signaling Pathway," J. Biol. Chem., vol. 274, 18659-18666, 1999.

(Continued)

*Primary Examiner* — Bruck Kifle
(74) *Attorney, Agent, or Firm* — McCarter & English, LLP; Steven G. Davis; Wei Song

(57) ABSTRACT

There is provided compounds of formula I, wherein R1, $R^{2a}$, $R^{2b}$, $R^{2c}$, X, Y, Z, $R^3$ and ring A/B have meanings given in the description, and pharmaceutically-acceptable esters, amides, solvates or salts thereof, which compounds are useful in the treatment of diseases in which inhibition of a protein or lipid kinase (e.g. PI3-K, particularly class I PI3K, PIM family kinase and/or mTOR) is desired and/or required, and particularly in the treatment of cancer. The invention also relates to combinations containing such compounds.

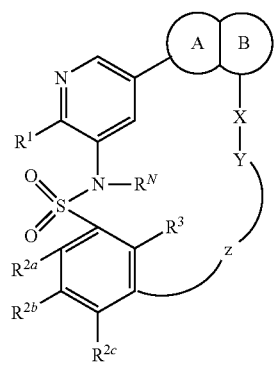

9 Claims, No Drawings

(56) References Cited

U.S. PATENT DOCUMENTS

| | | | |
|---|---|---|---|
| 5,583,024 | A | 12/1996 | McElroy et al. |
| 5,674,713 | A | 10/1997 | McElroy et al. |
| 5,698,582 | A | 12/1997 | Bastart et al. |
| 5,700,670 | A | 12/1997 | Yamagishi et al. |
| 5,714,512 | A | 2/1998 | Bastart et al. |
| 5,750,561 | A | 5/1998 | Bastart et al. |
| 6,602,677 | B1 | 8/2003 | Wood et al. |
| 6,713,485 | B2 | 3/2004 | Carter et al. |
| 6,727,256 | B1 | 4/2004 | Carter et al. |
| 6,933,299 | B1 | 8/2005 | Cockerill et al. |
| 6,960,614 | B2 | 11/2005 | Barrett et al. |
| 6,972,298 | B2 | 12/2005 | Baragi et al. |
| 7,084,147 | B2 | 8/2006 | Cockerill et al. |
| 7,109,333 | B2 | 9/2006 | Carter et al. |
| 7,141,576 | B2 | 11/2006 | Lackey et al. |
| 7,157,466 | B2 | 1/2007 | McClure et al. |
| 2004/0147478 | A1 | 7/2004 | Merriman |
| 2005/0085550 | A1 | 4/2005 | Macikenas et al. |
| 2010/0190804 | A1 | 7/2010 | Combs et al. |
| 2014/0256717 | A1 | 9/2014 | Fernandez et al. |

FOREIGN PATENT DOCUMENTS

| | | | |
|---|---|---|---|
| EA | 200970419 | A1 | 10/2009 |
| EA | 201100450 | A1 | 10/2011 |
| JP | 2006501271 | | 1/2006 |
| WO | 97/18207 | A2 | 5/1997 |
| WO | 2007/044515 | A1 | 4/2007 |
| WO | WO-2008049902 | A2 | 5/2008 |
| WO | 2008/150827 | A1 | 12/2008 |
| WO | 2009/040552 | A2 | 4/2009 |
| WO | 2009/055418 | A1 | 4/2009 |
| WO | WO-2010028116 | A1 | 3/2010 |
| WO | 2010/105008 | A2 | 9/2010 |
| WO | 2010/108074 | A2 | 9/2010 |
| WO | 2010/112874 | A1 | 10/2010 |
| WO | 2011/022439 | A1 | 2/2011 |
| WO | 2013/001310 | A1 | 1/2013 |

OTHER PUBLICATIONS

Montesinos-Rongen M. et al., "Primary diffuse large B-cell lymphomas of the central nervous system are targeted by aberrant somatic hypermutation," Blood Journal, vol. 103, 1869-1875, 2004.

Nicolau K.C. et al., "Metathesis Reactions in Total Synthesis," Angewandte Chemie Int. Ed., vol. 44, 4490-4257, 2005.

Nicolau K.C. et al., "Palladium-Catalyzed Cross-Coupling Reactions in Total Synthesis," Angewandte Chemie Int. Ed., vol. 44, 4442-4489, 2005.

Parsons W. et al., "Mutations in a signaling pathway," Nature, vol. 436, p. 792, 2005.

Pasqualucci L. et al., "Hypermutation of multiple proto-oncogenes in B-cell diffuse large-cell lymphomas," Nature, vol. 412, 341-346, 2001.

Paul, H. et al., "Uber cinige Umsetzungen von 2,5-Diamino—sowic 2-Amino-1,3,4-thiadiazolen mit a—Halongenketonen zu Imidazo[2,1-b]-1,3,4-thiadiazolen," Monatshefte fur Chemie, 1977, 108, 665-680.

Paulin R. et al., "Signal Transducers and Activators of Transcription-3/Pim1 Axis Plays a Critical Role in the Pathogenesis of Human Pulmonary Arterial Hypertension," Circulation, vol. 123(11), 1-20, 2011.

Plotkin M. et al., "A practical approach to highly functionalized benzodihydrofurans," Tetrahedron Letters, vol. 41, 2269-2273, 2000.

Qian C.K., "Structural Basis of Constitutive Activity and a Unique Nucleotide Binding Mode of Human Pim-1 Kinase," J. Biol. Chem., vol. 280, No. 7, 6130-6137, 2005.

Ringel I. et al., "Studies with RP 56976 (Taxotere): A Semisynthetic Analogue of Taxol," Journal of the National Cancer Institute, vol. 83, 288-291, 1991.

Roh M. et al., "Overexpression of the Oncogenic Kinase Pim-1 Leads to Genomic Instability," Cancer Research, vol. 63, 8079-8084, 2003.

Saris J.M.C. et al., "The pim-1 oncogene encodes two related protein-serine/threonine kinases by alternative initiation at AUG and CUG," The EMBO Journal, vol. 10, No. 3, 665-664, 1991.

Schlosser, Manfred, "Organometallics in Synthesis, a Manual," Wiley & Sons, Ltd., Chichester UK, 1-5, 2002.

Schmidt T. et al., "Evidence implicating Gfi-1 and Pim-1 in pre-T-cell differentiation steps associated with beta-selection," The EMBO Journal, vol. 17, No. 18, 5349-5359, 1998.

Severinsen R. et al., "Versatile strategies for the solid phase synthesis of small heterocyclic scaffolds: [1,3,4]-thiadiazoles and [1,3,4]-oxadiazoles," Tetrahedron, vol. 61, 5565-5575, 2005.

Seyden-Penne, J., "Reduction by the Alumino-and Borohydrides in Organic Synthesis," VCH Publishers, Inc. NY, 1-5, 1991.

Shintani R. et al., "Carbon-Carbon Bond Forming Enantioselective Synthesis of Chiral Organosilicon Compunds by Rhodium/Chiral Diene-Catalyzed Asymmetric 1,4-Addition Reaction," Organic Letters, vol. 7, No. 21, 4757-4759, 2005.

Shirogane T. et al., "Synergistic Roles for Pim-1 and c-Myc in STAT 3-Mediated Cell Cycle Progression and Antiapoptosis," Immunity, vol. 11, 709-719, 1999.

Toker, A., "Phosphoinositides and signal transduction," CMLS Cellular and Molecular Life Sciences, vol. 59, No. 5, 761-779, 2002.

Valdman, A. et al., "Pim-1 Expression in Prostatic Intraepithelial Neoplasia and Human Prostate Cancer," The Prostate, vol. 60, 367-371, 2004.

Van Der Heijden M.S. and Bernards R., "Inhibition of the P13K Pathway: Hope We Can Believe in?," Clinical Cancer Research, vol. 16, 3094-3099, 2010.

Van Lohuizen, M. et al., "Identification of Cooperating Oncogenes in Ep-myc Transgenic Mice by Provirus Tagging," Cell, vol. 65, 737-752, 1991.

Van Lohuizen, M. et al., "Predisposition to Lymphomagenesis in pim-1 Transgenic Mice: Cooperation with c-myc and N-myc in Murice Leukemia Virus-Induced Tumors," Cell., vol. 56, 673-682, 1989.

Vanhaesebroeck, B. et al., "Phosphoinositide 3-kinases: a conserved family of signal transducers," Trends BioChem Sci., vol. 22, No. 87, 267-272, 1997.

Vanhaesebroeck, B. et al., "Signaling by Distinct Classes of Phosphoinositide 3-Kinases," Experimental Cell Research, vol. 253, No. 1, 239-254, 1999.

Wang, Z. et al., "Phosphorylation of the cell cycle inhibitor p21Cip1/WAF1 by Pim-1 kinase," Biochimica et Biophysica Acta, vol. 1593, 45-55, 2002.

Wang, Z. et al., "Pim-1 a serine/threonine kinase with a role in cell survival, proliferation, differentiation and tumorigenesis," J. Vet. Sci., vol. 2, 167-179, 2001.

Wenwei, L. et al., "Preparation of highly functionalized arylmagnesium reagents by the addition of magnesium phenylselenide to arynes," Tetrahedron Letters, vol. 47, 1941-1944, 2006.

Werber, G. et al., "The Synthesis and Reactivity of some 2-Amino-5-bromo-1,3,4-thiadiazoles and the Corresponding $D^2$-1,3,4-Thiadiazolines," J. Heterocyclic Chem., vol. 14, 823-827, 1977.

Wiggins J. Mark, "A Convenient Procedure for the Reduction of Diarylmethanols with Dichlorodimethysilane/Sodium Iodide," Synthetic Communications, vol. 18, No. 7, 741-749, 1988.

Wipf, P. and Jung J.K., "Formal Total Synthesis of (+)-Diepoxin s," J. Org. Chem., vol. 65, 6319-6337, 2000.

Abdel-Magid A.F., et al., "Reductive Amination of Aldehydes and Ketones with Sodium Triacetoxyborohydride," Synlett, (9) pp. 537-539, 1990.

Abdel-Magid A.F., et al., "Reductive Amination of Aldehydes and Ketones with Sodium Triacetoxyborohydride. Studies on Direct and Indirect Reductive Amination Procedures," J. Org. Chem., 61, 3849-3862, 1996.

(56) References Cited

OTHER PUBLICATIONS

Abignente E. et al., "Research on Heterocyclic Compounds. XXVII. Synthesis and antiinflammatory activity of 2-phenylimidazo[1,2-b]pyridazine-3-carboxylic acids," II Farmaco, vol. 45, 1075-1087, 1990.

Akasaka H. et al., "Molecular Anatomy of BCL6 Translocations Revealed by Long-Distance Polymerase Chain Reaction-based Assays," Cancer Res., vol. 60, 2335-2341, 2000.

Albert, Sebastien et al. "New inhibitors of the mammalian target of rapamycin signaling pathway for cancer", Expert Opin Investig. Drugs. 18(8), 2010, pp. 919-930.

Andanappa K.G. et al., "Synthesis and anti-tubercular activity of a series of 2-sulfonamido/trifluoromethyl-6-substituted imidazo-[2,1-b]-1,3,4-thiadiazole derivatives," Bioorg. Med. Chem. vol. 12, 5651-5659, 2004.

Bachmann M. and Moroy T., "The serine/threonine kinase Pim-1," The International Journal of Biochemistry & Cell Biology, vol. 37, 726-730, 2005.

Baytel D. et al., "The human Pim-2 proto-oncogene and its testicular expression," Biochimica et Biophysica Acta vol. 1442, 274-285, 1998.

Bellamy F.D. and Ou K., "Selective reduction of aromatic niteo compounds with stannous chloride in non acidic and non aqueous medium," Tetrahedron Letters, vol. 25, 839-842, 1984.

Bissery M.C. et al., "Experimental Antitumor Activity of Taxotere (RP 56976, NSC 628503), a Taxol Analogue," Cancer Res., vol. 51, 4845-4852, 1991.

Borlado L.R. et al., "Increased phosphoinositide 3-kinase activity induces a lymphoproliferative disorder and contributes to tumor generation in vivo," FASEB J., vol. 14, No. 7, 895-903, 2000.

Bretonnet A-S et al., "NMR Screening Applied to the Fragment-Based Generation of Inhibitors of Creatine Kinase Exploiting a New Interaction Proximate to the ATP Binding Site," J. Med. Chem., vol. 50, 1865-1875, 2007.

Breuer M. et al., "Very high frequency of lymphoma induction by a chemical carcinogen in pim-1 transgenic mice," Letters to Nature, vol. 340, 61-63, 1989.

Bundgaard, Hans, "Design of prodrugs: Bioversible derivatives for various functional groups and chemical entities," Elsevier Science Publishers B.V., 1-92, 1985.

Bunney T.D. and Katan M., "Phosphoinositide signalling in cancer: beyond PI3K and PTEN," Nature Reviews Cancer, vol. 10, No. 5, 342-352, 2010.

Castillo J.J. et al., "CAL-101: a phosphatidylinositol-3-kinase p110-delta inhibitor for the treatment of lymphoid malignancies," Expert Opinion Investig. Drugs, vol. 21, No. 1, 15-22, 2012.

Cleary J.M. and Shapiro G.I., "Development of Phosphoinositide-3 Kinase Pathway Inhibitors for Advanced Cancer," Current Oncology Report, vol. 12, 87-94, 2010.

Cohen, Philip, "The development and therapeutic potential of protein kinase inhibitors," Current Opinion in Chemical Biology, vol. 3, 459-465, 1999.

Cree I.A. et al., "Methotrexate chemosensitivity by ATP luminescence in human leukemia cell lines and in breast cancer primary cultures: comparison of the TCA-100 assay with a clonogenic assay," Anti-Cancer Drugs, vol. 6, 398-404, 1995.

Crouch S.P.M. et al., "The use of ATP bioluminescence as a measure of cell proliferation and cytotoxity," Journal of Immunological Methods, vol. 160, 81-88, 1993.

Cuypers H.T. et al., "Murine Leukemia Virus-Induced T-Cell Lymphomagenesis: Integration of Proviruses in a Distinct Chromosomal Region," Cell, vol. 37, 141-150, 1984.

Davies M.A. et al., "Docetaxel in non-small cell lung cancer: a review," Expert Opinion Pharmacother, vol. 4, 553-565, 2003.

Defacqz N. et al., "Synthesis of C-5-substituted imidazolines," Tetrahedron Letters, vol. 44, 9111-9114, 2003.

Dermer C. Otis, "Metallic Salts of Alcohols and Alcohol Analogs," Chem. Rev., vol. 14, 385-430, 1934.

Domen J. et al, "Inpaired Interleukin-3 Response in Pim-1-Deficient Bone Marrow-Derived Mast Cells," Blood, vol. 82, 1445-1452, 1993.

Easton JB and Houghton PJ, "mTOR and cancer therapy," Oncogene, vol. 25, No. 48, 6436-6446, 2006.

El-Sherbeny M.A. et al., "Synthesis and cardiotonic activity of certain imidazo[2,1-b]-1,3,4-thiadiazole derivatives," Boll. Chim. Farm. vol. 136, 253-256, 1997.

Fabio P.F. et al., "Synthesis of carbon-14 and deuterium labeled 3-nitro-6-propoxymidazo [1,2-B]Pyridazine—An antiparasitic agent," Journal or Labelled Compunds and Radiopharmaceuticals, vol. 15, 407-412, 1978.

Feldman J. et al., "KID-1, a Protein Kinase Induced by Depolarization in Brain," J. Biol. Chem. vol. 273, 16535-16543, 1998.

Gaidano G. et al., "Aberrant somatic hypermutation in multiple subtypes of AIDS-associated non-Hodgkin lymphoma," Blood, vol. 102, 1833-1841, 2003.

Greene T.W. and Wuts P.G.M., "Protective Groups in Organic Synthesis," A Wiley-Interscience Publication, 1-6, 1999.

Gregson S.J. et al., "Linker Length Modulates DNA Cross-Linking Reactivity and Cytotoxic Potency of C8/C8 Ether-Linked C2-exo-Unsaturated Pyrrolol[2,1-c] [1,4] benzodiazepine (PBD) Dimers," J. Med. Chem., vol. 47, 1161-1174, 2004.

Han S.Y. and Kim Y-A., "Recent development of peptide coupling reagents in organic synthesis," Tetrahedron, vol. 60, 2447-2467, 2004.

Hennessey B.T. et al., "Exploiting the PI3K/AKT Pathway for Cancer Drug Discovery," Nature Review Drug Discovery, vol. 4, 988-1004, 2003.

Herbst R.S. and Khuri F.R., "Mode of action of docetaxel—a basis for combination with novel anticancer agents," Cancer Treatment Reviews, vol. 229, 407-415, 2003.

Hirano T. et al., "Roles of STAT3 in mediating the cell growth, differentiation and survival signals relayed through the IL-6 family of cytokine receptors," Oncogene, vol. 19, 2548-2556, 2000.

Ikemoto T. and Wakimasu M., "Reactions with N-Chlorosuccinimide of Various 5-Methylimidazo[1,2-a]Pyridine Derivatives with an Electron-Wtihdrawing Group Substituted at the 3-position," Heterocycles, vol. 55, No. 1, 99-108, 2001.

Ikemoto T. et al., "A Practical Synthesis of the Chronic Renal Disease Agent, 4,5-Dihydro-3H-1,4,8b-triazaacenaphthylen-3-one Derivatives, Using Regioselective Chlorination of Ethyl 5-methylimidazol[1,2-a]pyridine-3-carboxylate with N-Chlorosuccinimide," Tetrahedron, vol. 56, 7915-7921, 2000.

International Search Report and Written Opinion of the International Searching Authority. PCT/GB2012/051134 (WO 2012/156756), mailed Jul. 11, 2012.

Jacobs, H. et al., "PIM1 Reconstitutes Thymus Cellularity in Interleukin 7- and Common g Chain-Mutant Mice and Permits Thymocyte Maturation in Rag—but Not CD3g-deficient Mice," Journal of Experimental Medicine, vol. 190, pp. 1059-1068, 1999.

Katso R. et al., "Cellular Function of Phospoinositide 3-Kinases: Implications for Development, Immunity, Homeostasis, and Cancer," Annual Review of Cell and Developmental Biology, vol. 17, 615-675, 2001.

Kim O. et al., "Design and Synthesis of Imidazopyridine Analogues as Inhibitors of Phosphoinositide 3-kinase Signaling and Angiogenesis," Journal of Medical Chemistry, vol. 54, 2455-2466, 2011.

Kobe J. et al., "Synthesis of Pyridazine Derivatives-XV Some Electrophilic Substitutions on Imidazo[1,2-b]-Pyridazines," Tetrahedron, vol. 24, 239-245, 1968.

Koike N. et al., "Identification of heterochromatin protein 1 (HP1) as a phosphorylation target by Pim-1 kinase and the effect of phosphorylation on the transcriptional repression function of HP1," FEBS Letters, vol. 467, 17-21, 2000.

Kuwahara M. et al., "Synthetic Studies on Condensed-Azole Derivatives. IV. Synthesis and Anti-asthmatic Activities of w-Sulfamoylalkyloxyimidazo[1,2-b]pyridazines," Chem. Pharm. Bull., vol. 44, No. 1, pp. 121-131, 1996.

Lainton A.H.J. et al., "Design and Synthesis of a Diverse Morpholine Template Library," J. Comb. Chem., vol. 5, 400-407, 2003.

(56) References Cited

OTHER PUBLICATIONS

Leslie R.N. et al., "Phospoinositide-Regulated Kinases and Phosphoinositide Phosphatases," Chem. Rev., vol. 101, 2365-2380, 2001.

Lilly M. et al., "The PIM-1 serine kinase prolongs survival and inhibits apoptosis-related mitochondrial dysfunction in part through a bcl-2-dependent pathway," Oncogene, vol. 18, 4022-4031, 1999.

Mangatal L. et al., "Application of the vicinal oxyamination reaction with asymmetric induction to the hemisynthesis of taxol and analogues," Tetrahedron, vol. 45, 4177-4190, 1989.

Marin A. et al., "Synthesis and Athelmintic Activity of Carbamates Derived from Imidazo[2,1-b][1,3,4]Thiadiazole and Imidazo[2,1-b]Thiazole," IL Farmaco, vol. 47 (1), 63-75, 1992.

MACROCYCLIC COMPOUNDS AS PROTEIN KINASE INHIBITORS

RELATED APPLICATIONS

This application is a continuation of U.S. patent application Ser. No. 14/118,009, filed Nov. 15, 2013, which is a U.S. National Stage of International Application No. PCT/GB/2012/051134, filed May 18, 2012; which, in turn, claims priority to European Patent Application No. 12275024.3, filed Mar. 9, 2012 and European Patent Application No. 11382158.1, filed May 19, 2011. The entire teachings of each of the aforementioned applications are incorporated herein by reference.

FIELD OF THE INVENTION

This invention relates to novel pharmaceutically-useful compounds, which compounds are useful as inhibitors of protein or lipid kinases (such as inhibitors of the phosphoinositide 3'OH kinase (PI3 kinase) family, particularly the PI3K class I sub-type). The compounds may also be useful as inhibitors of the mammalian target of rapamycin (mTOR), and may optionally also be useful as inhibitors of a PIM family kinase (e.g. PIM-3 and, especially PIM-1). The compounds are of potential utility in the treatment of diseases such as cancer. The invention also relates to the use of such compounds as medicaments, to the use of such compounds for in vitro, in situ and in vivo diagnosis or treatment of mammalian cells (or associated pathological conditions), to pharmaceutical compositions containing them, and to synthetic routes for their production.

BACKGROUND OF THE INVENTION

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis. PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, *Current Opinion in Chemical Biology* 1999, 3, 459-465.

Phosphatidylinositol 3-kinases (PI3Ks) are a family of lipid and serine/threonine kinases that catalyze the phosphorylation of the membrane lipid phosphatidylinositol (PI) on the 3'-OH of the inositol ring to produce phosphoinositol-3-phosphate (PIP), phosphoinositol-3,4-diphosphate ($PIP_2$) and phosphoinositol-3,4,5-triphosphate ($PIP_3$), which act as recruitment sites for various intracellular signalling proteins, which in turn form signalling complexes to relay extracellular signals to the cytoplasmic face of the plasma membrane. These 3'-phosphoinositide subtypes function as second messengers in intracellular signal transduction pathways (see e.g. Trends Biochem. Sci 22 87, 267-72 (1997) by Vanhaesebroeck et al.; Chem. Rev. 101 (8), 2365-80 (2001) by Leslie et al (2001); Annu. Rev. Cell. Dev. Boil. 17, 615-75 (2001) by Katso et al; and Cell. Mol. Life Sci. 59 (5), 761-79 (2002) by Toker et al).

Multiple PI3K isoforms categorized by their catalytic subunits, their regulation by corresponding regulatory subunits, expression patterns and signalling specific functions (p110α, β, δ, γ) perform this enzymatic reaction (Exp. Cell. Res. 25 (1), 239-54 (1999) by Vanhaesebroeck and Katso et al., 2001, above).

The closely related isoforms p110α and β are ubiquitously expressed, while δ and γ are more specifically expressed in the haematopoietic cell system, smooth muscle cells, myocytes and endothelial cells (see e.g. Trends Biochem. Sci. 22 (7), 267-72 (1997) by Vanhaesebroeck et al). Their expression might also be regulated in an inducible manner depending on the cellular, tissue type and stimuli as well as disease context. Inductibility of protein expression includes synthesis of protein as well as protein stabilization that is in part regulated by association with regulatory subunits.

Eight mammalian PI3Ks have been identified so far, including four class I PI3Ks. Class Ia includes PI3Kα, PI3Kβ and PI3Kδ. All of the class Ia enzymes are heterodimeric complexes comprising a catalytic subunit (p110α, p110β or p110δ) associated with an SH2 domain containing p85 adapter subunit. Class Ia PI3Ks are activated through tyrosine kinase signalling and are involved in cell proliferation and survival. PI3Kα and PI3Kβ have also been implicated in tumorigenesis in a variety of human cancers. Thus, pharmacological inhibitors of PI3Kα and PI3Kβ are useful for treating various types of cancer.

The potential role of PI3K over-signaling in the development of lymphoid malignancies was initially identified in an experiment by Borlado et al. (Borlado LR, Redondo C, Alvarez B, et al. Increased phosphoinositide 3-kinase activity induces a lymphoproliferative disorder and contributes to tumor generation in viva, FASEB J 2000; 14(7):895-903). In that study, a mouse model with PI3K over-signaling developed infiltrating lymphoproliferative disorders as well as autoimmune disease. The PI3K pathway plays an important role in the development of B-cell malignancies, mainly through activation of the p110δ subunit. Inhibition of p110δ could have a role in the management of B-cell malignancies such as chronic lymphocytic leukemia (CLL), non-Hodgkin's lymphoma (NHL), plasma cell myeloma (PCM) and Hodgkin's lymphoma (HL). (for a review, see Expert Opin Investig Drugs. 2012 January; 21(1):15-22. CAL-101: a phosphatidylinositol-3-kinase p110-delta inhibitor for the treatment of lymphoid malignancies, Castillo J J, Furman M, Winer E S).

PI3Kγ, the only member of the Class Ib PI3Ks, consists of a catalytic subunit p110γ, which is associated with a p110 regulatory subunit. PI3Kγ is regulated by G protein coupled receptors (GPCRs) via association with βγ subunits of heterotrimeric G proteins. PI3Kγ is expressed primarily in hematopoietic cells and cardiomyocytes and is involved in inflammation and mast cell function. Thus, pharmacological inhibitors of PI3Kγ are useful for treating a variety of inflammatory diseases, allergies and cardiovascular diseases.

These observations show that deregulation of phosphoinositol-3-kinase and the upstream and downstream components of this signalling pathway is one of the most common deregulations associated with human cancers and proliferative diseases (see e.g. Parsons et al., Nature 436:792 (2005); Hennessey et al., Nature Rev. Drug Discovery 4: 988-1004 (2005).

The mammalian target of rapamycin (mTOR) also known as FK506 binding protein 12-rapamycin associated protein 1 (FRAP1) is a protein which in humans is encoded by the FRAP1 gene. mTOR is a serine/threonine protein kinase that regulates cell growth, cell proliferation, cell motility, cell survival, protein synthesis, and transcription. The inhibition of mTORs are believed to be useful for treating various diseases/conditions, such as cancer (for example, as described in Easton et al. (2006). "mTOR and cancer therapy". *Oncogene* 25 (48): 6436-46).

The listing or discussion of an apparently prior-published document in this specification should not necessarily be taken as an acknowledgement that the document is part of the state of the art or is common general knowledge.

For the treatment of cancer, targeted therapies are becoming more important. That is, therapy that has the effect of interfering with specific target molecules that are linked to tumor growth and/or carcinogenesis. Such therapy may be more effective than current treatments (e.g. chemotherapy) and less harmful to normal cells (e.g. because chemotherapy has the potential to kill normal cells as well as cancerous cells). This, and also the fact that targeted therapies may be selective (i.e. it may inhibit a certain targeted molecule more selectively as compared to other molecular targets, e.g. as described hereinafter), may have the benefit of reducing side effects and may also have the benefit that certain specific cancers can be treated (also selectively). The latter may in turn also reduce side effects.

PIM-1 is the protooncogene activated by murine leucemia virus (Provirus Integration site for Moloney murine leucemia virus—MoMuLV) that induces T-cell lymphoma [Cuypers, H. T., et. al. *Cell*, 1984, 37, 141-150].

The expression of the protooncogene produces a non-transmembrane serine/threonine kinase of 313 residues, including a kinase domain consisting of 253 amino acid residues. Two isoforms are known through alternative initiation (p44 and p33) [Saris, C. J. M. et al. *EMBO J.* 1991, 10, 655-664].

PIM-1, PIM-2 and PIM-3 phosphorylate protein substrates that are important in cancer neogenesis and progression. For example, PIM-1 phosphorylates inter alia p21, Bad, c-myb, Cdc 25A and eIF4B (see e.g. Quian, K. C. et al, *J. Biol. Chem.* 2005, 280(7), 6130-6137, and references cited therein).

Two PIM-1 homologs have been described [Baytel, D. *Biochem. Biophys. Acta* 1998, 1442, 274-285; Feldman, J. et al. *J. Biol. Chem.* 1998, 273, 16535.16543]. PIM-2 and PIM-3 are respectively 58% and 69% identical to PIM-1 at the amino acid level. PIM-1 is mainly expressed in thymus, testis, and cells of the hematopoietic system [Mikkers, H.; Nawijn, M.; Allen, J.; Brouwers, C.; Verhoeven, E.; Jonkers, J.; Berns, *Mol. Cell. Biol.* 2004, 24, 6104; Bachmann, M.; Moroy, T. *Int. J. Biochem. Cell Biol.* 2005, 37, 726-730. 6115]. PIM-1 expression is directly induced by STAT (Signal Transducers and Activators of Transcription) transcription factors, and PIM-1 expression is induced by many cytokine signalling pathways such as interleukins (IL), granulocyte-macrophage colony stimulating factor (GM-CSF), α- and γ-interferon, erythropoietin, and prolactin [Wang, Z et al. *J. Vet. Sci.* 2001, 2, 167-179].

PIM-1 has been implicated in lymphoma development. Induced expression of PIM-1 and the protooncogene c-myc synergise to increase the incidence of lymphomagenesis [Breuer, M. et al. Nature 1989, 340, 61-63; van Lohuizen M. et al. Cell, 1991, 65, 737-752]. PIM-1 functions in cytokine signalling pathways and has been shown to play a role in T cell development [Schmidt, T. et al. EMBO J. 1998, 17, 5349-5359; Jacobs, H. et al. JEM 1999, 190, 1059-1068]. Signalling through gp130, a subunit common to receptors of the IL-6 cytokine family, activates the transcription factor STAT3 and can lead to the proliferation of hematopioetic cells [Hirano, T. et al. Oncogene 2000, 19, 2548-2556]. A kinase-active PIM-1 appears to be essential for the gp130-mediated STAT3 proliferation signal. In cooperation with the c-myc PIM-1 can promote STAT3-mediated cell cycle progression and antiapoptosis [Shirogane, T. et al., immunity, 1999, 11, 709-719]. PIM-1 also appears to be necessary for IL-3-stimulated growth in bone marrow-derived mast cells [Domen, J. et al., Blood, 1993, 82, 1445-1452] and survival of FDCP1 cells after IL-3 withdrawal [Lilly, M. et al., Oncogene, 1999, 18, 4022-4031].

Additionally, control of cell proliferation and survival by PIM-1 may be effected by means of its phosphorylation of the well-established cell cycle regulators cdc25 [Mochizuki, T. et al., J. Biol. Chem. 1999, 274, 18659-18666] and/or p21(Cip1WAF1) [Wang Z. et al. Biochim. Biophys. Acta 2002, 1593, 45-55] or phosphorylation of heterochromatin protein 1, a molecule involved in chromatin structure and transcriptional regulation [Koike, N. et al, FEBS Lett. 2000, 467, 17-21].

Mice deficient for all three PIM genes showed an impaired response to hematopoietic growth factors and demonstrated that PIM proteins are required for efficient proliferation of peripheral T lymphocyes. In particular, it was shown that PIM function is required for efficient cell cycle induction of T cells in response to synergistic T-cell receptor and IL-2 signalling. A large number of interaction partners and substrates of PIM-1 have been identified, suggesting a pivotal role for PIM-1 in cell cycle control, proliferation, as well as in cell survival.

The oncogenic potential of this kinase has been first demonstrated in E μ PIM-1 transgenic mice in which PIM-1 over-expression is targeted to the B-cell lineage which leads to formation of B-cell tumors [van Lohuizen, M. et al.; *Cell* 1989, 56, 673-682. Subsequently PIM-1 has been reported to be over-expressed in a number of prostate cancers, erythroleukemias, and several other types of human leukemias [Roh, M. et al.; *Cancer Res.* 2003, 63, 8079-8084; Valdman, A. et al; *Prostate* 2004, 60, 367-371;

For example, chromosomal translocation of PIM-1 leads to overexpression of PIM-1 in diffuse large cell lymphoma. [Akasaka, H. et al.; *Cancer Res.* 2000, 60, 2335-2341]. Furthermore, a number of missense mutations in PIM-1 have been reported in lymphomas of the nervous system and AIDS-induced non-Hodgkins' lymphomas that probably affect PIM-1 kinase activity or stability [Pasqualucci, L. et al, *Nature* 2001, 412, 341-346; Montesinos-Rongen, M. et al., *Blood* 2004, 103, 1869-1875; Gaidano, G. et al., *Blood* 2003, 102, 1833-184]. Thus, the strong linkage between reported overexpression data and the occurrence of PIM-1 mutations in cancer suggests a dominant role of PIM-1 in tumorigenesis.

Several other protein kinases have been described in the literature, in which the activity and/or elevated activity of such protein kinases have been implicated in diseases such as cancer, in a similar manner to PIM-1, PIM-2 and PIM-3.

It has also been reported that PIM-1 has a role in pulmonary artery hypertension (PAH), see the journal article by Paulin et al, "Signal transducers and activators of transcription-3/PIM-1 axis plays a critical role in the pathogenesis of human pulmonary arterial hypertension".

There is a constant need to provide alternative and/or more efficacious inhibitors of protein kinases, and particularly inhibitors of PIM-1, PIM-2 and/or PIM-3. Such modulators are expected to offer alternative and/or improved approaches for the management of medical conditions associated with activity and/or elevated activity of PIM-1, PIM-2 and/or PIM-3 protein kinases.

For the treatment of cancer, targeted therapies are becoming more important. That is, therapy that has the effect of interfering with specific target molecules that are linked to tumor growth and/or carcinogenesis. Such therapy may be more effective than current treatments (e.g. chemotherapy) and less harmful to normal cells (e.g. because chemotherapy has the potential to kill normal cells as well as cancerous cells). This, and also the fact that targeted therapies may be selective (i.e. it may inhibit a certain targeted molecule more selectively as compared to other molecular targets, e.g. as described hereinafter), may have the benefit of reducing side effects and may also have the benefit that certain specific cancers can be treated (also selectively). The latter may in turn also reduce side effects.

Hence, it is a clear goal of current oncologists to develop targeted therapies (e.g. ones that are selective). In this respect, it should be pointed out that several different molecular targets may exist that are linked to certain diseases (e.g. cancer). However, one simply cannot predict if a therapy (e.g. a small molecule as a therapeutic) that interferes with or inhibits one target molecule could inhibit a different molecular target (be it one that will ultimately have the effect of treating the same disease or a different one).

International patent applications WO 2009/055418, WO 2010/108074, WO 2009/040552, WO 2010/112874 and WO 2011/022439 (as well as journal article *J Med Chem* by Okseon Kim et al *"Design and Synthesis of Imidazopyridine Analogues as Inhibitors of PI3K Signaling and Angiogenesis"*) all disclose various compounds for use as kinase inhibitors. However, none of these documents disclose macrocycles.

The listing or discussion of an apparently prior-published document in this specification should not necessarily be taken as an acknowledgement that the document is part of the state of the art or is common general knowledge.

DISCLOSURE OF THE INVENTION

According to the invention, there is provided a compound of formula I,

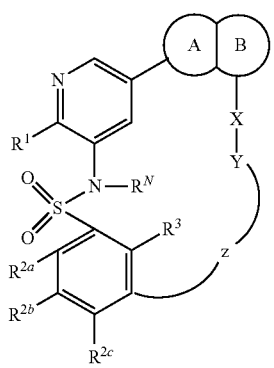

wherein:
ring A and ring B represent a fused bicyclic group of any one of the following formulae:

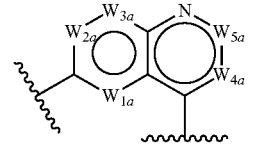

IA

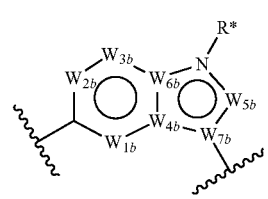

IB

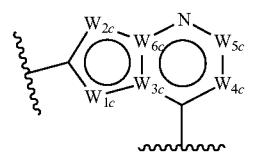

IC

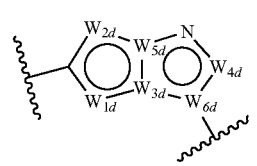

ID wherein
in formula IA: $W^{1a}$ is CH, CF or N; $W^{2a}$ is CH, CF or N; $W^{3a}$ is $CR^{4a}$ or N; $W^{4a}$ is $CR^{5a}$ or N; $W^{5a}$ is $CR^{6a}$ or N;

in formula IB: $W^{1b}$ is CH, CF or N; $W^{2b}$ is CH, CF or N; $W^{3b}$ is $CR^{4b}$ or N; $W^{4b}$ is C or N; $W^{5b}$ is $CR^{6b}$ or N; $W^{6b}$ is C or N; $W^{7b}$ is C or N, and wherein when $W^{3b}$ represents N, $W^{4b}$ and $W^{6b}$ represent C and $W^{5b}$ represents C or N, then R* is hydrogen (in all other cases R* is absent);

in formula IC: $W^{1c}$ is CH, $CR^{r1}$, N, $NR^{q1}$, O or S; $W^{2c}$ is CH, $CR^{r2}$, N, $NR^{q2}$, O or S; $W^{3c}$ is C or N; $W^{4c}$ is $CR^{5c}$ or N; $W^{5c}$ is $CR^{6c}$ or N; $W^{6x}$ is C or N;

in formula ID: $W^{1d}$ is CH, $CR^{r3}$, N, $NR^{q3}$, O or S; $W^{2d}$ is CH, $CR^{r4}$, N, $NR^{q4}$, O or S; $W^{3d}$ is C or N; $W^{4d}$ is $CR^{5d}$ or N; $W^{5d}$ is C or N; $W^{6d}$ is C or N;

each $R^{r1}$, $R^{r2}$, $R^{r3}$ and $R^{r4}$ is independently selected from halo, $C_{1-3}$ alkyl (e.g. acyclic $C_{1-3}$ alkyl or cyclopropyl), a 3- to 5-membered heterocycloalkyl group, $—OR^{s1}$, $—CN$, $—N(R^{s2})R^{s3}$, $—S(O)_{w1}CH_3$ or $—C(O)CH_3$;

w1 represents 0, 1 or 2;

each $R^{s1}$, $R^{s2}$ and $R^{3s}$ independently represent hydrogen or $C_{1-2}$ alkyl;

each $R^{q1}$, $R^{q2}$, $R^{q3}$ and $R^{q4}$ is independently selected from $C_{1-3}$ alkyl (e.g. acyclic $C_{1-3}$ alkyl or cyclopropyl), a 3- to 5-membered heterocycloalkyl group or $—C(O)CH_3$;

each $R^1$, $R^{2a}$, $R^{2b}$, $R^{2c}$, $R^3$, $R^{4a}$, $R^{5a}$, $R^{6a}$, $R^{4b}$, $R^{6b}$, $R^{5c}$, $R^{6c}$ and $R^{5d}$ are independently selected from hydrogen or a substituent selected from halo, $—CN$, $—C(O)N(R^{f1})R^{f2}$, $—C(O)R^{f3}$, $—N(R^{f4})R^{f5}$, $—C(O)OR^{f6}$, $—OR^{f7}$, $—OC(O)—R^{f8}$, $—S(O)_{w2}CH_3$ or $C_{1-8}$ alkyl (e.g. acyclic $C_{1-6}$ alkyl or $C_{3-7}$ cycloalkyl) and a 3- to 8-membered heterocycloalkyl groups, which alkyl and heterocycloalkyl groups are optionally substituted by one or more substituents selected from $=O$ and $E^1$;

w2 represents 0, 1 or 2;

$R^{f1}$, $R^{f2}$, $R^{f4}$, $R^{f5}$ and $R^{f7}$ independently represent hydrogen or $C_{1-6}$ alkyl optionally substituted by one or more substituents selected from $=O$ and $E^2$; or $R^{f1}$ and $R^{f2}$ and/or $R^{f4}$ and $R^{f5}$ may be linked together to form a 4- to 8- (e.g. 5- to 6-) membered ring optionally substituted by one or more substituents selected from $C_{1-3}$ alkyl and halo;

$R^{f3}$, $R^{f6}$ and $R^{f8}$ independently represent $C_{1-6}$ alkyl optionally substituted by one or more substituents selected from =O and $E^2$;

X represents a direct bond, —C($R^a$)($R^b$)—, —O—, —S—, —N($R^c$)—, —N($R^d$)C(O)—, —C(O)N($R^e$)— or —N($R^f$)—C(O)—N($R^g$)—;

Y represents -arylene-, -heteroarylene- (which latter two groups are optionally substituted by one or more substituents selected from $E^3$), -heterocycloalkylene- or —$C_{1-12}$alkylene- (which latter two groups are optionally substituted by one or more substituents selected from =O and $E^4$);

$R^N$ represents hydrogen or $C_{1-6}$ alkyl optionally substituted by one or more substituents selected from =O and $E^5$;

Z represents -($A^x$)$_{1-7}$- or, particularly, -($A^x$)$_{2-7}$-, wherein each $A^x$ independently represents —C($R^{x1}$)($R^{x2}$)—, —N($R^{x3}$)—, —C(O)—, —O—, —S—, —S(O)— or —S(O)$_2$—;

$R^{x1}$, $R^{x2}$ and $R^{x3}$ each independently represent hydrogen or a substituent selected from $E_x$;

each $E_x$ independently represents halo, —C(O)$R^{y1}$, —N($R^{y2}$)—C(O)—N($R^{y3}$)($R^{y4}$), $C_{1-6}$ alkyl or heterocycloalkyl (both of which latter two groups are optionally substituted by one or more halo atoms);

$R^{y1}$, $R^{y2}$, $R^{y3}$ and $R^{y4}$ each independently represent hydrogen or $C_{1-3}$ alkyl optionally substituted by one or more halo atoms;

each $R^a$, $R^b$, $R^c$, $R^d$, $R^e$, $R^f$ and $R^g$ independently represent hydrogen or $C_{1-6}$ alkyl optionally substituted by one or more halo atoms;

each $E^1$, $E^2$, $E^3$, $E^4$ and $E^5$ independently represents, on each occasion when used herein:

(i) $Q^4$;

(ii) $C_{1-12}$ alkyl or heterocycloalkyl, both of which are optionally substituted by one or more substituents selected from =O and $Q^5$;

any two $E^1$, $E^2$, $E^3$, $E^4$ and/or $E^5$ groups (for example on $C_{1-12}$ alkyl groups, e.g. when they are attached to the same or adjacent carbon atoms, or, on aromatic groups, when attached to adjacent atoms), may be linked together to form a 3- to 12-membered ring, optionally containing one or more (e.g. one to three) unsaturations (preferably, double bonds), and which ring is optionally substituted by one or more substituents selected from =O and $J^1$;

each $Q^4$ and $Q^5$ independently represent, on each occasion when used herein: halo, —CN, —N($R^{20}$)$R^{21}$, —O$R^{20}$, —C(=$Y^1$)—$R^{20}$, —C(=$Y^1$)—O$R^{20}$, —C(=$Y^1$)N($R^{20}$)$R^{21}$, —C(=$Y^1$)N($R^{20}$)—O—$R^{21a}$, —OC(=$Y^1$)—$R^{20}$, —OC(=$Y^1$)—O$R^{20}$, —OC(=$Y^1$)N($R^{20}$)$R^{21}$, —OS(O)$_2$O$R^{20}$, —OP(=$Y^1$)(O$R^{20}$)(O$R^{21}$), —OP(O$R^{20}$)(O$R^{21}$), —N($R^{22}$)C(=$Y^1$)$R^{21}$, —N($R^{22}$)C(=$Y^1$)O$R^{21}$, —N($R^{22}$)C(=$Y^1$)N($R^{20}$)$R^{21}$, —N$R^{22}$S(O)$_2$$R^{20}$, —N$R^{22}$S(O)$_2$N($R^{20}$)$R^{21}$, —S(O)$_2$N($R^{20}$)$R^{21}$, —SC(=$Y^1$)$R^{20}$, —SC(=$Y^1$)O$R^{20}$, —SC(=$Y^1$)N($R^{20}$)$R^{21}$, —S(O)$_2$$R^{20}$, —S$R^{20}$, —S(O)$R^{20}$, —S(O)$_2$O$R^{20}$, $C_{1-6}$ alkyl or heterocycloalkyl (which latter two groups are optionally substituted by one or more substituents selected from =O and $J^2$);

each $Y^1$ independently represents, on each occasion when used herein, =O, =S, =N$R^{23}$ or =N—CN;

each $R^{21a}$ represents $C_{1-6}$ alkyl or heterocycloalkyl (which latter two groups are optionally substituted by one or more substituents selected from $J^4$ and =O);

each $R^{20}$, $R^{21}$, $R^{22}$ and $R^{23}$ independently represent, on each occasion when used herein, hydrogen, $C_{1-6}$ alkyl or heterocycloalkyl (which latter two groups are optionally substituted by one or more substituents selected from $J^4$ and =O); or any relevant pair of $R^{20}$, $R^{21}$ and $R^{22}$, may (for example, when attached to the same atom, adjacent atom (i.e. 1,2-relationship) or to atoms that are two atoms apart, i.e. in a 1,3-relationship) be linked together to form (e.g. along with the requisite nitrogen atom to which they may be attached) a 4- to 20- (e.g. 4- to 12-) membered ring, optionally containing one or more heteroatoms (for example, in addition to those that may already be present, e.g. (a) heteroatom(s) selected from oxygen, nitrogen and sulfur), optionally containing one or more unsaturations (preferably, double bonds), and which ring is optionally substituted by one or more substituents selected from $J^6$ and =O;

each $J^1$, $J^2$, $J^4$ and $J^6$ independently represents, on each occasion when used herein:

(i) $Q^7$;

(ii) $C_{1-6}$ alkyl or heterocycloalkyl, both of which are optionally substituted by one or more substituents selected from =O and $Q^8$;

each $Q^7$ and $Q^8$ independently represents, on each occasion when used herein:

halo, —CN, —N($R^{50}$)$R^{51}$, —O$R^{50}$, —C(=$Y^a$)—$R^{50}$, —C(=$Y^a$)—O$R^{50}$, —C(=$Y^a$)N($R^{50}$)$R^{51}$, —N($R^{52}$)C(=$Y^a$)$R^{51}$, —N$R^{52}$S(O)$_2$$R^{50}$, —S(O)$_2$N($R^{50}$)$R^{51}$, —N($R^{52}$)—C(=$Y^a$)—N($R^{50}$)$R^{51}$, —S(O)$_2$$R^{50}$, —S$R^{50}$, —S(O)$R^{50}$, $C_{1-6}$ alkyl (optionally substituted by one or more fluoro atoms) or heterocycloalkyl (optionally substituted by one or more substituents selected from halo, —O$R^{60}$ and —N($R^{61}$)$R^{62}$);

each $Y^a$ independently represents, on each occasion when used herein, =O, =S, =N$R^{53}$ or =N—CN;

each $R^{50}$, $R^{51}$, $R^{52}$ and $R^{53}$ independently represents, on each occasion when used herein, hydrogen or $C_{1-6}$ alkyl optionally substituted by one or more substituents selected from fluoro, —O$R^{60}$ and —N($R^{61}$)$R^{62}$; or any relevant pair of $R^{50}$, $R^{51}$ and $R^{52}$ may (for example when attached to the same or adjacent atoms) be linked together to form, a 3- to 8-membered ring, optionally containing one or more heteroatoms (for example, in addition to those that may already be present, heteroatoms selected from oxygen, nitrogen and sulfur), optionally containing one or more unsaturations (preferably, double bonds), and which ring is optionally substituted by one or more substituents selected from =O and $C_{1-3}$ alkyl;

$R^{60}$, $R^{61}$ and $R^{62}$ independently represent hydrogen or $C_{1-6}$ alkyl optionally substituted by one or more fluoro atoms;

or a pharmaceutically acceptable ester, amide, solvate or salt thereof, which compounds, esters, amides, solvates and salts are referred to hereinafter as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

By "pharmaceutically acceptable ester, amide, solvate or salt thereof", we include salts of such an ester or amide, and solvates of such an ester, amide or salt. For instance, pharmaceutically acceptable esters and amides such as those defined herein may be mentioned, as well as pharmaceutically acceptable solvates or salts.

Pharmaceutically acceptable esters and amides of the compounds of the invention are also included within the scope of the invention. Pharmaceutically acceptable esters and amides of compounds of formula I may have an appropriate group, for example an acid group, converted to the appropriate ester or amide. For example, pharmaceutically acceptable esters (of carboxylic acids) that may be mentioned include optionally substituted $C_{1-6}$ alkyl, $C_{5-10}$ aryl and/or $C_{5-10}$ aryl-$C_{1-6}$ alkyl- esters. Pharmaceutically acceptable amides (of carboxylic acids) that may be mentioned include those of the formula —$C(O)N(R^{z1})R^{z2}$, in which $R^{z1}$ and $R^{z2}$ independently represent optionally substituted $C_{1-6}$ alkyl, $C_{5-10}$ aryl, or $C_{5-10}$ aryl-$C_{1-6}$ alkylene-. Preferably, $C_{1-6}$ alkyl groups that may be mentioned in the context of such pharmaceutically acceptable esters and amides are not cyclic, e.g. linear and/or branched.

Preferably, specific esters and amides of compounds of the invention that may be mentioned include those esters and amides those mentioned herein in respect of compounds of formula I (or compounds of the invention).

Further compounds of the invention that may be mentioned include carbamate, carboxamido or ureido derivatives, e.g. such derivatives of existing amino functional groups.

For the purposes of this invention, therefore, prodrugs of compounds of the invention are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. I-92, Elesevier, New York-Oxford (1985).

Compounds of the invention may contain double bonds and may thus exist as E (entgegen) and Z (zusammen) geometric isomers about each individual double bond. Positional isomers may also be embraced by the compounds of the invention. All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of the invention may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{38}Cl$, $^{123}I$, and $^{125}I$. Certain isotopically-labeled compounds of the present invention (e.g., those labeled with $^3H$ and $^{14}C$) are useful in compound and for substrate tissue distribution assays. Tritiated ($^3H$) and carbon-I4 ($^{14}C$) isotopes are useful for their ease of preparation and detectability. Further, substitution with heavier isotopes such as deuterium (i.e., $^2H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in e.g. the schemes and/or Examples hereinbelow, by substituting an isotopically labeled reagent for a non-isotopically labeled reagent.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). Such cycloalkyl groups may be monocyclic or bicyclic and may further be bridged. Further, when there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

Unless otherwise stated, the term $C_{1-q}$ alkylene (where q is the upper limit of the range) defined herein may be straight-chain or, when there is a sufficient number of carbon atoms, be saturated or unsaturated (so forming, for example, an alkenylene or alkynylene linker group). However, such $C_{1-q}$ alkylene groups are preferably not branched. Such "alkylene" groups may be appropriate linker groups that are a part of the macrocyclic structure of formula I. For the avoidance of doubt, any optional substituents on the alkylene groups are not an integral part of the linking moiety, i.e. when "Y" represents substituted alkylene, then the substituent(s) are not linked to "X" or "Z", but are located on the alkylene moiety.

$C_{3-q}$ cycloalkyl groups (where q is the upper limit of the range) that may be specifically mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double or triple bonds (forming for example a cycloalkenyl or cycloalkynyl group). Substituents may be attached at any point on the cycloalkyl group. Further, where there is a sufficient number (i.e. a minimum of four) such cycloalkyl groups may also be part cyclic. For the avoidance of doubt, optional substituents may also be other cyclic groups, which may be attached via a single carbon atom common to both rings, so forming a spiro-cycle.

The term "halo", when used herein, includes fluoro, chloro, bromo and iodo.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is from five to ten (between five and ten). Such heterocycloalkyl groups may also be bridged. Further, such heterocycloalkyl groups may be saturated or unsaturated containing one or more double and/or triple bonds, forming for example a $C_{3-q}$ heterocycloalkenyl (where q is the upper limit of the range) or a $C_7$ heterocycloalkynyl group. $C_{3-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo-[3.2.1]octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form (i.e. those heteroatoms may be substituted with one or two =O substituents, as appropriate). As stated herein other carbon atoms of the heterocycloalkyl groups mentioned herein may also be substituted by one or more =O substituents. For the avoidance of doubt, optional substituents may also be other cyclic groups, which may be attached via a single carbon atom common to both rings (so forming a Spiro cycle).

The term "-heterocycloalkylene-" refers to a heterocycloalkyl group that is a part of a linker group. Each hyphen therefore represents the point of attachment to the moieties to which they are attached. For instance when Y represents -heterocycloalkylene-, then the hyphens represent the point of attachment to "X" and "Z". The point of attachment may be via any appropriate atom (e.g. a nitrogen or carbon atom of that heterocycloalkyl moiety). Where it is indicated that such a moiety may be substituted, the optional substituents are not an integral part of the macrocycle, i.e. in the case where Y represents substituted -heterocycloalkylene-, then those substituents are not directly linked to "X" or "Z".

For the avoidance of doubt, the term "bicyclic" (e.g. when employed in the context of heterocycloalkyl groups) refers to groups in which the second ring of a two-ring system is formed between two adjacent atoms of the first ring. The term "bridged" (e.g. when employed in the context of cycloalkyl or heterocycloalkyl groups) refers to monocyclic or bicyclic groups in which two non-adjacent atoms are linked by either an alkylene or heteroalkylene chain (as appropriate).

Aryl groups that may be mentioned include $C_{6-10}$ aryl groups. Such groups may be monocyclic, bicyclic or tricyclic and have from 6 to 10 (between 6 and 10) ring carbon atoms, in which at least one ring is aromatic. $C_{6-10}$ aryl groups include phenyl, naphthyl and the like, such as 1,2,3,4-tetrahydronaphthyl. The point of attachment of aryl groups may be via any atom of the ring system. However, when aryl groups are bicyclic or tricyclic, they are linked to the rest of the molecule via an aromatic ring. For the avoidance of doubt, optional substituents include those defined herein and also include =O substituents that may be attached to any non-aromatic rings of a polycyclic (e.g. bicyclic) aryl group (however, in an embodiment, =O substituents are not included). For the avoidance of doubt, optional substituents may also be other cyclic groups, which may be, when attached to a non-aromatic ring of an aryl group, attached via a single carbon atom common to both rings (so forming a spiro-cycle).

Unless otherwise specified, the term "heteroaryl" when used herein refers to an aromatic group containing one or more heteroatom(s) (e.g. one to four heteroatoms) preferably selected from N, O and S. Heteroaryl groups include those which have from 5 to 10 (between 5 and 10) members and may be monocyclic, bicyclic or tricyclic, provided that at least one of the rings is aromatic (so forming, for example, a mono-, bi-, or tricyclic heteroaromatic group). However, when heteroaryl groups are bicyclic or tricyclic, they are linked to the rest of the molecule via an aromatic ring. Heteroaryl groups that may be mentioned include acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. For the avoidance of doubt, optional substituents include those defined herein and also include =O substituents that may be attached to any non-aromatic rings of a polycyclic (e.g. bicyclic) heteroaryl group (but, in an embodiment, =O substituents are not included). For the avoidance of doubt, optional substituents may also be other cyclic groups, which may be, when attached to a non-aromatic ring of a heteroaryl group, attached via a single carbon atom common to both rings (so forming a spiro-cycle). The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form.

The terms "-arylene-" and "-heteroarylene-" refer to aryl/heteroaryl groups that are a part of a linker group. Each hyphen therefore represents the point of attachment to the moieties to which they are attached. For instance when Y represents "-arylene-" and "-heteroarylene-", then the hyphens represent the point of attachment to "X" and "Z". The point of attachment may be via any appropriate atom (e.g. a nitrogen or carbon atom of those moieties). Where it is indicated that those moieties may be substituted, the optional substituents are not an integral part of the macrocycle, i.e. in the case where Y represents substituted -arylene- or -heteroarylene-, then those substituents are not directly linked to "X" or "Z".

It may be specifically stated that the heteroaryl group is monocyclic or bicyclic. In the case where it is specified that the heteroaryl is bicyclic, then it may consist of a five-, six- or seven-membered monocyclic ring (e.g. a monocyclic heteroaryl ring) fused with another a five-, six- or seven-membered ring (e.g. a monocyclic aryl or heteroaryl ring).

Heteroatoms that may be mentioned include phosphorus, silicon, boron and, preferably, oxygen, nitrogen and sulphur.

Linker groups, for example as defined by X and Z are specified with hyphens ("-"s) at the respective ends, depicting the points of attachment with the rest of the compound of formula I. For the avoidance of doubt, in relation to the linker groups defined by Z, the first hyphen of the linking moiety is the point at which that moiety links to the requisite phenyl ring (bearing $R^2$ and $R^3$ groups) and the last hyphen depicts the linking point to the Y group. Similarly, for the X linker group the first hyphen represents the point of attachment to the Y group and the last hyphen represents the point of attachment to ring NB.

For the avoidance of doubt, in cases in which the identity of two or more substituents in a compound of the invention may be the same, the actual identities of the respective substituents are not in any way interdependent. For example, in the situation in which there is more than one $Q^4$ substituent present, then those $Q^4$ substituents may be the same or different. Further, in the case where there are two $Q^4$ substituents present, in which one represents —$OR^{20}$ and the other represents —$C(O)$—$R^{20}$, then those $R^{20}$ groups are not to be regarded as being interdependent.

For the avoidance of doubt, in the instance where cyclic substituents (e.g. cycloalkyl or heterocycloalkyl groups) are present on groups (such as alkyl groups), then those cyclic substituents may be attached to the same carbon atom, so forming for example a spiro-cyclic group.

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

For instance, it is indicated herein that $A^x$ may represent various integers. However, certain integers may not be linked together if unstable groups are formed, e.g. —O— may not be linked to —S—, etc. The skilled person will appreciate the combinations that are possible, in order for the group to be sufficiently stable and/or for the rules of valency to be adhered to.

For the avoidance of doubt, when a term such as "$E^1$ to $E^4$" is employed herein, this will be understood by the skilled person to mean $E^1$, $E^2$, $E^3$ and $E^4$, inclusively. Likewise, a term such as "$R^1$ to $R^6$" when employed herein, will be understood by the skilled person to mean every single $R^1$ to $R^6$ group, i.e. $R^1$, $R^{2a}$, $R^{2b}$, $R^{2c}$, $R^3$, $R^{4a}$, $R^{5a}$, $R^{6a}$, $R^{4b}$, $R^{6b}$, $R^{5c}$, $R^{6c}$ and $R^{5d}$, inclusively.

In another embodiment of the invention, $R^N$ represents hydrogen and Z represents -$(A^x)_{2-7}$-.

In an embodiment of the invention, $R^N$ represents $C_{1-3}$ alkyl (e.g methyl) or, particularly, hydrogen.

In another embodiment of the invention:

$R^N$ represents $C_{1-6}$ alkyl (e.g. $C_{1-3}$ alkyl) optionally substituted by one or more substituents selected from =O and $E^5$; and/or Z represents -$(A^x)$-.

Preferred compounds of the invention include those in which:

$R^{4a}$ and $R^{6a}$ (or, $R^{4a}$, $R^{5a}$ and $R^{6a}$) independently represent hydrogen;

in formula IA: $W^{3a}$ is CH or N; $W^{5a}$ is CH or N (or, $W^{3a}$ is CH or N; $W^{4a}$ is CH or N; $W^{5a}$ is CH or N);

$R^{6b}$ (or, $R^{4b}$ and $R^{6b}$ independently) represents hydrogen;

in formula IB: $W^{3b}$ is CH or N (or, $W^{3b}$ is CH or N; $W^{5b}$ is CH or N);

$R^{5c}$ and $R^{6c}$ independently represent hydrogen;

in formula IC: $W^{4c}$ is CH or N; $W^{5c}$ is CH or N;

$R^{5d}$ represents hydrogen;

in formula ID: $W^{4d}$ is CH or N;

$R^{1}$ represents a substituent selected from hydrogen or, particularly, $C_{1-6}$ alkyl (e.g. acyclic $C_{1-6}$ alkyl and $C_{3-6}$ cycloalkyl, such as cyclopropyl; which alkyl groups are optionally substituted by one or more substituents selected from $E^{1}$, e.g. fluoro), halo, —CN, —N($R^{f4}$)$R^{f5}$ and —O$R^{f7}$;

when $R^{1}$ represents —N($R^{N}$)$R^{f5}$, then $R^{f4}$ and $R^{f5}$ preferably and independently represent hydrogen or $C_{1-6}$ alkyl (optionally substituted by one or more halo atoms);

when $R^{1}$ represents —O$R^{f7}$, then $R^{f7}$ preferably represents $C_{1-6}$ alkyl (optionally substituted by one or more halo atoms);

more preferably $R^{1}$ represents a substituent selected from hydrogen, —OCH($CH_{3}$)$_{2}$ or, particularly, —OH, or, preferably, halo, —CN, —OCH$_{3}$, —OCH$_{2}$CH$_{3}$, —N($R^{f4}$)$R^{f5}$ (e.g. —NH$_{2}$), —CH$_{3}$, —CH$_{2}$CH$_{3}$ and —CF$_{3}$.

Other preferred compounds of the invention that may be mentioned include those in which ring A and ring B represent a fused bicyclic group of the following structure:

Formula IA

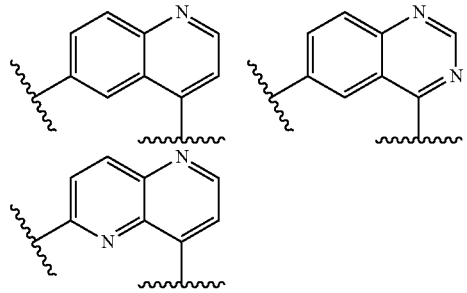

Formula IB

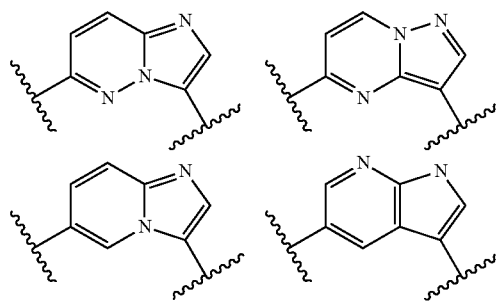

Formula IC

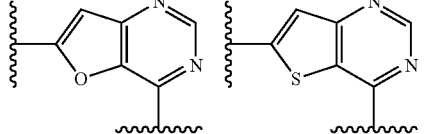

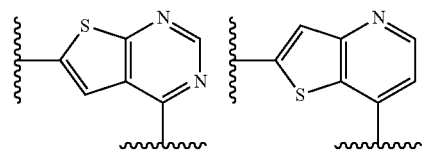

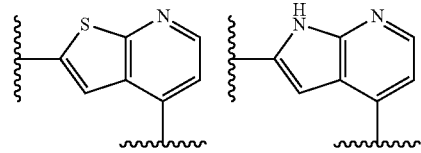

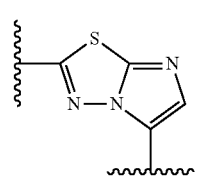

Formula ID

Other preferred compounds of the invention that may be mentioned include those in which ring A and ring B represent a fused bicyclic group of the following structure:

Formula IA

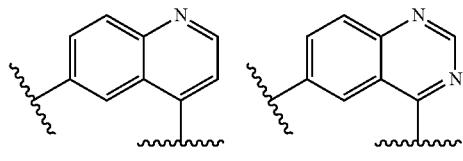

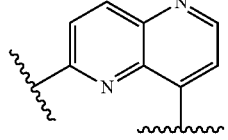

Formula IB

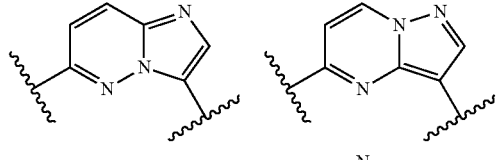

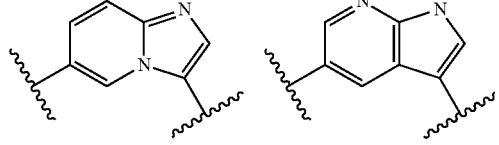

Formula IC

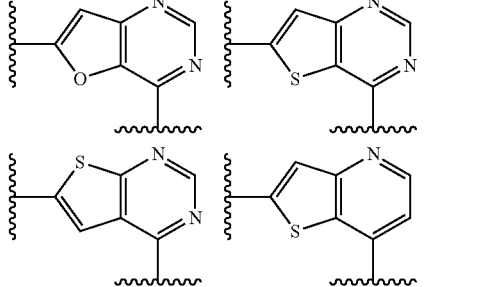

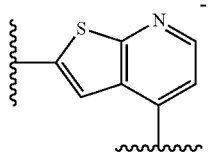

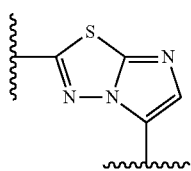

Formula ID

In some embodiments, these fused bicyclic groups are unsubstituted. In other embodiments they are substituted as described above in connection with rings A and B. In particular embodiments, the above-listed fused, bicyclic groups are optionally substituted by one or more substituents selected from halo, $C_{1-3}$ alkyl, or —CN.

Particularly, for compounds in which ring A and ring B together represent a fused bicyclic group of formula IC, formula IC represents:

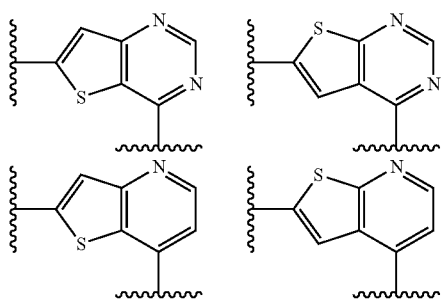

Hence preferred ring A/ring B bicyclic structures include those in which:

in formula IA: $W^{1a}$ is CF, preferably, CH or N; $W^{2a}$ is CF or, preferably, CH; $W^{3a}$ is $CR^{4a}$; $W^{4a}$ is $CR^{5a}$ or N; $W^{5a}$ is $CR^{6a}$;

$R^{4a}$ and $R^{6a}$ (particularly, $R^{4a}$, $R^{5a}$ and $R^{6a}$) independently represent hydrogen;

one of $W^{1a}$, $W^{2a}$ and $W^{3a}$ (preferably $W^{1a}$) may represent N or CH and the others represent CH;

one of $W^{4a}$ and $W^{5a}$ (preferably $W^{4a}$) represents N or CH and the other represents CH;

in formula IB: $W^{1b}$ is CF or, preferably, CH or N; $W^{2b}$ is CF or, preferably, CH; $W^{3b}$ is $CR^{4b}$ or N; $W^{4b}$ is C or N; $W^{5b}$ is $CR^{6b}$; $W^{6b}$ is C or N; $W^{7b}$ is C;

$R^{6b}$ (particularly, $R^{4b}$ and $R^{6b}$ independently) represents hydrogen;

one of $W^{4b}$ and $W^{6b}$ represents C or N and the other represents C;

one of $W^{1b}$, $W^{2b}$ and $W^{3b}$ (preferably $W^{1b}$ or $W^{3b}$) may represent N or CH and the others represent CH;

in formula IC: $W^{1c}$ is O or, particularly, $CR^{r1}$, preferably, CH or S; $W^{2c}$ is $CR^{r2}$, preferably, CH or S; $W^{3c}$ is C; $W^{4c}$ is N or $CR^{5c}$ (preferably N); $W^{5c}$ is $CR^{6c}$; $W^{6c}$ is C;

$R^{6c}$ represents a $C_{1-3}$ alkyl group or, particularly, hydrogen;

one of $W^{1c}$ and $W^{2c}$ represents CH and the other represents O or, particularly, S;

one of $W^{3c}$ and $W^{6c}$ may represent N but preferably both represent C;

one of $W^{4c}$ and $W^{5c}$ (preferably $W^{4c}$) may represent N (or $CR^{5c}$ or $CR^{6c}$) and the other (preferably $W^{5c}$) represents $CR^{5c}$ or $CR^{6c}$;

in formula ID: $W^{1d}$ is N; $W^{2d}$ is S; $W^{3d}$ is N; $W^{4d}$ is $CR^{5d}$; $W^{5d}$ is C; $W^{6d}$ is C;

$R^{5d}$ represents hydrogen;

one of $W^{3d}$ and $W^{5d}$ may represent N and the other represents C;

one of $W^{1d}$ and $W^{2d}$ (preferably $W^{1d}$) represents N and the other represents S.

Other preferred compounds of the invention that may be mentioned include those in which:

Y represents -arylene- (e.g. -phenylene-), -heteroarylene- (e.g. 1,2,3,4-tetrahydroisoquinolinyl, thiophenyl (i.e. thienyl), furanyl or, particularly, pyridyl or pyrazolyl), -heterocycloalkylene- (e.g. piperidinyl or morpholinyl, optionally containing a double bond) or —$C_{1-6}$alkylene-, all of which groups are optionally substituted as defined herein (e.g. by $E^3$, $E^4$ and, if appropriate by =O);

more preferably Y represents a cyclic group, e.g. optionally substituted arylene, heteroarylene or heterocycloalkylene;

more preferably still Y represents one of the following groups (in which, preferably, the upper squiggly line represents the point of attachment to the Z group):

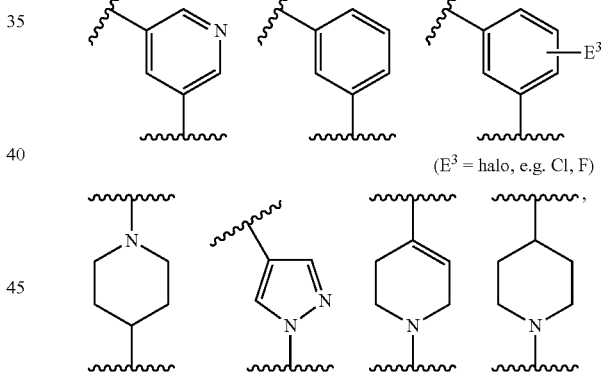

($E^3$ = halo, e.g. Cl, F)

e.g. more preferably:

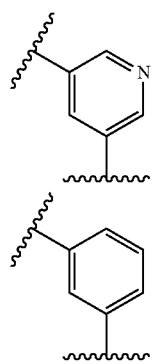

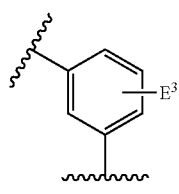
($E^3$ = halo, e.g. Cl, F)
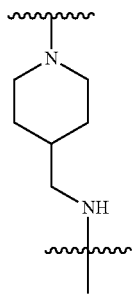
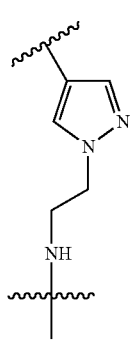
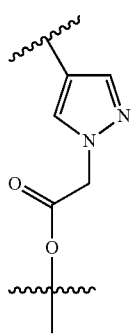
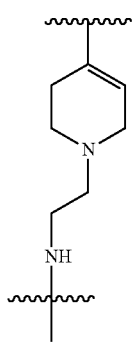
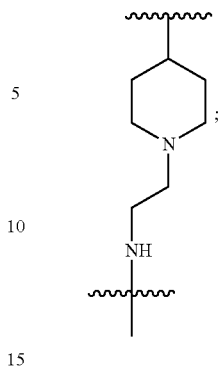
more preferably still Y represents one of the following groups (in which, preferably, the upper squiggly line represents the point of attachment to the X group):
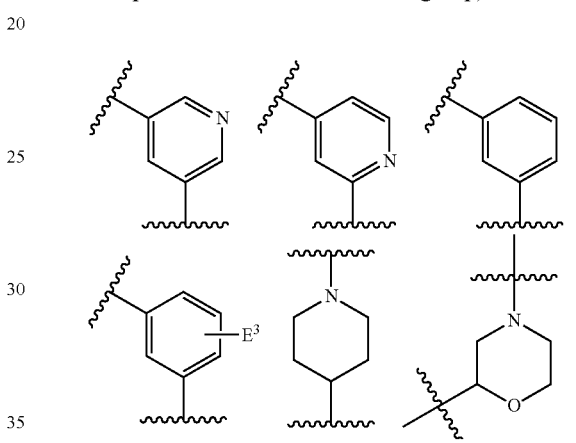
($E^3$ = halo, e.g. Cl, F)
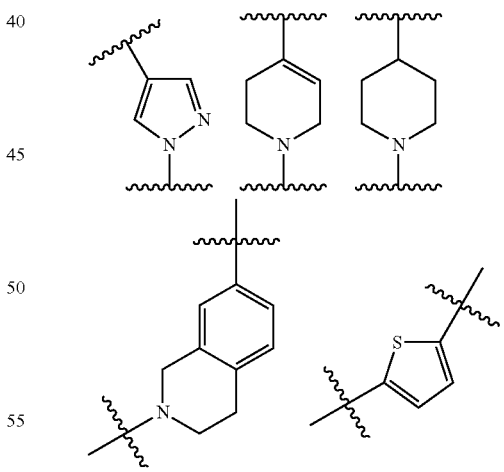
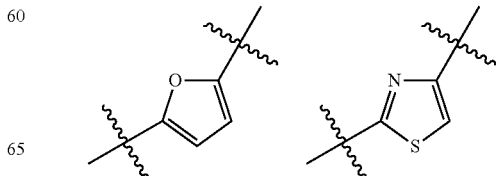

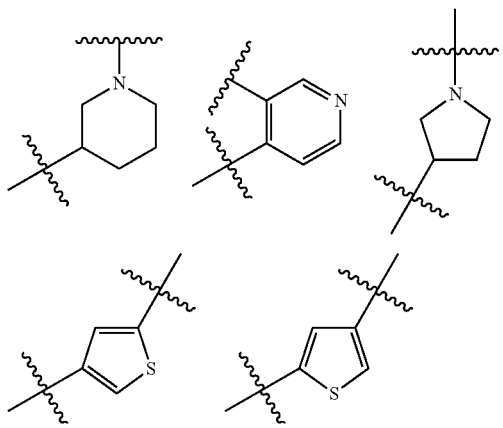

or particularly, Y represents one of the following groups (in which, preferably, the upper squiggly line represents the point of attachment to the X group):

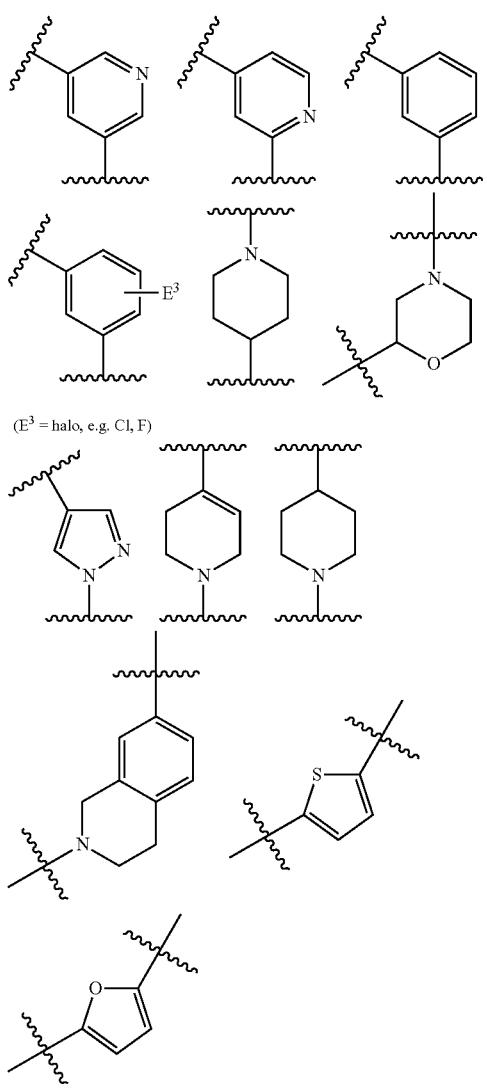

($E^3$ = halo, e.g. Cl, F)

Other preferred compounds of the invention include those in which:

X represents —N($R^c$)— or, more preferably a direct bond;

X may represent a linker group (i.e. other than a direct bond) particularly in the case when Y represents a non-cyclic group (e.g. acyclic $C_{1-12}$alkylene, optionally substituted as defined herein);

$R^c$ represents hydrogen;

Z represents -($A^x$)$_{1-6}$- (e.g. -($A^x$)$_{2-6}$-);

each $A^x$ independently represents —C($R^{x1}$)($R^{x2}$)—, —N($R^{x3}$)— and —C(O)—.

Further preferred compounds of the invention that may be mentioned include those in which:

$R^{x1}$ and $R^{x2}$ independently represent hydrogen, halo or $C_{1-6}$ (e.g. $C_{1-3}$) alkyl (preferably unsubstituted);

$R^{x3}$ represents hydrogen or $C_{1-6}$ (e.g. $C_{1-3}$) alkyl (preferably unsubstituted);

more preferably, $R^{x1}$, $R^{x2}$ and $R^{x3}$ each independently represent $C_{1-3}$ alkyl or, particularly, hydrogen;

each $E_x$ independently represents halo, —C(O)$R^{y1}$, $C_{1-6}$ alkyl or heterocycloalkyl (which latter two groups may be attached to a single carbon atom, and both of which are optionally substituted by one or more halo, e.g. fluoro, atoms) (more preferably each $E_x$ represents halo or unsubstituted $C_{1-6}$ alkyl); and/or each $R^a$, $R^b$, $R^c$, $R^d$, $R^e$, $R^f$, $R^g$, $R^{y1}$, $R^{y2}$, $R^{y3}$ and $R^{y4}$ independently represent hydrogen or $C_{1-2}$ alkyl optionally substituted by one or more fluoro atoms.

Most preferred compounds of the invention include those in which:

$E^1$, $E^2$, $E^3$, $E^4$ and $E^5$ independently represent, on each occasion when used herein, $Q^4$ or $C_{1-6}$ (e.g. $C_{1-3}$) alkyl optionally substituted by one or more substituents selected from =O and, preferably, $Q^5$ (most preferably such $E^1$ to $E^5$ groups represent $Q^4$);

each $Q^4$ and $Q^5$ independently represents, on each occasion when used herein halo, —CN, —N($R^{20}$)$R^{21}$, —O$R^{20}$, —C(=$Y^1$)—$R^{20}$, —C(=$Y^1$)—O$R^{20}$, —C(=$Y^1$)N($R^{20}$)$R^{21}$, —N($R^{22}$)C(=$Y^1$)$R^{21}$, —N($R^{22}$)C(=$Y^1$)O$R^{21}$, —N$R^{22}$S(O)$_2R^{20}$, —S(O)$_2$N($R^{20}$)$R^{21}$, —S(O)$_2R^{20}$, —S$R^{20}$, —S(O)$R^{20}$, or $C_{1-6}$ alkyl optionally substituted by one or more substituents selected from fluoro;

each $Y^1$ independently represents, on each occasion when used herein, =O;

each $R^{20}$, $R^{21}$, $R^{22}$ and $R^{23}$ independently represent, on each occasion when used herein, hydrogen or $C_{1-3}$ alkyl optionally substituted by one or more substituents selected from $J^4$ and =O; or any pair of $R^{20}$, $R^{21}$ and $R^{22}$ (e.g. $R^{20}$ and $R^{21}$)) may be linked together to form (e.g. when attached to the same nitrogen atom, along with the requisite nitrogen atom to which they are attached) a 4- to 8-membered ring, optionally containing one or more double bonds (e.g. one or two), and which ring may contain a further two or, preferably, one heteroatom (preferably selected from nitrogen and, especially, oxygen), and which ring is optionally substituted by one or more substituents selected from $J^6$ and =O;

each $J^1$, $J^2$, $J^4$ and $J^6$ independently represents, on each occasion when used herein: (i) $Q^7$; or (ii) $C_{1-8}$ (e.g. $C_{1-3}$) alkyl optionally substituted by one or more substituents selected from =O and $Q^8$ (more preferably, each $J^1$, $J^2$, $J^4$ and $J^6$ (e.g. each $J^1$ and $J^2$) independently represents $Q^7$);

each $Q^7$ and $Q^8$ (e.g. $Q^7$) independently represents —N($R^{50}$)$R^{51}$, —O$R^{50}$ or, preferably, halo (e.g. fluoro) or $C_{1-3}$ alkyl (e.g. methyl) optionally substituted by one or more fluoro atoms;

each $Y^a$ independently represents =O;

each $R^{50}$, $R^{51}$, $R^{52}$ and $R^{53}$ substituent independently represents, on each occasion when used herein, hydrogen or $C_{1-6}$ (e.g. $C_{1-3}$) alkyl optionally substituted by one or more substituents selected from fluoro;

$R^{60}$, $R^{61}$ and $R^{62}$ independently represent methyl or hydrogen.

Preferred aryl/arylene and heteroaryl/heteroarylene groups that Y may independently represent include optionally substituted 1,2,3,4-tetrahydroisoquinolinyl or, particularly, optionally substituted phenyl, naphthyl, pyrrolyl, furanyl, thienyl, imidazolyl, oxazolyl, isoxazolyl, thiazolyl, pyrazolyl, pyridyl, indazolyl, indolyl, indolinyl, isoindolinyl, quinolinyl, isoquinolinyl, quinolizinyl, benzoxazolyl, benzofuranyl, isobenzofuranyl, chromanyl, benzothienyl, pyridazinyl, pyrimidinyl, pyrazinyl, indazolyl, benzimidazolyl, quinazolinyl, quinoxalinyl, 1,3-benzodioxolyl, tetrazolyl, benzothiazolyl, and/or benzodioxanyl.

Preferred compounds of the invention include those in which:

each $E^1$, $E^2$, $E^3$, $E^4$ and $E^5$ independently represent $C_{1-6}$ (e.g. $C_{1-3}$) alkyl, heterocycloalkyl (which latter two groups are optionally substituted by one or more substituents selected from =O and, preferably, $Q^5$) or $E^1$ to $E^5$ independently (and more preferably) represent $Q^4$ (in which $E^4$ is preferably halo (e.g. fluoro));

each $Q^4$ and $Q^5$ (e.g. $Q^4$) independently represent halo (e.g fluoro), —C(=Y$^1$)—OR$^{20}$, —N(R$^{20}$)R$^{21}$, —C(=Y$^1$)N(R$^{20}$)R$^{21}$ or —N(R$^{22}$)C(=Y$^1$)OR$^{21}$ (preferably, halo (e.g fluoro), —C(=Y$^1$)—OR$^{20}$, —N(R$^{20}$)R$^{21}$ or —C(=Y$^1$)N(R$^{20}$)R$^{21}$);

each $Y^1$ independently represents =S or, preferably, =O;

$R^{20}$, $R^{21}$ and $R^{22}$ (e.g. $R^{20}$ and $R^{21}$) independently represent hydrogen or, preferably, $C_{1-4}$ alkyl; or $R^{20}$ and $R^{21}$, when attached to the same nitrogen atom are linked together to form a 5- or 6-membered ring, optionally containing a further heteroatom (e.g. nitrogen, or, preferably, oxygen) so forming, e.g. a morpholinyl group;

$R^{22}$ represents hydrogen.

More preferred compounds of the invention include those in which:

each $R^1$, $R^{2a}$, $R^{2b}$, $R^{2c}$, $R^3$, $R^{4a}$, $R^{5a}$, $R^{6a}$, $R^{4b}$, $R^{6b}$, $R^{5c}$, $R^{6c}$ and $R^{5d}$ are independently selected from:

(i) hydrogen;
(ii) halo, —CN, —OR$^{f7}$ and/or —N(R$^{f4}$)R$^{f5}$; and/or
(iii) $C_{1-6}$ alkyl optionally substituted by one or more substituents selected from =O and $E^1$;

X represents a direct bond, —O—, —S— or —N(R$^c$)—;

each $R^a$, $R^b$, $R^c$, $R^d$, $R^e$, $R^f$ and $R^g$ independently represent hydrogen or $C_{1-4}$ alkyl optionally substituted by one or more halo atoms.

Most preferred compounds of the invention that may be mentioned include those in which:

ring A/B represents formula IA, formula IB or formula ID, optionally substituted as indicated above, especially one of the following formulae (optionally substituted as indicated above):

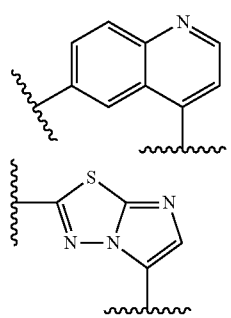

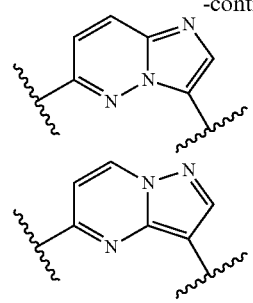

$R^1$ represents a substituent selected from —OR$^{f7}$ (in which R$^{f7}$ preferably represents hydrogen or, especially, $C_{1-4}$ alkyl, which is preferably unsubstituted, e.g. R$^{f7}$ is most preferably unsubstituted $C_{1-3}$ alkyl (particularly unsubstituted $C_{1-2}$ alkyl (e.g. methyl));

$R^{2a}$ and $R^{2c}$ independently represent hydrogen, $C_{1-3}$ alkyl optionally substituted by halo (e.g. fluoro), or a substituent selected from halo (e.g. fluoro);

$R^{2b}$ and $R^3$ independently represent hydrogen;

X represents a direct bond or —N(R$^c$)—;

$R^c$ represents hydrogen;

Y preferably represents pyrazolyl (e.g. 1,4-linked; i.e. linked at the 4-position to the requisite bicycle of formula I), 1,2,3,4-tetrahydroisoquinolinyl (e.g. 2,7-linked;

i.e. linked at the 7-position to the requisite bicycle of formula I), thiophenyl (e.g. 2,5-linked), furanyl (e.g. 2,5-linked), dihydropiperidinyl (e.g. 1,4-linked; i.e. linked at the 4-position to the requisite bicycle of formula I), morpholinyl (e.g. 2,4-linked; i.e. linked at the 4-position to the requisite bicycle of formula I) or, particularly, pyridyl (e.g. 3,5-linked or 2,4-linked; in the latter case, linked to the requisite bicycle of formula I at the 4-position of the pyridyl), phenyl (1,3-linked), piperidinyl (1,4-linked; i.e. linked at the 1-position to the requisite bicycle of formula I) or unsubstituted acyclic $C_{1-4}$ alkylene;

when Y represents arylene or heteroarylene, such groups are optionally substituted by one or more (e.g. two or preferably one) substituent(s) selected from $E^3$ (which $E^3$ substituent may be located at either of the positions ortho to the point of attachment to the requisite bicycle of formula I);

when Y represents pyridyl (or pyridylene), then that moiety is linked to Z and X via non-adjacent atoms that are in a 1,3-relative relationship;

when Y represents heterocycloalkylene or alkylene, such groups are preferably unsubstituted;

when Y represents alkylene, then X may represent —N(R$^c$)— (e.g. —Y—X— may represent —$C_{1-4}$alkylene-N(R$^c$)—);

when Y represents -arylene-, -heteroarylene- or -heterocycloalkylene-, then X preferably represents a direct bond;

$E^3$ represents $Q^4$;

$Q^4$ represents halo (e.g. fluoro);

Z represents —C(O)-[T$^1$]- or —C(O)N(R$^{x3}$)-[T$^1$]-, in which T$^1$ represents —(CH$_2$)$_{0-4}$-T$^2$- (e.g. —(CH$_2$)$_4$-T$^2$-, —CH$_2$-T$^2$- or, particularly, -T$^2$-) and T$^2$ represents a direct bond or —C(O)—N(H)—CH$_2$—; or, particularly, Z represents —C(O)N(H)-[T$^1$], in which T$^1$ represents —(CH$_2$)$_{1-4}$-T$^2$- (e.g. —(CH$_2$)$_4$-T$^2$- or preferably —CH$_2$-T$^2$-) and T$^2$ represents a direct bond or —C(O)—N(H)—CH$_2$—.

In certain embodiments of the invention, ring A and ring B represent a fused bicyclic group of any one of the following formulae:

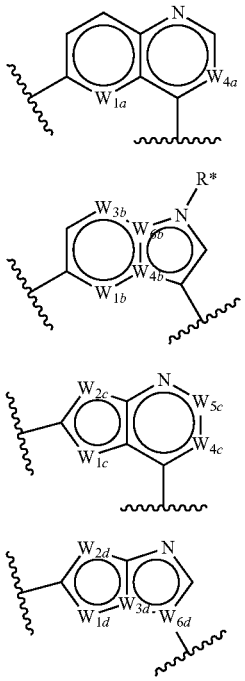

IA

IB

IC

ID wherein in formula IA: $W^{1a}$ is CH, CF or N; $W^{4a}$ is $CR^{5a}$ or N;

in formula IB: $W^{1b}$ is CH, CF or N; $W^{3b}$ is $CR^{4b}$ or N; $W^{4b}$ is C or N; $W^{6b}$ is C or N;

and wherein when $W^{3b}$ represents N and $W^{4b}$ and $W^{6b}$ represent C, then R* is hydrogen (in all other cases R* is absent);

in formula IC: $W^{1c}$ is CH, $CR^{t1}$, N, $NR^{q1}$, O or S; $W^{2c}$ is CH, $CR^{t2}$, N, $NR^{q2}$, O or S;

$W^{4c}$ is $CR^{5c}$ or N; $W^{5c}$ is $CR^{6c}$ or N;

in formula ID: $W^{1d}$ is CH, $CR^{t3}$, N, $NR^{q3}$, O or S; $W^{2d}$ is CH, $CR^{t4}$, N, $NR^{q4}$, O or S; $W^{3d}$ is C or N; $W^{6d}$ is C or N;

each $R^{t1}$, $R^{t2}$, $R^{t3}$ and $R^{t4}$ is independently selected from halo, $C_{1-3}$ alkyl (e.g. acyclic $C_{1-3}$ alkyl or cyclopropyl), $-OR^{s1}$, or $-CN$;

$R^{s1}$ represents hydrogen or $C_{1-2}$ alkyl;

each $R^{q1}$, $R^{q2}$, $R^{q3}$ and $R^{q4}$ is independently selected from $C_{1-3}$ alkyl (e.g. acyclic $C_{1-3}$ alkyl or cyclopropyl), or $-C(O)CH_3$;

each $R^1$, $R^{2a}$, $R^{2b}$, $R^{2c}$, $R^3$, $R^{5a}$, $R^{6a}$, $R^{4b}$, $R^{5a}$, $R^{5c}$ and $R^{6c}$ are independently selected from hydrogen or a substituent selected from halo, $-C(O)R^{f3}$, $-N(R^{f4})R^{f5}$, $-OR^{f7}$ or $C_{1-8}$ alkyl (e.g. acyclic $C_{1-6}$ alkyl or $C_{3-7}$ cycloalkyl) which alkyl group is optionally substituted by one or more substituents selected from $=O$ and $E^1$;

$R^{f4}$, $R^{f5}$ and $R^{f7}$ independently represent hydrogen or $C_{1-6}$ alkyl optionally substituted by one or more substituents selected from $=O$ and $E^2$;

$R^{f3}$ represents $C_{1-6}$ alkyl optionally substituted by one or more substituents selected from $=O$ and $E^2$;

X represents a direct bond, $-C(R^a)(R^b)-$, $-O-$, $-S-$, $-N(R^c)-$;

Y represents -arylene-, -heteroarylene- (which latter two groups are optionally substituted by one or more substituents selected from $E^3$), -heterocycloalkylene- or $-C_{1-6}$alkylene- (which latter two groups are optionally substituted by one or more substituents selected from $=O$ and $E^4$);

$R^N$ represents hydrogen or $C_{1-3}$ alkyl optionally substituted by one or more substituents selected from $=O$ and $E^5$;

Z represents $-(A^x)_{1-6}-$ wherein each $A^x$ independently represents $-C(R^{x1})(R^{x2})-$, $-N(R^{x3})-$, $-C(O)-$, $-O-$;

$R^{x1}$, $R^{x2}$ and $R^{x3}$ each independently represents hydrogen, halo, $-C(O)R^{y1}$ or $C_{1-6}$ alkyl (which latter group is optionally substituted by one or more halo atoms);

$R^{y1}$ represents hydrogen or $C_{1-3}$ alkyl;

each $R^a$, $R^b$ and $R^c$ independently represent hydrogen or $C_{1-3}$ alkyl optionally substituted by one or more halo atoms; and/or each $E^1$, $E^2$, $E^3$, $E^4$ and $E^5$ independently represents, on each occasion when used herein, halo or $C_{1-4}$ alkyl or heterocycloalkyl, both of which are optionally substituted by one or more halo atoms.

In certain embodiments of the invention, ring A and ring B represent a fused bicyclic group of any one of the following formulae:

IA

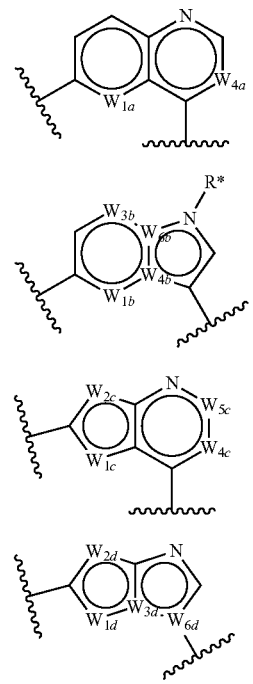

IB

IC

ID wherein in formula IA: $W^{1a}$ is CH, CF or N; $W^{4a}$ is $CR^{5a}$ or N;

in formula IB: $W^{1b}$ is CH, CF or N; $W^{3b}$ is $CR^{4b}$ or N; $W^{4b}$ is C or N; $W^{6b}$ is C or N;

and wherein when $W^{3b}$ represents N and $W^{4b}$ and $W^{6b}$ represent C, then R* is hydrogen (in all other cases R* is absent);

in formula IC: $W^{1c}$ is CH, $CR^{t1}$, N, $NR^{q1}$, O or S; $W^{2c}$ is CH, $CR^{t2}$, N, $NR^{q2}$, O or S; $W^{4c}$ is $CR^{5c}$ or N; $W^{5c}$ is $CR^{6c}$ or N;

in formula ID: $W^{1d}$ is CH, $CR^{t3}$, N, $NR^{q3}$, O or S; $W^{2d}$ is CH, $CR^{t4}$, N, $NR^{q4}$, O or S; $W^{3d}$ is C or N; $W^{6d}$ is C or N;

each $R^{t1}$, $R^{t2}$, $R^{t3}$ and $R^{t4}$ is independently selected from halo, $C_{1-3}$ alkyl (e.g. acyclic $C_{1-3}$ alkyl or cyclopropyl), $-OR^{s1}$, or $-CN$;

$R^{s1}$ represents hydrogen or $C_{1-2}$ alkyl;

each $R^{q1}$, $R^{q2}$, $R^{q3}$ and $R^{q4}$ is independently selected from $C_{1-3}$ alkyl (e.g. acyclic $C_{1-3}$ alkyl or cyclopropyl), or $-C(O)CH_3$;

each $R^1$, $R^{2a}$, $R^{2b}$, $R^{2c}$, $R^3$, $R^{5a}$, $R^{6a}$, $R^{4b}$, $R^{5a}$, $R^{5c}$ and $R^{6c}$ are independently selected from hydrogen or a substituent selected from halo, —C(O)$R^{f3}$, —N($R^{f4}$)$R^{f5}$, —O$R^{f7}$ or $C_{1-8}$ alkyl (e.g. acyclic $C_{1-6}$ alkyl or $C_{3-7}$ cycloalkyl) which alkyl group is optionally substituted by one or more substituents selected from =O and $E^1$;

$R^{f4}$, $R^{f5}$ and $R^{f7}$ independently represent hydrogen or $C_{1-6}$ alkyl optionally substituted by one or more substituents selected from =O and $E^2$;

$R^{f3}$ represents $C_{1-6}$ alkyl optionally substituted by one or more substituents selected from =O and $E^2$;

X represents a direct bond, —C($R^a$)($R^b$)—, —O—, —S—, —N($R^c$)—;

Y represents -arylene-, -heteroarylene- (which latter two groups are optionally substituted by one or more substituents selected from $E^3$), -heterocycloalkylene- or —$C_{1-6}$alkylene- (which latter two groups are optionally substituted by one or more substituents selected from =O and $E^4$);

$R^N$ represents hydrogen or $C_{1-3}$ alkyl optionally substituted by one or more substituents selected from =O and $E^5$;

Z represents -($A^x$)$_{1-6}$- wherein each $A^x$ independently represents —C($R^{x1}$)($R^{x2}$)—, —N($R^{x3}$)—, —C(O)—, —O—;

$R^{x1}$, $R^{x2}$ and $R^{x3}$ each independently represents hydrogen, halo, —C(O)$R^{y1}$ or $C_{1-6}$ alkyl (which latter group is optionally substituted by one or more halo atoms);

$R^{y1}$ represents hydrogen or $C_{1-3}$ alkyl;

each $R^a$, $R^b$ and $R^c$ independently represent hydrogen or $C_{1-3}$ alkyl optionally substituted by one or more halo atoms; and/or each $E^1$, $E^2$, $E^3$, $E^4$ and $E^5$ independently represents, on each occasion when used herein, halo, $C_{1-4}$ alkyl, —O—$C_{1-4}$ alkyl or heterocycloalkyl, which latter three groups are optionally substituted by one or more halo atoms.

In a further embodiment of the invention, ring A and ring B represent a fused bicyclic group of any one of the following formulae:

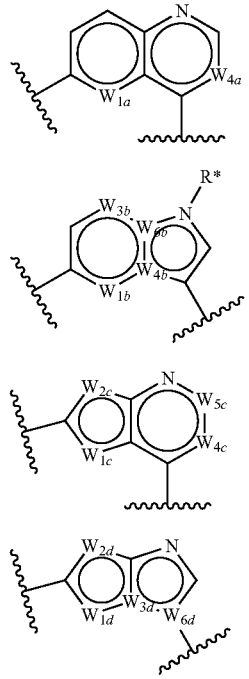

wherein
in formula IA: $W^{1a}$ is CH or N; $W^{4a}$ is CH or N;
in formula IB: $W^{1b}$ is CH or N; $W^{3b}$ is CH or N; $W^{4b}$ is C or N; $W^{6b}$ is C or N; and
wherein when $W^{3b}$ represents N and $W^{4b}$ and $W^{6b}$ represent C, then R* is hydrogen (in all other cases R* is absent);
in formula IC: $W^{1c}$ is CH or S; $W^{2c}$ is CH, C(CH$_3$) or S; $W^{4c}$ is CH, C(CN) or N; $W^{5c}$ is CH, C(CH$_3$) or C—CH(CH$_3$)$_2$;
in formula ID: $W^{1d}$ is N; $W^{2d}$ is S; $W^{3d}$ is N; $W^{6d}$ is C;
each $R^1$, $R^{2a}$, $R^{2b}$, $R^{2c}$, $R^3$, are independently selected from hydrogen or a substituent selected from halo, —O$R^{f7}$ or $C_{1-4}$ alkyl;

$R^{f7}$ independently represent hydrogen or $C_{1-4}$ alkyl optionally substituted by one or more substituents selected from $E^2$;

X represents a direct bond;

Y represents -arylene-, -heteroarylene- (which latter two groups are optionally substituted by one or more substituents selected from $E^3$), -heterocycloalkylene- or —$C_{1-6}$alkylene- (which latter two groups are optionally substituted by one or more substituents selected from $E^4$);

$R^N$ represents hydrogen;

Z represents -($A^x$)$_{1-4}$- wherein each $A^x$ independently represents —C($R^{x1}$)($R^{x2}$)—, —N($R^{x3}$)—, —C(O)—;

$R^{x1}$, $R^{x2}$ and $R^{x3}$ each independently represents hydrogen, halo, $C_{1-6}$ alkyl (which latter group is optionally substituted by one or more halo atoms);

each $E^2$, $E^3$ and $E^4$ independently represents, on each occasion when used herein, halo, $C_{1-4}$ alkyl, —O—$C_{1-4}$ alkyl or heterocycloalkyl, which latter three groups are optionally substituted by one or more halo atoms.

In a further embodiment of the invention, ring A and ring B represent a fused bicyclic group of any one of the following formulae:

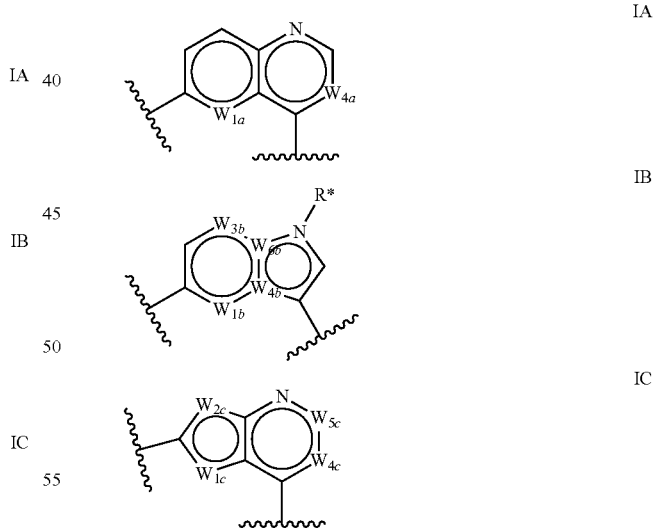

wherein
in formula IA: $W^{1a}$ is CH or N; $W^{4a}$ is CH or N;
in formula IB: $W^{1b}$ is CH or N; $W^{3b}$ is CH; $W^{4b}$ is C or N; $W^{6b}$ is C or N; and wherein R* is absent;
in formula IC: $W^{1c}$ is S; $W^{2c}$ is CH or C(CH$_3$); $W^{4c}$ is N; $W^{6b}$ is CH or C(CH$_3$);
each $R^1$, $R^{2a}$, $R^{2b}$, $R^{2c}$, $R^3$, are independently selected from hydrogen or a substituent selected from halo, —O$R^{f7}$ or $C_{1-4}$ alkyl;

$R^{r7}$ independently represent hydrogen or $C_{1-4}$ alkyl optionally substituted by one or more substituents selected from $E^2$;

X represents a direct bond;

Y represents -phenyl-, -pyridinyl-, -piperidinyl-, -pyrazolyl-, tetrahydroisoquinolinyl- or -thiophenyl- (which groups are optionally substituted by one or more substituents selected from $E^3$), -tetrahydropyridinyl-, -morpholinyl- or -pyrrolidinyl- (which latter three groups are optionally substituted by one or more substituents selected from $E^4$);

$R^N$ represents hydrogen;

Z represents $-(A^x)_{1-4}-$ wherein each $A^x$ independently represents —$C(R^{x1})(R^{x2})$—, —$N(R^{x3})$—, —$C(O)$—;

$R^{x1}$, $R^{x2}$ and $R^{x3}$ each independently represents hydrogen, halo, $C_{1-6}$ alkyl (which latter group is optionally substituted by one or more halo atoms);

each $E^2$, $E^3$ and $E^4$ independently represents, on each occasion when used herein, halo, $C_{1-4}$ alkyl, —O—$C_{1-4}$ alkyl or heterocycloalkyl, which latter three groups are optionally substituted by one or more halo atoms.

In a further embodiment of the invention, ring A and ring B represent a fused bicyclic group of any one of the following formulae:

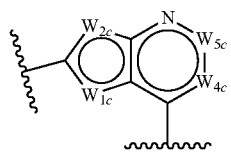

IC wherein in formula IC: $W^{1c}$ is S; $W^{2c}$ is CH or C(CH$_3$); $W^{4c}$ is CH, C(CN) or N; $W^{5c}$ is CH;

each $R^1$, $R^{2a}$, $R^{2b}$, $R^{2c}$, $R^3$, are independently selected from hydrogen or a substituent selected from halo, or —$OR^{r7}$;

$R^{r7}$ independently represent hydrogen or $C_{1-3}$ alkyl optionally substituted by one or more substituents selected from $E^2$;

X represents a direct bond;

Y represents -pyridyl-, -thiophenyl- (which two groups are optionally substituted by one or more substituents selected from $E^3$), -morpholinyl- or -pyrrolidinyl- (which latter two groups are optionally substituted by one or more substituents selected from $E^4$);

$R^N$ represents hydrogen;

Z represents $-(A^x)_{1-3}-$ wherein each $A^x$ independently represents —$C(R^{x1})(R^{x2})$—, —$N(R^{x3})$—, —$C(O)$—;

$R^{x1}$, $R^{x2}$ and $R^{x3}$ each independently represents hydrogen, or $C_{1-3}$ alkyl;

each $E^2$, $E^3$ and $E^4$ independently represents, on each occasion when used herein, halo, $C_{1-4}$ alkyl or heterocycloalkyl, which latter three groups are optionally substituted by one or more halo atoms.

In particular embodiments, the compounds of the invention may be in an isolated form, and/or ex vivo.

Particularly preferred compounds of the invention include those of the examples described hereinafter.

Compounds of the invention may be made in accordance with techniques that are well known to those skilled in the art, for example as described hereinafter.

According to a further aspect of the invention there is provided a process for the preparation of a compound of formula I which process comprises:

(i) compounds of formula I in which Z contains a —$C(O)N(R^{x3})$— or —$N(R^{x3})C(O)$— moiety, may be prepared by intramolecular reaction of a compound of formula II,

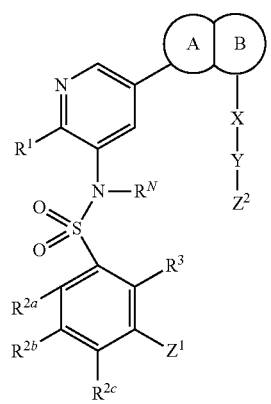

II wherein $Z^1$ and $Z^2$ independently represent —$C(O)OH$, —$N(R^{x3})H$ or a partial Z moiety with a terminal —$C(O)OH$ group or terminal —$N(R^{x3})H$ group (or derivatives thereof, such as carboxylic acid ester derivatives) and wherein one of $Z^1$ and $Z^2$ contains the —$C(O)OH$ group (or derivative) and the other contains the —$N(R^{x3})H$ group (or derivative), and ring A/ring B, $R^1$, $R^{2a}$, $R^{2b}$, $R^{2c}$, $R^3$, X and Y are as hereinbefore defined, which reaction is an amide coupling, which may be performed under standard reaction conditions, for instance the reaction may be performed in the presence of a suitable coupling reagent (e.g. 1,1'-carbonyldiimidazole, N,N'-dicyclohexylcarbodiimide, 1-(3-dimethylaminopropyl)-3-ethylcarbodiimide (or hydrochloride thereof), N,N'-disuccinimidyl carbonate, benzotriazol-1-yloxytris(dimethylamino)phosphonium hexafluorophosphate, 2-(1H-benzotriazol-1-yl)-1, 1,3, 3-tetramethyluronium hexa-fluorophosphate, benzotriazol-1-yloxytris-pyrrolidinophosphonium hexafluoro-phosphate, bromo-tris-pyrrolidinophosponium hexafluorophosphate, 2-(1H-benzotriazol-1-yl)-1,1,3,3-tetramethyluronium tetrafluorocarbonate, 1-cyclohexyl-carbodiimide-3-propyloxymethyl polystyrene, O-(7-azabenzotriazol-1-yl)-N,N,N',N'-tetramethyluronium hexafluorophosphate, O-benzotriazol-1-yl-N, N,N',N'-tetramethyluronium tetrafluoroborate and/or 1-hydroxy-7-azabenzotriazole), optionally in the presence of a suitable base (e.g. sodium hydride, sodium bicarbonate, potassium carbonate, pyridine, triethylamine, dimethylaminopyridine, diisopropylamine, diisopropylethylamine, sodium hydroxide, potassium tert-butoxide, dimethylaminopyridine and/or lithium diisopropylamide (or variants thereof), an appropriate solvent (e.g. tetrahydrofuran, pyridine, toluene, dichloromethane, chloroform, acetonitrile, dimethylformamide, trifluoromethylbenzene, dioxane or triethylamine) and a further additive (e.g. 1-hydroxybenzotriazole hydrate). Preferred amide coupling reaction conditions include reaction in the presence of a coupling reagent HATU, PyBOP and/or HOAt, in the presence of a base (preferably DIPEA and, optionally DMAP) and solvent (preferably DMF). In the case when reaction is performed on an ester functional group (e.g. —$C(O)OCH_3$ or —$C(O)OCH_2CH_3$), in the presence of e.g. trimethylaluminium, or, alternatively the —$C(O)OH$ group may first be activated to the corresponding acyl halide (e.g —$C(O)Cl$, by treatment with oxalyl chloride, thionyl chloride, phosphorous pentachloride, phosphorous oxychloride, or the like), under standard conditions known to those skilled in the art (e.g. optionally in the presence of a suitable solvent, suitable base and/or in an inert atmosphere);

(ii) compounds of formula I in which Z contains —O—, —S— or —N($R^{x3}$)—, may be prepared by reaction of a compound of formula III,

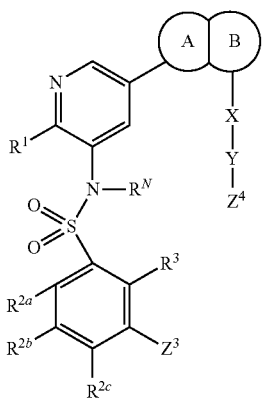

wherein $Z^3$ represents —OH, —SH, —N($R^{x3}$)H or -$L^x$ (in which $L^x$ is a suitable leaving group, such as chloro, bromo, iodo or a sulfonate group such as —OS(O)$_2$CF$_3$, —OS(O)$_2$CH$_3$ or —OS(O)$_2$PhMe), or $Z^3$ contains a partial Z moiety with a terminal —OH, —N($R^{x3}$)H or -$L^x$ group and $Z^4$ represents $L^y$-, HO—, HS— or H($R^{x3}$)N— (as appropriate) or a partial Z moiety with a terminal $L^y$-, HO— or H($R^{x3}$)N—, $L^y$ is a suitable leaving group (such as one defined for $L^x$) and ring A/ring B, $R^1$, $R^{2a}$, $R^{2b}$, $R^{2c}$, $R^3$, X and Y are as hereinbefore defined (in which one of $Z^3$ and $Z^4$ contains a —OH, —SH or —N($R^{x3}$)H moiety and the other contains the $L^x$ or $L^y$ moiety), which reaction may be performed under standard nucleophilic substitution reaction conditions, for instance in the presence of a suitable base (e.g. sodium hydride, sodium bicarbonate, potassium carbonate, pyrrolidinopyridine, pyridine, triethylamine, tributylamine, trimethylamine, dimethylaminopyridine, diisopropylamine, diisopropylethylamine, 1,8-diazabicyclo[5.4.0]undec-7-ene, sodium hydroxide, N-ethyldiisopropylamine, N-(methylpolystyrene)-4-(methylamino)pyridine, potassium bis(trimethylsilyl)-amide, sodium bis(trimethylsilyl)amide, potassium tert-butoxide, lithium diisopropylamide, lithium 2,2,6,6-tetramethylpiperidine or mixtures thereof) and an appropriate solvent (e.g. tetrahydrofuran, pyridine, toluene, dichloromethane, chloroform, acetonitrile, dimethylformamide, trifluoromethylbenzene, dioxane or triethylamine). However, if there is a $L^x$ or $L^y$ group directly attached to an aromatic ring, and reaction is performed with a nucleophilic —OH or —N($R^{x3}$)H (or the like) moiety, the reaction may be performed in the presence of an appropriate metal catalyst (or a salt or complex thereof) such as Cu, Cu(OAc)$_2$, CuI (or CuI/diamine complex), copper tris(triphenyl-phosphine)bromide, Pd(OAc)$_2$, tris(dibenzylideneacetone)-dipalladium(0) (Pd$_2$(dba)$_3$) or NiCl$_2$ and an optional additive such as Ph$_3$P, 2,2'-bis(diphenylphosphino)-1,1'-binaphthyl, xantphos, NaI or an appropriate crown ether such as 18-crown-6-benzene, in the presence of an appropriate base such as NaH, Et$_3$N, pyridine, N,N'-dimethylethylenediamine, Na$_2$CO$_3$, K$_2$CO$_3$, K$_3$PO$_4$, Cs$_2$CO$_3$, t-BuONa or t-BuOK (or a mixture thereof, optionally in the presence of 4 Å molecular sieves), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof). This reaction may be carried out under microwave irradiation reaction conditions or, alternatively, the reaction may be performed in the absence of other reagents such as catalyst, base and even solvent;

(iii) compounds of formula I in which $R^{x3}$, $R^{y2}$, $R^{y3}$ and/or $R^{y4}$ represent optionally substituted $C_{1-6}$ or $C_{1-3}$ alkyl, may be prepared by reaction of a corresponding compound of formula I in which $R^{x3}$, $R^{y2}$, $R^{y3}$ and/or $R^{y4}$ represent hydrogen, with a compound of formula IV, $$L^1-R^{12-14} \qquad IV$$

wherein $R^{12-14}$ represents $R^{x3}$, $R^{y2}$, $R^{y3}$ or $R^{y4}$ (as appropriate/required) and $L^1$ represents a suitable leaving group as defined for $L^x$ (e.g. under standard alkylation reaction conditions, such as reaction in the presence of base and solvent, e.g. under conditions such as those mentioned in step (ii) above), or with a compound of formula V, $$H(O)C—R^{12a-14a} \qquad V$$

wherein $R^{12a-14a}$ represents $C_{1-5}$ or $C_{1-2}$ alkyl optionally substituted by one or more halo atoms, under reductive amination reaction conditions (for example in the presence of a chemoselective reducing agent such as sodium triacetoxyborohydride or sodium cyanoborohydride, or alternatively, as a two-step process including condensation and then reduction, which reduction step in this instance may be performed in the presence of a stronger reducing agent such as sodium borohydride or LiAlH$_4$);

(iv) compounds of formula I containing a —N(R)—CH$_2$— moiety (e.g. when Z contains a —N($R^{x3}$)—CH$_2$— moiety) may be prepared by reduction of a corresponding compound of formula I containing a —N(R)C(O)— moiety (e.g. when Z contains a —N($R^{x3}$)—C(O)— moiety), for example in the presence of appropriate reduction reaction conditions, e.g. in the presence of a chemoselective reducing agent such as LiAlH$_4$.

Compounds of formula II and III may be prepared by reaction of a compound of formula VI,

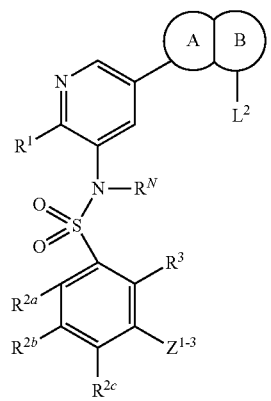

wherein $L^2$ represents a suitable leaving group, such as such as iodo, bromo, chloro, a sulfonate group (e.g. —OS(O)$_2$CF$_3$, —OS(O)$_2$CH$_3$ or —OS(O)$_2$PhMe), or a sulfide group (e.g. —S—C$_{1-6}$ alkyl, such as —SCH$_3$), $Z^{1-3}$ represents $Z^1$ or $Z^3$ (depending on whether compound of formula II or III is being prepared) and $R^1$, $R^{2a}$, $R^{2b}$, $R^{2c}$, $R^3$ and ring A/B are as hereinbefore defined, with a compound of formula VII,

  VII wherein $Z^{2-4}$ represents $Z^2$ or $Z^4$, $L^3$ represents a suitable group, such as:

(a) —B(OH)$_2$, —B(OR$^{wx}$)$_2$ or —Sn(R$^{wx}$)$_3$, in which each R$^{wx}$ independently represents a C$_{1-6}$ alkyl group, or, in the case of —B(OR$^{wx}$)$_2$, the respective R$^{wx}$ groups may be linked together to form a 4- to 6-membered cyclic group (such as a 4,4,5,5-tetramethyl-1,3,2-dioxaborolan-2-yl group), thereby forming e.g. a pinacolato boronate ester group, (or L$^3$ may represent iodo, bromo or chloro, provided that L$^2$ and L$^3$ are mutually compatible), for instance when X represents a direct bond or —C(R$^a$)(R$^b$)—; or (b) hydrogen, for instance when X represents —O—, —S— or —N(R$^c$)—, and X and Y are as hereinbefore defined, under standard reaction conditions, for instance for (b) above, under reaction conditions such as those hereinbefore described in respect of process (ii) above (e.g. catalytic reaction conditions) or for (a) above may be performed for example in the presence of a suitable catalyst system, e.g. a metal (or a salt or complex thereof) such as Pd, CuI, Pd/C, PdCl$_2$, Pd(OAc)$_2$, Pd(Ph$_3$P)$_2$Cl$_2$, Pd(Ph$_3$P)$_4$ (i.e. palladium tetrakistriphenylphosphine), Pd$_2$(dba)$_3$ and/or NiCl$_2$ (preferred catalysts include palladium) and a ligand such as PdCl$_2$(dppf).DCM, t-Bu$_3$P, (C$_6$H$_{11}$)$_3$P, Ph$_3$P, AsPh$_3$, P(o-Tol)$_3$, 1,2-bis(diphenylphosphino)ethane, 2,2'-bis(di-tert-butylphosphino)-1,1'-biphenyl, 2,2'-bis(diphenylphosphino)-1,1'-bi-naphthyl, 1,1'-bis(diphenyl-phosphino-ferrocene), 1,3-bis(diphenylphosphino)propane, xantphos, or a mixture thereof (preferred ligands include PdCl$_2$(dppf).DCM), together with a suitable base such as, Na$_2$CO$_3$, K$_3$PO$_4$, Cs$_2$CO$_3$, NaOH, KOH, K$_2$CO$_3$, CsF, Et$_3$N, (i-Pr)$_2$NEt, t-BuONa or t-BuOK (or mixtures thereof; preferred bases include Na$_2$CO$_3$ and K$_2$CO$_3$) in a suitable solvent such as dioxane, toluene, ethanol, dimethylformamide, dimethoxyethane, ethylene glycol dimethyl ether, water, dimethylsulfoxide, acetonitrile, dimethylacetamide, N-methylpyrrolidinone, tetrahydrofuran or mixtures thereof. When L$^3$ represents a sulfide (e.g. —SCH$_3$), then an additive such as CuMeSal (copper(I) 3-methylsalicylate) or CuTC (copper(I)thiophene-2-carboxylate) may also be employed. The reaction may be carried out for example at room temperature or above (e.g. at a high temperature such as at about the reflux temperature of the solvent system). Alternative reaction conditions include microwave irradiation conditions, for example at elevated temperature, e.g. of about 130° C.

Alternatively, compounds of formula II or III may be prepared by reaction of a compound of formula VIII,

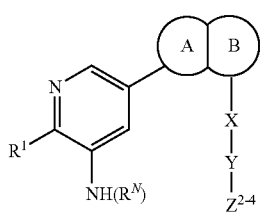  VIII wherein $R^1$, X, Y, $Z^{2-4}$ and ring A/B are as hereinbefore defined, with a compound of formula IX,

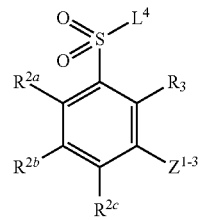  IX wherein L$^4$ represents —OH or chloro, bromo or iodo (preferably, chloro), and $Z^{1-3}$, $R^{2a}$, $R^{2b}$, $R^{2c}$ and $R^3$ are as hereinbefore defined, for example under reaction conditions such as those hereinbefore described in respect of process step (i) above (sulfonamide coupling reaction conditions).

Compounds of formula II or III in which X represents —C(O)N(R$^e$)— or —N(R$^f$)—C(O)—N(R$^g$)— may be prepared by reaction of a corresponding compound of formula X,

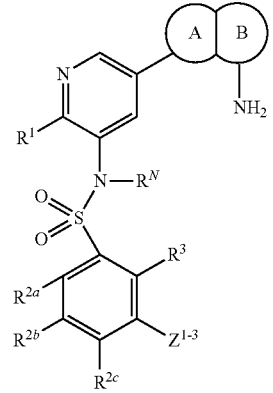  X wherein $Z^{1-3}$, $R^1$, $R^{2a}$, $R^{2b}$, $R^{2c}$, $R^3$ and ring A/B are as hereinbefore defined, with a compound of formula XI,

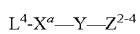  XI wherein X$^a$ represents —C(O)— or —C(O)—N(R$^f$)— and L$^4$ represents a suitable leaving group (such as one hereinbefore defined in respect of L$^x$) and Y and $Z^{2-4}$ are as hereinbefore defined, under standard reaction conditions, such as those hereinbefore described in respect of process step (i);

Compounds of formula II or III in which X represents —N(R$^d$)C(O)— may be prepared by reaction of a corresponding compound of formula XII,

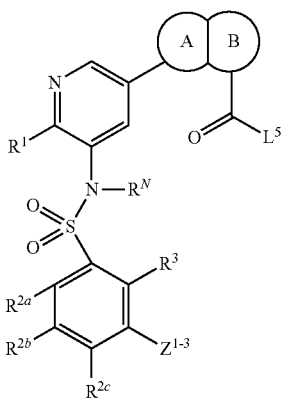

XII wherein $L^5$ represents —OH or a suitable leaving groups (such as one hereinbefore defined for $L^x$, e.g. chloro) and $Z^{1-3}$, $R^1$, $R^{2a}$, $R^{2b}$, $R^{2c}$, $R^3$ and ring A/B are as hereinbefore defined, with a compound of formula XIII,

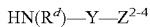  XIII wherein $R^d$, Y and $Z^{2-4}$ are as hereinbefore defined, under standard reaction conditions, such as those hereinbefore described in respect of process step (i).

Compounds of formula VI may be prepared by reaction of a compound of formula XIV,

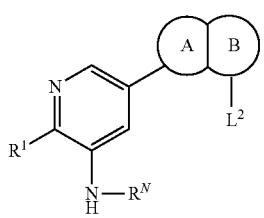

XIV wherein $L^2$, $R^1$ and ring A/B are as hereinbefore defined, with a compound of formula IX as hereinbefore defined, under reaction conditions such as those hereinbefore described in respect of process step (i) above (sulfonamide coupling reaction conditions).

Compounds of formula VI and XIV in which $L^2$ represents halo, may be prepared by reaction of a compound corresponding to a compound of formula VI and XIV but in which $L^2$ represents hydrogen, with a source of halide ions, for instance an electrophile that provides a source of iodide ions includes iodine, diiodoethane, diiodotetrachloroethane or, preferably, N-iodosuccinimide, a source of bromide ions includes N-bromosuccinimide and bromine, and a source of chloride ions includes phosphorus oxychloride ($POCl_3$), N-chlorosuccinimide, chlorine and iodine monochloride.

Other compounds of formula VI and XIV may be prepared under standard conditions, for instance such as those described herein, for example, for synthesis of those compounds in which $L^2$ represents a sulfonate group, reaction of a corresponding compound but in which $L^2$ represents —OH with an appropriate sulfonyl halide, under standard reaction conditions, such as in the presence of a base (e.g. as hereinbefore described in respect of preparation of compounds of formula I (process step (ii)).

Compounds of formula XII may be prepared by reaction of a compound of formula VI as hereinbefore defined, with an appropriate reagent for the introduction of the —C(O)OH (or —C(O)Cl) group, for instance by metallation of the $L^2$ group (e.g. conversion to the corresponding lithiated derivative) and then quench with e.g. $CO_2$ or phosgene, triphosgene or the like, under conditions known to those skilled in the art.

Compounds of formula XIV may be prepared by reaction of a compound of formula XV,

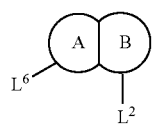

XV wherein $L^6$ represents a suitable leaving group such as one hereinbefore defined by $L^2$, and $L^2$, ring A/B are as hereinbefore defined, with a compound of formula XVI,

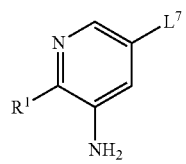

XVI wherein $L^7$ represents a suitable group, such as one hereinbefore defined by $L^3$, and $R^1$ is as hereinbefore defined, under standard reaction conditions known to those skilled in the art, for example those described in respect of preparation of compounds of formula II or III (reaction of a compound of formula VI and VII; see step (a)).

The core bicyclic ring structures A/B (e.g. of formulae VI, X and XIV) may be commercially available or prepared in accordance with known standard procedures (e.g. starting from known commercially available starting materials), for instance they may be prepared in accordance with the procedures described in e.g. WO2009/040552, WO2008/150827 and WO 2010/112874.

Certain other intermediate compounds may also be commercially available, known in the literature, or may be obtained either by analogy with the processes described herein, or by conventional synthetic procedures, in accordance with standard techniques, from available starting materials using appropriate reagents and reaction conditions. Further, the skilled person will appreciate that where reactions to introduce the 3-pyridyl moiety of compounds of formula I is described, similar reactions may be performed to introduce the "—X—Y—Z" moiety in compounds of formula I and vice versa. Further, processes to prepare compounds of formula I may be described in the literature, for example in:

Werber, G. et al.; *J. Heterocycl. Chem.*; EN; 14; 1977; 823-827;

Andanappa K. Gadad et al. *Bioorg. Med. Chem.* 2004, 12, 5651-5659;

Paul Heinz et al. *Monatshefte für Chemie,* 1977, 108, 665-680;

M. A. El-Sherbeny et al. *Boll. Chim. Farm.* 1997, 136, 253-256;

Nicolaou, K. C.; Bulger, P. G.; Sarlah, D. *Angew. Chem. Int. Ed.* 2005, 44, 2-49;

Bretonnet et al. *J. Med. Chem.* 2007, 50, 1872;

Asunción Marin et al. *Farmaco* 1992, 47 (1), 63-75;
Severinsen, R. et al. *Tetrahedron* 2005, 61, 5565-5575;
Nicolaou, K. C.; Bulger, P. G.; Sarlah, D. *Angew. Chem. Int. Ed.* 2005, 44, 2-49;
M. Kuwahara et al., *Chem. Pharm Bull.*, 1996, 44, 122;
Wipf, P.; Jung, J.-K. *J. Org. Chem.* 2000, 65(20), 6319-6337;
Shintani, R.; Okamoto, K. *Org. Lett.* 2005, 7 (21), 4757-4759;
Nicolaou, K. C.; Bulger, P. G.; Sarlah, D. *Angew. Chem. Int. Ed.* 2005, 44, 2-49;
J. Kobe et at, *Tetrahedron*, 1968, 24, 239;
P. F. Fabio, A. F. Lanzilotti and S. A. Lang, *Journal of Labelled Compounds and Pharmaceuticals*, 1978, 15, 407;
F. D. Bellamy and K. Ou, *Tetrahedron Lett.*, 1985, 25, 839;
M. Kuwahara et al., *Chem. Pharm Bull.*, 1996, 44, 122;
A. F. Abdel-Magid and C. A Maryanoff. *Synthesis*, 1990, 537;
M. Schlosser et al. *Organometallics in Synthesis. A Manual*, (M. Schlosser, Ed.),
Wiley &Sons Ltd: Chichester, U K, 2002, and references cited therein;
L. Wengwei et al., *Tetrahedron Lett.*, 2006, 47, 1941;
M. Plotkin et al. *Tetrahedron Lett.*, 2000, 41, 2269;
Seyden-Penne, J. *Reductions by the Alumino and Borohydrides*, VCH, NY, 1991;
O. C. Dermer, *Chem. Rev.*, 1934, 14, 385;
N. Defacqz, et al., *Tetrahedron Lett.*, 2003, 44, 9111;
S. J. Gregson et al., *J. Med. Chem.*, 2004, 47, 1161;
A. M. Abdel Magib, et al., *J. Org. Chem.*, 1996, 61, 3849;
A. F. Abdel-Magid and C. A Maryanoff. *Synthesis*, 1990, 537;
T. Ikemoto and M. Wakimasu, *Heterocycles*, 2001, 55, 99;
E. Abignente et al, *II Farmaco*, 1990, 45, 1075;
T. Ikemoto et al., *Tetrahedron*, 2000, 56, 7915;
T. W. Greene and P. G. M. Wuts, *Protective Groups in Organic Synthesis*, Wiley, N Y, 1999;
S. Y. Han and Y.-A. Kim. *Tetrahedron*, 2004, 60, 2447;
J. A. H. Lainton et al., *J. Comb. Chem.*, 2003, 5, 400; or
Wiggins, J. M. *Synth. Commun.*, 1988, 18, 741.

Other specific transformation steps (including those that may be employed in order to form compounds of formula I) that may be mentioned include:
(i) reductions, for example of a carboxylic acid (or ester) to either an aldehyde or an alcohol, using appropriate reducing conditions (e.g. —C(O)OH (or an ester thereof), may be converted to a —C(O)H or —CH$_2$—OH group, using DIBAL and LiAlH$_4$, respectively (or similar chemoselective reducing agents));
(ii) reductions of an aldehyde (—C(O)H) group to an alcohol group (—CH$_2$OH), using appropriate reduction conditions such as those mentioned at point (i) above;
(iii) oxidations, for example of a moiety containing an alcohol group (e.g. —CH$_2$OH) to an aldehyde (e.g. —C(O)H) or of a —S— moiety to a —S(O)— or —S(O)$_2$— moiety (or the reverse reduction reaction), for example in the presence of a suitable oxidising agent, e.g. MnO$_2$ or mcpba or the like;
(iv) reductive amination of an aldehyde and an amine, under appropriate reaction conditions, for example in "one-pot" procedure in the presence of an appropriate reducing agent, such as a chemoselective reducing agent such as sodium cyanoborohydride or, preferably, sodium triacetoxyborohydride, or the like. Alternatively, such reactions may be performed in two steps, for example a condensation step (in the presence of e.g. a dehydrating agent such as trimethyl orthoformate or MgSO$_4$ or molecular sieves, etc) followed by a reduction step (e.g. by reaction in the presence of a reducing agent such as a chemoselective one mentioned above or NaBH$_4$, AlH$_4$, or the like), for instance the conversion of —NH$_2$ to —N(H)-isopropyl by condensation in the presence of acetone (H$_3$C—C(O)—CH$_3$) followed by reduction in the presence of a reducing agent such as sodium cyanaoborohydride (i.e. overall a reductive amination);
(v) formation of an amide or sulfonamide, for example by reaction of a sulfonyl chloride with an amine or by an amide coupling reaction, i.e. the formation of an amide from a carboxylic acid (or ester thereof), for example —C(O)OH (or an ester thereof), may be converted to —C(O)N(R$^{20}$)R$^{21}$ group (in which R$^{20}$ and R$^{21}$ are as hereinbefore defined, and may be linked together, e.g. as defined above), and which reaction may (e.g. for —COOH) be performed in the presence of a suitable coupling reagent (e.g. 1,1'-carbonyldiimidazole, N,N'-dicyclohexylcarbodiimide, or the like) or, in the case of an ester (e.g. —C(O)OCH$_3$ or —C(O)OCH$_2$CH$_3$), be performed in the presence of e.g. trimethylaluminium, or, alternatively the —C(O)OH group may first be activated to the corresponding acyl halide (e.g —C(O)Cl, by treatment with oxalyl chloride, thionyl chloride, phosphorous pentachloride, phosphorous oxychloride, or the like), and, in all cases, the relevant compound is reacted with a compound of formula HN(R$^{20}$R$^{21}$ (in which R$^{20}$ and R$^{21}$ are as hereinbefore defined), under standard conditions known to those skilled in the art (e.g. optionally in the presence of a suitable solvent, suitable base and/or in an inert atmosphere);
(vi) conversion of a primary amide to a nitrile functional group, for example under dehydration reaction conditions, e.g. in the presence of POCl$_3$, or the like;
(vii) nucleophilic substitution (e.g. aromatic nucleophilic substitution) reactions, where any nucleophile replaces a leaving group, e.g. an amine may replace a —S(O)CH$_3$ leaving group;
(viii) transformation of a methoxy group to a hydroxy group, by reaction in the presence of an appropriate reagent, such as boron fluoride-dimethyl sulfide complex or BBr$_3$ (e.g. in the presence of a suitable solvent such as dichloromethane);
(ix) haolgenation, alkylation, acylation or sulfonylation reactions, which may be performed in the presence of base and solvent (such as those described hereinbefore);
(x) specific deprotection steps, such as deprotection of an N-Boc protecting group by reaction in the presence of an acid, or, a hydroxy group protected as a silyl ether (e.g. a tert-butyl-dimethylsilyl protecting group) may be deprotected by reaction with a source of fluoride ions, e.g. by employing the reagent tetrabutylammonium fluoride (TBAF);
(xi) aromatic nitration reactions (for instance which may be performed on compounds corresponding to compounds of formula X, but in which the —NH$_2$ group is replaced with a —NO$_2$ group; subsequent conversion of the nitro group may take place separately—see (xii) below); e.g. by reaction in the presence of nitric acid at low temperature, followed by addition of conc. H$_2$SO$_4$);
(xii) reductions of nitro groups to amino groups under standard conditions, e.g. iron-based reduction), which may be followed by an acylation reaction (see (ix) above) or a reductive amination (see (iv) above).

The substituents R$^1$, R$^{2a}$, R$^{2b}$, R$^{2c}$, R$^3$, Z, X and Y (or substituents on the main core structure, including substituents on ring A/B) in final compounds of the invention or relevant intermediates may be modified one or more times, after or during the processes described above by way of methods that are well known to those skilled in the art. Examples of such methods include substitutions, reductions, oxidations, alkylations, acylations, hydrolyses, esterifications, etherifications, halogenations or nitrations. Such reactions may result in the formation of a symmetric or asymmetric final compound of the invention or intermediate. The precursor groups can be changed to a different such group, or to the groups defined in formula I, at any time during the reaction sequence. For example, in cases in which there is a —$CO_2H$ present, the skilled person will appreciate that at any stage during the synthesis (e.g. the final step), the relevant ester group may be hydrolysed to form a carboxylic acid functional group.

Compounds of the invention bearing a carboxyester functional group may be converted into a variety of derivatives according to methods well known in the art to convert carboxyester groups into carboxamides, N-substituted carboxamides, N,N-disubstituted carboxamides, carboxylic acids, and the like. The operative conditions are those widely known in the art and may comprise, for instance in the conversion of a carboxyester group into a carboxamide group, the reaction with ammonia or ammonium hydroxide in the presence of a suitable solvent such as a lower alcohol, dimethylformamide or a mixture thereof; preferably the reaction is carried out with ammonium hydroxide in a methanol/dimethylformamide mixture, at a temperature ranging from about 50° C. to about 100° C. Analogous operative conditions apply in the preparation of N-substituted or N,N-disubstituted carboxamides wherein a suitable primary or secondary amine is used in place of ammonia or ammonium hydroxide. Likewise, carboxyester groups may be converted into carboxylic acid derivatives through basic or acidic hydrolysis conditions, widely known in the art. Further, amino derivatives of compounds of the invention may easily be converted into the corresponding carbamate, carboxamido or ureido derivatives.

Compounds of the invention may be isolated from their reaction mixtures using conventional techniques (e.g. recrystallisations).

It will be appreciated by those skilled in the art that, in the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Synthesis*", 3$^{rd}$ edition, T. W. Greene & P. G. M. Wutz, Wiley-Interscience (1999).

Medical and Pharmaceutical Uses

Compounds of the invention are indicated as pharmaceuticals. According to a further aspect of the invention there is provided a compound of the invention, for use as a pharmaceutical.

For the avoidance of doubt, although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the "active" compounds to which they are metabolised) may therefore be described as "prodrugs" of compounds of the invention.

A "prodrug of a compound of the invention" is as hereinbefore defined, including compounds that form a compound of the invention, in an experimentally-detectable amount, within a predetermined time (e.g. about 1 hour), following oral or parenteral administration. All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the "active" compounds of the invention to which they are metabolised), may also be described as "prodrugs".

Thus, the compounds of the invention are useful because they possess pharmacological activity, and/or are metabolised in the body following oral or parenteral administration to form compounds which possess pharmacological activity.

Compounds of the invention may inhibit protein or lipid kinases, such as a PI3 kinase (especially a class I PI3K), or a PIM family kinase (e.g. PIM-1, PIM-2 and/or PIM-3), for example as may be shown in the tests described below (for example, the test for PI3Kα and PIM inhibition described below) and/or in tests known to the skilled person. The compounds of the invention may also inhibit mTOR. Thus, the compounds of the invention may be useful in the treatment of those disorders in an individual in which the inhibition of such protein or lipid kinases (e.g. PI3K, particularly class I PI3K, mTOR and/or a PIM family kinase, e.g. PIM-1, PIM-2 or PIM-3) is desired and/or required (for instance compounds of the invention may inhibit PI3K, particularly class I PI3K and, optionally, may also inhibit either (or both of) mTOR and PIM). Hence, certain compounds of the invention may be "dual" (e.g. PI3K and mTOR; PI3K and PIM; or mTOR and PIM) inhibitors. Further, certain compounds of the invention may be "triple" (e.g. PI3K, PIM and mTOR) inhibitors.

The term "inhibit" may refer to any measurable reduction and/or prevention of catalytic kinase (e.g. PI3K, particularly class I PI3K, mTOR and/or PIM) activity. The reduction and/or prevention of kinase activity may be measured by comparing the kinase activity in a sample containing a compound of the invention and an equivalent sample of kinase (e.g. PI3K, particularly class I PI3K, mTOR and/or PIM) in the absence of a compound of the invention, as would be apparent to those skilled in the art. The measurable change may be objective (e.g. measurable by some test or marker, for example in an in vitro or in vivo assay or test, such as one described hereinafter, or otherwise another suitable assay or test known to those skilled in the art) or subjective (e.g. the subject gives an indication of or feels an effect).

Compounds of the invention may be found to exhibit 50% inhibition of a protein or lipid kinase (e.g. PI3K, such as class I PI3K, mTOR and/or PIM) at a concentration of 100 µM or below (for example at a concentration of below 50 µM, or even below 10 µM, such as below 1 µM), when tested in an assay (or other test), for example as described hereinafter, or otherwise another suitable assay or test known to the skilled person.

Compounds of the invention are thus expected to be useful in the treatment of a disorder in which a protein or lipid kinase (e.g. PI3K, such as class I PI3K, mTOR and/or PIM) is known to play a role and which are characterised by or associated with an overall elevated activity of that kinase (due to, for example, increased amount of the kinase or increased catalytic activity of the kinase). Hence, compounds of the invention are expected to be useful in the treatment of a disease/disorder arising from abnormal cell growth, function or behaviour associated with the protein or lipid kinase (e.g. PI3K, such as class I PI3K, mTOR and/or PIM). Such conditions/disorders include cancer, immune disorders, cardiovascular diseases, viral infections, inflammation, metabolism/endocrine function disorders and neurological disorders.

Compounds of the invention (alone or in combination with another active) may be shown to be active e.g. in the biochemical assays described herein, may be shown to have predictive activity based on e.g. the phosphorylation assay described herein, and/or may reduce the rate of cell proliferation e.g. as may be shown in the cell proliferation assays described herein (for instance using cancer cell lines (e.g. known commercially available ones), such as those described herein or others that are known and publically available).

The disorders/conditions that the compounds of the invention may be useful in treating hence includes cancer (such as lymphomas, solid tumours or a cancer as described hereinafter), obstructive airways diseases, allergic diseases, inflammatory diseases (such as asthma, allergy and Crohn's disease), immunosuppression (such as transplantation rejection and autoimmune diseases), disorders commonly connected with organ transplantation, AIDS-related diseases and other associated diseases. Other associated diseases that may be mentioned (particularly due to the key role of kinases in the regulation of cellular proliferation) include other cell proliferative disorders and/or non-malignant diseases, such as benign prostate hyperplasia, familial adenomatosis, polyposis, neuro-fibromatosis, psoriasis, bone disorders, atherosclerosis, vascular smooth cell proliferation associated with atherosclerosis, pulmonary fibrosis, arthritis glomerulonephritis and post-surgical stenosis and restenosis. Other disease states that may be mentioned include cardiovascular disease, stroke, diabetes, hepatomegaly, Alzheimer's disease, cystic fibrosis, hormone-related diseases, immunodeficiency disorders, destructive bone disorders, infectious diseases, conditions associated with cell death, thrombin-induced platelet aggregation, chronic myelogenous leukaemia, liver disease, pathologic immune conditions involving T cell activation, CNS disorders and pulmonary artery hypertension (PAH).

As stated above, the compounds of the invention may be useful in the treatment of cancer. More, specifically, the compounds of the invention may therefore be useful in the treatment of a variety of cancer including, but not limited to: carcinoma such as cancer of the bladder, breast, colon, kidney, liver, lung (including non-small cell cancer and small cell lung cancer), esophagus, gall-bladder, ovary, pancreas, stomach, cervix, thyroid, prostate, skin, squamous cell carcinoma, testis, genitourinary tract, larynx, glioblastoma, neuroblastoma, keratoacanthoma, epidermoid carcinoma, large cell carcinoma, non-small cell lung carcinoma, small cell lung carcinoma, lung adenocarcinoma, bone, adenoma, adenocarcinoma, follicular carcinoma, undifferentiated carcinoma, papilliary carcinoma, seminona, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukaemia; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xeroderma pigmentosum, keratoxanthoma, thyroid follicular cancer and Kaposi's sarcoma.

Further, the protein or lipid kinases (e.g. PI3K, such as class I PI3K, mTOR and/or PIM) may also be implicated in the multiplication of viruses and parasites. They may also play a major role in the pathogenesis and development of neurodegenerative disorders. Hence, compounds of the invention may also be useful in the treatment of viral conditions, parasitic conditions, as well as neurodegenerative disorders.

Compounds of the invention are indicated both in the therapeutic and/or prophylactic treatment of the above-mentioned conditions.

According to a further aspect of the present invention, there is provided a method of treatment of a disease (e.g. cancer or another disease as mentioned herein) which is associated with the inhibition of protein or lipid kinase (e.g. PI3K, such as class I PI3K, mTOR and/or PIM) is desired and/or required (for example, a method of treatment of a disease/disorder arising from abnormal cell growth, function or behaviour associated with protein or lipid kinases, e.g. PI3K, such as class I PI3K, mTOR and/or PIM), which method comprises administration of a therapeutically effective amount of a compound of the invention, as hereinbefore defined, to a patient suffering from, or susceptible to, such a condition.

"Patients" include mammalian (including human) patients. Hence, the method of treatment discussed above may include the treatment of a human or animal body.

The term "effective amount" refers to an amount of a compound, which confers a therapeutic effect on the treated patient. The effect may be objective (e.g. measurable by some test or marker) or subjective (e.g. the subject gives an indication of or feels an effect).

Compounds of the invention may be administered orally, intravenously, subcutaneously, buccally, rectally, dermally, nasally, tracheally, bronchially, sublingually, by any other parenteral route or via inhalation, in a pharmaceutically acceptable dosage form.

Compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like. The type of pharmaceutical formulation may be selected with due regard to the intended route of administration and standard pharmaceutical practice. Such pharmaceutically acceptable carriers may be chemically inert to the active compounds and may have no detrimental side effects or toxicity under the conditions of use.

Such formulations may be prepared in accordance with standard and/or accepted pharmaceutical practice. Otherwise, the preparation of suitable formulations may be achieved non-inventively by the skilled person using routine techniques and/or in accordance with standard and/or accepted pharmaceutical practice.

According to a further aspect of the invention there is thus provided a pharmaceutical formulation including a compound of the invention, as hereinbefore defined, in admixture with a pharmaceutically acceptable adjuvant, diluent and/or carrier.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The amount of compound of the invention in the formulation will depend on the severity of the condition, and on the patient, to be treated, as well as the compound(s) which is/are employed, but may be determined non-inventively by the skilled person.

The invention further provides a process for the preparation of a pharmaceutical formulation, as hereinbefore defined, which process comprises bringing into association a compound of the invention, as hereinbefore defined, or a pharmaceutically acceptable ester, amide, solvate or salt thereof with a pharmaceutically-acceptable adjuvant, diluent or carrier.

Compounds of the invention may also be combined with other therapeutic agents that are inhibitors of protein or lipid kinases (e.g. PI3K (such as class I PI3K), mTOR, Flt3, a PIM family kinase (e.g. PIM-1, PIM-2 or PIM-3), EGFR and/or MEK) and/or useful in the treatment of a cancer and/or a proliferative disease. Compounds of the invention may also be combined with other therapies (e.g. radiation).

For instance, compounds of the invention may be combined with one or more treatments independently selected from surgery, one or more anti-cancer/anti-neoplastic/anti-tumoral agent, one or more hormone therapies, one or more antibodies, one or more immunotherapies, radioactive iodine therapy, and radiation.

More specifically, compounds of the invention may be combined with an agent that modulates the Ras/Raf/Mek pathway (e.g. an inhibitor of MEK), the Jak/Stat pathway (e.g. an inhibitor of Jak), the PI3K/Akt pathway (e.g. an inhibitor of Akt), the DNA damage response mechanism (e.g. an inhibitor of ATM or ATR) or the stress signaling pathway (an inhibitor of p38 or NF-KB).

For instance, compounds of the invention may be combined with:
  (i) a targeted kinase inhibitor;
  (ii) a receptor tyrosine kinase (RTK) inhibitor;
  (iii) a PIM family kinase inhibitor, such as SGI-1776;
  (iv) an Flt-3 inhibitor;
  (v) an EGFR or HER2 inhibitor, such as lapatanib;
  (vi) a therapeutic monoclonal antibody, such as the HER2 inhibitor trastuzumab;
  (vii) a MEK inhibitor, such as PD-0325901;
  (vii) a BRaf inhibitor, such as GDC-0879;
  (viii) an anthracyclin, such as doxorubicin;
  (ix) a taxane, such as paclitaxel or, particularly, docetaxel;
  (x) a platin, such as carboplatin or, particularly, cisplatin;
  (xi) a nucleotide analog, such as 5-fluorouracil (5-FU) or gemcitabine);
  (xii) an alkylating agent, such as temozolomide;
  (xiii) a hormone therapeutic agent, such as an estrogen receptor antagonist e.g. tamoxifen;
  (xiv) an anti-tumour compound that has potential radio-sensitising and/or chemosensitising effects, such as chloroquine;
  (xv) an mTOR inhibitor, such as rapamycin;
  (xvi) an Akt or PI3-K inhibitor, such as GDC-0941;
  (xvii) a JAK inhibitor;
  (xviii) an agent that modulates the DNA damage response mechanism and/or the stress signaling pathway, e.g. an inhibitor of ATM or ATR, an inhibitor of p38 and/or NF-KB; and/or
  (xix) a BCL-2 family inhibitor, such as AB5-737.

According to a further aspect of the invention, there is provided a combination product comprising:
(A) a compound of the invention, as hereinbefore defined; and
(B) another therapeutic agent that is useful in the treatment of cancer and/or a proliferative disease,
wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, another therapeutic agent that is useful in the treatment of cancer and/or a proliferative disease, and a pharmaceutically-acceptable adjuvant, diluent or carrier; and
(2) a kit of parts comprising components:
(a) a pharmaceutical formulation including a compound of the invention, as hereinbefore defined, in admixture with a pharmaceutically-acceptable adjuvant, diluent or carrier; and
(b) a pharmaceutical formulation including another therapeutic agent that is useful in the treatment of cancer and/or a proliferative disease in admixture with a pharmaceutically-acceptable adjuvant, diluent or carrier,
which components (a) and (b) are each provided in a form that is suitable for administration in conjunction with the other.

In a particularly preferred aspect of the invention, compounds of the invention may be combined with other therapeutic agents (e.g. chemotherapeutic agents) for use as medicaments (e.g. for use in the treatment of a disease or condition as mentioned herein, such as one in which the inhibition of growth of cancer cells are required and/or desired e.g. for treating hyperproliferative disorders such as cancer (e.g. specific cancers that may be mentioned herein, e.g. in the examples) in mammals, especially humans). Such active ingredients in combinations may act in synergy.

In particular, compounds of the invention may be combined with known chemotherapeutic agents (as may be demonstrated by the examples, for instance where a compound of the examples is employed in combination and inhibits cellular proliferation in vitro; in particular such combinations may be useful in treating lung and/or ovarian cancer), for instance:

(i) a MEK inhibitor, such as PD-0325901;
(ii) an EGFR inhibitor, such as Lapatinib; and/or
(iii) docetaxel (Taxotere®, Sanofi-Aventis).

The MEK inhibitor PD-0325901 (CAS RN 391210-10-9, Pfizer) is a second-generation, non-ATP competitive, allosteric MEK inhibitor for the potential oral tablet treatment of cancer (U.S. Pat. Nos. 6,960,614 ;6,972,298; US 2004/1147478; US 2005/085550). Phase II clinical trials have been conducted for the potential treatment of breast tumors, colon tumors, and melanoma. PD-0325901 is named (R)—N-(2,3-dihydroxypropoxy)-3,4-difluoro-2-(2-fluoro-4-iodophenylamino)benz-amide, and has the structure:

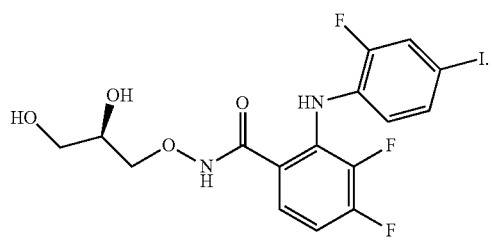 [SMILES: O=C(NOC[C@H](O)CO)c1ccc(F)c(F)c1Nc1ccc(I)cc1F]

Docetaxel (TAXOTERE®, Sanofi-Aventis) is used to treat breast, ovarian, and NSCLC cancers (U.S. Pat. Nos. 4,814,470; 5,438,072; 5,698,582; 5,714,512; 5,750,561; Mangatal et al (1989) Tetrahedron 45:4177; Ringel et al (1991) J. Natl. Cancer Inst. 83:288; Bissery et al (1991) Cancer Res. 51:4845; Herbst et al (2003) Cancer Treat. Rev. 29:407-415; Davies et al (2003) Expert. Opin. Pharmacother. 4:553-565). Docetaxel is named as (2R,3S)—N-carboxy-3-phenylisoserine, N-tert-butyl ester, 13-ester with 5, 20-epoxy-1, 2, 4, 7, 10, 13-hexahydroxytax-11-en-9-one 4-acetate 2-benzoate, trihydrate (U.S. Pat. No. 4,814,470; EP 253738; CAS Reg. No. 114977-28-5) (or named as 1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}) and has the structure:

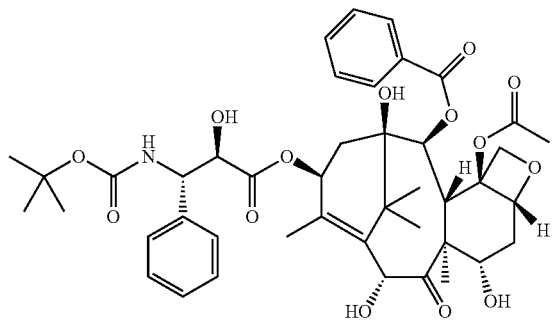 [SMILES: CC(=O)O[C@@]12CO[C@@H]1C[C@H](O)[C@@]1(C)C(=O)[C@H](O)C3=C(C)[C@@H](OC(=O)[C@H](O)[C@@H](NC(=O)OC(C)(C)C)c4ccccc4)C[C@](O)([C@@H](OC(=O)c4ccccc4)[C@H]21)C3(C)C]

Lapatinib (TYKERB®, GW572016, Glaxo SmithKline) has been approved for use in combination with capecitabine (XELODA®, Roche) for the treatment of patients with advanced or metastatic breast cancer whose tumors over-express HER2 (ErbB2) and who have received prior therapy including an anthracycline, a taxane and trastuzumab. Lapatinib is an ATP-competitive epidermal growth factor (EGFR) and HER2/neu (ErbB-2) dual tyrosine kinase inhibitor (U.S. Pat. Nos. 6,727,256; 6,713,485; 7,109,333; 6,933,299; 7,084,147; 7,157,466; 7,141,576) which inhibits receptor autophosphorylation and activation by binding to the ATP-binding pocket of the EGFR/HER2 protein kinase domain. Lapatinib is named as N-(3-chloro-4-(3-fluorobenzyloxy)phenyl)-6-(5-((2-(methylsulfonyl)ethylamino)-methyl)furan-2-yl)quinazolin-4-amine (or alternatively named as N-[3-chloro-4-[(3-fluorophenyl)methoxy]phenyl]-6-[5-[(2-methylsulfonylethylamino)methyl]-2-furyl]quinazolin-4-amine), and has the structure:

The invention further provides a process for the preparation of a combination product as hereinbefore defined, which process comprises bringing into association a compound of the invention, as hereinbefore defined, or a pharmaceutically acceptable ester, amide, solvate or salt thereof with the other therapeutic agent that is useful in the treatment of cancer and/or a proliferative disease, and at least one pharmaceutically-acceptable adjuvant, diluent or carrier.

For instance, compounds of the invention may be combined with a chemotherapeutic agent. A "chemotherapeutic agent" is a biological (large molecule) or chemical (small molecule) compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, proteins, antibodies, photosensitizers, and kinase inhibitors. Chemotherapeutic agents include compounds used in "targeted therapy" and non-targeted, conventional chemotherapy.

Examples of chemotherapeutic agents include those mentioned in e.g. WO 2010/105008, for instance: dexamethasone, thioTEPA, doxorubicin, vincristine, rituximab, cyclophosphamide, prednisone, melphalan, lenalidomide, bortezomib, rapamycin, and cytarabine.

Examples of chemotherapeutic agents also include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), doxorubicin (ADRIAMYCIN®), Akti-1/2, HPPD, rapamycin, and lapatinib (TYKERB®, Glaxo SmithKline).

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (MEK inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), ABT-869 (multi-targeted inhibitor of VEGF and PDGF family receptor tyrosine kinases, Abbott Laboratories and Genentech), ABT-263 (Bcl-2/Bcl-xL inhibitor, Abbott Laboratories and Genentech), PTK787/ZK 222584 (Novartis), fulvestrant (FASLODEX®, AstraZeneca), leucovorin (folinic acid), lonafamib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), capecitabine (XELODA®, Roche), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thioTepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma II, calicheamicin omega II, dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; antiadrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; tiaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thioTepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; ibandronate; CPT-11; topoisomerase inhibitor RFS 2000; difluoromethylomithine (DMFO); retinoids such as retinoic acid; and pharmaceutically acceptable salts, acids and derivatives of any of the above.

Also included in the definition of "chemotherapeutic agent" are: (i) antihormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTN®, Genentech); cetuximab (ERBITUX®, lmclone); panitumumab (VECTIBIX®, Amgen), rituximab (RITUXAN®, Genentech/Biogen Idec), pertuzumab (OMNITARG™, rhuMab 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanised monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, rolizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Depending on the disorder, and the patient, to be treated, as well as the route of administration, compounds of the invention may be administered at varying therapeutically effective doses to a patient in need thereof. However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of the invention.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

Compounds of the invention may have the advantage that they are effective inhibitors of protein or lipid kinases (e.g. PI3K, such as class I PI3K, mTOR and/or PIM). In an embodiment, compounds of the invention may have the advantage that they are both PI3K (e.g. class I PI3K, such as PI3Kα) inhibitors and mTOR inhibitors, i.e. they may exhibit dual kinase inhibition. In a further embodiment, compounds of the invention may have the advantage that they are PIM inhibitors and are also either PI3K (e.g. class I PI3K, such as PI3Kα) inhibitors or mTOR inhibitors, i.e. they may exhibit dual kinase inhibition. In a yet further embodiment, compounds of the invention may have the advantage that they are PI3K (e.g. class I PI3K, such as PI3Kα) inhibitors, mTOR inhibitors and PIM inhibitors, i.e. they may exhibit triple kinase inhibition.

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

Pharmacokinetic data for a selection of the compounds of the invention are shown in Table 4. These data demonstrate that the macrocyclic compounds are stable under physiological conditions. Without wishing to be bound by theory, it is believed that the activity that is observed for the compounds of the invention is associated with the compounds in their macrocyclic forms, as opposed to in ring-open forms.

As stated hereinbefore, compounds of the invention may have the advantage that they may exhibit triple (e.g. dual) kinase inhibitory activity (e.g. may act as inhibitors of combinations of PI3K (such PI3Kα), mTOR and PIM (e.g. PI3K (such PI3Kα) and mTOR). In this respect, advantageously, compounds of the invention may be considered as multi-targeted kinase inhibitors. Compounds of the invention that exhibit single selectivity for a kinase may have the additional benefit that they exhibit less side effects, whereas compounds of the invention that exhibit multiple kinase selectivity may have the additional benefit that they exhibit better potency and/or efficacy.

To date, clinical development of PI3K and dual PI3K/mTOR inhibitors have shown moderate activities, suggesting that either more potent/efficacious inhibitors are required or that inhibition of multiple targets or even pathways might be required for effective treatments (see e.g. Bunney, Tom D., Katan, Matilda, Phosphoinositide signalling in cancer: beyond PI3K and PTEN, Nature Reviews Cancer (2010), 10(5), 342-352; Cleary, James M. and Shapiro, Geoffrey I., Development of phosphoinositide-3 kinase pathway inhibitors for advanced cancer, Current Oncology Report (2010), 12, 87-94; and van der Heijden, Michiel S. and Bernards, Rene; Inhibition of the PI3K Pathway: Hope We Can Believe in? Clinical Cancer Research (2010), 16, 3094-3099).

Advantageously, the compounds of the invention may have the benefit that they inhibit multiple targets (or even multiple pathways). For instance, in addition to being inhibitors of PI3K, mTOR and PIM (e.g. PI3K (e.g PI3Kα) and mTOR), they may also be effective inhibitors of other protein or lipid kinases (as may be demonstrated by known tests). In this respect, compounds of the invention may be considered to have an improved kinase inhibition cross-reactivity profile, e.g. by being selective against multiple kinases of therapeutic interest, for instance compared to compounds known in the prior art. They may have advantages in the clinic.

Compounds of the invention may combine dual PI3K/mTOR activity (optionally together with PIM activity) with activity on other key kinases (indeed, combination products covering this spectrum of kinases are currently being evaluated as mentioned above), thereby allowing single-agent administration (or, potentially, combination products with reduced dosages) and providing the associated benefits, e.g. reducing the risk of drug-drug interactions, etc.

Compounds of the invention may be beneficial as they are medicaments with targeted therapy, i.e. which target a particular molecular entity by inferring or inhibiting it (e.g. in this case by inhibiting one or more protein or lipid kinases as hereinbefore described). Compounds of the invention may therefore also have the benefit that they have a new effect (for instance as compared to known compounds in the prior art), for instance, the new effect may be a particular mode of action or another effect resultant of the targeted therapy. Targeted therapies may be beneficial as they may have the desired effect (e.g. reduce cancer, by reducing tumor growth or carcinogenesis) but may also have the advantage of reducing side effects (e.g. by preventing the killing of normal cells, as may occur using e.g. chemotherapy).

Furthermore, compounds of the invention may selectively target particular protein or lipid kinases (e.g. the ones described herein) compared to other known protein or lipid kinases. Accordingly, compounds of the invention may have the advantage that certain, specific, cancers may be treated selectively, which selective treatment may also have the effect of reducing side effects.

EXAMPLES/BIOLOGICAL TESTS

Determination of PI3 and PIM kinase activity of compounds of the invention (such as those exemplified) is possible by a number of direct and indirect detection methods. Certain exemplary compounds described herein were prepared, characterized, and assayed for their PI3Kα, PIM and mTOR enzymatic activities using the methods described herein. The compounds may also be tested in cell-based assays.

PI3K Activity Assay

The kinase activity was measured by using the commercial ADP Hunter™ Plus assay available from DiscoveR$_x$ (#33-016), which is a homogeneous assay to measure the accumulation of ADP, a universal product of kinase activity. The enzyme, PI3K (p110α/p85α was purchased from Carna Biosciences (#07CBS-0402A). The assay was done following the manufacturer recommendations with slight modifications: Mainly the kinase buffer was replace by 50 mM HEPES, pH 7.5, 3 mM MgCl$_2$, 100 mM NaCl, 1 mM EGTA, 0.04% CHAPS, 2 mM TCEP and 0.01 mg/ml BGG. The PI3K was assayed in a titration experiment to determine the optimal protein concentration for the inhibition assay. To calculate the IC$_{50}$ of the ETP-compounds, serial 1:5 dilutions of the compounds were added to the enzyme at a fixed concentration (2.5 μg/ml). The enzyme was preincubated with the inhibitor and 30 μM PIP$_2$ substrate (P9763, Sigma) for 5 min and then ATP was added to a final 50 μM concentration. Reaction was carried out for 1 hour at 25° C. Reagent A and B were sequentially added to the wells and plates were incubated for 30 min at 37° C. Fluorescence counts were read in a Victor instrument (Perkin Elmer) with the recommended settings (544 and 580 nm as excitation and emission wavelengths, respectively). Values were normalized against the control activity included for each enzyme (i.e., 100% PI3 kinase activity, without compound). These values were plotted against the inhibitor concentration and were fit to a sigmoid dose-response curve by using the Graphad software.

mTOR Assay

The enzymatic mTOR activity was measured using a LanthaScreen™ kinase activity assay (Invitrogen). The enzyme was purchased from Invitrogen (PV4754), as well as the GFP-labeled substrate (4EBP1-GFP; PV4759) and the Tb-anti-p4EBP1(pThr46) antibody (PV4757). The assay was performed in 50 mM HEPES buffer, pH 7.5, containing 1.5 mM MnCl$_2$, 10 mM MgCl$_2$, 1 mM EGTA, 2.5 mM DTT and 0.01% Tween-20. The concentration of the assay components were the following: 0.24 nM mTOR kinase, 400 nM 4EBP1-GFP, 10 mM ATP and serial dilutions of the compound (inhibitor) to be evaluated. After 1 h incubation at room temperature, 20 mM EDTA was used to stop the reaction and terbium-labeled antibody (4 nM) added to detect phosphorylated product. The antibody associates with the phosphorylated product resulting in an increased TR-FRET value. The TR-FRET value (a dimensionless number) was calculated as the ratio of the acceptor signal (GFP, emission at 520 nm) to the donor signal (terbium, emission at 495 nm). Values were plotted against the inhibitor concentration and fitted to a sigmoid dose-response curve using GraphPad software.

PIM-1 Biochemical Assay

The biochemical assay to measure PIM-1 activity relies on the ADP Hunter assay kit (DiscoveRx Corp., Cat. #90-0077), that determines the amount of ADP as direct product of the kinase enzyme activity.

The enzyme has been expressed and purified in-house as a recombinant human protein with a C-terminal histidine tag. The protein is active and stable.

Assay conditions were as indicated by the kit manufacturers with the following adaptations for the kinase activity step:

Kinase assay buffer and assay volume stay as recommended (15 mM HEPES, pH 7.4, 20 mM NaCl, 1 mM EGTA, 0.02% Tween 20, 10 mM MgCl$_2$ and 0.1 mg/ml bovine γ-globulins/75 μl assay volume)

Incubation time and temperature: 60 min at 30° C.

PIM-1 concentration: 50 pg/μl

ATP concentration: 100 μM

PIM-1 substrate peptide: PIMtide (ARKRRRHPS-GPPTA) (SEQIDNO. 1)

Peptide concentration: 60 μM

Positive control for kinase activity inhibition: 1-10 μM Staurosporine

DMSO concentration have to stay below 2% during the kinase reaction

Assays were performed in either 96 or 384-well plates. The final outcome of the coupled reactions provided by the kit is the release of the fluorescent product Resorufin and has been measured with a multilabel HTS counter VICTOR V (PerkinElmer) using an excitation filter at 544 nm and an emission filter at 580 nm.

Pharmacokinetic

Experiments were done using BALB-c female mice, 10 weeks old. Compounds were dissolved in selected vehicles at a concentration calculated in order to administer the dose selected in 0.1 mL. Animals were administered by i.v and oral route (by gavage), and sacrificed at different time points (n=3 at each time point). Time points were 0.08, 0.25, 0.5, 1, 4 and 8 h for the i.v branch, and 0.08, 0.16, 0.25, 0.5, 1, 4, 8 and 24 h for oral branch. Blood was collected and processed for plasma which was analyzed and quantified by means of tandem mass spectrometry coupled with liquid chromatography. Pharmacokinetic parameters were estimated by fitting the experimental data to a compartmental model using Winnonlin software for pharmacokinetic analysis.

Cellular Mode of Action

Cell culture: The cell lines are obtained from the American Type Culture Collection (ATCC). U2OS (human osteosarcoma) is cultured in Dulbecco's modified Eagle's medium (DMEM). PC3 (human prostate carcinoma), MCF7 (human breast cardinoma), HCT116 (human colon carcinoma), 768-0 (human neuroblastoma), U251 (human glyoblastoma) are grown in RPMI. All media are supplemented with 10% fetal bovine serum (FBS) (Sigma) and antibiotics-antimycotics. Cells are maintained in a humidified incubator at 37° C. with 5% $CO_2$ and passaged when confluent using trypsin/EDTA.

Cytotoxicity Assessment

Cell viability in the presence of test compounds is measured by the CellTiter-Glo® Luminescent Cell Viability Assay, commercially available from Promega Corp., Madison, Wis. This homogeneous assay method is based on the recombinant expression of Coleoptera luciferase (U.S. Pat. Nos. 5,583,024;5,674,713; 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiterGlo® Assay was conducted in 96 making it amenable to automated highthroughput screening (HTS) (Cree et al (1995) AntiCancer Drugs 6:398-404).

The homogeneous assay procedure involves adding the single reagent (CellTiter-Glut Reagent) directly to cells cultured in serum-supplemented medium. Cell washing, removal of medium and multiple pipetting steps are not required. The system detects as few as 15 cells/well in a 96-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

PI3K Cellular Activity (ELISA Assay)

Activity is measured as endogenous levels of phospho-Akt1 (Ser473) protein. Osteosarcoma U2OS cells are plated in 96 Poly-D-Lysine coating tissue culture plates (18.000 cells/well). After the treatment with serial dilutions of the compound during 3 h, the cells are fixed directly in the wells with 4% paraformaldehyde.

After fixing, individual wells go through the same series of steps used for a conventional immunoblot: including blocking with 5% BSA, incubation with 1/1000 of primary antibody-AKT (Ser 74) in PBS containing 5% BSA at 4° C. overnight (Cell Signalling), washing and incubation with second antibody HRP-anti-mouse IgG for 1 h at RT (Amersham). After the addition of SuperSignal ELISA Femto maximum sensitivity chemiluminescent substrate (Pierce) the results are read using a luminescence plate reader (Victor).

PIM-1 Cellular Assay (BAD S112 Phosphorylation Inhibition Assay)

The efficacy of compounds of the invention in inhibiting BAD phosphorylation was measured by an In Cell ELISA. EC50 values were established for the tested compounds.

Assay Conditions:

Cells: H1299 cells overexpressing PIM1 (H1299Pim1)

DMSO Plates: 96-well-Polystyrene, Untreated, Round-Bottom plates from Costar (Cat #3797)

Cell Plates: 96-Flat bottom biocoated with Poly-D-Lysin plates with lid from Becton Dickinson (Cat#354651)

Cell Culture Medium: DMEM high glucose, 10% Fetal Bovine Serum, 2 mM L-Glutamine, P/S Antibodies: phosphor Bad S112 antibody from Cell Signaling (cat. #9291S), anti rabbit conjugated with peroxidise from Amersham (cat.#3619)

Reagent: SuperSignal ELISA femto from Pierce (cat.#1001110)

Procedure:

Cells were seeded in 15000 cells per 200 µl per well into 96-well plates and incubated for 16 h at 37° C., 5% $CO_2$. On day two, nine serial 1:2 compound dilutions were made in DMSO in a 96-well plate. The compounds were added to duplicate wells in 96-well cell plates using a FX BECKMAN robot (Beckman Coulter) and incubated at 37° C. with $CO_2$ atmosphere. After 4 hours, relative levels of Bad S112 phosphorylation were measured in Cell ELISA using SuperSignal ELISA Femto substrate (Pierce) and read on VICTOR (Perkin Elmer). EC50 values were calculated using ActivityBase from IDBS.

EXAMPLES

The following Examples illustrate the invention.

Experimental Part

Hereinafter, the term "DCM" means dichloromethane, "MeOH" means methanol, "THF" means tetrahydrofuran, "DMF" means dimethylformamide, "DME" means 1,2-dimethoxyethane, "EtOAc" means ethyl acetate, "BOP" means (Benzotriazol-1-yloxy)tris(dimethylamino)phosphonium hexafluorophosphate, "HOAt" means 1-hydroxy-7-azabenzotriazole, "PyBOP" means (benzotriazol-1-yloxy)tripyrrolidinophosphonium hexafluorophosphate, "DMAP" means 4-dimethylaminopyridine, "HATU" means O-(7-azabenzotriazole-1-yl)-1,1,3,3-tetramethyluronium hexafluorophosphate, "Pd(PPh$_3$)$_4$" means tetrakis(triphenylphosphine)palladium, "PdCl$_2$(dppf)-DCM" means 1,1'-bis(diphenylphosphino)ferrocenepalladium(II) dichloride, dichloromethane, "DIPEA" means diisopropylethylamine, "TFA" means trifluoroacetic acid, "min" means minutes, "h" means hours, "RT" means room temperature, "eq" means equivalents, "nBuOH" means n-butanol, "mw" means microwave.

General Procedure

NMR spectra were recorded in a Bruker Avance II 300 spectrometer and Bruker Avance II 700 spectrometer fitted with 5 mm QXI 700 S4 inverse phase, Z-gradient unit and variable temperature controller.

The HPLC measurements were performed using a HP 1100 from Agilent Technologies comprising a pump (binary) with degasser, an autosampler, a column oven, a diode-array detector (DAD) and a column as specified in the respective methods below. Flow from the column was split to a MS spectrometer. The MS detector was configured with an electrospray ionization source or API/APCI. Nitrogen was used as the nebulizer gas. Data acquisition was performed with ChemStation LC/MSD quad, software.

Method 1

Reversed phase HPLC was carried out on a Gemini-NX C18 (100×2.0 mm; 5 um).

Solvent A: water with 0.1% formic acid; Solvent B: acetonitrile with 0.1% formic acid. Gradient: 5% to 100% of B within 8 min at 50° C., DAD.

Method 2

Reversed phase HPLC was carried out on a Gemini-NX C18 (100×2.0 mm; 5 um).

Solvent A: water with 0.1% formic acid; Solvent B: acetonitrile with 0.1% formic acid. Gradient: 5% to 40% of B within 8 min at 50° C., DAD.

Method 3

Reversed phase HPLC was carried out on a Gemini-NX C18 (100×2.0 mm; 5 um).

Solvent A: water with 0.1% formic acid; Solvent B: acetonitrile with 0.1% formic acid. Gradient: 0% to 30% of B within 8 min at 50° C., DAD.

Method 4

Reversed phase HPLC was carried out on a Gemini C18 column (50×2 mm, 3 urn).

Solvent A: water with 0.1% formic acid; Solvent B: acetonitrile with 0.1% formic acid. Gradient: 10% to 95% of B within 4 min at 50° C., DAD.

Method 5

Reversed phase HPLC was carried out on a Gemini C18 column (50×2 mm, 3 um). Solvent A: water with 0.1% formic acid; Solvent B: acetonitrile with 0.1% formic acid. Gradient: 0% to 30% of B within 4 min at 50° C., DAD.

"Found mass" refers to the most abundant isotope detected in the HPLC-MS.

The compound names given herein may be generated in accordance with IUPAC using the AutoNom naming program in MDL ISIS Draw.

Preparation of Intermediates

The synthesis of the some intermediates may have already been described in international patent applications WO2009/040552, WO2008/150827 and WO 2010/112874.

Synthesis of Intermediate I-01

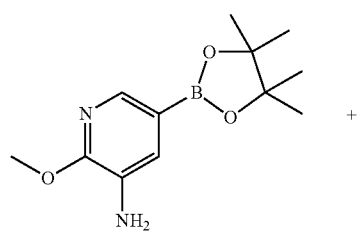

+

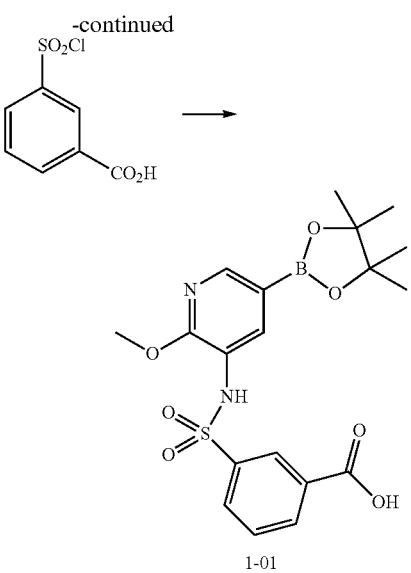

To a solution of (5-amino-6-methoxypyridin-3-yl)boronic acid pinacol ester (1.0 g, 3.99 mmol) in pyridine (13.3 mL) at 0° C. was added 3-(chlorosulfonyl)benzoic acid (1.11 g, 4.79 mmol). The reaction mixture was stirred at 0° C. for 3 h. The mixture was concentrated and the residue was purified by column chromatography (Biotage, cHex:EtOAc 100:0 to 0:100) to give Intermediate I-01 (1.15 g, 82%).

Synthesis of Intermediate 1-02

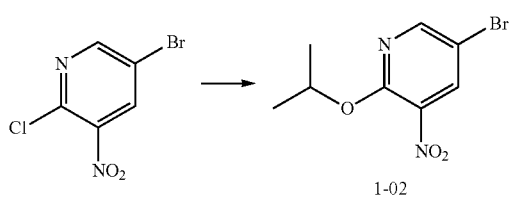

To a mixture of 5-bromo-2-chloro-3-nitropyridine (5 g, 21.06 mmol) in 2-propanol (60 mL) was added DBU (15.7 mL, 105.3 mmol). The reaction mixture was stirred at 50° C. for 17 h. After cooling to RT, 1N HCl was added and the mixture was concentrated under reduced pressure. Aqueous layer was extracted with EtOAc (×4). Combined organic layers were washed with 1N HCl, dried, filtered and evaporated. The residue was purified on silica gel (Biotage, cHex/EtOAc 100:0 to 90:10) to give Intermediate 1-02 (974 mg, 18%).

Synthesis of Intermediate 1-03

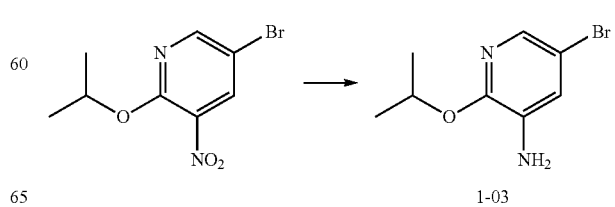

To a solution of Intermediate I-02 (978 mg, 3.75 mmol) in a 4:1 mixture of acetic acid/water (10 mL) was added Iron (628 mg, 11.24 mmol). The reaction mixture was stirred at RT for 4 h. EtOAc was added, and the mixture was filtered through a plug of celite. The filtrate was basified by addition of 5N NaOH. The mixture was extracted with EtOAc (×3) and the combined organic layers were dried, filtered and evaporated. The residue was purified on silica gel (Biotage, cHex/EtOAc 100:0, 80:20) to obtain Intermediate I-03 (338 mg, 39%).

Synthesis of Intermediate I-04

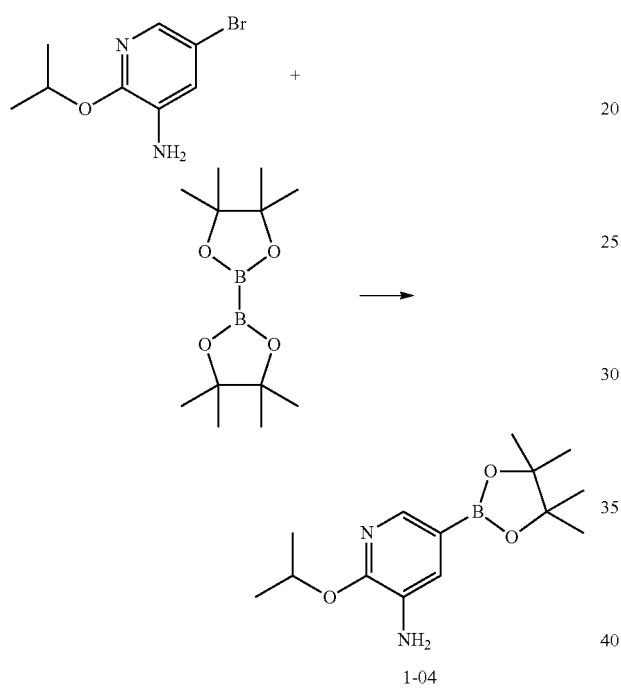

1-04

To a mixture of Intermediate I-03 (338 mg, 1.46 mmol), bis(pinacolato)diboron (446 mg, 1.75 mmol) and KOAc (431 mg, 4.39 mmol) in 1,4-dioxane/DMF (2 mL/0.2 mL) was added PdCl$_2$(dppf). DCM (121 mg, 0.15 mmol). The reaction mixture was heated under microwave conditions at 150° C. for 10 min. On cooling, the mixture was filtered through a column of silica gel (isolute Si II, 5 g) with a pad of celite on its top eluting with EtOAc. The filtrate was evaporated and the residue was purified on silica gel (Biotage, cHex/EtOAc 90:10 to 0:100) to obtain Intermediate I-04 (169 mg, 42%).

Synthesis of Intermediate I-05

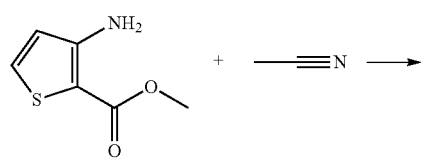

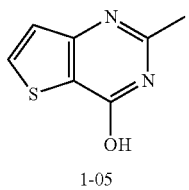

1-05

A mixture of methyl 3-aminothiophene-2-carboxylate (1 g, 6.362 mmol) and acetonitrile (0.50 mL, 9.542 mmol) in HCl (4M in 1,4-dioxane, 12.70 mL) was placed into a sealed tube and left under sonication at RT for 4 h. The reaction mixture was then heated at 100° C. for 16 h. More HCl (4M in 1,4-dioxane, 2 mL) and CH$_3$CN (0.25 mL) were added and the mixture was heated at 100° C. for 2 h. NaOH (5 N, 12 mL) was added and the mixture was refluxed for 30 min. On cooling, H$_2$O was added and the mixture was extracted with EtOAc. The combined organic layers were dried (Na$_2$SO$_4$), filtered and concentrated to give Intermediate I-05 (184 mg). The aqueous layer was evaporated under vacuum and the residue was triturated from H$_2$O to give Intermediate I-05 (463 mg) as a pale yellow solid. Total yield: 61%.

Synthesis of Intermediate I-06

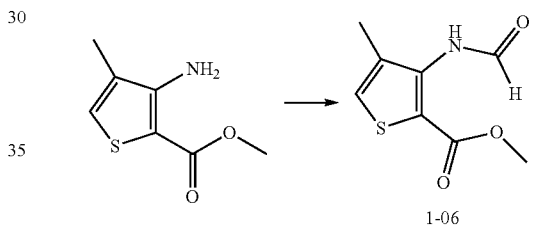

1-06

To acetic anhydride (18 mL) at 0° C. was added dropwise formic acid (12 mL) followed by the portionwise addition of methyl 3-amino-4-methylthiophene-2-carboxylate (5 g, 29.2 mmol). The reaction mixture was stirred at RT for 18 h. The mixture was poured into a solution of Na$_2$CO$_3$ (30 g) in water (100 mL) at 0° C. The resulting white solid was filtered off, washed with water and dried to give Intermediate I-06 (4.69 g, 81%) as a white solid.

$^1$H NMR (300 MHz, DMSO) δ 9.85 (s, 1H), 8.24 (s, 1H), 7.55 (s, 1H), 3.76 (s, 3H), 2.07 (s, 3H).

Synthesis of Intermediate I-07

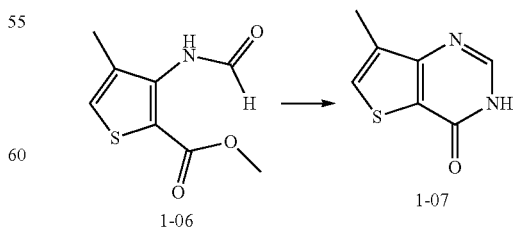

1-06        1-07

A mixture of Intermediate I-06 (4.65 g, 23.25 mmol) and ammonium formate (10 g, 200 mmol) in formamide (6 mL) was heated at 160° C. for 18 h. On cooling, the resulting solid was filtered, washed with acetone and dried to give Intermediate I-07 (3.85 g, 99%) as a white solid.

¹H NMR (300 MHz, DMSO) δ 8.18 (s, 1H), 7.81 (d, J=0.7 Hz, 1H), 2.31 (d, J=0.9 Hz, 3H).

Synthesis of Intermediate I-08

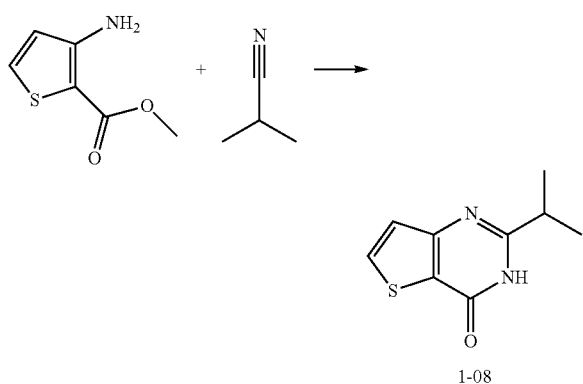

1-08

A mixture of methyl 3-aminothiophene-2-carboxylate (2 g, 12.72 mmol) and isobutyronitrile (1.71 mL, 19.08 mmol) in HCl (4M in 1,4-dioxane, 25 mL) was placed into a seated tube and left under sonication at RT for 4 h. The reaction mixture was then heated at 100° C. for 16 h. More HCl (4M in 1,4-dioxane, 4 mL) and isobutyronitrile (0.9 mL) were added and the mixture was stirred at RT for 20 h. 5N NaOH (24 mL) was added and the mixture was refluxed for 1 h. The solvent was evaporated and H₂O and 6N HCl were added to the residue. The resulting suspension was filtered off and washed with a lot of H₂O and Et₂O to give Intermediate I-08 (2.40 g, 97%).

LC-MS: $R_t$=2.64 min, [M+H]⁺=195.0.

¹H NMR (300 MHz, CDCl₃) δ 11.76 (s, 1H), 7.82 (d, J=5.3 Hz, 1H), 7.36 (d, J=5.3 Hz, 1H), 3.09 (m, 1H), 1.43 (d, 6H).

Synthesis of Intermediate I-09

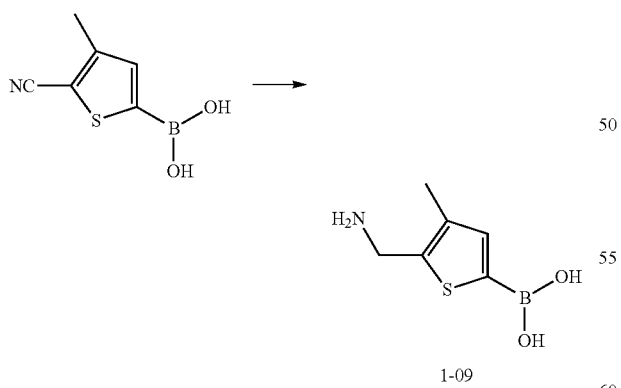

1-09

A solution of 5-cyano-4-methylthiophene-2-boronic acid (0.2 g, 1.20 mmol) in 7N NH₃ in MeOH was hydrogenated in an H-cube apparatus (Raney Nickel, flow 1 mL/min, 50 bar, 50° C., recirculating mode) for 2 h 45 min. Solvent was evaporated under reduced pressure to give Intermediate I-09 (164 mg, 80%).

Method A-1

Synthesis of Intermediate I-01

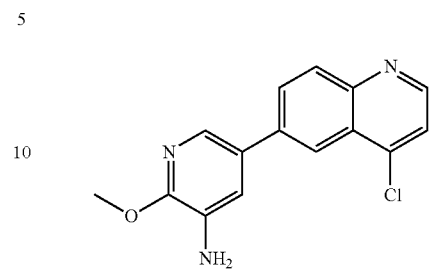

To a sealed tube charged with 6-Bromo-4-chloro-quinoline 1-00 (2.3 g, 9.48 mmol) in 1,4-dioxane (75 ml), 2-Methoxy-5-(4,4,5,5-tetramethyl-1,3,2-dioxaborolan-2-yl)-pyridin-3-yl amine (2.85 g, 11.38 mmol), K₂CO₃ (aq. sol. 1M) (40 ml) and tetrakis(triphenylphosphine)palladium (0) (1.096 g, 0.948 mmol) were added. The reaction mixture was heated at 100° C. for 1 h. The mixture was concentrated and purified by flash chromatography in a Biotage using cyclohexane-EtOAc gradient to give intermediate I-01 (2.2 g, Y: 81%).

Synthesis of Intermediate II-01

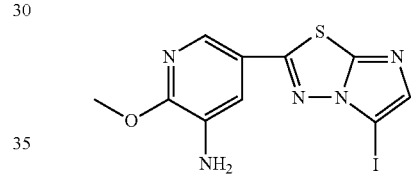

To a solution of 2-Bromo-5-iodo-imidazo[2,1-b]-1,3,4-thiadiazole (0.55 g, 1.67 mmol) in 1,4-dioxane (9 mL), 2-Methoxy-5-(4,4,5,5-tetramethyl-1,3,2-dioxaborolan-2-yl)-pyridin-3-yl amine (0.5 g, 2 mmol), Na₂CO₃ (aq. sol. 2M) (5 mL) and PdCl₂(PPh₃)₂ (117 mg, 0.167 mmol) were added. The reaction mixture was heated (sand bath) in a sealed tube at 110° C. for 2.5 h. On cooling, water was added and the suspension was filtered and rinsed with H₂O and Et₂O. The solid was purified through a path of silica (EtOAc:DCM 10:90 to 50:50) to give the intermediate II-01 (2.16 g, Y: 23%) as a beige solid.

Synthesis of Intermediate III-02

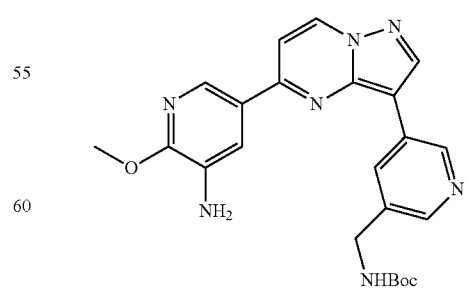

To a solution of 3-bromo-5-chloropyrazolo[1,5-a]pyrimidine (III-01) (0.5 g, 2.151 mmol) in DME (10 mL) was added (5-amino-6-methoxypyridin-3-yl)boronic acid pinacol ester (538 mg, 2.151 mmol), K$_2$CO$_3$ 2M (3.3 mL, 6.452 mmol) and PdCl$_2$(PPh$_3$)$_2$ (45 mg, 0.065 mmol). The reaction mixture was heated in a sealed tube at 80° C. for 30 min. 3-(N-Boc-aminomethyl)pyridine-5-boronic acid pinacol ester (719 mg, 2.151 mmol) and PdCl$_2$(PPh$_3$)$_2$ (45 mg, 0.065 mmol) were added and the mixture was heated at 80° C. for 22 h. On cooling, the mixture was diluted with EtOAc and washed with brine. The organic layer was dried, filtered and evaporated. The residue was purified by flash chromatography in a Biotage using MeOH:DCM 4:96 to 10:90 gradient to give intermediate III-02 (545 mg, 56%) as a yellow solid.

Synthesis of Intermediate IV-02

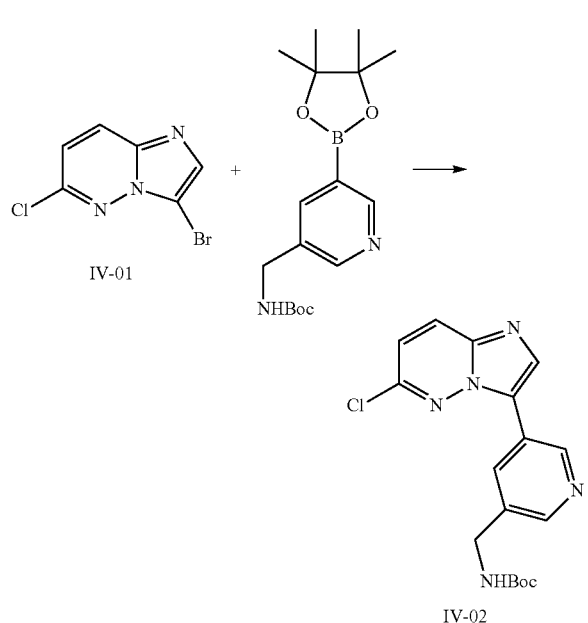

To a solution of 3-bromo-6-chloroimidazo[1,2-b]pyridazine (IV-01) (450 mg, 1.936 mmol) in 1,4-dioxane (8 mL) was added 3-(N-Boc-aminomethyl)pyridine-5-boronic acid pinacol ester (679 mg, 2.033 mmol), aq. Na$_2$CO$_3$ 2M (3 mL, 6 mmol) and PdCl$_2$(PPh$_3$)$_2$ (136 mg, 0.194 mmol). The resulting mixture was heated at 80° C. in a sealed tube for 8 h. On cooling, the mixture was diluted with DCM and water. Layers were separated and the aqueous phase was extracted twice with DCM. The combined organic extracts were dried (Na$_2$SO$_4$), filtered and concentrated. The residue was purified by flash chromatography (Biotage) using MeOH:DCM 0:100 to 20:80 as eluent to afford intermediate IV-02 (525 mg, 75%).

Synthesis of Intermediate VIII-18

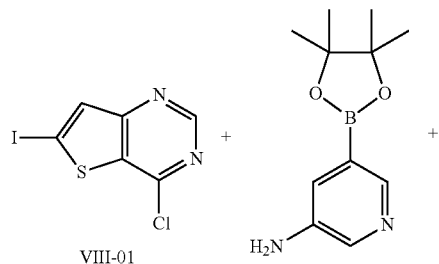

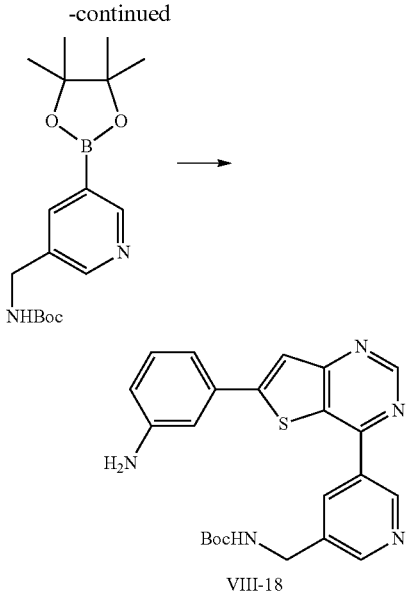

To a solution of 4-chloro-6-iodothieno[3,2-d]pyrimidine VIII-01 (30 mg, 0.101 mmol) in 1,2-dioxane (0.81 mL) was added 3-aminopyridine-5-boronic acid, pinacol ester (27 mg, 0.121 mmol), K$_2$CO$_3$ 1M (0.42 mL) and Pd(PPh$_3$)$_4$ (12 mg, 0.010 mmol). The reaction mixture was heated at 100° C. for 1 h. Then 3-(N-Boc-aminomethyl)pyridine-5-boronic acid, pinacol ester (50 mg, 0.142 mmol), K$_2$CO$_3$ 1M (0.42 mL) and Pd(PPh$_3$)$_4$ (12 mg, 0.010 mmol) were added. The reaction mixture was heated at 100° C. for 1 h. On cooling, the mixture was concentrated and the residue was purified by column chromatography (Biotage, cHex:EtOAc 100:0 to 0:100 and EtOAc:MeOH 100:0 to 80:20) to give intermediate VIII-18 (17 mg, 39%).

Method A-2

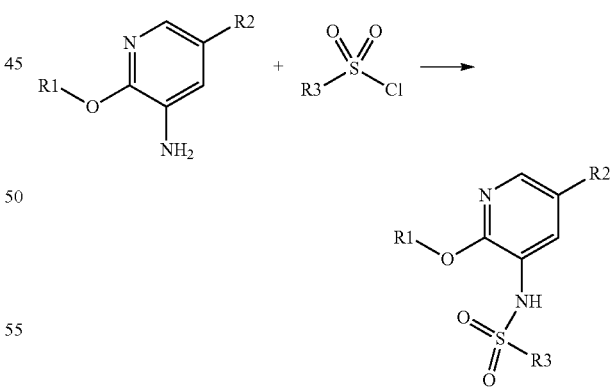

To a solution of the corresponding 2-methoxy-pyridin-3ylamine intermediate (1 eq.) in pyridine (10 mL/mmol) at 0° C. was added the required sulfonyl chloride (1.2 eq.). The reaction mixture was stirred at 0° C. for 1 h, MeOH was added and the mixture was evaporated. The residue was purified either by flash chromatography in a Biotage using MeOH:EtOAc gradient or by precipitation from MeOH to give the desired sulfonilated product.

Synthesis of Intermediate IX-10

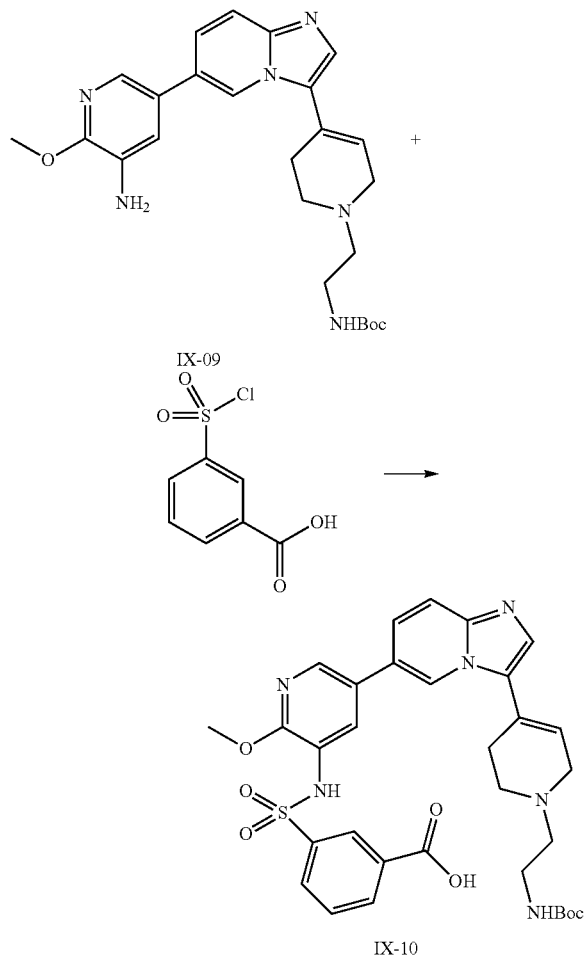

A mixture of Intermediate IX-09 (0.7 g, 1.507 mmol), 3-chlorosulfonyl-benzoic acid (0.83 g, 3.773 mmol), pyridine (7 mL) and DCM (35 mL) was stirred at 40° C. overnight. Methanol (20 mL) was added to the reaction mixture. The mixture was concentrated and diluted into 20 mL of 1N NaOH at 0° C. The mixture was extracted with EtOAc. The aqueous phase was adjusted to pH=3 by 1N HCl and extracted with EtOAc. The organic phase was dried over $Na_2SO_4$, filtered and concentrated. The residue was purified by flash chromatography to give Intermediate IX-10 (0.4 g, yield: 41%).

Method A-3

In a sealed tube charged with the halogenated starting material (1 eq.) in 1,4-dioxane (10 mL/mmol), the corresponding boronic acid (1.2 eq.), $K_2CO_3$ (aq. sol. 1M) (3 eq.) and tetrakis(triphenylphosphine)palladium(0) (0.1 eq.) were added. The reaction mixture was heated at 100° C. for 1-2 h. The mixture was concentrated and the crude was purified by flash chromatography in a Biotage using Cyclohexane/EtOAc followed by EtOAc/MeOH gradient to give the desired product.

Synthesis of Intermediate II-02

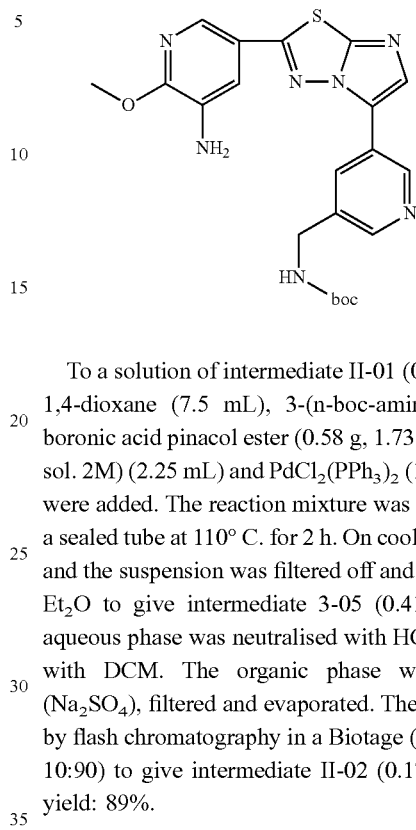

To a solution of intermediate II-01 (0.54 g, 1.44 mmol) in 1,4-dioxane (7.5 mL), 3-(n-boc-aminomethyl)pyridine-5-boronic acid pinacol ester (0.58 g, 1.73 mmol), $Na_2CO_3$ (aq. sol. 2M) (2.25 mL) and $PdCl_2(PPh_3)_2$ (102 mg, 0.144 mmol) were added. The reaction mixture was heated (sand bath) in a sealed tube at 110° C. for 2 h. On cooling, water was added and the suspension was filtered off and rinsed with $H_2O$ and $Et_2O$ to give intermediate 3-05 (0.412 g, Y: 63%). The aqueous phase was neutralised with HCl 25% and extracted with DCM. The organic phase was separated, dried ($Na_2SO_4$), filtered and evaporated. The residue was purified by flash chromatography in a Biotage (MeOH:DCM 2:98 to 10:90) to give intermediate II-02 (0.17 g, Y: 26%), global yield: 89%.

Synthesis of Intermediate VII-07

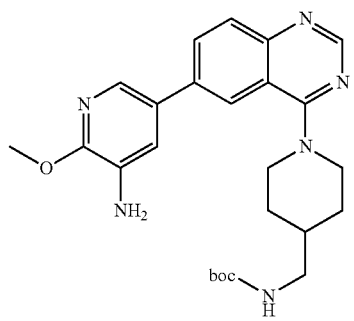

A mixture of intermediate VII-06 (3.76 g, 8.95 mmol), 2-methoxy-6-(4,4,5,5-tetramethyl-[1,3,2]dioxaborolan-2-yl)-pyridin-3-ylamine (2.35 g, 9.40 mmol), $Na_2CO_3$ (1.9 g, 17.9 mmol), Pd(dppf)$Cl_2$ (0.36 g, 0.45 mmol) in $H_2O$ (8 mL) and DME (60 mL) was stirred at 120° C. under $N_2$ overnight. The mixture was poured into ice water and extracted with EtOAc. The organic layer was washed with brine, dried over $Na_2SO_4$, and concentrated. The residue was purified by column chromatography to give the intermediate VII-07 (3.48 g, 84%).

Synthesis of Intermediate VII-10

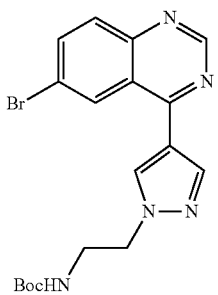 [SMILES: CC(C)(C)OC(=O)NCCn1cc(-c2ncnc3ccc(Br)cc23)cn1]

A mixture of intermediate VII-01 (0.50 g, 2.06 mmol), {2-[4-(4,4,5,5-tetramethyl-[1,3,2]dioxaborolan-2-yl)-pyrazol-1-yl]-ethyl}-carbamic acid tert-butyl ester (0.73 g, 2.16 mmol), Pd(dppf)Cl$_2$ (84 mg, 0.10 mmol), and Na$_2$CO$_3$ (0.65 g, 6.17 mmol) in DME (8 mL) and H$_2$O (2.5 mL) was heated under microwave irradiation at 140° C. for 40 min. The mixture was poured into water and extracted with EtOAc. The organic layer was washed with brine, dried over Na$_2$SO$_4$, and concentrated. The residue was purified by chromatography column on silica gel to give intermediate VII-10 (125 mg, 15%).

Synthesis of Intermediate VIII-09

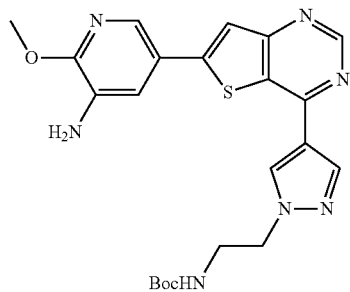 [SMILES: COc1ncc(-c2cc3ncnc(-c4cnn(CCNC(=O)OC(C)(C)C)c4)c3s2)cc1N]

To a mixture of Intermediate VIII-02 (2 g, 6.8 mmol), {2-[4-(4,4,5,5-tetramethyl-[1,3,2]dioxaborolan-2-yl)-pyrazol-1-yl]-ethyl}-carbamic acid tert-butyl ester (2.2 g, 6.8 mmol) and K$_2$CO$_3$ (2.8 g, 20.4 mmol) in dioxane (20 mL) and H$_2$O (10 mL) was added Pd(dppf)Cl$_2$ (0.5 g, 0.7 mmol) under N$_2$. The mixture was heated to 85° C. and stirred 2 h. The reaction mixture was cooled to RT, poured into water, and extracted with CH$_2$Cl$_2$ (50 mL×4). The combined organic layers were washed with brine, dried over Na$_2$SO$_4$, filtered and concentrated. The residue was purified by column chromatography to give Intermediate VIII-09 (1.7 g, 53%) as a yellow solid.

Synthesis of Intermediate XVII-03

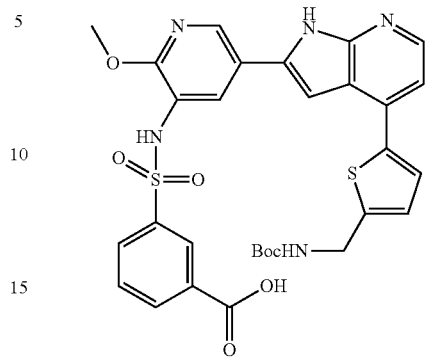

A mixture of Intermediate XVII-02 (233 mg, 0.49 mmol), 5-(Boc-aminomethyl)thiophene-2-boronic acid (159 mg, 0.62 mmol), K$_3$PO$_4$ (178 mg, 0.80 mmol), tricyclohexylphosphine (28 mg, 0.11 mmol) and Pd(dba)$_2$ (47 mg) in degassed dioxane (10 mL) and water (0.6 mL) was heated for 3 h at 120° C. under microwave irradiation. On cooling, the mixture was evaporated and the residue was purified by column chromatography (hexanes/EtOAc, 90:10 to 0:100) to give the ester intermediate as a brown solid (205 mg). By eluting the column with EtOAc/MeOH 80:20 the acid Intermediate XVII-03 was obtained (50 mg).

The ester (205 mg) was dissolved in EtOH (10 mL), the mixture was cooled to 0° C., 4N KOH (10 mL) was added and the mixture was stirred for 4 h at RT. The EtOH was carefully removed, water (5 mL) was added, and the mixture was cooled to 0° C. Acetic acid was added until the solution had a pH of ~4, and the resulting solid was filtered, washed with water and dried to give the acid as a grey solid (183 mg). Both collected acids (50 mg+183 mg) were combined and purified by column chromatography (EtOAc/MeOH, 100:0 to 80:20) to give Intermediate XVII-03 as a brown solid (193 mg, 61%).

Method A-4

Synthesis of Intermediate I-03

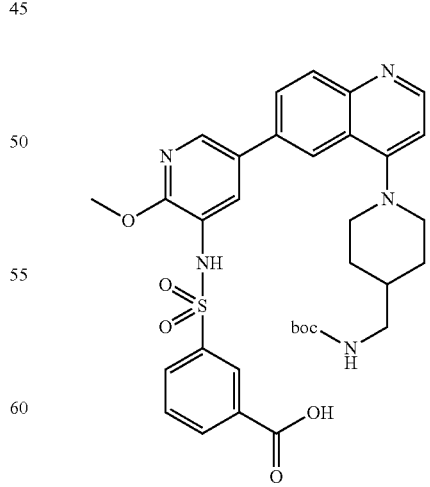

In a sealed tube charged with intermediate I-02 (250 mg, 0.532 mmol) in 1-methyl-2-pyrrolidinone (4.5 ml), 4-(tert-butoxycarbonylaminomethyl)piperidine (238 mg, 1.064 mmol) was added. The reaction mixture was heated at 150° C. for 1 h. The mixture was concentrated. The crude was purified by flash chromatography in a Biotage using Cyclohexane/AcOEt gradient followed by AcOEt/MeOH gradient to give intermediate I-03 (154 mg, Y: 45%).

Synthesis of Intermediate I-04

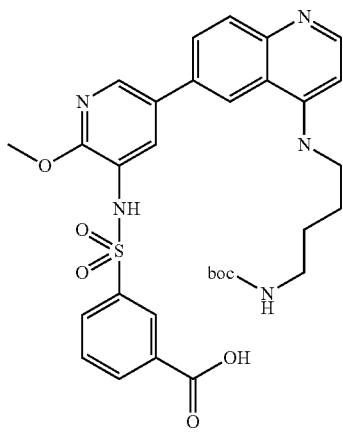

In a sealed tube charged with intermediate I-02 (260 mg, 0.553 mmol) in 1-methyl-2-pyrrolidinone (3 ml), N-boc-1,4-diaminobutane (214 mg, 1.107 mmol) was added. The reaction mixture was heated at 150° C. for 1.5 h. The mixture was concentrated. The crude was purified by flash chromatography in a Biotage using Cyclohexane/AcOEt gradient followed by AcOEt/MeOH gradient to give intermediate I-04 (137 mg, Y: 40%).

Synthesis of Intermediate VII-06

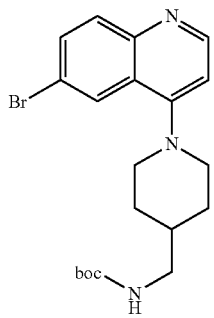

To a solution of intermediate VII-01 (2.08 g, 8.56 mmol) in ClCH$_2$CH$_2$Cl (40 mL) was added 4-(tert-butoxycarbonylaminomethyl)piperidine (1.92 g, 8.99 mmol) and Et$_3$N (1.73 g, 17.12 mmol) at 0° C. The mixture was stirred at RT overnight. The mixture was poured into ice water and extracted with EtOAc. The organic layer was washed with brine, dried over Na$_2$SO$_4$, and concentrated to give the intermediate VII-06 (3.45 g, crude), which was used in the next step with no further treatment.

Synthesis of Intermediate VIII-12

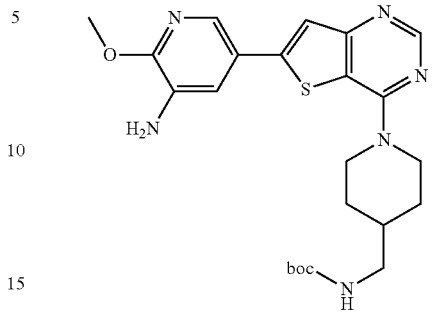

To a solution of intermediate VIII-02 (0.6 g, 2.05 mmol) and Et$_3$N (0.62 g, 0.15 mmol) in n-Butanol (30 mL) was added 4-(tert-butoxycarbonylaminomethyl)piperidine (0.66 g, 3.08 mmol). The mixture was heated to reflux and stirred for 3 h. On cooling, the reaction mixture was concentrated. The residue was purified by column chromatography to give Intermediate VIII-12 (0.8 g, 83%) as a yellow solid.

Method A-5

Synthesis of Intermediates I-07 & I-08

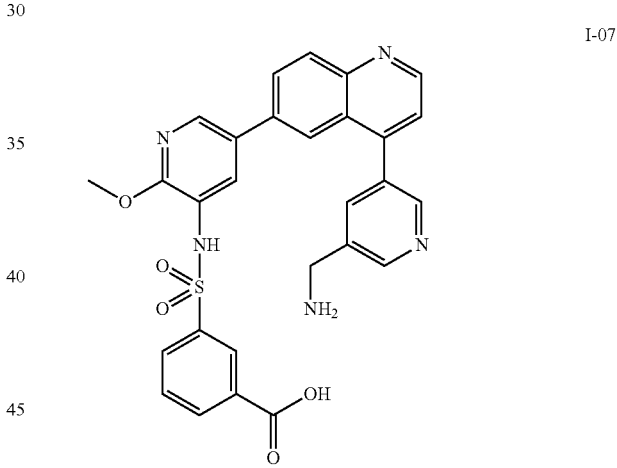

I-07

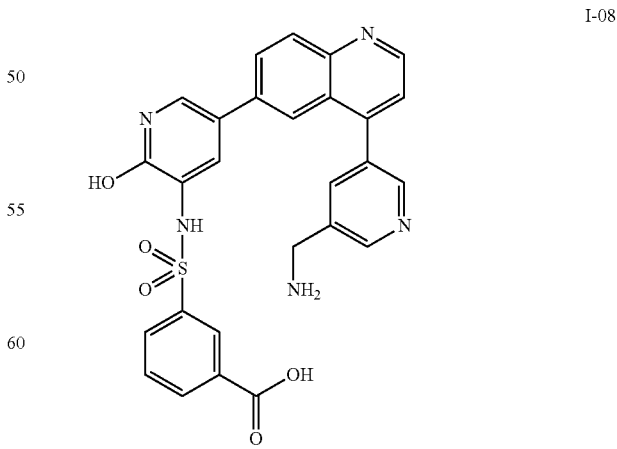

I-08

To a solution of intermediate I-06 (620 mg, 0.966 mmol) in dioxane (8 ml) at 0° C. was added dropwise a solution of HCl (4 N in water) (8 ml). The reaction mixture was stirred for 2 h. Additional amount of HCl (4 N) (8 ml) was added and the mixture was stirred at RT for 2 h. The reaction was evaporated till dryness. The residue, mixture of intermediates I-07 and I-08, was used in the next step without further purification.

Synthesis of Intermediates II-04 & II-05

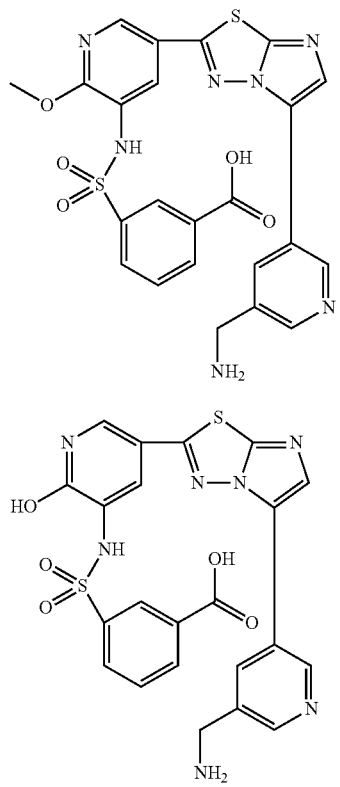

To a solution of intermediate II-03 (80 mg, 0.125 mmol) in dioxane (1.25 mL) was added HCl (4 M in dioxane) (1.25 mL). Two more additions of HCl (1 mL) were made and the mixture was finally stirred at RT over the weekend. The reaction was concentrated in vacuo and coevaporated with toluene. The residue, mixture of intermediates II-04 and II-05, was used in the next step without further purification.

Synthesis of Intermediate VIII-24

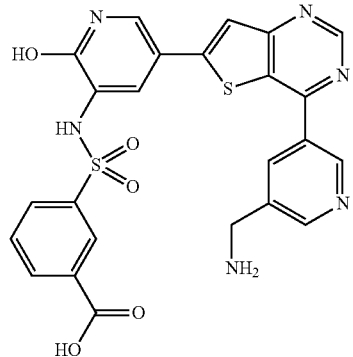

To a suspension of Intermediate VIII-04 (200 mg, 0.308 mmol) in 1,4-dioxane (3 mL) was added HCl 4N in dioxane (3.85 mL, 15.415 mmol). The reaction mixture was heated in a pressure tube at 100° C. for 4 h. On cooling, the mixture was filtered and washed with Et$_2$O to give Intermediate VIII-24 (200 mg, quant.) contaminated with aprox. 5% of the methoxy-derivative.

Method A-6

Synthesis of Intermediate II-10

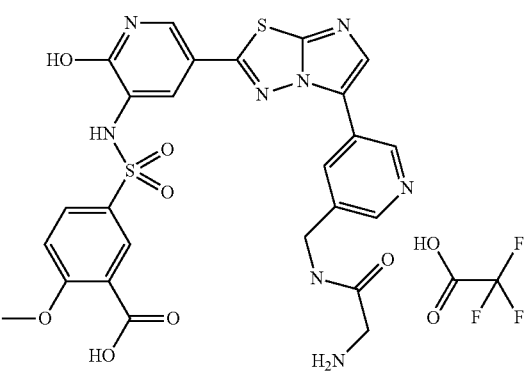

To a suspension of the corresponding Boc-amino (1 eq.) in DCM (5 mL/mmol) was added TFA (5 mL/mmol). The solution was stirred at RT for 1-18 h. The mixture was concentrated and coevaporated with toluene three times to give the desired product as trifluoroacetic salt. It was used in the next experiment without further purification. Quantitative yield was assumed.

Synthesis of Intermediate XIII-38

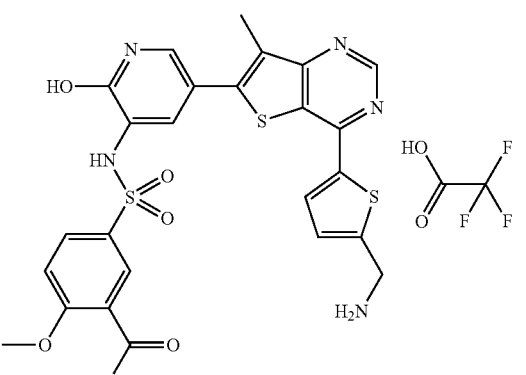

The corresponding acid (1 eq.) was suspended in DCE (5 mL/mmol), the mixture cooled to 0° C. and TFA (5 mL/mmol) was added. The mixture was stirred for 4 h at room temperature and the solvents were removed in vacuo to give the desired compound as trifluoroacetic salt. It was used in subsequent reactions without further purification. A quantitative yield was assumed.

Method A-7

Synthesis of Intermediate II-08

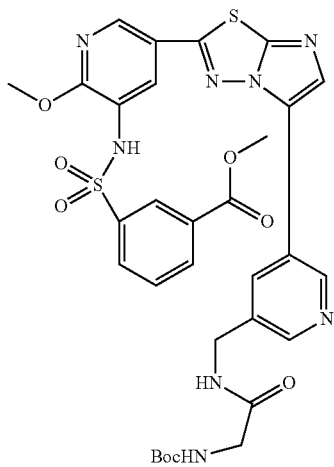

II-08

To a solution of Intermediate II-07 (trifluoroacetic salt, raw material, 290 mg, 0.436 mmol) in DCM (8 mL) and DMF (1 mL) was added DIPEA (0.38 mL, 2.18 mmol), Boc-Gly-OH (153 mg, 0.871 mmol), BOP (385 mg, 0.871 mmol) and DMAP (5 mg, 0.044 mmol). The mixture was stirred at RT for 2 h and evaporated. The residue was taken up in EtOAc and washed with H$_2$O and HCl 1.2 M. The organic layer was dried, filtered and evaporated to give Intermediate II-08 (510 mg). It was used in the next experiment with no further treatment. Quantitative yield was assumed.

Method A-8

Synthesis of Intermediate II-09

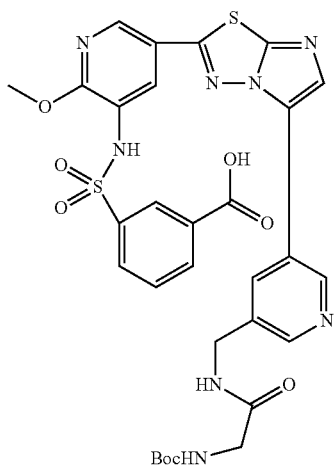

II-09

To a solution of Intermediate II-08 (raw material, 310 mg, 0.437 mmol) in MeOH (8 mL) was added LiOH.H$_2$O (184 mg, 4.37 mmol). The reaction mixture was stirred at RT for 8 h and more LiOH H$_2$O (184 mg) was added. The mixture was stirred overnight and evaporated to give Intermediate II-09. It was used in the next experiment with no further treatment. Quantitative yield was assumed.

Synthesis of Intermediate VIII-22

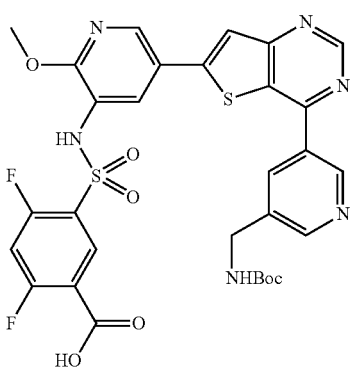

VIII-22

To a mixture of Intermediate VIII-21 (157 mg, 0.225 mmol) in 1,4-dioxane/water (3:1, 4 mL) was added potassium carbonate. The reaction was heated at 100° C. for 5 h. On cooling, the mixture was evaporated, water was added, and the pH was adjusted to 5 with 1N HCl. The mixture was extracted with EtOAc. The aqueous layer was further acidified until pH 3 and extracted with 1:1 CHCl$_3$/$^i$PrOH. All the organic layers were combined, dried and filtered to give Intermediate VIII-22 (127 mg, 83%).

Synthesis of Intermediate VIII-65

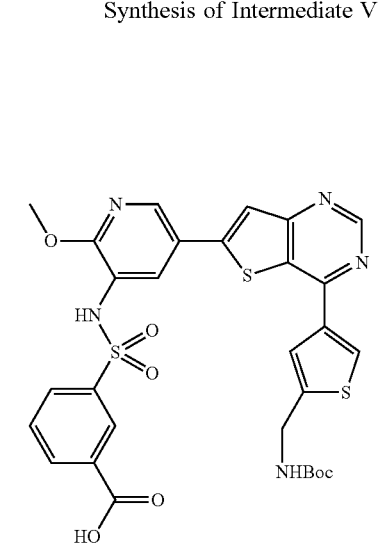

VIII-65

To a solution of Intermediate VIII-64 (275 mg, 0.41 mmol) in 1,4-dioxane (3 mL) was added 2M KOH (1 mL, 2 mmol). The reaction mixture was stirred at RT for 4.5 h. The mixture was partially evaporated under reduced pressure without heating. Water was added and pH was adjusted to pH 2 with 2M HCl. The aqueous layer was extracted twice with EtOAc, dried, filtered and evaporated to afford Intermediate VIII-65 (248 mg, 92%).

Method A-9

Synthesis of Intermediate V-02

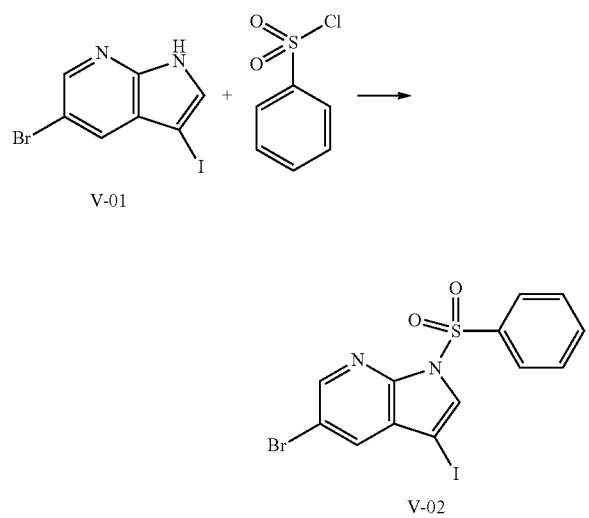

To a solution of 5-bromo-3-iodo-1H-pyrrolo[2,3-b]pyridine V-01 (1.58 g, 4.64 mmol) in DCM (47 mL) was added benzenesulfonyl chloride (1.32 mL, 10.22 mmol), tetrabutylammonium hydrogen sulfate (55% in water, 0.75 mL, 1.16 mmol) and NaOH (50% aq., 14 mL). The reaction mixture was stirred at RT for 12 h. The mixture was quenched with brine and the aqueous layer was extracted with DCM (2×20 mL). The combined organic layers were dried over Na$_2$SO$_4$, filtered and evaporated. Ice-cold methanol was added to the residue and the mixture was stirred at 0° C. for 1 h. The suspension was filtered off and the solid was washed with ice-cold methanol to afford Intermediate V-02 (1.72 g, 80%) as a pale yellow solid.

Method A-10

Synthesis of Intermediate XII-01

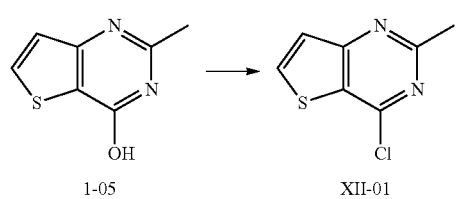

A mixture of Intermediate I-05 (647 mg, 3.893 mmol) and POCl$_3$ (32 mL) was refluxed for 5 h. The reaction mixture was cooled down to RT and poured very carefully into sat. Na$_2$CO$_3$. The aqueous layer was extracted with EtOAc. The combined organic layers were dried (Na$_2$SO$_4$), filtered and evaporated to give Intermediate XII-01 (518 mg, 72%) as a pale brown solid.

Synthesis of Intermediate XIII-01

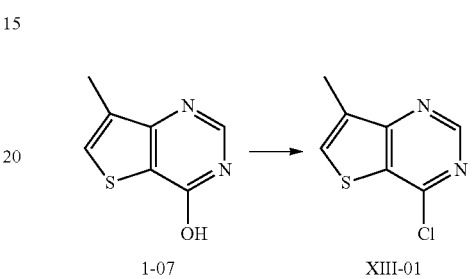

A mixture of Intermediate 1-07 (4.85 g, 24.34 mmol) and POCl$_3$ (20 mL) was refluxed for 3 h. On cooling, the solvents were removed in vacuo, the residue was suspended in water and the suspension was cooled to 0° C. Aqueous saturated Na$_2$CO$_3$ was added dropwise at 0° C. up to pH~8. The resulting solid was filtered, washed with water and dried to give Intermediate XIII-01 (1.1 g, 20%) as a white solid.

$^1$H NMR (300 MHz, DMSO) δ 9.01 (s, 1H), 8.19 (q, J=1.1 Hz, 1H), 2.39 (d, J=1.1 Hz, 3H).

Method A-11

Synthesis of Intermediate XII-02

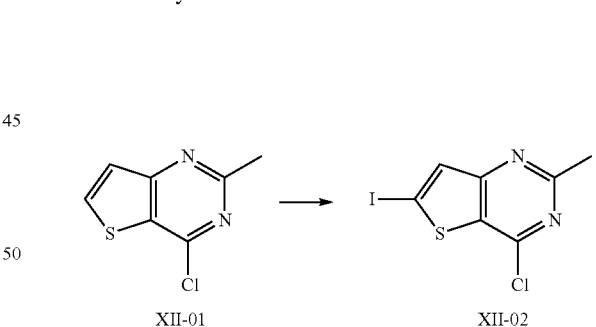

To a mixture of Intermediate XII-01 (429 mg, 2.323 mmol) in THF (12 mL) was added LDA (1.8 M in THF/heptane/ethylbenzene, 1.55 mL, 2.788 mmol) at −78° C. After stirring at −78° C. for 1 h, a solution of I$_2$ (737 mg, 2.904 mmol) in THF (2.6 mL) was slowly added. The reaction mixture was stirred at −78° C. for 2 h. EtOAc was added to the mixture at −78° C. followed by the addition of H$_2$O. The aqueous layer was extracted with EtOAc and the combined organic layers were dried (Na$_2$SO$_4$), filtered and concentrated. The residue was triturated from MeCN to give Intermediate XII-02 (515 mg, 71%) as a pale brown solid.

TABLE 1

Intermediates

[Quinoline core structure with R1 at 6-position and R2 at 4-position]

| No. | R1 | R2 | Starting Material | Method | Yield % |
|---|---|---|---|---|---|
| I-02 | [2-methoxy-3-(3-carboxyphenylsulfonamido)pyridin-5-yl] | Cl | I-01 | A-2 | 54 |
| I-05 | [2-methoxy-3-(methyl 2,4-difluoro-5-sulfamoylbenzoate)pyridin-5-yl] | Cl | I-01 | A-2 | 43 |
| I-06 | [2-methoxy-3-(3-carboxyphenylsulfonamido)pyridin-5-yl] | [5-(BocNHCH2)pyridin-3-yl] | I-02 | A-3 | 84 |
| I-09 | [2-methoxy-3-(3-carboxyphenylsulfonamido)pyridin-5-yl] | [3-(BocNHCH2)phenyl] | I-02 | A-3 | 82 |

TABLE 1-continued

Intermediates

| | | | | | |
|---|---|---|---|---|---|
| I-10 | [structure: 2-methoxypyridine with NH-SO2-benzoic acid] | [structure: BocHN-CH2-phenyl-F] | I-02 | A-3 | 57 |
| I-11 | [structure: 2-methoxypyridine with NH-SO2-benzoic acid] | [structure: H2N-CH2-phenyl-F] | I-02 | A-3 | 62 |
| I-12 | [structure: 2-methoxypyridine with NH-SO2-difluorobenzoic acid] | [structure: BocHN-CH2-pyridine] | I-05 | A-3 | 66 |
| I-13 | [structure: 2-methoxypyridine with NH-SO2-benzoic acid] | [structure: H2N-CH2-phenyl] | I-09 | A-6 | Quant. |
| I-14 | [structure: 2-methoxypyridine with NH-SO2-benzoic acid] | [structure: piperidine-CH2-NH2] | I-03 | A-6 | Quant. |

TABLE 1-continued

| Intermediates | | | | | |
|---|---|---|---|---|---|
| I-15 | [structure] | [structure] | I-04 | A-6 | Quant. |
| I-16 | [structure] | [structure] | I-12 | A-6 | Quant. |
| I-17 | [structure] | [structure] | I-10 | A-6 | Quant. |
| I-18 | [structure] | [structure] | I-02 | A-3 | 73 |
| I-19 | [structure] | [structure] | I-18 | A-6 | Quant. |

TABLE 1-continued

Intermediates

| | | | | | |
|---|---|---|---|---|---|
| I-02 | [pyridine-OMe, sulfonamide-benzoic acid structure] | Cl | I-00 | A-1 | Quant. |
| I-20 | [pyridine-OMe, sulfonamide-benzoic acid structure] | [pyrazole-CH2CH2-NHBoc] | I-02 | A-1 | 88 |
| I-21 | [pyridine-OMe, sulfonamide-benzoic acid structure] | [pyrazole-CH2CH2-NH2] | I-20 | A-6 | Quant. |
| I-22 | [pyridine-OMe, sulfonamide-benzoic acid structure] | [piperidine-CH2-N(Me)Boc] | I-02 | A-4 | 64 |

TABLE 1-continued

Intermediates

| | | | | | |
|---|---|---|---|---|---|
| I-23 | [pyridine with OMe, NH-SO2-phenyl-COOH] | [N-piperidine-CH2-NHMe] | I-22 | A-6 | Quant. |
| I-24 | [pyridine with OMe, NH-SO2-difluorophenyl-COOH] | [BocHN-CH2-phenyl] | I-05 | A-3 | 65 |
| I-25 | [pyridine with OMe, NH-SO2-difluorophenyl-COOH] | [H2N-CH2-phenyl] | I-24 | A-6 | Quant. |
| I-26 | [methoxypyridine-NH2] | [Boc-tetrahydroisoquinoline] | I-01 | A-1 | 83 |
| I-27 | [pyridine with OMe, NH-SO2-phenyl-COOH] | [Boc-tetrahydroisoquinoline] | I-26 | A-2 | 31 |

TABLE 1-continued

Intermediates

| ID | Structure 1 | Structure 2 | Ref | Method | Yield |
|---|---|---|---|---|---|
| I-28 | 2-methoxy-3-(sulfonamido)pyridine with benzoic acid | 1,2,3,4-tetrahydroisoquinoline (7-position) | I-27 | A-6 | Quant. |
| I-29 | 3-aminopyridine (5-position) | Cl | I-00 | A-1 | 83 |
| I-30 | 3-(pyridin-3-ylsulfamoyl)benzoic acid | Cl | I-29 | A-2 | 47 |
| I-31 | 3-(pyridin-3-ylsulfamoyl)benzoic acid | BocHN-CH₂-pyridine (5-position) | I-30 | A-1 | 90 |
| I-32 | 3-(pyridin-3-ylsulfamoyl)benzoic acid | H₂N-CH₂-pyridine (5-position) | I-31 | A-6 | Quant. |

TABLE 1-continued

Intermediates

R1 — [imidazo[2,1-b][1,3,4]thiadiazole core] — R2

| No. | R1 | R2 | Starting Material | Method | Yield % |
|---|---|---|---|---|---|
| II-03 | 2-methoxy-5-(pyridin-3-yl) with 3-NH-SO₂-C₆H₄-COOH substituent | BocNH-CH₂-(pyridin-3-yl) | II-02 | A-2 | 45 |
| II-06 | 2-methoxy-5-(pyridin-3-yl) with 3-NH-SO₂-C₆H₄-COOMe substituent | BocNH-CH₂-(pyridin-3-yl) | II-02 | A-2 | 20 |
| II-07 | 2-methoxy-5-(pyridin-3-yl) with 3-NH-SO₂-C₆H₄-COOMe substituent | H₂N-CH₂-(pyridin-3-yl) | II-06 | A-6 | Quant. |
| II-10 | 2-methoxy-5-(pyridin-3-yl) with 3-NH-SO₂-C₆H₄-COOH substituent | NH₂-CH₂-C(O)-NH-CH₂-(pyridin-3-yl) | II-09 | A-6 | Quant. |
| II-11 | 3-amino-2-methoxy-5-(pyridin-3-yl) | BocNH-CH₂-phenyl | II-01 | A-3 | 53 |

TABLE 1-continued

Intermediates

| | | | | | |
|---|---|---|---|---|---|
| II-12 | [3-carboxyphenyl sulfonamide linked to 2-methoxypyridin-3-yl, with attachment at pyridine 5-position] | [BocNH-CH2- attached to meta position of phenyl] | II-11 | A-2 | 44 |
| II-13 | [3-carboxyphenyl sulfonamide linked to 2-methoxypyridin-3-yl, with attachment at pyridine 5-position] | [H2N-CH2- attached to meta position of phenyl] | II-12 | A-6 | Quant. |
| II-14 | [2-methoxy-3-aminopyridine with attachment at 5-position] | [BocNH-CH2- attached to 4-position of pyridine (N at 1)] | II-01 | A-3 | 26 |
| II-15 | [3-carboxyphenyl sulfonamide linked to 2-methoxypyridin-3-yl, with attachment at pyridine 5-position] | [BocNH-CH2- attached to 4-position of pyridine] | II-14 | A-2 | Quant. |
| II-16 | [3-carboxyphenyl sulfonamide linked to 2-methoxypyridin-3-yl, with attachment at pyridine 5-position] | [H2N-CH2- attached to 4-position of pyridine] | II-15 | A-6 | Quant. |

TABLE 1-continued

Intermediates

[Pyrazolo[1,5-a]pyrimidine core structure with R1 at 5-position and R2 at 3-position]

| No. | R1 | R2 | Starting Material | Method | Yield % |
|---|---|---|---|---|---|
| III-03 | 2-methoxy-3-(3-carboxyphenylsulfonamido)pyridin-5-yl | 5-(BocNHCH₂)pyridin-3-yl | III-02 | A-2 | 71 |
| III-04 | 2-methoxy-3-(3-carboxyphenylsulfonamido)pyridin-5-yl | 5-(H₂NCH₂)pyridin-3-yl | III-03 | A-6 | Quant. |
| III-05 | 2-methoxy-3-aminopyridin-5-yl | 3-(BocNHCH₂)phenyl | III-01 | A-1 | 29 |
| III-06 | 2-methoxy-3-(3-carboxyphenylsulfonamido)pyridin-5-yl | 3-(BocNHCH₂)phenyl | III-05 | A-2 | 72 |
| III-07 | 2-methoxy-3-(3-carboxyphenylsulfonamido)pyridin-5-yl | 3-(H₂NCH₂)phenyl | III-06 | A-6 | Quant. |

TABLE 1-continued
Intermediates
| | | | | | |
|---|---|---|---|---|---|
| III-08 | 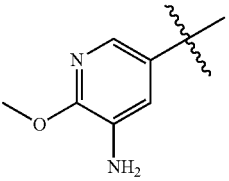 [SMILES: *c1cnc(OC)c(N)c1] | Br | III-01 | A-1 | 98 |
| III-09 | 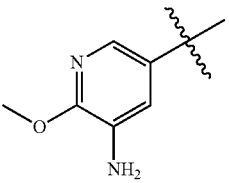 | 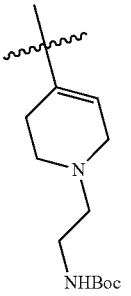 [SMILES: *C1=CCN(CCNC(=O)OC(C)(C)C)CC1] | III-08 | A-1 | 25 |
| III-10 | 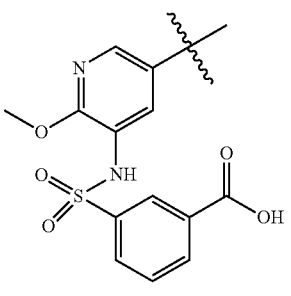 [SMILES: *c1cnc(OC)c(NS(=O)(=O)c2cccc(C(=O)O)c2)c1] | 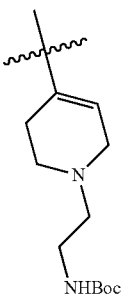 | III-09 | A-2 | 40 |
| III-11 | 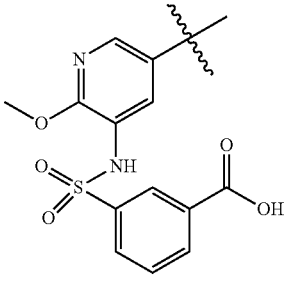 [SMILES: *c1cnc(OC)c(NS(=O)(=O)c2cccc(C(=O)O)c2)c1] | 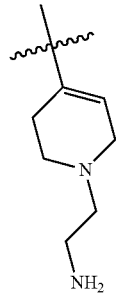 [SMILES: *C1=CCN(CCN)CC1] | III-10 | A-6 | Quant. |
| III-12 | 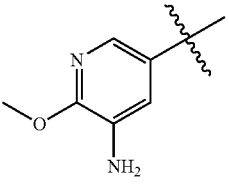 | 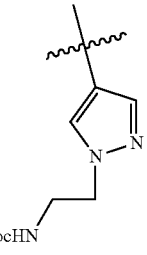 | III-08 | A-1 | 50 |

TABLE 1-continued
| | | | | | |
|---|---|---|---|---|---|
| III-13 | 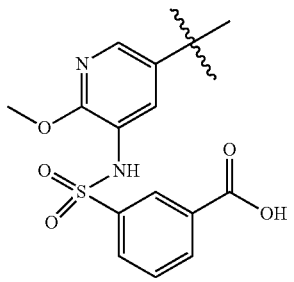 [SMILES: *c1cnc(OC)c(NS(=O)(=O)c2cccc(C(=O)O)c2)c1] | | III-12 | A-2 | 46 |
| III-14 | 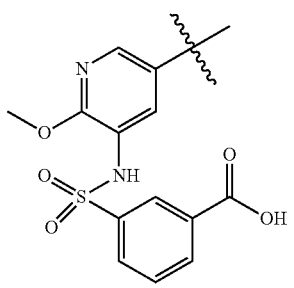 [SMILES: *c1cnc(OC)c(NS(=O)(=O)c2cccc(C(=O)O)c2)c1] | | III-13 | A-6 | Quant. |
| III-15 | 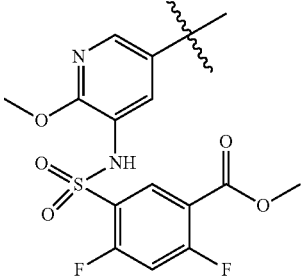 | | III-05 | A-2 | 48 |
| III-16 | 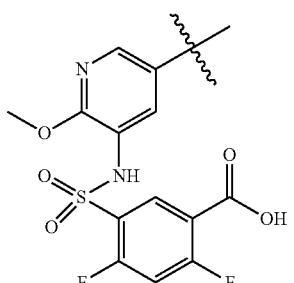 | | III-15 | A-8 | 50 |
| III-17 | 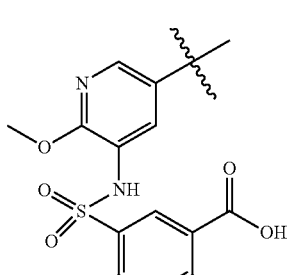 | | III-16 | A-6 | Quant. |

TABLE 1-continued

Intermediates

| No. | Structure | | Starting Material | Method | Yield % |
|---|---|---|---|---|---|
| III-18 | pyridine with HO, NH-SO2-benzoic acid substituent | III-06 benzyl amine (H2N-CH2-phenyl) | | A-5 | Quant. |

Imidazo[1,2-b]pyridazine core with R1 and R2 substituents:

| No. | R1 | R2 | Starting Material | Method | Yield % |
|---|---|---|---|---|---|
| IV-03 | 2-methoxypyridin-5-yl with 3-NH2 | BocHN-CH2-pyridin-3-yl | IV-02 | A-3 | 67 |
| IV-04 | 2-methoxypyridin-5-yl with 3-NHSO2-benzoic acid | BocHN-CH2-pyridin-3-yl | IV-03 | A-2 | 57 |
| IV-05 | 2-methoxypyridin-5-yl with 3-NHSO2-benzoic acid | H2N-CH2-pyridin-3-yl | IV-04 | A-6 | Quant. |
| IV-06 | Cl | BocHN-CH2-phenyl | IV-01 | A-1 | 90 |

TABLE 1-continued
Intermediates
| | | | | | |
|---|---|---|---|---|---|
| IV-07 | 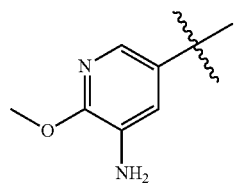 [SMILES: *c1cnc(OC)c(N)c1] | 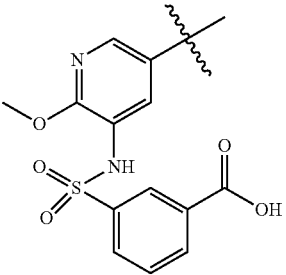 [SMILES: *c1cnc(OC)c(NS(=O)(=O)c2cccc(C(=O)O)c2)c1] | IV-06 | A-3 | 83 |
| IV-08 | 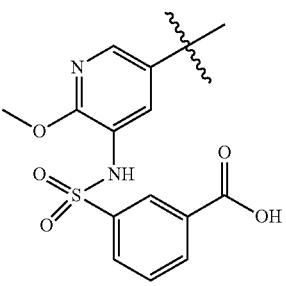 [SMILES: *c1cnc(OC)c(NS(=O)(=O)c2cccc(C(=O)O)c2)c1] | 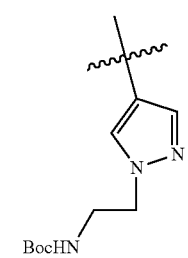 [SMILES: *c1cnn(CCNC(=O)OC(C)(C)C)c1] | IV-07 | A-2 | 75 |
| IV-09 | 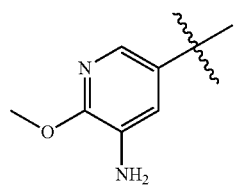 [SMILES: *c1cnc(OC)c(N)c1] | 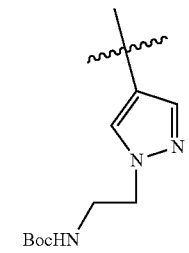 [SMILES: *c1cnn(CCNC(=O)OC(C)(C)C)c1] | IV-08 | A-6 | Quant. |
| IV-10 | Cl | 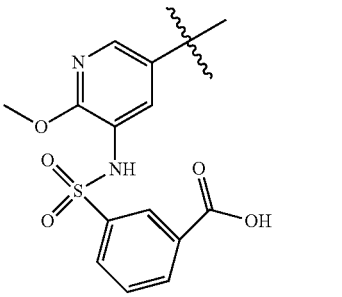 [SMILES: *c1cnc(OC)c(NS(=O)(=O)c2cccc(C(=O)O)c2)c1] | IV-01 | A-1 | 62 |
| IV-11 | 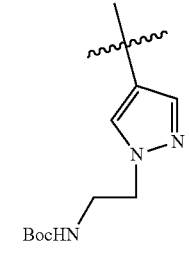 [SMILES: *c1cnn(CCNC(=O)OC(C)(C)C)c1] | | IV-10 | A-3 | 94 |
| IV-12 | | | IV-11 | A-2 | 65 |

TABLE 1-continued

Intermediates

| | | | | | |
|---|---|---|---|---|---|
| IV-13 | [pyridine with OMe, NH-SO2-benzoic acid, wavy bond] | [pyrazole-N-CH2CH2-NH2, wavy bond] | IV-12 | A-6 | Quant. |
| IV-14 | Cl | [tetrahydropyridine-N-CH2CH2-NHBoc, wavy bond] | IV-01 | A-1 | 90 |
| IV-15 | [pyridine with OMe, NH2, wavy bond] | [tetrahydropyridine-N-CH2CH2-NHBoc, wavy bond] | IV-14 | A-1 | 72 |
| IV-16 | [pyridine with OMe, NH-SO2-benzoic acid, wavy bond] | [tetrahydropyridine-N-CH2CH2-NHBoc, wavy bond] | IV-15 | A-2 | 84 |
| IV-17 | [pyridine with OMe, NH-SO2-benzoic acid, wavy bond] | [tetrahydropyridine-N-CH2CH2-NH2, wavy bond] | IV-16 | A-6 | Quant. |

TABLE 1-continued
Intermediates
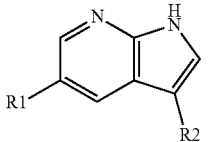
| No. | R1 | R2 | Starting Material | Method | Yield % |
|---|---|---|---|---|---|
| V-03 | Br | 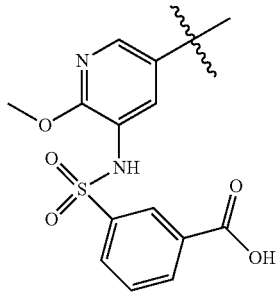 [SMILES: *c1cnc(OC)c(NS(=O)(=O)c2cccc(C(=O)O)c2)c1] | V-02 | A-1 | 60 |
| V-04 | 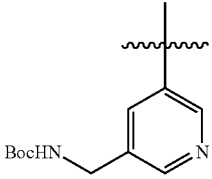 [SMILES: *c1cncc(CNC(=O)OC(C)(C)C)c1] | 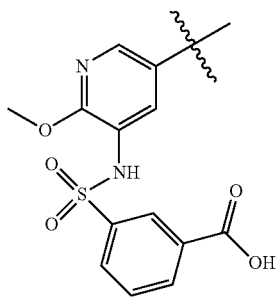 [SMILES: *c1cnc(OC)c(NS(=O)(=O)c2cccc(C(=O)O)c2)c1] | V-03 | A-1 | 62 |
| V-05 | 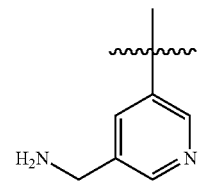 [SMILES: *c1cncc(CN)c1] | 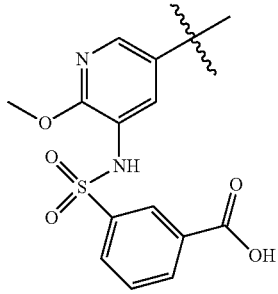 [SMILES: *c1cnc(OC)c(NS(=O)(=O)c2cccc(C(=O)O)c2)c1] | V-04 | A-6 | Quant. |
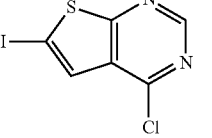
| No. | R1 | R2 | Starting Material | Method | Yield % |
|---|---|---|---|---|---|
| VI-02 | (structure) | Cl | VI-01 Commercially Available | A-1 | 20 |

TABLE 1-continued

Intermediates

| | | | | | |
|---|---|---|---|---|---|
| VI-03 | (structure) | (structure) | VI-02 | A-1 | 89 |
| VI-04 | (structure) | (structure) | VI-03 | A-6 | Quant. |
| VI-05 | (structure) | Cl | VI-01 | A-1 | 67 |
| VI-06 | (structure) | (structure) | VI-05 | A-1 | 78 |
| VI-07 | (structure) | (structure) | VI-06 | A-2 | 49 |
| VI-08 | (structure) | (structure) | VI-07 | A-6 | Quant. |

TABLE 1-continued

Intermediates

| No. | R1 | R2 | Starting Material | Method | Yield % |
|---|---|---|---|---|---|
| VII-02 | Br | 3-(BocNHCH₂)phenyl | VII-01 Commercially Available | A-1 | 68 |
| VII-03 | 5-(2-methoxy-3-aminopyridyl) | 3-(BocNHCH₂)phenyl | VII-02 | A-1 | 95 |
| VII-04 | 5-[2-methoxy-3-(3-carboxyphenylsulfonylamino)pyridyl] | 3-(BocNHCH₂)phenyl | VII-03 | A-2 | 62 |
| VII-05 | 5-[2-methoxy-3-(3-carboxyphenylsulfonylamino)pyridyl] | 3-(H₂NCH₂)phenyl | VII-04 | A-6 | Quant. |
| VII-06 | Br | 4-(BocNHCH₂)piperidin-1-yl | VII-01 | A-4 | Quant. |

TABLE 1-continued

Intermediates

| | | | | | |
|---|---|---|---|---|---|
| VII-07 | 2-methoxy-pyridin-3-amine (structure) | 4-((Boc-aminomethyl))piperidine (structure) | VII-06 | A-3 | 84 |
| VII-08 | 3-(sulfonamido)-2-methoxypyridine benzoic acid (structure) | 4-((Boc-aminomethyl))piperidine (structure) | VII-07 | A-2 | 37 |
| VII-09 | 3-(sulfonamido)-2-methoxypyridine benzoic acid (structure) | 4-(aminomethyl)piperidine (structure) | VII-08 | A-6 | Quant. |
| VII-10 | Br | 4-(Boc-aminoethyl)pyrazole (structure) | VII-01 | A-3 | 15 |
| VII-11 | 2-methoxy-pyridin-3-amine (structure) | 4-(Boc-aminoethyl)pyrazole (structure) | VII-10 | A-3 | 61 |

TABLE 1-continued

Intermediates

| | | | | | |
|---|---|---|---|---|---|
| VII-12 | [structure: 2-methoxy-pyridine with NH-SO2-phenyl-COOH] | [structure: pyrazole with BocHN-ethyl] | VII-11 | A-2 | 43 |
| VII-13 | [structure: 2-methoxy-pyridine with NH-SO2-phenyl-COOH] | [structure: pyrazole with H2N-ethyl] | VII-12 | A-6 | Quant. |
| VII-14 | Br | [structure: pyridine-CH2-NHBoc] | VII-01 | A-3 | 4 |
| VII-15 | [structure: 2-methoxy-3-amino-pyridine] | [structure: pyridine-CH2-NHBoc] | VII-14 | A-3 | 95 |
| VII-16 | [structure: 2-methoxy-pyridine with NH-SO2-phenyl-COOH] | [structure: pyridine-CH2-NHBoc] | VII-15 | A-2 | 31 |
| VII-17 | [structure: 2-methoxy-pyridine with NH-SO2-phenyl-COOH] | [structure: pyridine-CH2-NH2] | VII-16 | A-6 | Quant. |

TABLE 1-continued

Intermediates

[Structure: thieno[3,2-d]pyrimidine core with R1 at 6-position and R2 at 4-position]

| No. | R1 | R2 | Starting Material | Method | Yield % |
|---|---|---|---|---|---|
| VIII-02 | 2-methoxy-3-amino-pyridin-5-yl | Cl | VIII-01 Commercially Available (4-chloro-6-iodo-thieno[3,2-d]pyrimidine) | A-1 | 79 |
| VIII-03 | 2-methoxy-3-amino-pyridin-5-yl | 5-(BocNHCH2)-pyridin-3-yl | VIII-02 | A-3 | 63 |
| VIII-04 | 2-methoxy-3-(3-carboxyphenylsulfonamido)-pyridin-5-yl | 5-(BocNHCH2)-pyridin-3-yl | VIII-03 | A-2 | 37 |
| VIII-05 | 2-methoxy-3-(3-carboxyphenylsulfonamido)-pyridin-5-yl | 5-(H2NCH2)-pyridin-3-yl | VIII-04 | A-6 | Quant. |
| VIII-06 | 2-methoxy-3-amino-pyridin-5-yl | 3-(BocNHCH2)-phenyl | VIII-02 | A-1 | 64 |

TABLE 1-continued

Intermediates

| | | | | | |
|---|---|---|---|---|---|
| VIII-07 | methoxypyridine-sulfonamide-benzoic acid structure | BocHN-CH2-phenyl structure | VIII-06 | A-2 | 62 |
| VIII-08 | methoxypyridine-sulfonamide-benzoic acid structure | H2N-CH2-phenyl structure | VIII-07 | A-6 | Quant. |
| VIII-09 | methoxy-aminopyridine structure | BocHN-CH2CH2-pyrazole structure | VIII-02 | A-3 | 53 |
| VIII-10 | methoxypyridine-sulfonamide-benzoic acid structure | BocHN-CH2CH2-pyrazole structure | VIII-09 | A-2 | 61 |
| VIII-11 | methoxypyridine-sulfonamide-benzoic acid structure | H2N-CH2CH2-pyrazole structure | VIII-10 | A-6 | Quant. |

TABLE 1-continued

Intermediates

| | Structure 1 | Structure 2 | Starting | Method | Yield |
|---|---|---|---|---|---|
| VIII-12 | 2-methoxy-3-amino-pyridin-5-yl | 1-(BocNH-CH2)-piperidin-4-yl (N-linked) | VIII-02 | A-4 | 83 |
| VIII-13 | 2-methoxy-3-(3-carboxyphenylsulfonylamino)-pyridin-5-yl | 1-(BocNH-CH2)-piperidin-4-yl (N-linked) | VIII-12 | A-2 | 63 |
| VIII-14 | 2-methoxy-3-(3-carboxyphenylsulfonylamino)-pyridin-5-yl | 1-(H2N-CH2)-piperidin-4-yl (N-linked) | VIII-13 | A-6 | Quant. |
| VIII-15 | 2-methoxy-3-amino-pyridin-5-yl | 2-(BocNH-CH2)-pyridin-4-yl | VIII-02 | A-3 | 54 |
| VIII-16 | 2-methoxy-3-(3-carboxyphenylsulfonylamino)-pyridin-5-yl | 2-(BocNH-CH2)-pyridin-4-yl | VIII-15 | A-2 | 42 |

TABLE 1-continued

Intermediates

| | | | | | | |
|---|---|---|---|---|---|---|
| VIII-17 | (structure) | (structure) | VIII-16 | A-6 | Quant. | |
| VIII-18 | (structure) | (structure) | VIII-01 | A-1 | 39 | |
| VIII-19 | (structure) | (structure) | VIII-18 | A-2 | 26 | |
| VIII-20 | (structure) | (structure) | VIII-19 | A-6 | Quant. | |
| VIII-21 | (structure) | (structure) | VIII-03 | A-2 | 54 | |

TABLE 1-continued

Intermediates

| | | | | | |
|---|---|---|---|---|---|
| VIII-22 | pyridine-methoxy-sulfonamide-difluorobenzoic acid structure | BocHN-CH2-pyridine | VIII-21 | A-8 | 83 |
| VIII-23 | pyridine-methoxy-sulfonamide-difluorobenzoic acid structure | H2N-CH2-pyridine | VIII-22 | A-6 | Quant. |
| VIII-24 | pyridine-hydroxy-sulfonamide-benzoic acid structure | H2N-CH2-pyridine | VIII-04 | A-5 | Quant. |
| VIII-25 | pyridine-methoxy-sulfonamide-benzoic acid structure | Cl | VIII-02 | A-2 | 28 |
| VIII-26 | pyridine-methoxy-sulfonamide-benzoic acid structure | H2N-pyridine | VIII-25 | A-3 | 43 |

TABLE 1-continued

Intermediates

| | Structure 1 | Structure 2 | From | Method | Yield |
|---|---|---|---|---|---|
| VIII-27 | methoxypyridine-sulfonamide-fluorobenzoic acid | BocHN-CH2-pyridine | VIII-03 | A-2 | 70 |
| VIII-28 | methoxypyridine-sulfonamide-fluorobenzoic acid | H2N-CH2-pyridine | VIII-27 | A-6 | Quant. |
| VIII-29 | isopropoxy-aminopyridine | Cl | VIII-01 | A-3 | 98 |
| VIII-30 | isopropoxy-aminopyridine | BocHN-CH2-pyridine | VIII-29 | A-3 | 57 |
| VIII-31 | isopropoxypyridine-sulfonamide-benzoic acid | BocHN-CH2-pyridine | VIII-30 | A-2 | 62 |

TABLE 1-continued

Intermediates

| | | | | | |
|---|---|---|---|---|---|
| VIII-32 | (2-isopropoxypyridin-3-yl sulfonamide benzoic acid structure) | (aminomethyl pyridine structure) | VIII-31 | A-6 | Quant. |
| VIII-33 | (2-methoxypyridin-3-yl sulfonamide 4-fluorobenzoic acid structure) | (BocHN-methyl pyridine structure) | VIII-03 | A-2 | 44 |
| VIII-34 | (2-methoxypyridin-3-yl sulfonamide 4-fluorobenzoic acid structure) | (H₂N-methyl pyridine structure) | VIII-33 | A-6 | Quant. |
| VIII-35 | (2-methoxypyridin-3-yl sulfonamide 3-trifluoromethyl benzoic acid structure) | (BocHN-methyl pyridine structure) | VIII-03 | A-2 | 37 |

TABLE 1-continued

Intermediates

| ID | Structure 1 | Structure 2 | Ref | Method | Yield |
|---|---|---|---|---|---|
| VIII-36 | 2-methoxypyridine with sulfonamide-NH linked to 3-carboxy-5-(trifluoromethyl)phenyl | 5-(aminomethyl)pyridin-3-yl | VIII-35 | A-6 | Quant. |
| VIII-37 | 5-amino-6-methoxypyridin-3-yl | 5-(BocNHCH₂)thiophen-2-yl | VIII-02 | A-1 | 61 |
| VIII-38 | 2-methoxypyridine with sulfonamide-NH linked to 3-carboxyphenyl | 5-(BocNHCH₂)thiophen-2-yl | VIII-37 | A-2 | 64 |
| VIII-39 | 2-methoxypyridine with sulfonamide-NH linked to 3-carboxyphenyl | 5-(aminomethyl)thiophen-2-yl | VIII-38 | A-6 | Quant. |
| VIII-40 | 2-chloropyridine with sulfonamide-NH linked to 3-carboxyphenyl | Cl | VIII-01 | A-1 | 63 |

TABLE 1-continued

Intermediates

| | | | | | |
|---|---|---|---|---|---|
| VIII-41 | [2-chloropyridine with sulfonamide-benzoic acid substituent] | [BocHN-CH2-pyridine] | VIII-40 | A-1 | 74 |
| VIII-42 | [2-chloropyridine with sulfonamide-benzoic acid substituent] | [H2N-CH2-pyridine] | VIII-41 | A-6 | Quant. |
| VIII-43 | [2-isopropoxy-3-aminopyridine] | [BocHN-CH2CH2-pyrazole] | VIII-29 | A-1 | 56 |
| VIII-44 | [2-isopropoxypyridine with sulfonamide-benzoic acid substituent] | [BocHN-CH2CH2-pyrazole] | VIII-43 | A-2 | 34 |
| VIII-45 | [2-isopropoxypyridine with sulfonamide-benzoic acid substituent] | [H2N-CH2CH2-pyrazole] | VIII-44 | A-6 | Quant. |

TABLE 1-continued

Intermediates

| ID | Structure 1 | Structure 2 | From | Method | Yield |
|---|---|---|---|---|---|
| VIII-46 | 2-methoxy-3-amino-pyridin-5-yl | N-Boc-aminomethyl morpholine | VIII-02 | A-4 | 75 |
| VIII-47 | 2-methoxy-3-(3-carboxyphenylsulfonamido)pyridin-5-yl | N-Boc-aminomethyl morpholine | VIII-46 | A-2 | 71 |
| VIII-48 | 2-methoxy-3-(3-carboxyphenylsulfonamido)pyridin-5-yl | aminomethyl morpholine | VIII-47 | A-6 | Quant. |
| VIII-49 | 2-methoxy-3-amino-pyridin-5-yl | BocHN-CH2, fluorophenyl | VIII-02 | A-1 | 45 |
| VIII-50 | 2-methoxy-3-(3-carboxyphenylsulfonamido)pyridin-5-yl | BocHN-CH2, fluorophenyl | VIII-49 | A-2 | 40 |

TABLE 1-continued

| | | | | | |
|---|---|---|---|---|---|
| VIII-51 | [structure] | [structure] | VIII-50 | A-6 | Quant. |
| VIII-52 | [structure] | [structure] | VIII-02 | A-4 | 75 |
| VIII-53 | [structure] | [structure] | VIII-52 | A-2 | 65 |
| VIII-54 | [structure] | [structure] | VIII-53 | A-6 | Quant. |
| VIII-55 | [structure] | [structure] | VIII-02 | A-1 | 80 |

TABLE 1-continued

| Intermediates | | | | |
|---|---|---|---|---|
| VIII-56 | [pyridine with OMe, NH-SO2-C6H4-COOH structure] | [BocHN-CH2-furan structure] | VIII-55 | A-2 | 57 |
| VIII-57 | [pyridine with OMe, NH-SO2-C6H4-COOH structure] | [H2N-CH2-furan structure] | VIII-56 | A-6 | Quant. |
| VIII-58 | [pyridine with OMe, NH2 structure] | [HN-(CH2)4-NHBoc structure] | VIII-02 | A-4 | 93 |
| VIII-59 | [pyridine with OMe, NH-SO2-C6H4-COOH structure] | [HN-(CH2)4-NHBoc structure] | VIII-58 | A-2 | 74 |
| VIII-60 | [pyridine with OMe, NH-SO2-C6H4-COOH structure] | [HN-(CH2)4-NH2 structure] | VIII-59 | A-6 | Quant. |

TABLE 1-continued
Intermediates
| | | | | | |
|---|---|---|---|---|---|
| VIII-61 | 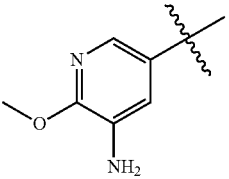 | 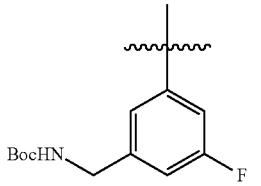 [SMILES: *c1cc(F)cc(CNC(=O)OC(C)(C)C)c1] | VIII-02 | A-1 | 100 |
| VIII-62 | 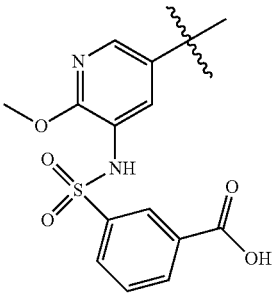 [SMILES: *c1cnc(OC)c(NS(=O)(=O)c2cccc(C(=O)O)c2)c1] | 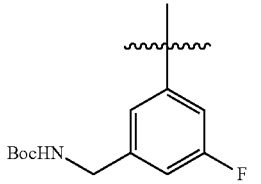 [SMILES: *c1cc(F)cc(CNC(=O)OC(C)(C)C)c1] | VIII-61 | A-2 | 18 |
| VIII-63 | 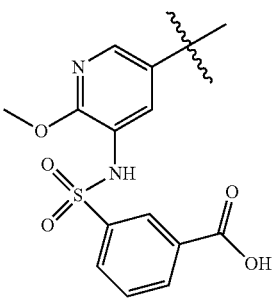 [SMILES: *c1cnc(OC)c(NS(=O)(=O)c2cccc(C(=O)O)c2)c1] | 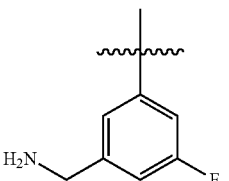 | VIII-62 | A-6 | Quant. |
| VIII-64 | 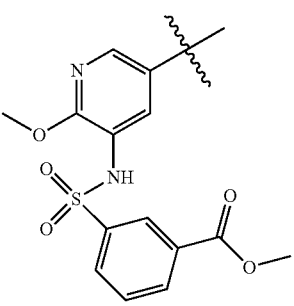 | Cl | VIII-02 | A-2 | 67 |
| VIII-65 | 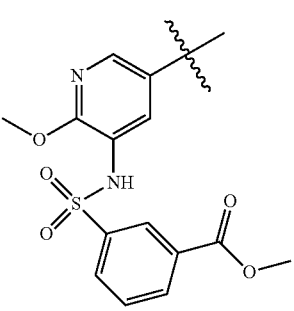 | 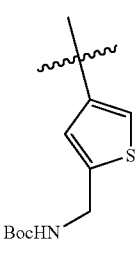 | VIII-64 | A-1 | 71 |

TABLE 1-continued

Intermediates

| | | | | | |
|---|---|---|---|---|---|
| VIII-66 | (pyridine-OMe, NH-SO2-benzoic acid structure) | (thiophene-CH2-NHBoc structure) | VIII-65 | A-8 | 92 |
| VIII-67 | (pyridine-OMe, NH-SO2-benzoic acid structure) | (thiophene-CH2-NH2 structure) | VIII-66 | A-6 | Quant. |
| VIII-68 | (pyridine-OMe-NH2 structure) | (piperidine-NHBoc structure) | VIII-02 | A-4 | 84 |
| VIII-69 | (pyridine-OMe, NH-SO2-benzoic acid structure) | (piperidine-NHBoc structure) | VIII-68 | A-2 | 80 |
| VIII-70 | (pyridine-OMe, NH-SO2-benzoic acid structure) | (piperidine-NH2 structure) | VIII-69 | A-6 | Quant. |
| VIII-71 | (pyridine-OMe-NH2 structure) | (piperidine-NHBoc structure) | VIII-02 | A-4 | 91 |

TABLE 1-continued

Intermediates

| | | | | | |
|---|---|---|---|---|---|
| VIII-72 | [pyridine-methoxy-sulfonamide-benzoic acid structure] | [BocHN-piperidine structure] | VIII-71 | A-2 | 68 |
| VIII-73 | [pyridine-methoxy-sulfonamide-benzoic acid structure] | [H₂N-piperidine structure] | VIII-72 | A-6 | Quant. |
| VIII-74 | [pyridine-methoxy-sulfonamide-benzoate methyl ester structure] | [BocHN-CH₂-thiophene structure] | VIII-64 | A-1 | 32 |
| VIII-75 | [pyridine-methoxy-sulfonamide-benzoic acid structure] | [BocHN-CH₂-thiophene structure] | VIII-74 | A-8 | Quant. |
| VIII-76 | [pyridine-methoxy-sulfonamide-benzoic acid structure] | [H₂N-CH₂-thiophene structure] | VIII-75 | A-6 | Quant. |

TABLE 1-continued
Intermediates
| | | | | | |
|---|---|---|---|---|---|
| VIII-77 | 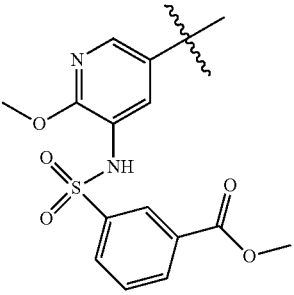 | 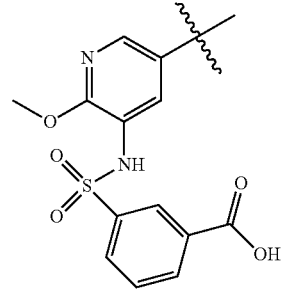 [SMILES: *c1cnc(OC)c(NS(=O)(=O)c2cccc(C(=O)O)c2)c1] | VIII-64 | A-1 | Quant. |
| VIII-78 | 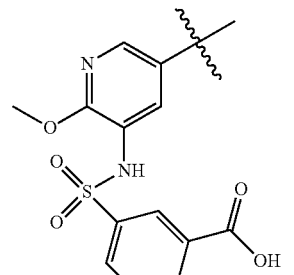 | | VIII-77 | A-8 | 16 |
| VIII-79 | | | VIII-78 | A-6 | Quant. |
| VIII-80 | 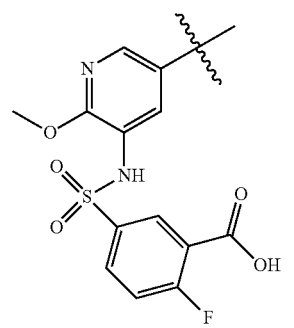 [SMILES: *c1cnc(OC)c(NS(=O)(=O)c2ccc(F)c(C(=O)O)c2)c1] | | VIII-37 | A-2 | 50 |
| VIII-81 | 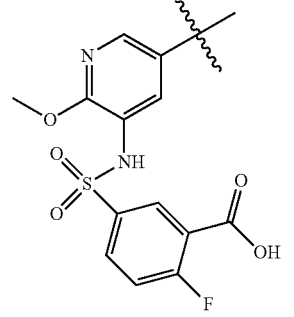 | | VIII-80 | A-6 | Quant. |

TABLE 1-continued
Intermediates
| | | | | | |
|---|---|---|---|---|---|
| VIII-82 | 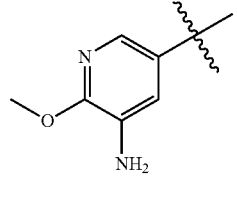 | | VIII-02 | A-4 | 91 |
| VIII-83 | 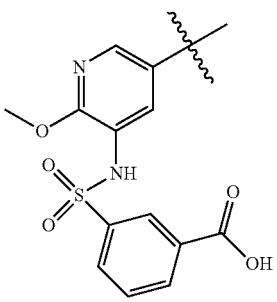 [SMILES: *c1cnc(OC)c(NS(=O)(=O)c2cccc(C(=O)O)c2)c1] | | VIII-82 | A-2 | 78 |
| VIII-84 | 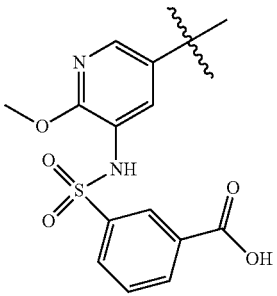 [SMILES: *c1cnc(OC)c(NS(=O)(=O)c2cccc(C(=O)O)c2)c1] | | VIII-83 | A-6 | Quant. |
| VIII-85 | 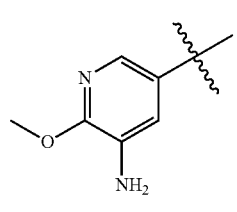 [SMILES: *c1cnc(OC)c(N)c1] | | VIII-02 | A-4 | 93 |
| VIII-86 | 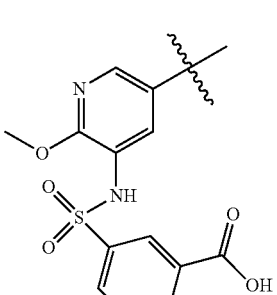 | | VIII-85 | A-2 | 77 |

TABLE 1-continued
Intermediates
| | | | | | |
|---|---|---|---|---|---|
| VIII-87 | 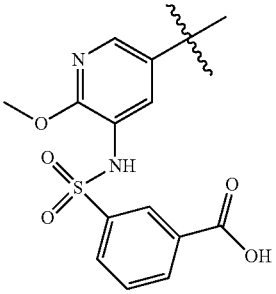 [SMILES: *c1cnc(OC)c(NS(=O)(=O)c2cccc(C(=O)O)c2)c1] | 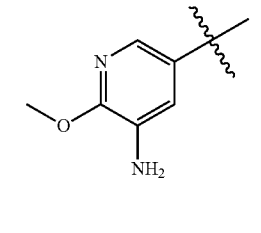 | VIII-86 | A-6 | Quant. |
| VIII-88 | 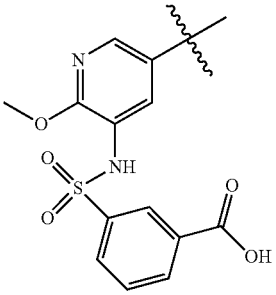 [SMILES: *c1cnc(OC)c(NS(=O)(=O)c2cccc(C(=O)O)c2)c1] | 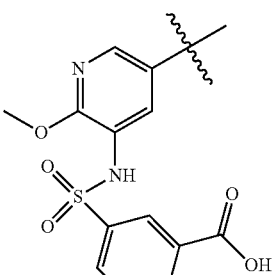 | VIII-02 | A-4 | 80 |
| VIII-89 | 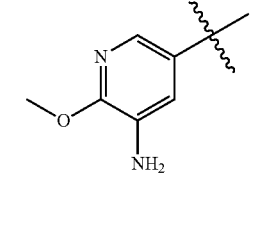 | | VIII-88 | A-2 | 85 |
| VIII-90 | | | VIII-89 | A-6 | Quant. |
| VIII-91 | | | VIII-02 | A-4 | 86 |

TABLE 1-continued

Intermediates

| | | | | | |
|---|---|---|---|---|---|
| VIII-92 | (structure) | (structure, NHBoc) | VIII-91 | A-2 | 90 |
| VIII-93 | (structure) | (structure, NH₂) | VIII-92 | A-6 | Quant. |
| VIII-94 | (structure) | (structure, H₂N) | VIII-64 | A-1 | Quant. |
| VIII-95 | (structure) | (structure, H₂N) | VIII-94 | A-8 | 95 |
| VIII-96 | (structure) | (structure, BocHN) | VIII-02 | A-1 | 17 |

TABLE 1-continued

Intermediates

| | | | | |
|---|---|---|---|---|
| VIII-97 | [structure] | VIII-96 | A-2 | 74 |
| VIII-98 | [structure] | VIII-97 | A-6 | 25 |
| VIII-99 | [structure] | VIII-02 | A-1 | 77 |
| VIII-100 | [structure] | VIII-99 | A-2 | 75 |

TABLE 1-continued

Intermediates

| | | | | | |
|---|---|---|---|---|---|
| VIII-101 | (structure) | (structure) | VIII-100 | A-6 | Quant. |
| VIII-102 | (structure) | (structure) | VIII-99 | A-2 | 56 |
| VIII-103 | (structure) | (structure) | VIII-102 | A-6 | Quant. |
| VIII-104 | (structure) | (structure) | VIII-99 | A-2 | 60 |

TABLE 1-continued
Intermediates
| No. | R1 | R2 | Starting Material | Method | Yield % |
|---|---|---|---|---|---|
| VIII-105 | 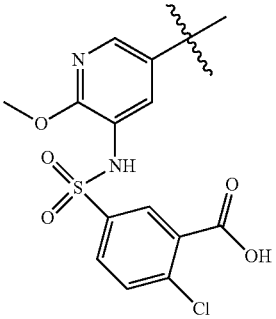 [SMILES: *c1cnc(OC)c(NS(=O)(=O)c2ccc(Cl)c(C(=O)O)c2)c1] | 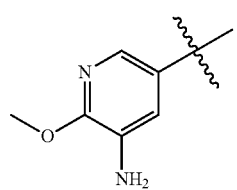 | VIII-104 | A-6 | Quant. |
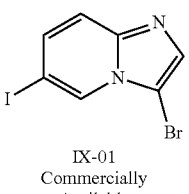
| No. | R1 | R2 | Starting Material | Method | Yield % |
|---|---|---|---|---|---|
| IX-02 | 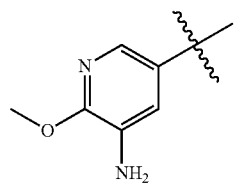 [SMILES: *c1cnc(OC)c(N)c1] | Br | 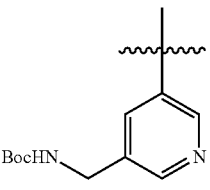 [SMILES: *c1cncc(CNC(=O)OC(C)(C)C)c1] IX-01 Commercially Available | A-3 | 57 |
| IX-03 | 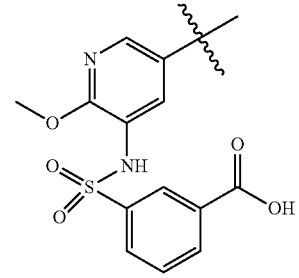 [SMILES: *c1cnc(OC)c(NS(=O)(=O)c2cccc(C(=O)O)c2)c1] | 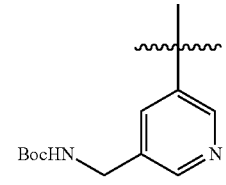 [SMILES: *c1cncc(CNC(=O)OC(C)(C)C)c1] | IX-02 | A-3 | 72 |
| IX-04 | 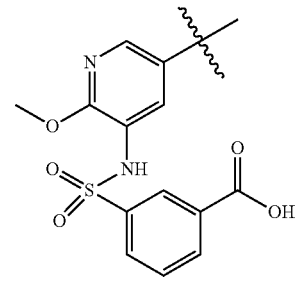 [SMILES: *c1cnc(OC)c(NS(=O)(=O)c2cccc(C(=O)O)c2)c1] | 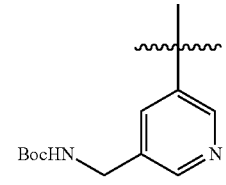 [SMILES: *c1cncc(CNC(=O)OC(C)(C)C)c1] | IX-03 | A-2 | 71 |
| IX-05 | 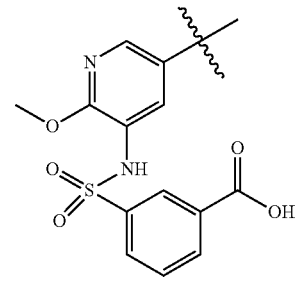 [SMILES: *c1cnc(OC)c(NS(=O)(=O)c2cccc(C(=O)O)c2)c1] | 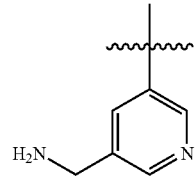 [SMILES: *c1cncc(CN)c1] | IX-04 | A-6 | Quant. |

TABLE 1-continued
Intermediates
| | | | | | |
|---|---|---|---|---|---|
| IX-06 | 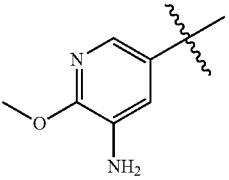 [SMILES: *c1cnc(OC)c(N)c1] | 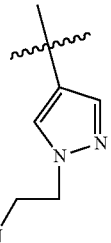 | IX-02 | A-3 | 69 |
| IX-07 | 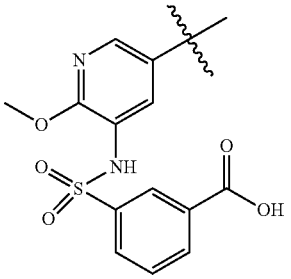 [SMILES: *c1cnc(OC)c(NS(=O)(=O)c2cccc(C(=O)O)c2)c1] | 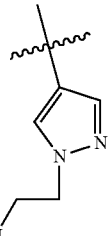 | IX-06 | A-2 | 58 |
| IX-08 | 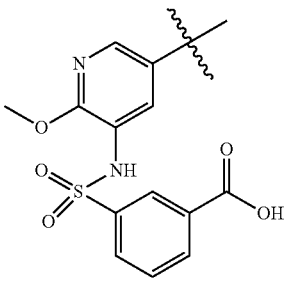 [SMILES: *c1cnc(OC)c(NS(=O)(=O)c2cccc(C(=O)O)c2)c1] | 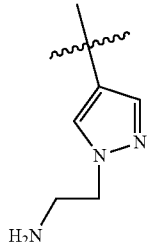 | IX-07 | A-6 | Quant. |
| IX-09 | 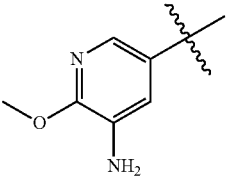 [SMILES: *c1cnc(OC)c(N)c1] | 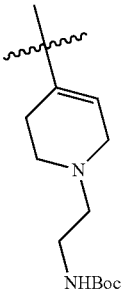 | IX-02 | A-1 | 66 |
| IX-10 | 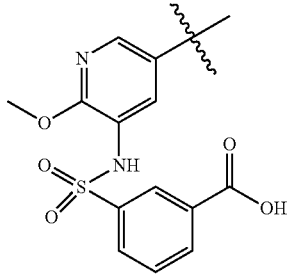 [SMILES: *c1cnc(OC)c(NS(=O)(=O)c2cccc(C(=O)O)c2)c1] | 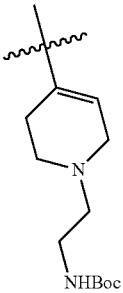 [SMILES: *C1=CCN(CCNC(=O)OC(C)(C)C)CC1] | IX-09 | A-2 | 41 |

TABLE 1-continued
Intermediates
| No. | | | Starting Material | Method | Yield % |
|---|---|---|---|---|---|
| IX-11 | 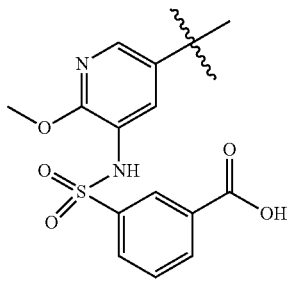 [SMILES: *c1cnc(OC)c(NS(=O)(=O)c2cccc(C(=O)O)c2)c1] | 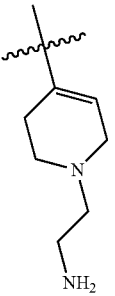 [SMILES: *C1=CCN(CCN)CC1] | IX-10 | A-6 | Quant. |
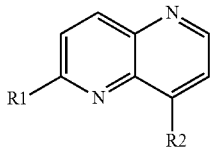
| No. | R1 | R2 | Starting Material | Method | Yield % |
|---|---|---|---|---|---|
| X-02 | 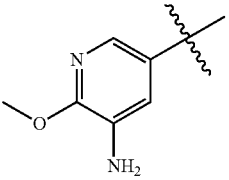 [SMILES: *c1cnc(OC)c(N)c1] | Cl | 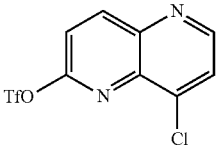 [SMILES: O=S(=O)(Oc1ccc2nccc(Cl)c2n1)C(F)(F)F]<br>X-01<br>Commercially Available | A-1 | 80 |
| X-03 | 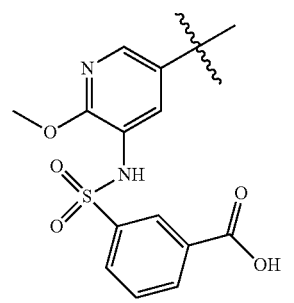 [SMILES: *c1cnc(OC)c(NS(=O)(=O)c2cccc(C(=O)O)c2)c1] | Cl | X-02 | A-2 | 24 |
| X-04 | 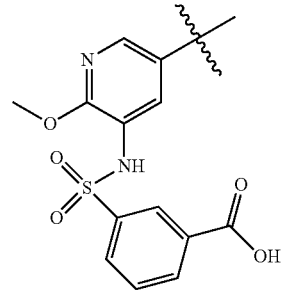 [SMILES: *c1cnc(OC)c(NS(=O)(=O)c2cccc(C(=O)O)c2)c1] | 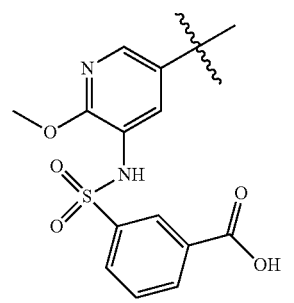 [SMILES: *c1cnc(OC)c(NS(=O)(=O)c2cccc(C(=O)O)c2)c1] | X-03 | A-1 | 51 |

TABLE 1-continued

Intermediates

| | | | | | |
|---|---|---|---|---|---|
| X-05 | (structure) | (structure) | X-04 | A-6 | Quant. |
| X-06 | (structure) | (structure) | X-03 | A-1 | 70 |
| X-07 | (structure) | (structure) | X-06 | A-6 | Quant. |
| X-08 | (structure) | (structure) | X-02 | A-1 | 18 |
| X-09 | (structure) | (structure) | X-08 | A-2 | 31 |

TABLE 1-continued

Intermediates

| No. | Structure | | Starting Material | Method | Yield % |
|---|---|---|---|---|---|
| X-10 | [structure: 2-methoxypyridine with sulfonamide linked to 4,5-difluorobenzoic acid] | [structure: BocHN-CH2-pyridine] | X-09 | A-8 | 48 |
| X-11 | [structure: 2-methoxypyridine with sulfonamide linked to 4,5-difluorobenzoic acid] | [structure: H2N-CH2-pyridine] | X-10 | A-6 | Quant. |

[structure: furo[3,2-d]pyrimidine core with R1 at 6-position and R2 at 4-position]

| No. | R1 | R2 | Starting Material | Method | Yield % |
|---|---|---|---|---|---|
| XI-02 | [structure: 3-amino-2-methoxypyridin-5-yl] | Cl | [structure: 6-iodo-4-chlorofuro[3,2-d]pyrimidine] XI-01 Commercially Available | A-1 | 92 |
| XI-03 | [structure: 3-amino-2-methoxypyridin-5-yl] | [structure: 1-(2-BocNH-ethyl)pyrazol-4-yl] | XI-02 | A-1 | Quant. |

TABLE 1-continued
Intermediates
| No. | | | Starting Material | Method | Yield % |
|---|---|---|---|---|---|
| XI-04 | 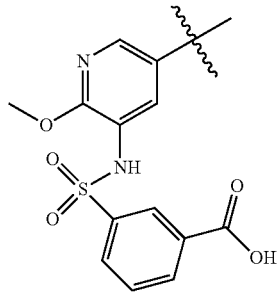 [SMILES: *c1cnc(OC)c(NS(=O)(=O)c2cccc(C(=O)O)c2)c1] | 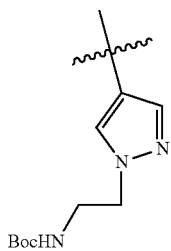 [SMILES: *c1cnn(CCNC(=O)OC(C)(C)C)c1] | XI-03 | A-2 | 96 |
| XI-05 | 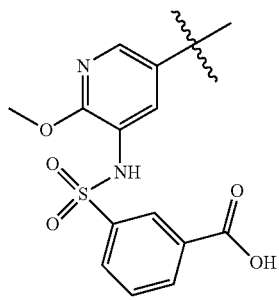 [SMILES: *c1cnc(OC)c(NS(=O)(=O)c2cccc(C(=O)O)c2)c1] | 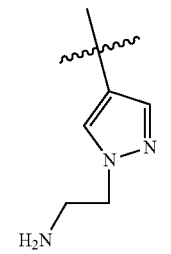 [SMILES: *c1cnn(CCN)c1] | XI-04 | A-6 | Quant. |
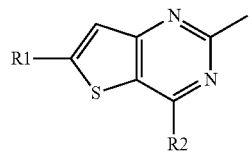
| No. | R1 | R2 | Starting Material | Method | Yield % |
|---|---|---|---|---|---|
| XII-01 | H | Cl | 1-05 | A-10 | 72 |
| XII-02 | I | Cl | XII-01 | A-11 | 71 |
| XII-03 | 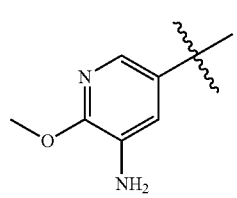 [SMILES: *c1cnc(OC)c(N)c1] | Cl | XII-02 | A-1 | 83 |
| XII-04 | 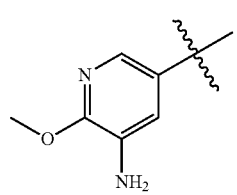 [SMILES: *c1cnc(OC)c(N)c1] | 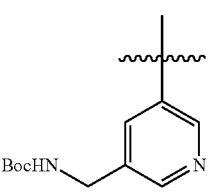 | XII-03 | A-1 | 100 |

TABLE 1-continued

Intermediates

| No. | Structure 1 | Structure 2 | Starting Material | Method | Yield % |
|---|---|---|---|---|---|
| XII-05 | 2-methoxypyridine with sulfonamide linked to benzoic acid | BocHN-CH2-pyridine | XII-04 | A-2 | 41 |
| XII-06 | 2-methoxypyridine with sulfonamide linked to benzoic acid | H2N-CH2-pyridine | XII-05 | A-6 | Quant. |

Thieno[3,2-d]pyrimidine core with R1 at 6-position and R2 at 4-position, methyl at 7-position

| No. | R1 | R2 | Starting Material | Method | Yield % |
|---|---|---|---|---|---|
| XIII-01 | H | Cl | 1-07 | A-10 | 20 |
| XIII-02 | I | Cl | XIII-01 | A-11 | 77 |
| XIII-03 | 3-amino-2-methoxypyridin-5-yl | Cl | XIII-02 | A-1 | 70 |
| XIII-04 | 3-amino-2-methoxypyridin-5-yl | BocHN-CH2-pyridin-5-yl | XIII-03 | A-1 | 50 |

TABLE 1-continued

Intermediates

| | | | | | |
|---|---|---|---|---|---|
| XIII-05 | [structure] | [structure] | XIII-04 | A-2 | 66 |
| XIII-06 | [structure] | [structure] | XIII-05 | A-6 | Quant. |
| XIII-07 | [structure] | [structure] | XIII-03 | A-1 | 64 |
| XIII-08 | [structure] | [structure] | XIII-07 | A-2 | 56 |
| XIII-09 | [structure] | [structure] | XIII-08 | A-6 | Quant. |

TABLE 1-continued

Intermediates

| | | | | | |
|---|---|---|---|---|---|
| XIII-10 | 6-methoxy-5-amino-pyridin-3-yl | 5-(BocNHCH2)-thiophen-2-yl | XIII-03 | A-1 | 64 |
| XIII-11 | 6-methoxy-5-(3-carboxyphenylsulfonylamino)-pyridin-3-yl | 5-(BocNHCH2)-thiophen-2-yl | XIII-10 | A-2 | 76 |
| XIII-12 | 6-methoxy-5-(3-carboxyphenylsulfonylamino)-pyridin-3-yl | 5-(H2NCH2)-thiophen-2-yl | XIII-11 | A-6 | Quant. |
| XIII-13 | 6-methoxy-5-(3-carboxy-4-fluorophenylsulfonylamino)-pyridin-3-yl | 5-(BocNHCH2)-thiophen-2-yl | XIII-10 | A-2 | 19 |
| XIII-14 | 6-methoxy-5-(3-carboxy-4-fluorophenylsulfonylamino)-pyridin-3-yl | 5-(H2NCH2)-thiophen-2-yl | XIII-13 | A-6 | Quant. |

TABLE 1-continued

Intermediates

| | | | | | |
|---|---|---|---|---|---|
| XIII-15 | (pyridine-OMe with NH-SO2-phenyl-CO2Me) | Cl | XIII-03 | A-2 | 50 |
| XIII-16 | (pyridine-OMe with NH-SO2-phenyl-CO2Me) | (methylthiophene-CH2NH2) | XIII-15 | A-1 | Quant. |
| XIII-17 | (pyridine-OMe with NH-SO2-phenyl-CO2H) | (methylthiophene-CH2NH2) | XIII-16 | A-8 | 95 |
| XIII-18 | (pyridine-OMe-NH2) | (morpholine-CH2NHboc) | XIII-03 | A-4 | 85 |
| XIII-19 | (pyridine-OMe with NH-SO2-phenyl-CO2Me) | (morpholine-CH2NHboc) | XIII-18 | A-2 | 93 |

TABLE 1-continued

Intermediates

| | | | | | |
|---|---|---|---|---|---|
| XIII-20 | (pyridine-methoxy-sulfonamide-benzoic acid structure) | (boc-NH-methyl morpholine structure) | XIII-19 | A-8 | Quant. |
| XIII-21 | (pyridine-methoxy-sulfonamide-benzoic acid structure) | (NH$_2$-methyl morpholine structure) | XIII-20 | A-6 | Quant. |
| XIII-22 | (methoxy-pyridine-NH$_2$ structure) | (boc-NH-CH$_2$-fluorophenyl structure) | XIII-03 | A-1 | Quant. |
| XIII-23 | (pyridine-methoxy-sulfonamide-benzoate methyl ester structure) | (boc-NH-CH$_2$-fluorophenyl structure) | XIII-22 | A-2 | 95% |
| XIII-24 | (pyridine-methoxy-sulfonamide-benzoic acid structure) | (boc-NH-CH$_2$-fluorophenyl structure) | XIII-23 | A-8 | 97% |

TABLE 1-continued

| ID | Structure 1 | Structure 2 | Ref | Method | Yield |
|---|---|---|---|---|---|
| XIII-25 | 2-methoxy-pyridin-3-yl sulfonamide benzoic acid | 3-fluoro-5-(aminomethyl)phenyl | XIII-24 | A-6 | Quant. |
| XIII-26 | 3-amino-2-methoxypyridin-5-yl | boc-NH-CH2-pyrrolidin-3-yl | XIII-03 | A-4 | 98 |
| XIII-27 | 2-methoxy-pyridin-3-yl sulfonamide benzoate methyl ester | boc-NH-CH2-pyrrolidin-3-yl | XIII-26 | A-2 | 80 |
| XIII-28 | 2-methoxy-pyridin-3-yl sulfonamide benzoic acid | boc-NH-CH2-pyrrolidin-3-yl | XIII-27 | A-8 | 86 |
| XIII-29 | 2-methoxy-pyridin-3-yl sulfonamide benzoic acid | H2N-CH2-pyrrolidin-3-yl | XIII-28 | A-6 | Quant. |

TABLE 1-continued
Intermediates
| | | | | | |
|---|---|---|---|---|---|
| XIII-30 | 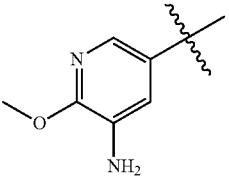 | | XIII-03 | A-1 | 98 |
| XIII-31 | | 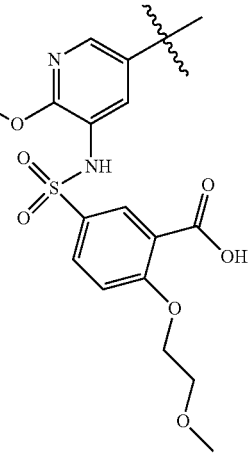 | XIII-30 | A-2 | 66 |
| XIII-32 | | 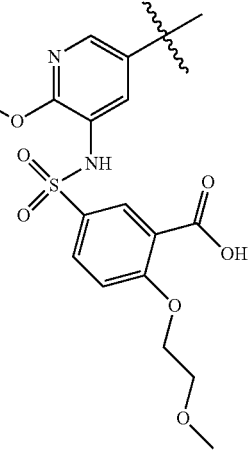 | XIII-31 | A-6 | Quant. |
| XIII-33 | 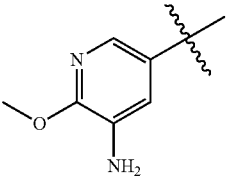 [SMILES: *c1cnc(OC)c(N)c1] | | XIII-03 | A-4 | 98 |

TABLE 1-continued

Intermediates

| | | | | |
|---|---|---|---|---|
| XIII-34 | | XIII-33 | A-2 | 82 |
| XIII-35 | | XIII-34 | A-8 | Quant. |
| XIII-36 | | XIII-35 | A-6 | Quant. |
| XIII-37 | | XIII-10 | A-2 | 56 |

TABLE 1-continued

Intermediates

| | | | | |
|---|---|---|---|---|
| XIII-38 | | XIII-37 | A-6 | Quant. |
| XIII-39 | | XIII-10 | A-2 | 80 |
| XIII-40 | | XIII-39 | A-8 | 95 |
| XIII-41 | | XIII-40 | A-6 | Quant. |

TABLE 1-continued
Intermediates
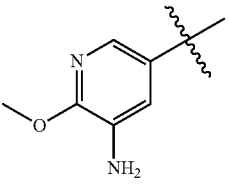 [SMILES: *c1cnc(OC)c(N)c1]
| No. | R1 | R2 | Starting Material | Method | Yield % |
|---|---|---|---|---|---|
| XIV-01 | H | Cl | 1-08 | A-10 | 91 |
| XIV-02 | I | Cl | XIV-01 | A-11 | 90 |
| XIV-03 | 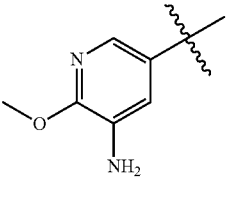 [SMILES: *c1cnc(OC)c(N)c1] | Cl | XIV-02 | A-1 | 74 |
| XIV-04 | 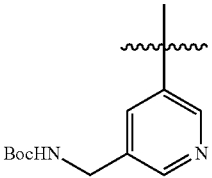 [SMILES: *c1cncc(CNC(=O)OC(C)(C)C)c1] | 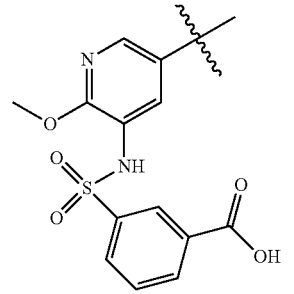 [SMILES: *c1cnc(OC)c(NS(=O)(=O)c2cccc(C(=O)O)c2)c1] | XIV-03 | A-1 | 99 |
| XIV-05 | 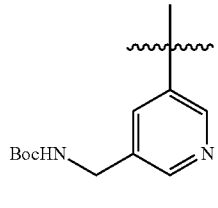 | 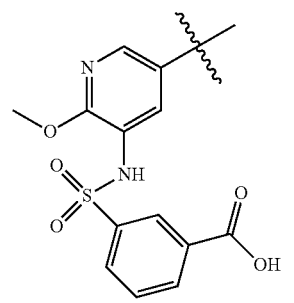 [SMILES: *c1cnc(OC)c(NS(=O)(=O)c2cccc(C(=O)O)c2)c1] | XIV-04 | A-2 | 40 |
| XIV-06 | 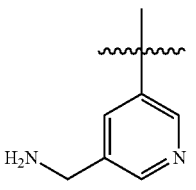 | 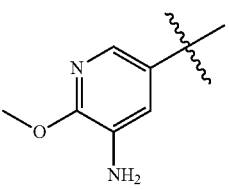 [SMILES: *c1cnc(OC)c(N)c1] | XIV-05 | A-6 | Quant. |
| XIV-07 | 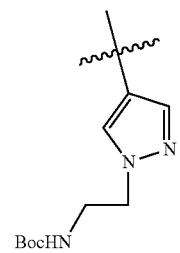 [SMILES: *c1cnn(CCNC(=O)OC(C)(C)C)c1] |  | XIV-03 | A-1 | 81 |

TABLE 1-continued
Intermediates
| No. | | | Starting Material | Method | Yield % |
|---|---|---|---|---|---|
| XIV-08 | 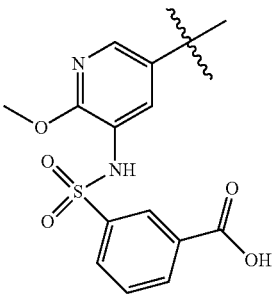 [SMILES: *c1cnc(OC)c(NS(=O)(=O)c2cccc(C(=O)O)c2)c1] | 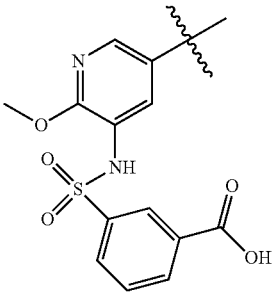 [SMILES: *c1cnc(OC)c(NS(=O)(=O)c2cccc(C(=O)O)c2)c1] | XIV-07 | A-2 | 30 |
| XIV-09 | 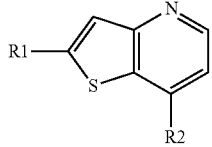 | 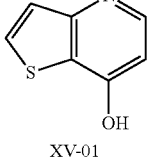 | XIV-08 | A-6 | Quant. |
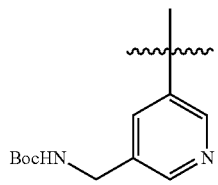 [SMILES: *c1cncc(CNC(=O)OC(C)(C)C)c1]
| No. | R1 | R2 | Starting Material | Method | Yield % |
|---|---|---|---|---|---|
| XV-02 | H | Cl | XV-01 Commercially Available | A-10 | 78 |
| XV-03 | I | Cl | XV-02 | A-11 | 88 |
| XV-04 | | Cl | XV-03 | A-1 | 79 |
| XV-05 | | | XV-04 | A-1 | 85 |

TABLE 1-continued

Intermediates

| | | | | | |
|---|---|---|---|---|---|
| XV-06 | (2-methoxy-pyridin-3-yl sulfonamide with benzoic acid) | (BocHN-CH2-pyridine) | XV-05 | A-2 | 44 |
| XV-07 | (2-methoxy-pyridin-3-yl sulfonamide with benzoic acid) | (H2N-CH2-pyridine) | XV-06 | A-6 | Quant. |
| XV-08 | (2-methoxy-pyridin-3-yl sulfonamide with fluorobenzoic acid) | (BocHN-CH2-pyridine) | XV-05 | A-2 | 32 |
| XV-09 | (2-methoxy-pyridin-3-yl sulfonamide with fluorobenzoic acid) | (H2N-CH2-pyridine) | XV-08 | A-6 | Quant. |
| XV-10 | (3-amino-2-methoxypyridine) | (BocHN-CH2-thiophene) | XV-04 | A-1 | 43 |

TABLE 1-continued

Intermediates

| No. | | | Starting Material | Method | Yield % |
|---|---|---|---|---|---|
| XV-11 | [structure: methoxypyridine with sulfonamide-benzoic acid] | [structure: thiophene with BocHN-CH2] | XV-10 | A-2 | 82 |
| XV-12 | [structure: methoxypyridine with sulfonamide-benzoic acid] | [structure: thiophene with H2N-CH2] | XV-11 | A-6 | Quant. |

[structure: thieno[3,2-b]pyridine core with R1, R2, CN substituents]

| No. | R1 | R2 | Starting Material | Method | Yield % |
|---|---|---|---|---|---|
| XVI-02 | I | Cl | [structure XVI-01: thienopyridine with R2 and CN] XVI-01 Commercially Available | A-11 | 23 |
| XVI-03 | [structure: 2-methoxy-3-aminopyridine] | [structure: thiophene with BocHN-CH2] | XVI-02 | A-1 | 96 |
| XVI-04 | [structure: methoxypyridine with sulfonamide-benzoic acid] | [structure: thiophene with BocHN-CH2] | XVI-03 | A-2 | 57 |

TABLE 1-continued

Intermediates

| No. | R1 | R2 | Starting Material | Method | Yield % |
|---|---|---|---|---|---|
| XVI-05 | (2-methoxypyridin-3-yl)sulfonamido-benzoic acid structure | 5-(aminomethyl)thiophen-2-yl | XVI-04 | A-6 | Quant. |

7-azaindole core with R1 at 2-position and R2 at 4-position

| No. | R1 | R2 | Starting Material | Method | Yield % |
|---|---|---|---|---|---|
| XVII-02 | (2-methoxypyridin-3-yl)sulfonamido-benzoic acid methyl ester structure | Cl | XVII-01 Commercially Available | A-1 | 44 |
| XVII-03 | (2-methoxypyridin-3-yl)sulfonamido-benzoic acid structure | 5-(BocNHCH₂)thiophen-2-yl | XVII-02 | A-3 | 61 |
| XVII-04 | (2-methoxypyridin-3-yl)sulfonamido-benzoic acid structure | 5-(aminomethyl)thiophen-2-yl | XVII-03 | A-6 | Quant. |

TABLE 1-continued

Intermediates

| No. | | | Starting Material | Method | Yield % |
|---|---|---|---|---|---|
| XVII-05 | 2-methoxypyridine with NH-SO2-phenyl-COOH substituent | BocHN-CH2-pyridine | XVII-02 | A-3 | 35 |
| XVII-06 | 2-methoxypyridine with NH-SO2-phenyl-COOH substituent | H2N-CH2-pyridine | XVII-05 | A-6 | Quant. |

Thieno[3,2-b]pyridine core with R1 at 2-position and R2 at 7-position, 3-methyl

| No. | R1 | R2 | Starting Material | Method | Yield % |
|---|---|---|---|---|---|
| XVIII-02 | I | Cl | XVIII-01 (3-methyl-7-chlorothieno[3,2-b]pyridine) Commercially Available | A-11 | 86 |
| XVIII-03 | 3-amino-2-methoxypyridin-5-yl | Cl | XVIII-02 | A-1 | 84 |
| XVIII-04 | 3-amino-2-methoxypyridin-5-yl | BocHN-CH2-thiophen-2-yl | XVIII-03 | A-3 | Quant. |

TABLE 1-continued

Intermediates

| | | | | |
|---|---|---|---|---|
| XVIII-05 | [pyridine with OMe, NH-SO2-phenyl-COOMe structure] | XVIII-04 | A-2 | 48 |
| XVIII-06 | [pyridine with OMe, NH-SO2-phenyl-COOH structure] | XVIII-05 | A-8 | 82 |
| XVIII-07 | [pyridine with OMe, NH-SO2-phenyl-COOH structure] | XVIII-06 | A-6 | Quant. |

The final examples of compounds of the invention were prepared according to the general methods B-1 to B-4 described hereinafter.

EXAMPLES

General Method B-1

The corresponding aminoacid intermediate (1 eq.) was dissolved in DMF (50 mL/mmol) and DI PEA (5 eq.) was added. The mixture was added using a syringe pump (2 mL/h) to a solution of PyBOP (1.1 eq.) and DMAP (1.1 eq.) in DMF (150 mL/mmol). After the addition, the mixture was stirred for 18 h and evaporated till dryness. The residue was purified by flash chromatography in a Biotage using cyclohexane/AcOEt gradient followed by AcOEt/MeOH gradient to give the expected compound.

General Method B-2

A solution of the indicated aminoacid intermediate (1 eq.) in DMF (50 mL/mmol) and DIPEA (5 eq.) was added via syringe pump (2 mL/h) to a solution of HATU (2 eq.) and HOAt (0.5 M in DMF, 2 eq.) in DMF (150 mL/mmol). The resulting mixture was stirred overnight under Ar. The mixture was concentrated under vacuum. The residue was purified by flash chromatography in a Biotage using DCM/MeOH gradient to give the expected compound.

General Method B-3

A solution of the indicated aminoacid intermediate (1 eq.) in DMF (50 mL/mmol) and DIPEA (5 eq.) was added via syringe pump (2 mL/h) to a solution of PyBroP (2 eq.) in DMF (150 mL/mmol). The resulting mixture was stirred overnight under Ar. The mixture was concentrated under vacuum. The residue was purified by flash chromatography in a Biotage using DCM/MeOH gradient to give the expected compound.

Method B-4

Synthesis of Final Product 46

To a solution of Final Product 27 (30 mg, 0.06 mmol) in DMF (0.6 mL) and DIPEA (10 µL 0.06 mmol) was added MeI (4 µL, 0.06 mmol) at 0° C. The mixture was stirred from 0° C. to rt. More DIPEA (10 µL) and MeI (5 µL) were added and the reaction was stirred at rt for 6 h. Water was added and the mixture was extracted with DCM. The organic layer was dried ($Na_2SO_4$), filtered and concentrated. The residue was purified by prep HPLC to give Final Product 46 (4 mg, 13%) and the dimethylated product (3 mg, 9%).

TABLE 2

| | Final products | | | |
|---|---|---|---|---|
| Cpd. Nr. | Structure | Starting Material | General Method | Yield % |
| 1 | | I-07 | B-1 | 12 |
| 2 | | I-08 | B-1 | 23 |
| 3 | | I-13 | B-1 | 31 |
| 4 | | I-17 | B-1 | 57 |

TABLE 2-continued

| | Final products | | | |
|---|---|---|---|---|
| Cpd. Nr. | Structure | Starting Material | General Method | Yield % |
| 5 | | I-11 | B-1 | 20 |
| 6 | | I-14 | B-1 | 38 |
| 7 | | I-15 | B-1 | 73 |
| 8 | | II-04 | B-2 | 19 |

TABLE 2-continued

Final products

| Cpd. Nr. | Structure | Starting Material | General Method | Yield % |
|---|---|---|---|---|
| 9 | 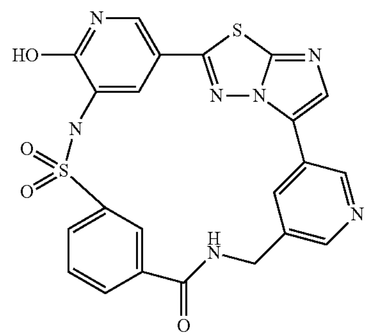 [SMILES: O=C1NCc2cncc(c2)-c2cnc3sc(nn23)-c2cnc(O)c(c2)NS(=O)(=O)c2cccc1c2] | II-05 | B-2 | 21 |
| 10 | 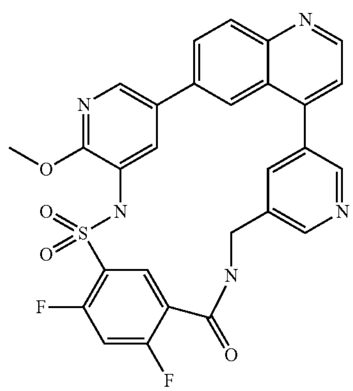 [SMILES: COc1ncc2cc1NS(=O)(=O)c1cc(c(F)cc1F)C(=O)NCc1cncc(c1)-c1ccnc3ccc-2cc13] | I-16 | B-1 | 26 |
| 11 | 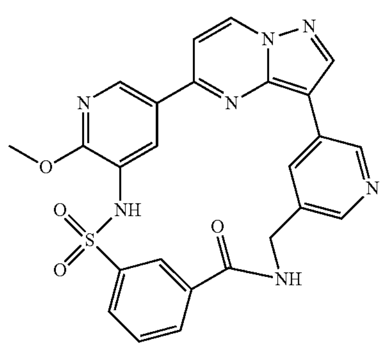 [SMILES: COc1ncc2cc1NS(=O)(=O)c1cccc(c1)C(=O)NCc1cncc(c1)-c1cnn3ccc-2nc13] | III-04 | B-2 | 40 |
| 12 | 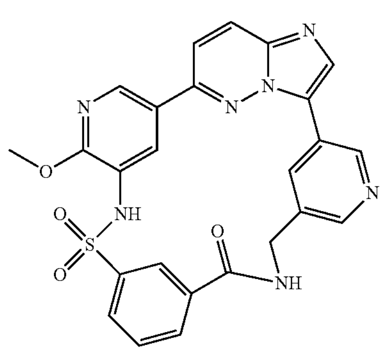 [SMILES: COc1ncc2cc1NS(=O)(=O)c1cccc(c1)C(=O)NCc1cncc(c1)-c1cnc3ccc-2nn13] | IV-05 | B-2 | 53 |

TABLE 2-continued
Final products
| Cpd. Nr. | Structure | Starting Material | General Method | Yield % |
|---|---|---|---|---|
| 13 | 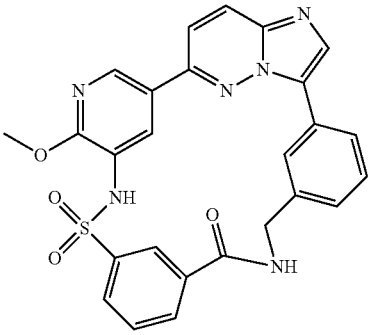 [SMILES: COc1ncc2cc1NS(=O)(=O)c1cccc(c1)C(=O)NCc1cccc(c1)-c1cnc3ccc-2nn13] | IV-09 | B-2 | 43 |
| 14 | 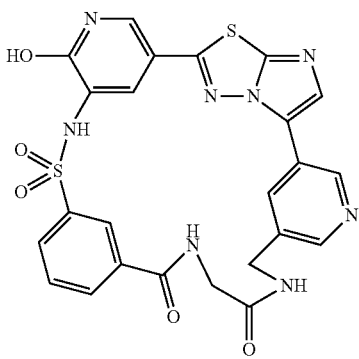 [SMILES: O=C1CNC(=O)c2cccc(c2)S(=O)(=O)Nc2cc(cnc2O)-c2nn3c(cnc3s2)-c2cncc(c2)CN1] | II-10 | B-2 | 1 |
| 15 | 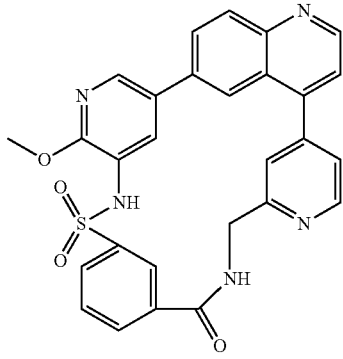 [SMILES: COc1ncc2cc1NS(=O)(=O)c1cccc(c1)C(=O)NCc1cc(ccn1)-c1ccnc3ccc-2cc13] | I-19 | B-1 | 14 |
| 16 | 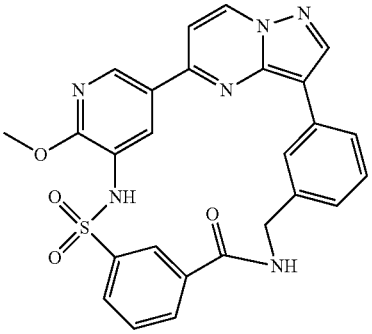 [SMILES: COc1ncc2cc1NS(=O)(=O)c1cccc(c1)C(=O)NCc1cccc(c1)-c1cnn3ccc-2nc13] | III-07 | B-2 | 18 |

TABLE 2-continued

Final products

| Cpd. Nr. | Structure | Starting Material | General Method | Yield % |
|---|---|---|---|---|
| 17 | 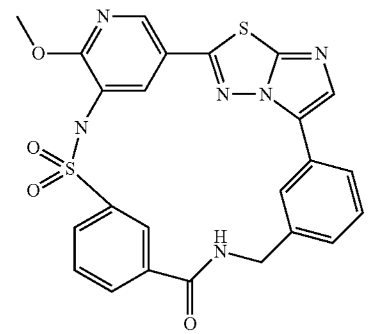 [SMILES: COc1ncc2cc1NS(=O)(=O)c1cccc(c1)C(=O)NCc1cccc(c1)-c1cnc3sc-2nn13] | II-13 | B-2 | 43 |
| 18 | 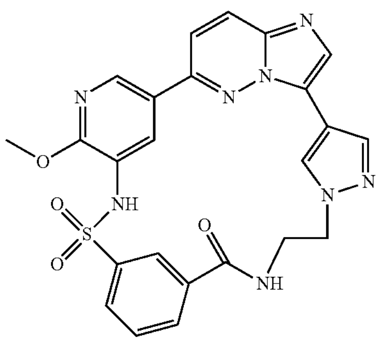 [SMILES: COc1ncc2cc1NS(=O)(=O)c1cccc(c1)C(=O)NCCn1cc(cn1)-c1cnc3ccc-2nn13] | IV-13 | B-2 | 12 |
| 19 | 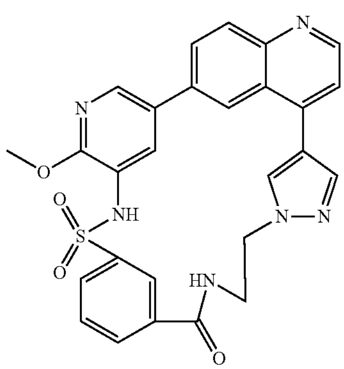 [SMILES: COc1ncc2cc1NS(=O)(=O)c1cccc(c1)C(=O)NCCn1cc(cn1)-c1ccnc3ccc-2cc13] | I-21 | B-1 | 5 |
| 20 | 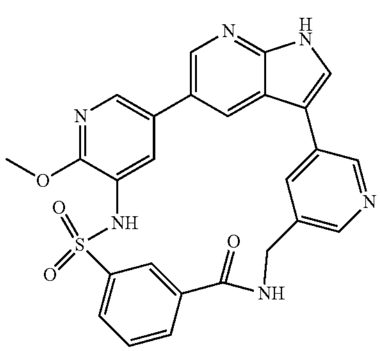 [SMILES: COc1ncc2cc1NS(=O)(=O)c1cccc(c1)C(=O)NCc1cncc(c1)-c1c[nH]c3ncc-2cc13] | V-05 | B-1 | 5 |

TABLE 2-continued

Final products

| Cpd. Nr. | Structure | Starting Material | General Method | Yield % |
|---|---|---|---|---|
| 21 | 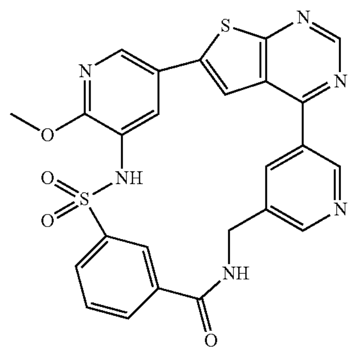 [SMILES: COc1ncc2cc1NS(=O)(=O)c1cccc(c1)C(=O)NCc1cncc(c1)-c1ncnc3sc-2cc13] | VI-04 | B-2 | 3 |
| 22 | 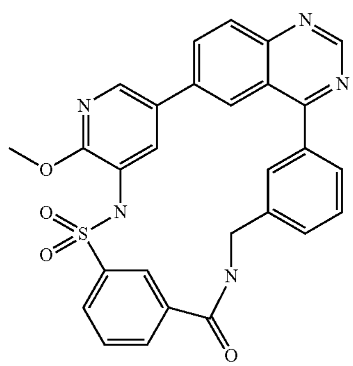 [SMILES: COc1ncc2cc1NS(=O)(=O)c1cccc(c1)C(=O)NCc1cccc(c1)-c1ncnc3ccc-2cc13] | VII-05 | B-2 | 36 |
| 23 | 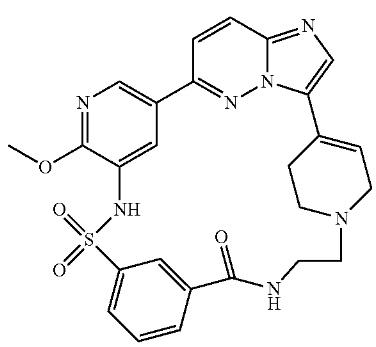 [SMILES: COc1ncc2cc1NS(=O)(=O)c1cccc(c1)C(=O)NCCN1CC=C(CC1)c1cnc3ccc-2nn13] | IV-17 | B-2 | 4 |
| 24 | 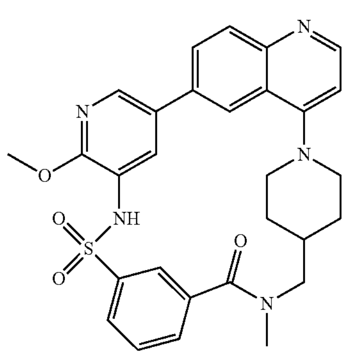 [SMILES: COc1ncc2cc1NS(=O)(=O)c1cccc(c1)C(=O)N(C)CC1CCN(CC1)c1ccnc3ccc-2cc13] | I-23 | B-3 | 6 |

TABLE 2-continued
Final products
| Cpd. Nr. | Structure | Starting Material | General Method | Yield % |
|---|---|---|---|---|
| 25 | 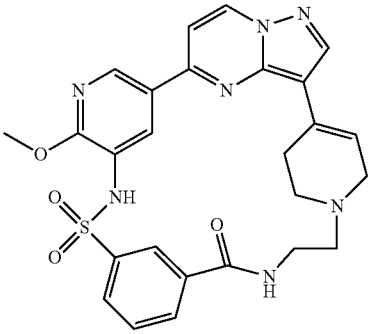 [SMILES: COc1ncc2cc1NS(=O)(=O)c1cccc(c1)C(=O)NCCN1CC=C(CC1)c1cnn3ccc-2nc13] | III-11 | B-2 | 4 |
| 26 | 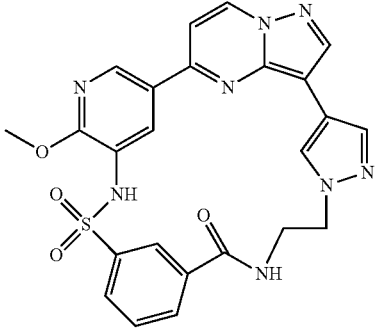 [SMILES: COc1ncc2cc1NS(=O)(=O)c1cccc(c1)C(=O)NCCn1cc(cn1)-c1cnn3ccc-2nc13] | III-14 | B-2 | 30 |
| 27 | 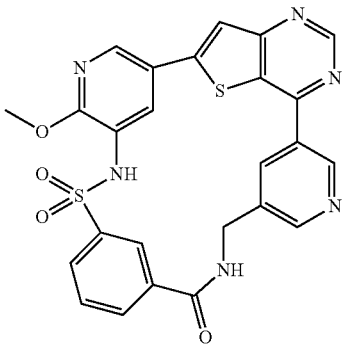 [SMILES: COc1ncc2cc1NS(=O)(=O)c1cccc(c1)C(=O)NCc1cncc(c1)-c1ncnc3c1SC2=C3] | VIII-05 | B-2 | 31 |
| 28 | 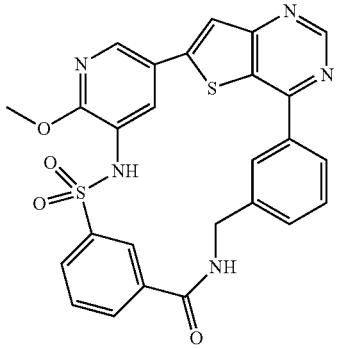 [SMILES: COc1ncc2cc1NS(=O)(=O)c1cccc(c1)C(=O)NCc1cccc(c1)-c1ncnc3c1SC2=C3] | VIII-08 | B-2 | 19 |

TABLE 2-continued

| Final products | | | | |
|---|---|---|---|---|
| Cpd. Nr. | Structure | Starting Material | General Method | Yield % |
| 29 | | I-25 | B-1 | 47 |
| 30 | | IX-05 | B-2 | 15 |
| 31 | | X-05 | B-2 | 18 |
| 32 | | VII-09 | B-2 | 53 |

TABLE 2-continued

Final products

| Cpd. Nr. | Structure | Starting Material | General Method | Yield % |
|---|---|---|---|---|
| 33 | 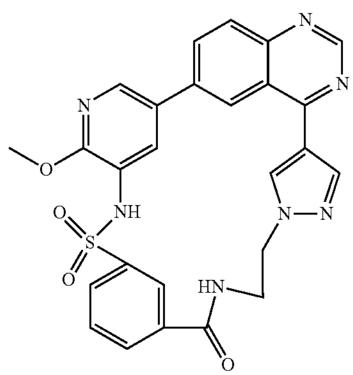 [SMILES: COc1ncc2cc1NS(=O)(=O)c1cccc(c1)C(=O)NCCn1cc(cn1)-c1ncnc3ccc-2cc13] | VII-13 | B-2 | 51 |
| 34 | 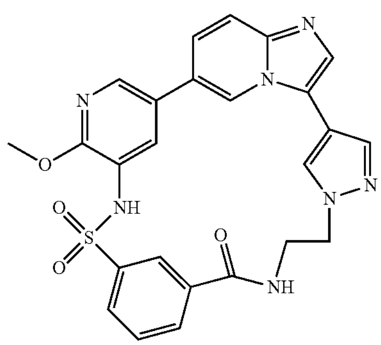 [SMILES: COc1ncc2cc1NS(=O)(=O)c1cccc(c1)C(=O)NCCn1cc(cn1)-c1cnc3ccc-2cn13] | IX-08 | B-2 | 38 |
| 35 | 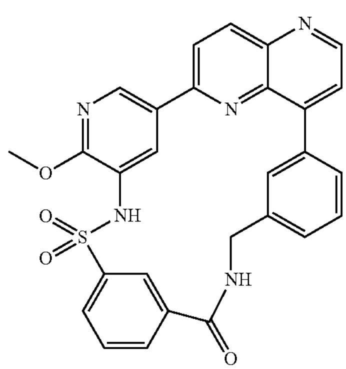 [SMILES: COc1ncc2cc1NS(=O)(=O)c1cccc(c1)C(=O)NCc1cccc(c1)-c1ccnc3ccc-2nc13] | X-07 | B-2 | 32 |
| 36 | 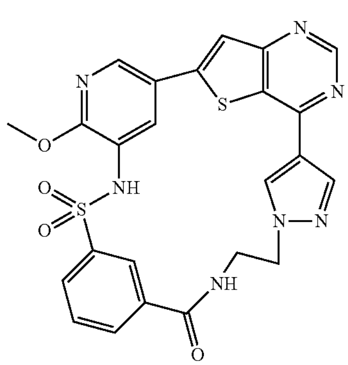 [SMILES: COc1ncc2cc1NS(=O)(=O)c1cccc(c1)C(=O)NCCn1cc(cn1)-c1ncnc3cc-2sc13] | VIII-11 | B-2 | 18 |

TABLE 2-continued

Final products

| Cpd. Nr. | Structure | Starting Material | General Method | Yield % |
|---|---|---|---|---|
| 37 | 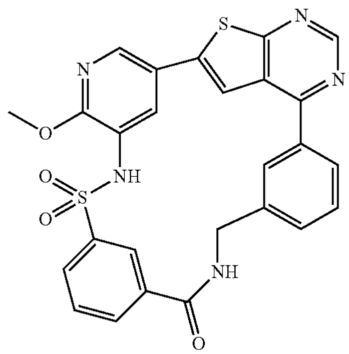 [SMILES: COc1ncc2cc1NS(=O)(=O)c1cccc(c1)C(=O)NCc1cccc(c1)-c1ncnc3sc-2cc13] | VI-08 | B-2 | 8 |
| 38 | 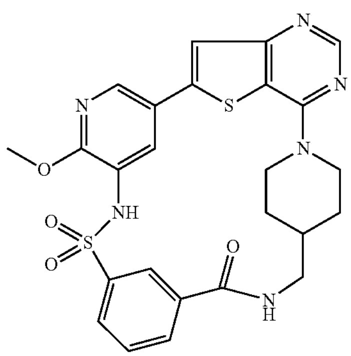 [SMILES: COc1ncc2cc1NS(=O)(=O)c1cccc(c1)C(=O)NCC1CCN(CC1)c1ncnc3cc-2sc13] | VIII-14 | B-2 | 6 |
| 39 | 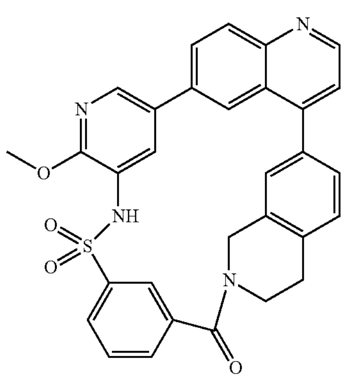 [SMILES: COc1ncc2cc1NS(=O)(=O)c1cccc(c1)C(=O)N1CCc3ccc(cc3C1)-c1ccnc3ccc-2cc13] | I-28 | B-2 | 34 |
| 40 | 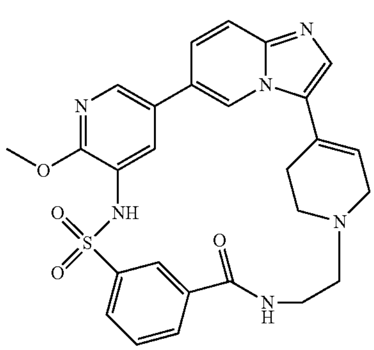 [SMILES: COc1ncc2cc1NS(=O)(=O)c1cccc(c1)C(=O)NCCN1CC=C(CC1)c1cnc3ccc-2cn13] | IX-11 | B-2 | 21 |

TABLE 2-continued

Final products

| Cpd. Nr. | Structure | Starting Material | General Method | Yield % |
|---|---|---|---|---|
| 41 | 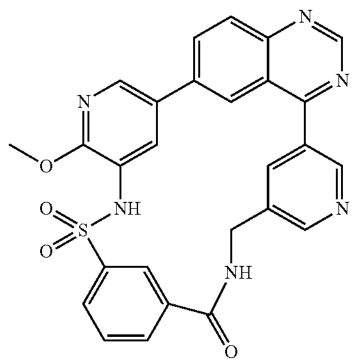 [SMILES: COc1ncc2cc1NS(=O)(=O)c1cccc(c1)C(=O)NCc1cncc(c1)-c1ncnc3ccc-2cc13] | VII-17 | B-2 | 29 |
| 42 | 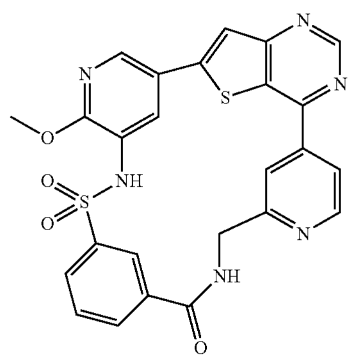 [SMILES: COc1ncc2cc1NS(=O)(=O)c1cccc(c1)C(=O)NCc1cc(ccn1)-c1ncnc3cc-2sc13] | VIII-17 | B-2 | 30 |
| 43 | 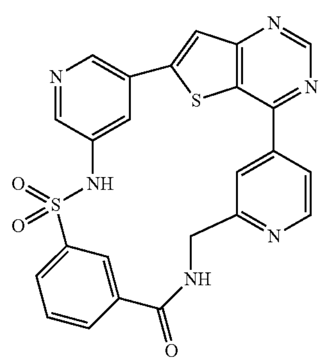 [SMILES: O=C1NCc2cc(ccn2)-c2ncnc3cc(sc23)-c2cncc(c2)NS(=O)(=O)c2cccc1c2] | VIII-20 | B-2 | 10 |
| 44 | 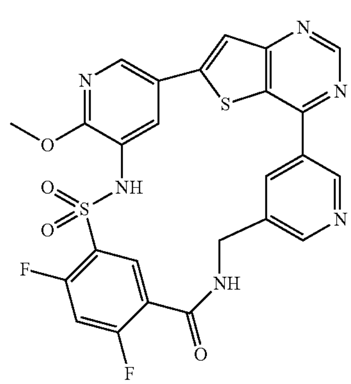 [SMILES: COc1ncc2cc1NS(=O)(=O)c1cc(c(F)cc1F)C(=O)NCc1cncc(c1)-c1ncnc3cc-2sc13] | VIII-23 | B-2 | 19 |

TABLE 2-continued

Final products

| Cpd. Nr. | Structure | Starting Material | General Method | Yield % |
|---|---|---|---|---|
| 45 | 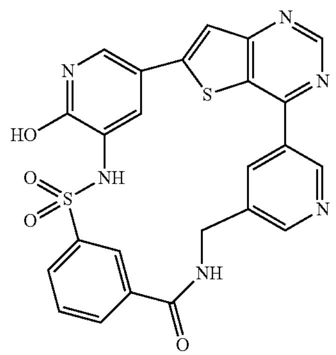 [SMILES: O=C1NCc2cncc(c2)-c2ncnc3cc(sc23)-c2cnc(O)c(c2)NS(=O)(=O)c2cccc1c2] | VIII-24 | B-2 | 10 |
| 46 | 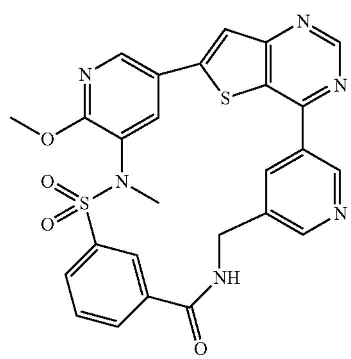 [SMILES: COc1ncc2cc1N(C)S(=O)(=O)c1cccc(c1)C(=O)NCc1cncc(c1)-c1ncnc3cc-2sc13] | 27 | B-4 | 13 |
| 47 | 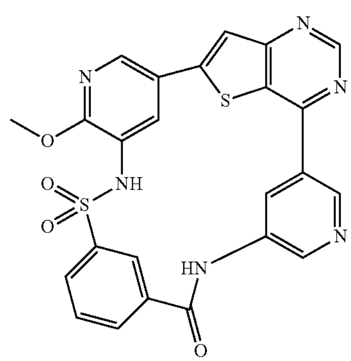 [SMILES: COc1ncc2cc1NS(=O)(=O)c1cccc(c1)C(=O)Nc1cncc(c1)-c1ncnc3cc-2sc13] | VIII-26 | B-2 | 14 |
| 48 | 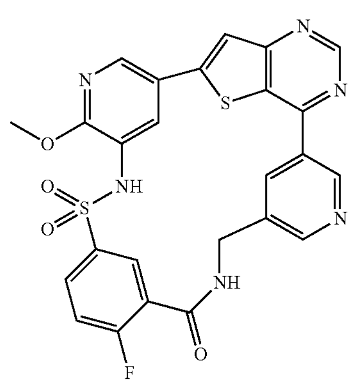 [SMILES: COc1ncc2cc1NS(=O)(=O)c1ccc(F)c(c1)C(=O)NCc1cncc(c1)-c1ncnc3cc-2sc13] | VIII-28 | B-2 | 38 |

TABLE 2-continued

Final products

| Cpd. Nr. | Structure | Starting Material | General Method | Yield % |
|---|---|---|---|---|
| 49 | 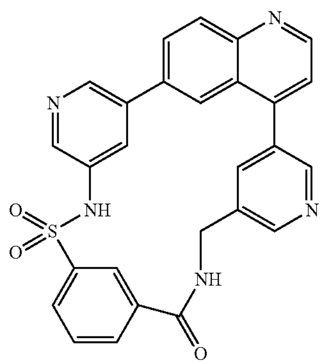 [SMILES: O=C1NCc2cncc(c2)-c2ccnc3ccc(cc23)-c2cncc(c2)NS(=O)(=O)c2cccc1c2] | I-32 | B-1 | 11 |
| 50 | 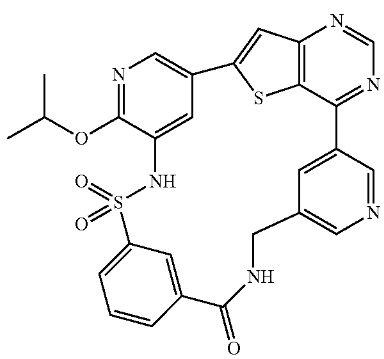 [SMILES: CC(C)Oc1ncc2cc1NS(=O)(=O)c1cccc(c1)C(=O)NCc1cncc(c1)-c1ncnc3cc-2sc13] | VIII-32 | B-2 | 19 |
| 51 | 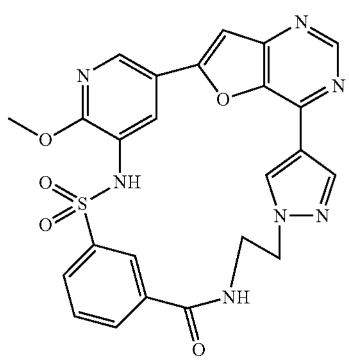 [SMILES: COc1ncc2cc1NS(=O)(=O)c1cccc(c1)C(=O)NCCn1cc(cn1)-c1ncnc3cc-2oc13] | XI-05 | B-2 | 7 |
| 52 | 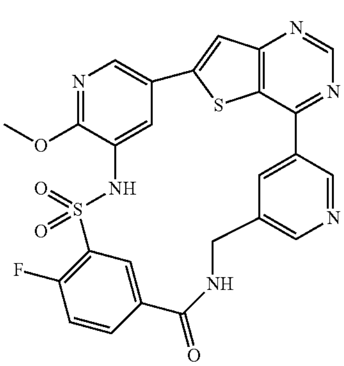 [SMILES: COc1ncc2cc1NS(=O)(=O)c1cc(ccc1F)C(=O)NCc1cncc(c1)-c1ncnc3cc-2sc13] | VIII-34 | B-2 | 34 |

TABLE 2-continued
Final products
| Cpd. Nr. | Structure | Starting Material | General Method | Yield % |
|---|---|---|---|---|
| 53 | 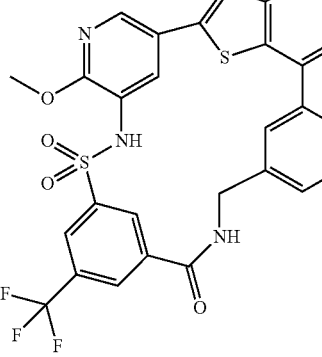 | VIII-36 | B-2 | 35 |
| 54 | 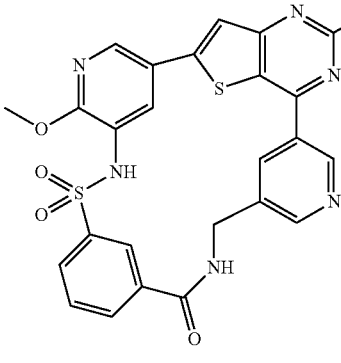 | XII-06 | B-2 | 29 |
| 55 | 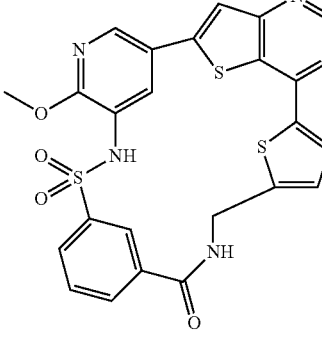 | VIII-39 | B-2 | 20 |
| 56 | 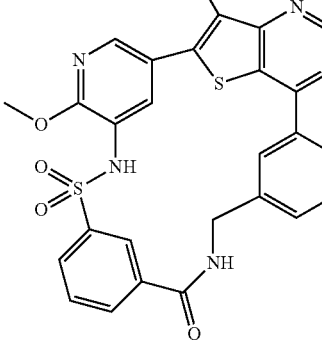 | XIII-06 | B-2 | 36 |

TABLE 2-continued

Final products

| Cpd. Nr. | Structure | Starting Material | General Method | Yield % |
|---|---|---|---|---|
| 57 | 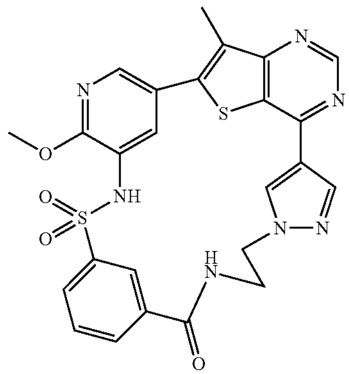 [SMILES: COc1ncc2cc1NS(=O)(=O)c1cccc(c1)C(=O)NCCn1cc(cn1)-c1ncnc3c(C)c-2sc13] | XIII-09 | B-2 | 25 |
| 58 | 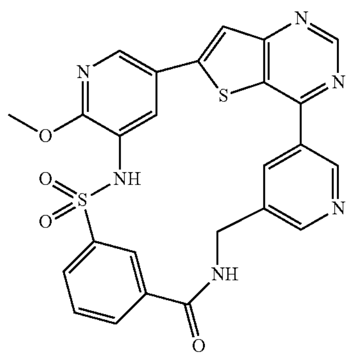 [SMILES: COc1ncc2cc1NS(=O)(=O)c1cccc(c1)C(=O)NCc1cncc(c1)-c1ncnc3cc-2sc13] | VIII-42 | B-2 | 13 |
| 59 | 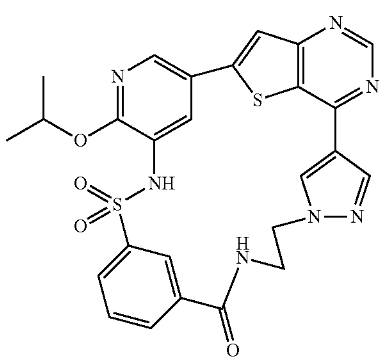 [SMILES: CC(C)Oc1ncc2cc1NS(=O)(=O)c1cccc(c1)C(=O)NCCn1cc(cn1)-c1ncnc3cc-2sc13] | VIII-45 | B-2 | 19 |
| 60 | 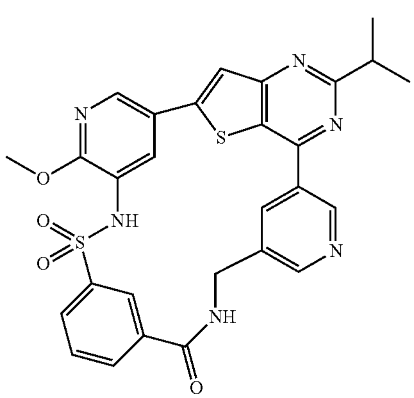 [SMILES: COc1ncc2cc1NS(=O)(=O)c1cccc(c1)C(=O)NCc1cncc(c1)-c1nc(C(C)C)nc3cc-2sc13] | XIV-06 | B-2 | 22 |

TABLE 2-continued

Final products

| Cpd. Nr. | Structure | Starting Material | General Method | Yield % |
|---|---|---|---|---|
| 61 | 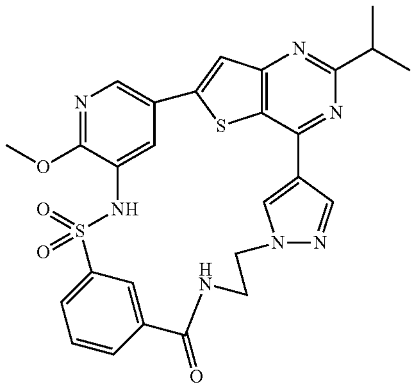 [SMILES: COc1ncc2cc1NS(=O)(=O)c1cccc(c1)C(=O)NCCn1cc(cn1)-c1nc(C(C)C)nc3cc-2sc13] | XIV-09 | B-2 | 13 |
| 62 | 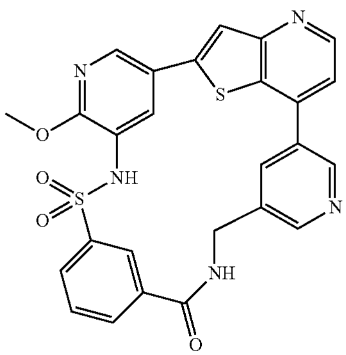 [SMILES: COc1ncc2cc1NS(=O)(=O)c1cccc(c1)C(=O)NCc1cncc(c1)-c1ccnc3cc-2sc13] | XV-07 | B-2 | 33 |
| 63 | 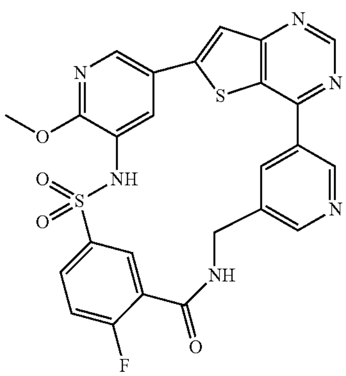 [SMILES: COc1ncc2cc1NS(=O)(=O)c1ccc(F)c(c1)C(=O)NCc1cncc(c1)-c1ncnc3cc-2sc13] | XV-09 | B-2 | 42 |
| 64 | 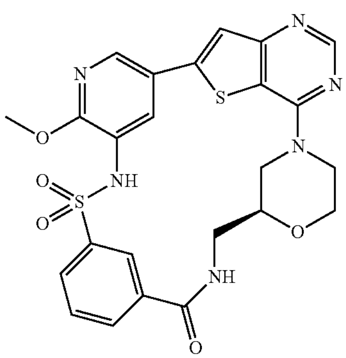 [SMILES: COc1ncc2cc1NS(=O)(=O)c1cccc(c1)C(=O)NC[C@H]1CN(CCO1)c1ncnc3cc-2sc13] | VIII-48 | B-2 | 27 |

TABLE 2-continued

Final products

| Cpd. Nr. | Structure | Starting Material | General Method | Yield % |
|---|---|---|---|---|
| 65 | 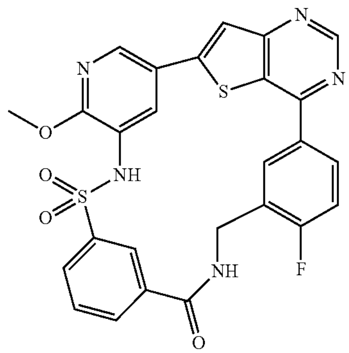 [SMILES: COc1ncc2cc1NS(=O)(=O)c1cccc(c1)C(=O)NCc1cc(ccc1F)-c1ncnc3cc-2sc13] | VIII-50 | B-2 | 59 |
| 66 | 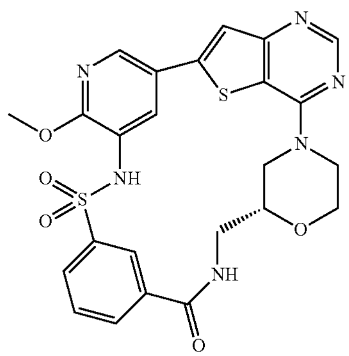 [SMILES: COc1ncc2cc1NS(=O)(=O)c1cccc(c1)C(=O)NC[C@@H]1CN(CCO1)c1ncnc3cc-2sc13] | VIII-54 | B-2 | 29 |
| 67 | 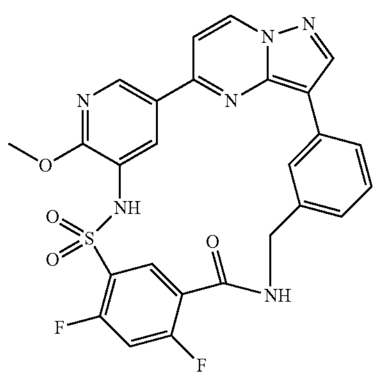 [SMILES: COc1ncc2cc1NS(=O)(=O)c1cc(c(F)cc1F)C(=O)NCc1cccc(c1)-c1cnn3ccc-2nc13] | III-17 | B-2 | 29 |
| 68 | 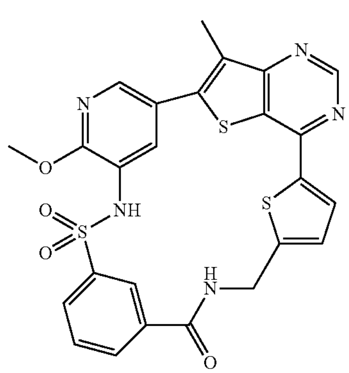 [SMILES: COc1ncc2cc1NS(=O)(=O)c1cccc(c1)C(=O)NCc1ccc(s1)-c1ncnc3c(C)c-2sc13] | XIII-12 | B-2 | 4 |

TABLE 2-continued

Final products

| Cpd. Nr. | Structure | Starting Material | General Method | Yield % |
|---|---|---|---|---|
| 69 | 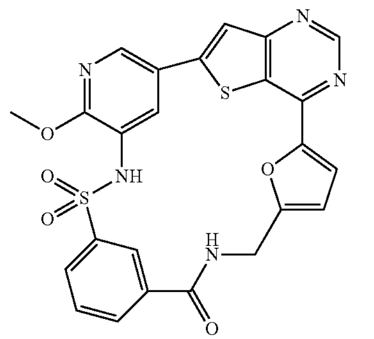 [SMILES: COc1ncc2cc1NS(=O)(=O)c1cccc(c1)C(=O)NCc1ccc(o1)-c1ncnc3cc-2sc13] | VIII-57 | B-2 | 15 |
| 70 | 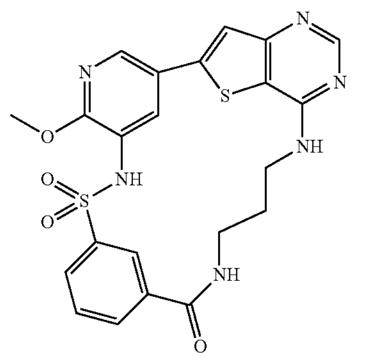 [SMILES: COc1ncc2cc1NS(=O)(=O)c1cccc(c1)C(=O)NCCCNc1ncnc3cc-2sc13] | VIII-60 | B-2 | 20 |
| 71 | 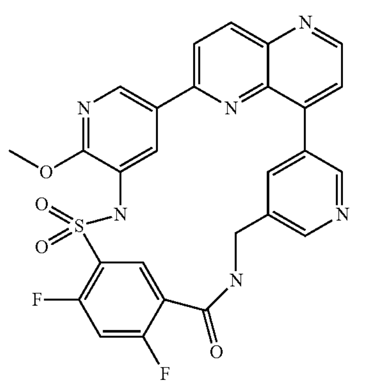 [SMILES: COc1ncc2cc1NS(=O)(=O)c1cc(c(F)cc1F)C(=O)NCc1cncc(c1)-c1ccnc3ccc-2nc13] | X-11 | B-2 | 9 |
| 72 | 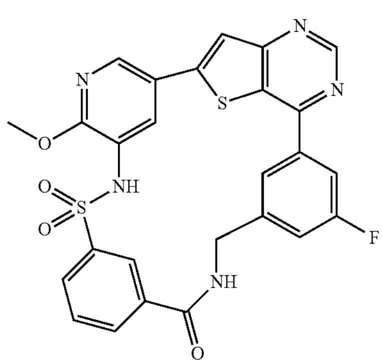 [SMILES: COc1ncc2cc1NS(=O)(=O)c1cccc(c1)C(=O)NCc1cc(F)cc(c1)-c1ncnc3cc-2sc13] | VIII-63 | B-2 | 17 |

TABLE 2-continued

Final products

| Cpd. Nr. | Structure | Starting Material | General Method | Yield % |
|---|---|---|---|---|
| 73 | 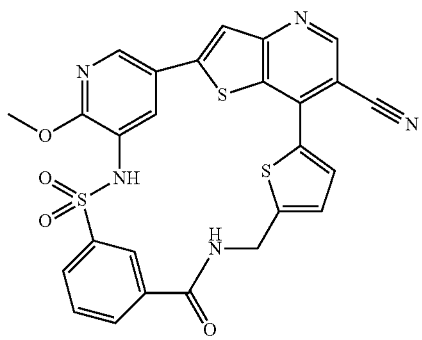 [SMILES: COc1ncc2cc1NS(=O)(=O)c1cccc(c1)C(=O)NCC1=CC=C(S1)c1c(C#N)cnc3cc-2sc13] | XVI-05 | B-2 | 34 |
| 74 | 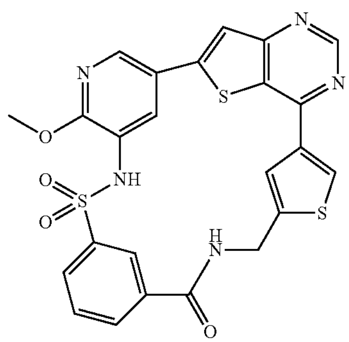 [SMILES: COc1ncc2cc1NS(=O)(=O)c1cccc(c1)C(=O)NCc1cc(cs1)-c1ncnc3cc-2sc13] | VIII-67 | B-2 | 16 |
| 75 | 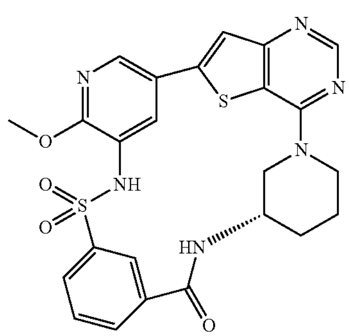 [SMILES: COc1ncc2cc1NS(=O)(=O)c1cccc(c1)C(=O)N[C@H]1CCCN(C1)c1ncnc3cc-2sc13] | VIII-70 | B-2 | 3 |
| 76 | 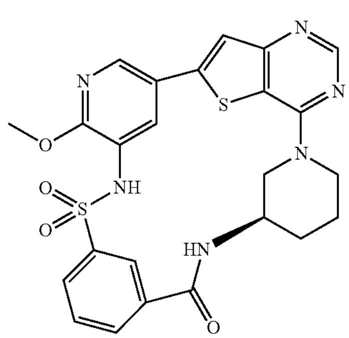 [SMILES: COc1ncc2cc1NS(=O)(=O)c1cccc(c1)C(=O)N[C@@H]1CCCN(C1)c1ncnc3cc-2sc13] | VIII-73 | B-2 | 43 |

TABLE 2-continued

| Cpd. Nr. | Structure | Starting Material | General Method | Yield % |
|---|---|---|---|---|
| 77 | 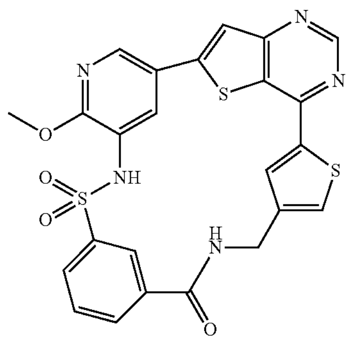 [SMILES: COc1ncc2cc1NS(=O)(=O)c1cccc(c1)C(=O)NCc1csc(c1)-c1ncnc3cc-2sc13] | VIII-76 | B-2 | 9 |
| 78 | 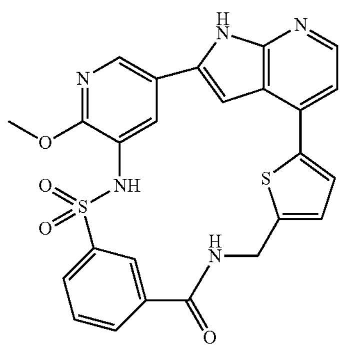 [SMILES: COc1ncc2cc1NS(=O)(=O)c1cccc(c1)C(=O)NCC1=CC=C(S1)c1ccnc3[nH]c-2cc13] | XVII-04 | B-2 | 26 |
| 79 | 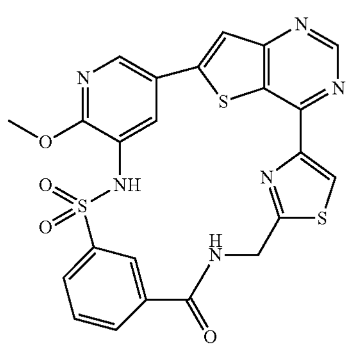 [SMILES: COc1ncc2cc1NS(=O)(=O)c1cccc(c1)C(=O)NCc1nc(cs1)-c1ncnc3cc-2sc13] | VIII-79 | B-2 | 52 |
| 80 | 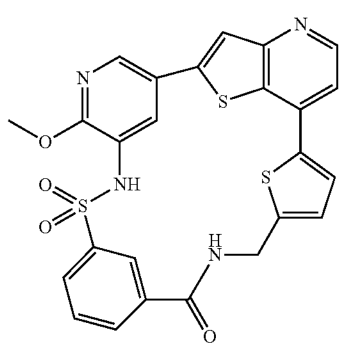 [SMILES: COc1ncc2cc1NS(=O)(=O)c1cccc(c1)C(=O)NCC1=CC=C(S1)c1ccnc3cc-2sc13] | XV-12 | B-2 | 18 |

TABLE 2-continued

Final products

| Cpd. Nr. | Structure | Starting Material | General Method | Yield % |
|---|---|---|---|---|
| 81 | 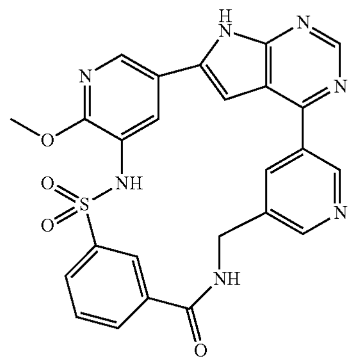 [SMILES: COc1ncc2cc1NS(=O)(=O)c1cccc(c1)C(=O)NCc1cncc(c1)-c1ncnc3[nH]c-2cc13] | XVII-06 | B-2 | 19 |
| 82 | 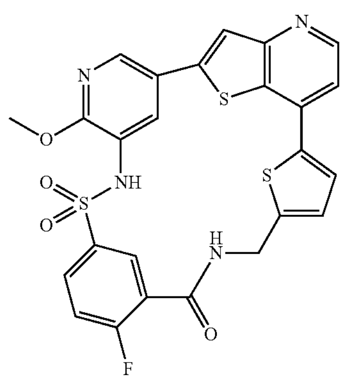 [SMILES: COc1ncc2cc1NS(=O)(=O)c1ccc(F)c(c1)C(=O)NCC1=CC=C(S1)c1ccnc3cc-2sc13] | VIII-81 | B-2 | 33 |
| 83 | 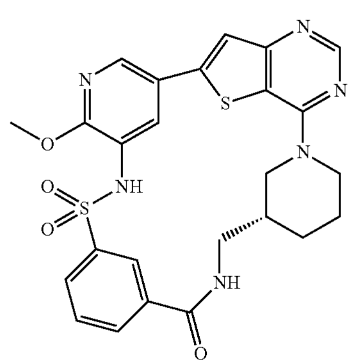 [SMILES: COc1ncc2cc1NS(=O)(=O)c1cccc(c1)C(=O)NC[C@H]1CCCN(C1)c1ncnc3cc-2sc13] | VIII-84 | B-2 | 25 |
| 84 | 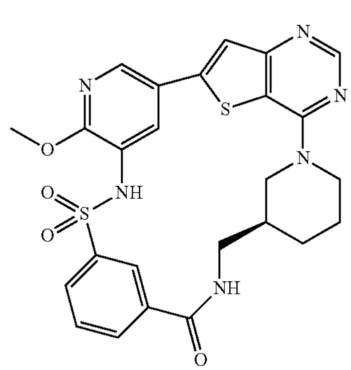 [SMILES: COc1ncc2cc1NS(=O)(=O)c1cccc(c1)C(=O)NC[C@@H]1CCCN(C1)c1ncnc3cc-2sc13] | VIII-87 | B-2 | 32 |

TABLE 2-continued
| Cpd. Nr. | Structure | Starting Material | General Method | Yield % |
|---|---|---|---|---|
| 85 | 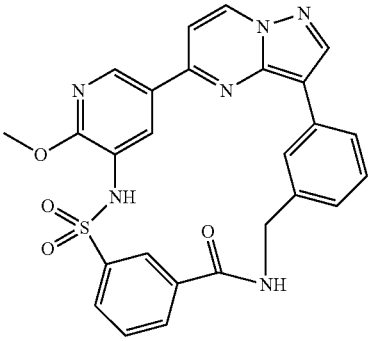 [SMILES: COc1ncc2cc1NS(=O)(=O)c1cccc(c1)C(=O)NCc1cccc(c1)-c1cnn3ccc-2nc13] | III-18 | B-2 | 3 |
| 86 | 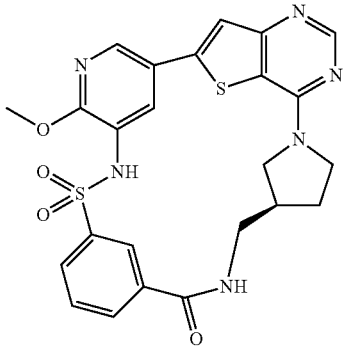 [SMILES: COc1ncc2cc1NS(=O)(=O)c1cccc(c1)C(=O)NC[C@@H]1CCN(C1)c1ncnc3cc-2sc13] | VIII-90 | B-2 | 20 |
| 87 | 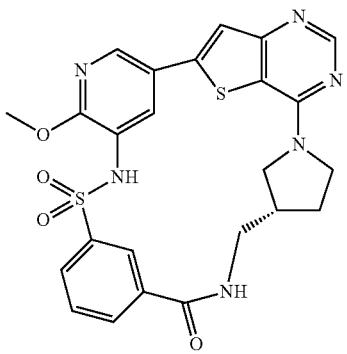 [SMILES: COc1ncc2cc1NS(=O)(=O)c1cccc(c1)C(=O)NC[C@H]1CCN(C1)c1ncnc3cc-2sc13] | VIII-93 | B-2 | 27 |
| 88 | 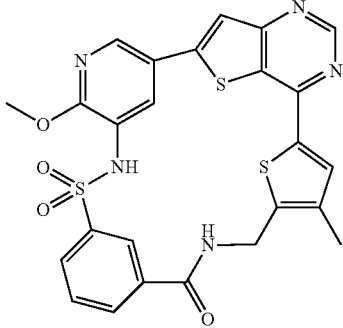 | VIII-95 | B-2 | 4 |

TABLE 2-continued

Final products

| Cpd. Nr. | Structure | Starting Material | General Method | Yield % |
|---|---|---|---|---|
| 89 | 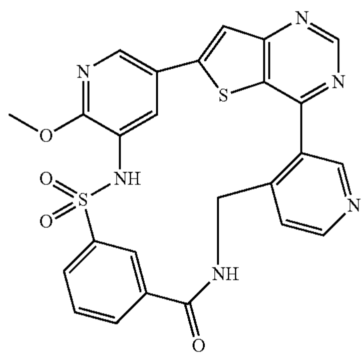 [SMILES: COc1ncc2cc1NS(=O)(=O)c1cccc(c1)C(=O)NCc1ccncc1-c1ncnc3cc-2sc13] | VIII-98 | B-2 | 25 |
| 90 | 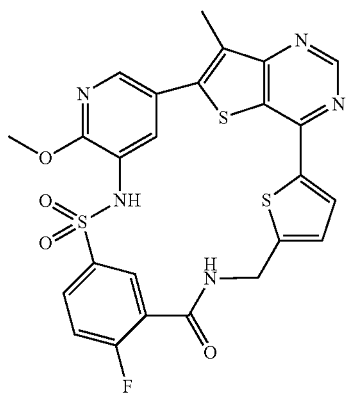 [SMILES: COc1ncc2cc1NS(=O)(=O)c1ccc(F)c(c1)C(=O)NCC1=CC=C(S1)c1ncnc3c(C)c-2sc13] | XIII-14 | B-2 | 16 |
| 91 | 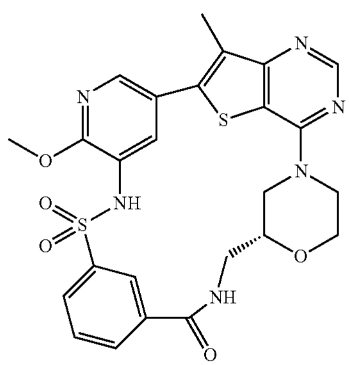 [SMILES: COc1ncc2cc1NS(=O)(=O)c1cccc(c1)C(=O)NC[C@@H]1CN(CCO1)c1ncnc3c(C)c-2sc13] | XIII-21 | B-2 | 49 |
| 92 | 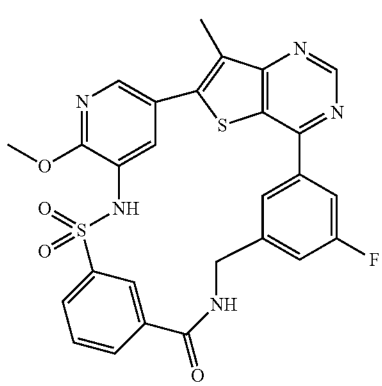 [SMILES: COc1ncc2cc1NS(=O)(=O)c1cccc(c1)C(=O)NCc1cc(F)cc(c1)-c1ncnc3c(C)c-2sc13] | XIII-25 | B-2 | 37 |

TABLE 2-continued

Final products

| Cpd. Nr. | Structure | Starting Material | General Method | Yield % |
|---|---|---|---|---|
| 93 | 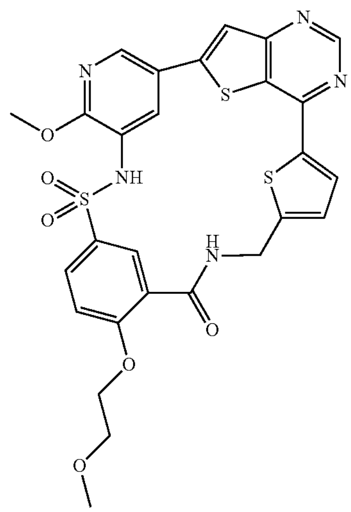 [SMILES: COCCOc1ccc2cc1C(=O)NCC1=CC=C(S1)c1ncnc3cc(sc13)-c1cnc(OC)c(c1)NS2(=O)=O] | VIII-101 | B-2 | 24 |
| 94 | 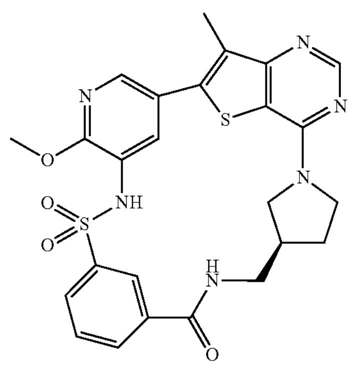 [SMILES: COc1ncc2cc1NS(=O)(=O)c1cccc(c1)C(=O)NC[C@@H]1CCN(C1)c1ncnc3c(C)c-2sc13] | XIII-29 | B-2 | 42 |
| 95 | 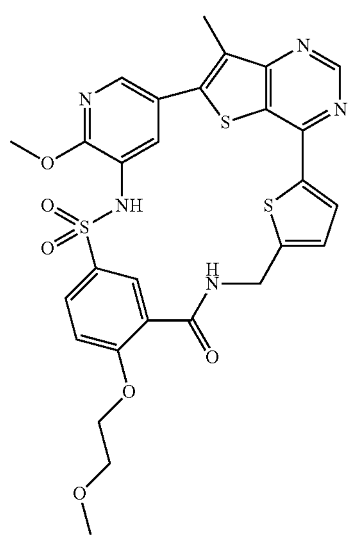 [SMILES: COCCOc1ccc2cc1C(=O)NCC1=CC=C(S1)c1ncnc3c(C)c(sc13)-c1cnc(OC)c(c1)NS2(=O)=O] | XIII-32 | B-2 | 29 |

TABLE 2-continued

Final products

| Cpd. Nr. | Structure | Starting Material | General Method | Yield % |
|---|---|---|---|---|
| 96 | 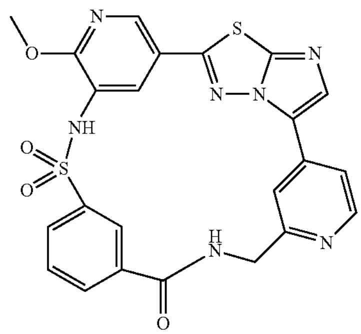 [SMILES: COc1ncc2cc1NS(=O)(=O)c1cccc(c1)C(=O)NCc1cc(ccn1)-c1cnc3sc-2nn13] | II-16 | B-2 | 1 |
| 97 | 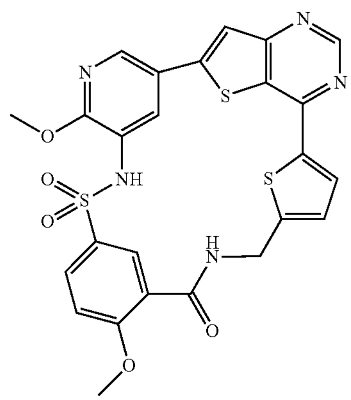 [SMILES: COc1ccc2cc1C(=O)NCC1=CC=C(S1)c1ncnc3cc(sc13)-c1cnc(OC)c(c1)NS2(=O)=O] | VIII-103 | B-2 | 17 |
| 98 | 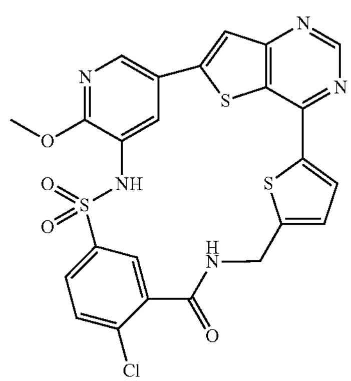 [SMILES: COc1ncc2cc1NS(=O)(=O)c1ccc(Cl)c(c1)C(=O)NCC1=CC=C(S1)c1ncnc3cc-2sc13] | VIII-105 | B-2 | 16 |
| 99 | 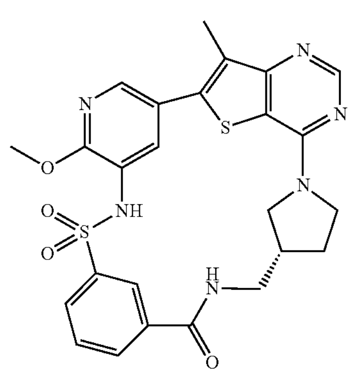 [SMILES: COc1ncc2cc1NS(=O)(=O)c1cccc(c1)C(=O)NC[C@H]1CCN(C1)c1ncnc3c(C)c-2sc13] | XIII-36 | B-2 | 29 |

TABLE 2-continued

Final products

| Cpd. Nr. | Structure | Starting Material | General Method | Yield % |
|---|---|---|---|---|
| 100 | 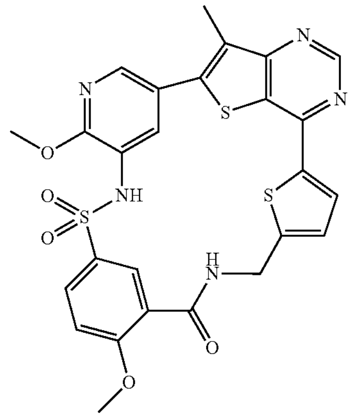 [SMILES: COc1ccc2cc1C(=O)NCC1=CC=C(S1)c1ncnc3c(C)c(sc13)-c1cnc(OC)c(c1)NS2(=O)=O] | XIII-38 | B-2 | 25 |
| 101 | 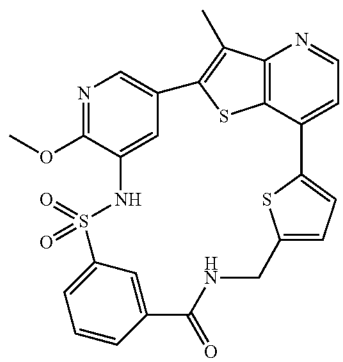 [SMILES: COc1ncc2cc1NS(=O)(=O)c1cccc(c1)C(=O)NCC1=CC=C(S1)c1ccnc3c(C)c-2sc13] | XVIII-07 | B-2 | 31 |
| 102 | 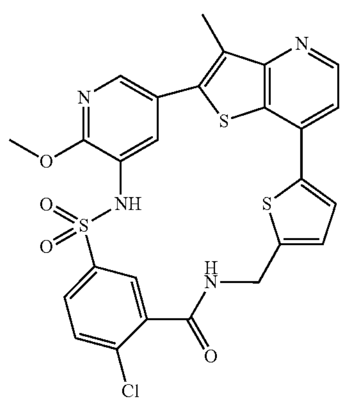 [SMILES: COc1ncc2cc1NS(=O)(=O)c1ccc(Cl)c(c1)C(=O)NCC1=CC=C(S1)c1ccnc3c(C)c-2sc13] | XIII-41 | B-2 | 26 |

Certain exemplary compounds of the invention described herein were prepared, characterised and assayed for their PI3Kα, PIM-1 and mTOR enzymatic activities.

TABLE 3

Analytical data and PI3K alpha, PIM-1 and mTOR activities

| Cpd. Nr. | $R_t$ | $[M + 1]^+$ | Meth. | PI3K | mTOR | PIM1 | $^1$H NMR (300 MHz; δ in ppm, J in Hz) |
|---|---|---|---|---|---|---|---|
| 1 | 3.67 | 524.3 | 1 | *** (2) | *** (64) | * | DMSO-$d_6$ δ 9.86 (s, 1H), 9.40 (t, J = 5.7 Hz, 1H), 9.01 (d, J = 4.4 Hz, 1H), 8.73 (m, 2H), 8.21 (d, J = 8.7 Hz, 1H), |

TABLE 3-continued

Analytical data and PI3K alpha, PIM-1 and mTOR activities

| Cpd. Nr. | $R_t$ | $[M + 1]^+$ | Meth. | PI3K | mTOR | PIM1 | $^1$H NMR (300 MHz; δ in ppm, J in Hz) |
|---|---|---|---|---|---|---|---|
| | | | | | | | 8.14 (m, 1H), 8.06 (m, 3H), 7.98 (m, 2H), 7.71 (m, 3H), 7.60 (d, J = 4.4 Hz, 1H), 4.56 (d, J = 5.5 Hz, 2H), 3.76 (s, 3H). |
| 2 | 3.11 | 510.0 | 1 | ** | * | * | DMSO-$d_6$ δ 11.96 (very broad s, 1H), 9.41 (t, J = 5.6 Hz, 1H), 8.99 (d, J = 4.4 Hz, 1H), 8.73 (d, J = 1.7 Hz, 1H), 8.72 (d, J = 1.9 Hz, 1H), 8.17 (m, 3H), 8.06 (m, 2H), 7.89 (dd, J = 8.7, 1.8 Hz, 1H), 7.70 (t, J = 7.8 Hz, 1H), 7.58 (m, 3H), 7.21 (d, J = 2.1 Hz, 1H), 4.54 (d, J = 5.5 Hz, 2H). |
| 3 | 4.21 | 523.1 | 1 | *** (1.6) | ** | * | DMSO-$d_6$ δ 9.84 (broad s, 1H), 9.37 (t, J = 5.9 Hz, 1H), 8.97 (d, J = 4.4 Hz, 1H), 8.18 (d, J = 8.7 Hz, 1H), 8.03 (m, 3H), 7.91 (m, 2H), 7.70 (m, 2H), 7.62 (m, 2H), 7.58 (d, J = 7.3 Hz, 1H), 7.51 (m, 3H), 4.50 (d, J = 5.7 Hz, 2H), 3.73 (s, 3H). |
| 4 | 4.69 | 541.1 | 1 | *** (3) | ** | * | DMSO-$d_6$ δ 9.86 (s, 1H), 9.31 (t, J = 5.8 Hz, 1H), 9.00 (d, J = 4.4 Hz, 1H), 8.20 (d, J = 8.7 Hz, 1H), 8.20 (m, 4H), 7.70 (t, J = 7.9 Hz, 1H), 7.58 (m, 5H), 7.43 (dd, J = 9.7, 8.5 Hz, 1H), 4.46 (m, 2H), 3.73 (s, 3H). |
| 5 | 4.55 | 541.1 | 1 | *** (23) | ** | * | DMSO-$d_6$ δ 9.83 (s, 1H), 9.35 (m, 1H), 9.02 (d, J = 4.3 Hz, 1H), 8.19 (d, J = 8.7 Hz, 1H), 8.13 (m, 1H), 8.03 (m, 3H), 7.97 (dd, J = 8.7, 1.9 Hz, 1H), 7.70 (m, 3H), 7.51 (m, 3H), 7.40 (t, J = 7.5 Hz, 1H), 4.69 (dd, J = 13.7, 6.5 Hz, 1H), 4.36 (dd, J = 13.9, 3.3 Hz, 1H), 3.80 (s, 3H). |
| 6 | 2.90 | 530.2 | 1 | *** (11) | *** (72) | * | DMSO-$d_6$ δ 10.16 (broad s, 1H), 8.93 (t, J = 6.2 Hz, 1H), 8.71 (d, J = 4.9 Hz, 1H), 8.31 (m, 1H), 8.24 (m, 2H), 8.01 (m, 2H), 7.95 (d, J = 2.2 Hz, 1H), 7.91 (m, 2H), 7.79 (t, J = 7.8 Hz, 1H), 7.05 (d, J = 4.9 Hz, 1H), 3.94 (s, 3H), 3.50 (m, 2H), 3.37 (m, 2H), 2.77 (m, 2H), 1.81 (m, 3H), 1.65 (m, 2H). |
| 7 | 3.07 | 504.1 | 1 | * | * | * | DMSO-$d_6$ δ 8.92 (m, 1H), 8.82 (t, J = 5.5 Hz, 1H), 8.62 (m, 2H), 8.53 (d, J = 7.1 Hz, 1H), 8.31 (d, J = 2.2 Hz, 1H), 8.24 (dd, J = 8.8, 1.4 Hz, 1H), 8.17 (m, 2H), 7.94 (d, J = 8.8 Hz, 1H), 7.88 (d, J = 2.2 Hz, 1H), 7.77 (t, J = 7.8 Hz, 1H), 6.94 (d, J = 7.2 Hz, 1H), 4.01 (s, 3H), 3.60 (m, 2H), 3.37 (m, 2H), 1.83 (m, 2H), 1.62 (m, 2H). |
| 8 | 3.87 | 520.2 | 1 | *** (7) | * | * | DMSO-$d_6$ δ 10.56 (s, 1H), 9.70 (t, J = 5.8 Hz, 1H), 8.95 (s, 1H), 8.79 (s, 1H), 8.57 (s, 1H), 8.34 (d, J = 2.0 Hz, 1H), 8.21 (m, 2H), 8.16 (d, J = 7.8 Hz, 1H), 7.97 (s, 1H), 7.89 (d, J = 2.1 Hz, 1H), 7.80 (t, J = 7.8 Hz, 1H), 4.68 (d, J = 5.6 Hz, 2H), 4.02 (s, 3H). |

TABLE 3-continued

Analytical data and PI3K alpha, PIM-1 and mTOR activities

| Cpd. Nr. | R$_t$ | [M + 1]$^+$ | Meth. | PI3K | mTOR | PIM1 | $^1$H NMR (300 MHz; δ in ppm, J in Hz) |
|---|---|---|---|---|---|---|---|
| 9 | 3.14 | 506.0 | 1 | ** | * | ** | DMSO-d$_6$ δ 9.60 (t, J = 5.5 Hz, 1H), 8.93 (d, J = 2.1 Hz, 1H), 8.64 (s, 1H), 8.55 (d, J = 1.9 Hz, 1H), 8.17 (t, J = 1.8 Hz, 1H), 8.12 (m, 1H), 8.04 (m, 1H), 7.90 (s, 1H), 7.72 (m, 1H), 7.59 (m, 1H), 7.35 (m, 1H), 4.66 (d, J = 5.5 Hz, 2H). |
| 10 | 3.94 | 560.1 | 1 | *** (0.03) | *** (22) | * | DMSO-d$_6$ δ 10.47 (s, 1H), 9.14 (t, J = 5.4 Hz, 1H), 9.02 (d, J = 4.4 Hz, 1H), 8.74 (m, 2H), 8.22 (d, J = 8.7 Hz, 1H), 7.99 (m, 3H), 7.72 (m, 3H), 7.60 (d, J = 4.4 Hz, 1H), 7.55 (d, J = 1.8 Hz, 1H), 4.52 (d, J = 5.5 Hz, 2H), 3.77 (s, 3H). |
| 11 | 3.27 | 514.1 | 1 | *** (0.4) | *** (4) | * | DMSO-d$_6$ δ 9.97 (s, 1H), 9.68 (t, J = 5.8 Hz, 1H), 9.23 (d, J = 7.4 Hz, 1H), 8.94 (d, J = 1.3 Hz, 1H), 8.81 (s, 1H), 8.74 (m, 2H), 8.49 (d, J = 1.3 Hz, 1H), 8.34 (t, J = 1.8 Hz, 1H), 8.15 (d, J = 2.2 Hz, 1H), 8.09 (m, 1H), 8.03 (m, 1H), 7.70 (t, J = 7.8 Hz, 1H), 7.65 (d, J = 7.5 Hz, 1H), 4.60 (d, J = 5.6 Hz, 2H), 4.02 (s, 3H). |
| 12 | 3.32 | 514.1 | 1 | *** (0.4) | *** (5) | * | DMSO-d$_6$ δ 9.93 (broad s, 1H), 9.56 (t, J = 5.6 Hz, 1H), 8.95 (d, J = 1.8 Hz, 1H), 8.60 (d, J = 1.6 Hz, 1H), 8.48 (m, 1H), 8.37 (m, 3H), 8.04 (m, 2H), 7.92 (d, J = 2.1 Hz, 1H), 7.73 (d, J = 7.8 Hz, 1H), 7.67 (d, J = 9.5 Hz, 1H), 4.56 (d, J = 5.5 Hz, 2H), 3.91 (s, 3H). |
| 13 | 4.09 | 513.1 | 1 | *** (0.4) | *** (10) | * | DMSO-d$_6$ δ 9.91 (broad s, 1H), 9.46 (t, J = 5.7 Hz, 1H), 8.37 (m, 2H), 8.27 (d, J = 9.4 Hz, 1H), 8.14 (s, 1H), 8.03 (m, 3H), 7.88 (d, J = 2.2 Hz, 1H), 7.69 (m, 2H), 7.61 (d, J = 9.5 Hz, 1H), 7.50 (t, J = 7.6 Hz, 1H), 7.40 (m, 1H), 4.54 (d, J = 5.6 Hz, 2H), 3.88 (s, 3H). |
| 14 | 3.37 | 577.1 | 1 | ** | * | ** | DMSO-d$_6$ δ 10.04 (broad s, 1H), 8.96 (t, J = 5.9 Hz, 1H), 8.92 (d, J = 2.0 Hz, 1H), 8.57 (t, J = 5.8 Hz, 1H), 8.50 (m, 2H), 8.44 (m, 1H), 8.16 (d, J = 2.2 Hz, 1H), 8.10 (m, 3H), 7.94 (s, 1H), 7.75 (m, 1H), 4.36 (d, J = 5.9 Hz, 2H), 3.84 (d, J = 5.8 Hz, 2H), 3.77 (s, 3H). |
| 15 | 3.89 | 524.1 | 1 | *** (20) | ** | * | DMSO-d$_6$ δ 9.87 (broad s, 1H), 9.49 (t, J = 5.8 Hz, 1H), 9.02 (d, J = 4.4 Hz, 1H), 8.75 (d, J = 5.1 Hz, 1H), 8.19 (d, J = 8.7 Hz, 1H), 8.15 (m, 1H), 8.09 (d, J = 7.8 Hz, 1H), 8.00 (m, 2H), 7.91 (dd, J = 8.7, 1.8 Hz, 1H), 7.70 (m, 2H), 7.65 (s, 1H), 7.57 (m, 2H), 7.51 (d, J = 2.0 Hz, 1H), 4.68 (d, J = 5.8 Hz, 2H), 3.79 (s, 3H). |
| 16 | 4.87 | 513.1 | 1 | *** (0.9) | *** (4) | * | DMSO-d$_6$ δ 9.90 (s, 1H), 9.57 (t, J = 5.7 Hz, 1H), 9.18 (d, J = 7.4 Hz, 1H), 8.72 (m, 2H), 8.62 (s, 1H), 8.12 (d, J = 2.0 Hz, 1H), 8.08 (d, J = 7.5 Hz, 1H), 7.99 (m, 2H), 7.69 |

TABLE 3-continued

Analytical data and PI3K alpha, PIM-1 and mTOR activities

| Cpd. Nr. | $R_t$ | $[M + 1]^+$ | Meth. | PI3K | mTOR | PIM1 | $^1$H NMR (300 MHz; δ in ppm, J in Hz) |
|---|---|---|---|---|---|---|---|
| | | | | | | | (d, J = 7.8 Hz, 1H), 7.65 (m, 1H), 7.59 (d, J = 7.5 Hz, 1H), 7.43 (t, J = 7.6 Hz, 1H), 7.27 (m, 1H), 4.58 (d, J = 5.7 Hz, 2H), 4.01 (s, 3H). |
| 17 | 4.97 | 519.0 | 1 | *** | ** | * | DMSO-d$_6$ δ 10.52 (s, 1H), 9.67 (t, J = 5.8 Hz, 1H), 8.79 (s, 1H), 8.31 (s, 1H), 8.16 (t, J = 8.0 Hz, 2H), 7.94 (s, 1H), 7.91 (d, J = 2.0 Hz, 1H), 7.82-7.73 (m, 2H), 7.68 (d, J = 7.8 Hz, 1H), 7.47 (t, J = 7.7 Hz, 1H), 7.35 (d, J = 7.6 Hz, 1H), 4.64 (d, J = 5.7 Hz, 2H), 4.01 (s, 3H). |
| | | | | (9) | | | |
| 18 | 3.29 | 517.2 | 1 | *** | *** | * | DMSO-d$_6$ δ 10.36 (s, 1H), 8.75 (t, J = 5.4 Hz, 1H), 8.62 (d, J = 1.9 Hz, 1H), 8.51 (m, 1H), 8.23 (d, J = 4.7 Hz, 2H), 8.18 (d, J = 9.5 Hz, 1H), 8.02 (m, 2H), 7.85 (d, J = 2.1 Hz, 1H), 7.82 (d, J = 7.8 Hz, 1H), 7.76 (d, J = 9.7 Hz, 1H), 7.59 (t, J = 7.8 Hz, 1H), 4.48 (s, 2H), 4.04 (s, 3H), 3.72 (s, 2H). |
| | | | | (5) | (67) | | |
| 19 | 3.24 | 527.1 | 1 | *** | *** | * | DMSO-d$_6$ δ 10.28 (bs, 1H), 8.86 (d, J = 4.5 Hz, 2H), 8.34 (s, 1H), 8.30 (s, 1H), 8.21 (s, 1H), 8.13-8.05 (m, 3H), 8.05-7.94 (m, 2H), 7.90 (s, 1H), 7.75-7.62 (m, 2H), 7.50 (d, J = 4.5 Hz, 1H), 4.43 (s, 2H), 3.95 (s, 3H), 3.78 (s, 2H). |
| | | | | (4) | (21) | | |
| 20 | 3.18 | 513.0 | 1 | *** | ** | * | DMSO-d$_6$ δ 12.26 (s, 1H), 10.12 (s, 1H), 9.62 (t, J = 5.6 Hz, 1H), 8.85 (d, J = 2.0 Hz, 1H), 8.81 (s, 1H), 8.50 (d, J = 2.0 Hz, 1H), 8.46 (d, J = 1.7 Hz, 1H), 8.22-8.11 (m, 4H), 8.07 (d, J = 1.8 Hz, 1H), 7.81-7.74 (m, 1H), 7.74 (d, J = 2.2 Hz, 1H), 4.61 (d, J = 5.5 Hz, 2H), 3.94 (s, 3H). |
| | | | | (80) | | | |
| 21 | 4.44 | 531.1 | 1 | *** | * | ** | DMSO-d$_6$ δ 9.56 (t, J = 5.3 Hz, 1H), 9.16 (s, 1H), 9.09 (s, 1H), 9.02 (s, 1H), 8.80 (s, 1H), 8.44 (s, 1H), 8.13 (m, 3H), 7.74 (m, 3H), 4.68 (d, J = 5.2 Hz, 2H), 3.94 (s, 3H). |
| | | | | (85) | | | |
| 22 | 4.67 | 524.1 | 1 | *** | *** | * | DMSO δ 9.87 (s, 1H), 9.42 (t, J = 5.5 Hz, 1H), 9.38 (s, 1H), 8.18 (s, 2H), 8.14 (s, 1H), 8.04 (m, 3H), 7.93 (s, 1H), 7.72 (m, 2H), 7.80 (m, 2H), 7.63 (m, 2H), 4.53 (d, J = 5.5 Hz, 2H), 3.76 (s, 3H). |
| | | | | (0.1) | (30) | | |
| 23 | 0.41 | 532.2 | 1 | *** | *** | * | DMSO δ 8.59 (t, J = 5.5 Hz, 1H), 8.52 (d, J = 1.8 Hz, 1H), 8.16 (s, 1H), 8.13 (d, J = 9.6 Hz, 1H), 8.04 (m, 1H), 7.96 (d, J = 2.0 Hz, 1H), 7.92 (m, 1H), 7.78 (d, J = 9.6 Hz, 1H), 7.75 (s, 1H), 7.65 (t, J = 7.8 Hz, 1H), 6.42 (m, 1H), 4.02 (s, 3H), 3.49 (m, 2H), 3.36 (m, 2H), 2.82 (t, J = 5.2 Hz, 2H), 2.76 (m, 2H), 2.61 (s, 2H). |
| | | | | (5) | (22) | | |
| 24 | 2.88 | 544.2 | 1 | *** | *** | * | DMSO δ 8.62 (d, J = 4.8 Hz, 1H), 8.15 (s, 1H), 8.02 (m, 2H), 7.96 (m, 2H), 7.67 (m, 4H), 6.91 (d, J = 4.9 Hz, 1H), 4.02 (s, 3H), 3.40 (m, 4H), |
| | | | | (3) | (4) | | |

TABLE 3-continued

Analytical data and PI3K alpha, PIM-1 and mTOR activities

| Cpd. Nr. | $R_t$ | $[M + 1]^+$ | Meth. | PI3K | mTOR | PIM1 | $^1$H NMR (300 MHz; δ in ppm, J in Hz) |
|---|---|---|---|---|---|---|---|
| 25 | 2.71 | 522.3 | 1 | *** (20) | *** (54) | * | 3.05 (s, 3H), 2.73 (m, 2H), 1.94 (m, 1H), 1.71 (m, 2H), 0.95 (m, 2H). DMSO δ 8.87 (d, J = 7.5 Hz, 1H), 8.68 (t, J = 5.3 Hz, 1H), 8.51 (s, 1H), 8.22 (s, 1H), 8.18 (s, 1H), 7.98 (d, J = 1.6 Hz, 1H), 7.91 (m, 2H), 7.56 (m, 2H), 6.20 (m, 1H), 3.9 (s, 3H), 3.48 (m, 2H), 3.34 (m, 2H), 2.90 (m, 2H), 2.77 (m, 2H), 2.60 (m, 2H). |
| 26 | 3.99 | 517.3 | 1 | *** (4) | *** (40) | * | DMSO δ 10.14 (s, 1H), 9.07 (d, J = 7.5 Hz, 1H), 8.84 (t, J = 5.2 Hz, 1H), 8.80 (d, J = 1.7 Hz, 1H), 8.71 (s, 1H), 8.49 (s, 1H), 8.00 (s, 1H), 7.96 (m, 1H), 7.86 (m, 1H), 7.81 (s, 1H), 7.75 (d, J = 2.1 Hz, 1H), 7.56 (m, 2H), 4.45 (m, 2H), 4.04 (s, 3H), 3.66 (s, 2H). |
| 27 | 4.18 | 531.1 | 1 | ** | * | *** (40) | DMSO δ 10.74 (s, 1H), 9.90 (t, J = 6.0 Hz, 1H), 9.29 (s, 1H), 9.26 (d, J = 1.9 Hz, 1H), 8.88 (m, 2H), 8.67 (s, 1H), 8.49 (m, 1H), 8.28 (d, J = 7.7 Hz, 1H), 8.21 (m, 2H), 7.83 (m, 1H), 7.44 (s, 1H), 4.73 (d, J = 5.8 Hz, 2H), 4.03 (s, 3H). |
| 28 | 4.92 | 530.2 | 1 | ** | * | ** | DMSO δ 10.71 (s, 1H), 9.90 (t, J = 5.7 Hz, 1H), 9.24 (s, 1H), 8.93 (s, 1H), 8.64 (s, 1H), 8.27 (d, J = 7.5 Hz, 1H), 8.19 (m, 4H), 7.81 (m, 1H), 7.65 (d, J = 4.5 Hz, 2H), 7.46 (d, J = 1.8 Hz, 1H), 4.70 (d, J = 5.6 Hz, 2H), 4.02 (s, 3H). |
| 29 | 4.51 | 559.3 | 1 | *** (6) | ** | * | DMSO δ 10.46 (s, 1H), 9.13 (t, J = 5.7 Hz, 1H), 8.98 (d, J = 4.4 Hz, 1H), 8.20 (d, J = 8.6 Hz, 1H), 7.97 (dd, J = 8.7, 1.9 Hz, 1H), 7.94 (d, J = 2.2 Hz, 1H), 7.74 (d, J = 2.2 Hz, 1H), 7.58 (m, 8H), 4.46 (m, 2H), 3.76 (s, 3H). |
| 30 | 2.58 | 513.1 | 1 | *** (11) | *** (49) | * | DMSO δ 9.40 (t, J = 5.2 Hz, 1H), 8.73 (d, J = 2.1 Hz, 1H), 8.69 (s, 1H), 8.61 (m, 2H), 8.44 (t, J = 1.9 Hz, 1H), 8.22-8.04 (m, 3H), 7.96 (s, 1H), 7.91 (d, J = 2.2 Hz, 1H), 7.82-7.66 (m, 2H), 7.59 (dd, J = 9.4, 1.5 Hz, 1H), 4.59 (d, J = 5.2 Hz, 2H), 3.93 (s, 3H). |
| 31 | 3.57 | 525.1 | 1 | *** (2) | *** (23) | * | DMSO δ 9.83 (s, 1H), 9.26 (t, J = 6.1 Hz, 1H), 9.09 (d, J = 4.4 Hz, 1H), 8.83 (m, 1H), 8.67 (m, 1H), 8.59 (d, J = 8.7 Hz, 1H), 8.32-8.17 (m, 2H), 8.08-7.93 (m, 4H), 7.91 (d, J = 4.4 Hz, 1H), 7.72 (t, J = 7.8 Hz, 1H), 7.59 (m, 1H), 4.50 (d, J = 5.9 Hz, 2H), 3.50 (s, 3H). |
| 32 | 2.83 | 531.2 | 1 | *** (2) | *** (5) | * | DMSO δ 10.09 (s, 1H), 8.85 (t, J = 6.1 Hz, 1H), 8.62 (s, 1H), 8.37-8.26 (m, 2H), 8.16 (m, 1H), 8.05 (m, 2H), 7.85 (d, J = 8.7 Hz, 1H), 7.81-7.65 (m, 3H), 4.05 (m, 2H), 3.98 (s, 3H), 3.59-3.44 (m, |

TABLE 3-continued

Analytical data and PI3K alpha, PIM-1 and mTOR activities

| Cpd. Nr. | $R_t$ | $[M + 1]^+$ | Meth. | PI3K | mTOR | PIM1 | $^1$H NMR (300 MHz; δ in ppm, J in Hz) |
|---|---|---|---|---|---|---|---|
| | | | | | | | 2H), 3.04 (t, J = 11.9 Hz, 2H), 2.01 (m, 1H), 1.93-1.61 (m, 4H). |
| 33 | 4.16 | 528.2 | 1 | *** (1.3) | *** (4.8) | * | DMSO δ 10.23 (s, 1H), 9.19 (s, 1H), 8.98 (t, J = 5.8 Hz, 1H), 8.69 (s, 1H), 8.42 (t, J = 1.9 Hz, 1H), 8.30-8.00 (m, 7H), 7.72 (t, J = 7.8 Hz, 1H), 7.67 (d, J = 2.2 Hz, 1H), 4.42 (m, 2H), 3.97 (s, 3H), 3.77 (m, 2H). |
| 34 | 3.14 | 516.1 | 1 | *** (7.6) | *** (66) | * | DMSO δ 10.15 (s, 1H), 9.02 (t, J = 5.7 Hz, 1H), 8.49 (m, 1H), 8.36 (s, 1H), 8.21 (s, 1H), 8.19-8.08 (m, 3H), 7.85 (s, 1H), 7.78-7.62 (m, 3H), 7.56 (d, J = 2.2 Hz, 1H), 7.47 (dd, J = 9.2, 1.8 Hz, 1H), 4.39 (m, 2H), 3.96 (s, 3H), 3.81-3.60 (m, 2H). |
| 35 | 4.69 | 524.3 | 1 | *** (5) | *** (16) | * | DMSO δ 9.81 (s, 1H), 9.20 (t, J = 6.0 Hz, 1H), 9.04 (d, J = 4.4 Hz, 1H), 8.56 (d, J = 8.8 Hz, 1H), 8.21 (d, J = 8.7 Hz, 1H), 8.07 (d, J = 2.3 Hz, 1H), 8.02-7.93 (m, 3H), 7.81 (m, 1H), 7.76 (d, J = 4.4 Hz, 1H), 7.74-7.58 (m, 3H), 7.53 (t, J = 7.5 Hz, 1H), 7.44(m, 1H), 4.45 (d, J = 6.0 Hz, 2H), 3.52 (s, 3H). |
| 36 | 4.11 | 534.2 | 1 | ** | * | ** | DMSO δ 10.76 (s, 1H), 9.20 (t, J = 5.4 Hz, 1H), 9.06 (s, 1H), 8.90 (m, 1H), 8.65 (d, J = 2.3 Hz, 1H), 8.52 (s, 1H), 8.19 (s, 1H), 8.14 (m, 2H), 8.09 (s, 1H), 7.73 (t, J = 7.8 Hz, 1H), 7.25 (d, J = 2.2 Hz, 1H), 4.61 (m, 2H), 4.03 (s, 3H), 3.70 (m, 2H). |
| 37 | 5.23 | 530.0 | 1 | *** (20) | * | * | DMSO δ 10.34 (s, 1H), 9.63 (t, J = 4.8 Hz, 1H), 9.14 (s, 1H), 9.11 (s, 1H), 8.21 (m, 3H), 8.05 (s, 1H), 7.97 (m, 1H), 7.88 (s, 1H), 7.83 (d, J = 2.2 Hz, 1H), 7.79 (t, J = 7.8 Hz, 1H), 7.63 (m, 2H), 4.65 (d, J = 4.9 Hz, 2H), 3.99 (s, 3H). |
| 38 | 3.15 | 537.2 | 1 | * | * | * | DMSO δ 10.49 (s, 1H), 8.64 (m, 1H), 8.53 (m, 2H), 8.41 (s, 1H), 7.97 (d, J = 8.5 Hz, 1H), 7.90 (d, J = 8.5 Hz, 1H), 7.62 (m, 2H), 6.85 (s, 1H), 4.38 (m, 2H), 4.01 (s, 3H), 3.50 (m, 2H), 3.23 (m, 2H), 2.14 (m, 1H), 1.67 (m, 2H), 1.25 (d, J = 7.0 Hz, 2H). |
| 39 | 4.47 | 549.3 | 1 | *** (0.05) | *** (0.3) | * | DMSO δ 10.18 (s, 1H), 8.91 (d, J = 4.4 Hz, 1H), 8.45 (d, J = 2.1 Hz, 1H), 8.16 (m, 2H), 7.96 (m, 1H), 7.91 (s, 1H), 7.75 (m, 3H), 7.66 (d, J = 2.2 Hz, 1H), 7.47 (m, 3H), 7.43 (s, 1H), 4.54 (s, 2H), 4.02 (s, 3H), 3.93 (m, 2H), 3.08 (m, 2H). |
| 40 | 1.19 | 531.3 | 1 | *** (3) | *** (36) | * | DMSO δ 10.55 (broad s, 1H), 8.62 (t, J = 5.5 Hz, 1H), 8.40 (m, 1H), 8.19 (d, J = 2.3 Hz, 1H), 8.06 (m, 2H), 8.00 (s, 1H), 7.70 (t, J = 7.8 Hz, 1H), 7.63 (d, J = 9.4 Hz, 1H), 7.53 (m, 3H), 6.04 (m, 1H), 3.97 |

TABLE 3-continued

Analytical data and PI3K alpha, PIM-1 and mTOR activities

| Cpd. Nr. | R$_t$ | [M + 1]$^+$ | Meth. | PI3K | mTOR | PIM1 | $^1$H NMR (300 MHz; δ in ppm, J in Hz) |
|---|---|---|---|---|---|---|---|
| | | | | | | | (s, 3H), 3.53 (m, 2H), 3.25 (m, 2H), 2.76 (m, 4H), 2.39 (m, 2H). |
| 41 | 3.96 | 525.0 | 1 | *** (3) | *** (16) | * | DMSO δ 9.88 (broad s, 1H), 9.44 (m, 2H), 8.95 (d, J = 1.8 Hz, 1H), 8.82 (d, J = 1.5 Hz, 1H), 8.25 (m, 4H), 8.08 (m, 3H), 7.99 (s, 1H), 7.84 (d, J = 2.1 Hz, 1H), 7.73 (t, J = 7.8 Hz, 1H), 4.59 (d, J = 5.3 Hz, 2H), 3.82 (s, 3H). |
| 42 | 4.42 | 531.0 | 1 | ** | * | ** | DMSO δ 10.76 (s, 1H), 9.97 (s, 1H), 9.33 (s, 1H), 8.92 (s, 1H), 8.84 (d, J = 5.2 Hz, 1H), 8.66 (s, 1H), 8.32-8.17 (m, 3H), 8.13 (m, 2H), 7.83 (t, J = 7.7 Hz, 1H), 7.43 (s, 1H), 4.77 (d, J = 5.6 Hz, 2H), 4.02 (s, 3H). |
| 43 | 3.75 | 501.1 | 1 | *** (44) | * | *** (41) | DMSO δ 9.86 (m, 1H), 9.32 (s, 1H), 9.26 (s, 1H), 8.93-8.79 (m, 3H), 8.51 (s, 1H), 8.30 (s, 2H), 8.22 (m, 1H), 8.01 (d, J = 7.9 Hz, 1H), 7.76 (t, J = 7.8 Hz, 1H), 7.48 (m, 1H), 4.73 (d, J = 5.5 Hz, 2H). |
| 44 | 4.26 | 567.0 | 1 | ** | * | * | DMSO δ 11.24 (s, 1H), 9.38 (m, 1H), 9.30 (s, 1H), 9.21 (d, J = 1.9 Hz, 1H), 8.83 (s, 1H), 8.68 (m, 1H), 8.61 (t, J = 7.9 Hz, 1H), 8.40 (m, 1H), 8.23 (s, 1H), 7.85 (t, J = 10.3 Hz, 1H), 7.36 (d, J = 1.9 Hz, 1H), 4.73 (d, J = 5.3 Hz, 2H), 4.01 (s, 3H). |
| 45 | 3.38 | 517.1 | 1 | * | * | ** | DMSO δ 9.87 (s, 1H), 9.25 (d, J = 2.0 Hz, 1H), 9.24 (s, 1H), 8.84 (s, 2H), 8.46 (s, 1H), 8.21 (t, J = 7.5 Hz, 2H), 8.03 (s, 1H), 8.01 (s, 1H), 7.80 (t, J = 7.8 Hz, 1H), 7.07 (s, 1H), 4.72 (d, J = 5.5 Hz, 2H). |
| 46 | 4.46 | 545.0 | 1 | * | * | * | DMSO δ 9.74 (t, J = 5.5 Hz, 1H), 9.30 (m, 2H), 8.97 (d, J = 2.1 Hz, 1H), 8.83 (m, 1H), 8.67 (m, 1H), 8.50 (s, 1H), 8.40 (d, J = 7.6 Hz, 1H), 8.26 (m, 1H), 8.23 (s, 1H), 7.89 (t, J = 7.9 Hz, 1H), 7.44 (d, J = 2.1 Hz, 1H), 4.73 (d, J = 5.4 Hz, 2H), 4.07 (s, 3H), 3.19 (s, 3H). |
| 47 | 4.09 | 517.0 | 1 | *** (99) | *** (8.5) | * | DMSO δ 10.86 (broad s, 1H), 10.62 (s, 1H), 9.24 (s, 1H), 8.96 (d, J = 2.1 Hz, 1H), 8.76 (d, J = 2.3 Hz, 1H), 8.56 (d, J = 2.3 Hz, 1H), 8.48 (m, 1H), 8.31 (t, J = 2.2 Hz, 1H), 8.03 (s, 1H), 7.85 (m, 1H), 7.60 (m, 2H), 7.21 (d, J = 2.3 Hz, 1H), 4.04 (s, 3H). |
| 48 | 4.29 | 549.1 | 1 | *** (48) | * | *** (52) | DMSO δ 10.74 (s, 1H), 9.47 (m, 1H), 9.29 (s, 1H), 9.22 (d, J = 2.2 Hz, 1H), 8.84 (d, J = 2.1 Hz, 1H), 8.66 (d, J = 2.2 Hz, 1H), 8.56 (dd, J = 6.4, 2.6 Hz, 1H), 8.44 (t, J = 2.2 Hz, 1H), 8.22 (m, 2H), 7.75 (dd, J = 10.2, 8.8 Hz, 1H), 7.46 (d, J = 2.2 Hz, 1H), 4.73 (d, J = 5.7 Hz, 2H), 4.03 (s, 3H). |

TABLE 3-continued

Analytical data and PI3K alpha, PIM-1 and mTOR activities

| Cpd. Nr. | $R_t$ | $[M + 1]^+$ | Meth. | PI3K | mTOR | PIM1 | $^1$H NMR (300 MHz; δ in ppm, J in Hz) |
|---|---|---|---|---|---|---|---|
| 49 | 3.39 | 494.1 | 1 | *** (68) | ** | * | DMSO δ 10.32 (s, 1H), 9.35 (t, J = 5.7 Hz, 1H), 9.03 (d, J = 4.4 Hz, 1H), 8.79 (d, J = 2.0 Hz, 1H), 8.73 (d, J = 2.1 Hz, 1H), 8.52 (d, J = 2.0 Hz, 1H), 8.46 (d, J = 2.3 Hz, 1H), 8.22 (d, J = 8.7 Hz, 1H), 8.01 (m, 5H), 7.67 (m, 2H), 7.61 (d, J = 4.4 Hz, 1H), 7.52 (t, J = 2.3 Hz, 1H), 4.50 (d, J = 5.7 Hz, 2H). |
| 50 | 4.91 | 559.2 | 1 | * | * | * | DMSO δ 10.54 (s, 1H), 9.90 (m, 1H), 9.27 (m, 2H), 8.88 (d, J = 12.0 Hz, 2H), 8.65 (d, J = 2.0 Hz, 1H), 8.49 (s, 1H), 8.25 (m, 3H), 7.84 (t, J = 7.8 Hz, 1H), 7.42 (d, J = 2.0 Hz, 1H), 5.37 (m, 1H), 4.74 (d, J = 5.4 Hz, 2H), 1.40 (d, J = 6.2 Hz, 6H). |
| 51 | 3.84 | 518.2 | 1 | ** | * | * | DMSO δ 10.19 (s, 1H), 9.07 (t, J = 4.7 Hz, 1H), 8.89 (s, 1H), 8.83 (m, 2H), 8.32 (s, 1H), 8.28 (s, 1H), 8.01 (d, J = 7.8 Hz, 1H), 7.85 (d, J = 7.9 Hz, 1H), 7.70 (s, 1H), 7.56 (t, J = 7.8 Hz, 1H), 7.35 (d, J = 1.7 Hz, 1H), 4.52 (m, 2H), 4.04 (s, 3H), 3.67 (m, 2H). |
| 52 | 4.24 | 549.1 | 1 | ** | * | ** | DMSO δ 11.16 (s, 1H), 9.90 (t, J = 5.6 Hz, 1H), 9.29 (s, 1H), 9.26 (d, J = 2.1 Hz, 1H), 8.92 (m, 1H), 8.85 (s, 1H), 8.66 (s, 1H), 8.45 (s, 1H), 8.37 (m, 1H), 8.21 (s, 1H), 7.67 (t, J = 9.2 Hz, 1H), 7.37 (d, J = 2.1 Hz, 1H), 4.73 (d, J = 5.5 Hz, 2H), 4.01 (s, 1H). |
| 53 | 4.88 | 599.1 | 1 | * | * | * | DMSO δ 10.78 (broad s, 1H), 10.12 (t, J = 5.6 Hz, 1H), 9.29 (s, 1H), 9.25 (d, J = 1.8 Hz, 1H), 9.18 (s, 1H), 8.88 (s, 1H), 8.71 (s, 1H), 8.64 (s, 1H), 8.61 (s, 1H), 8.51 (s, 1H), 8.22 (s, 1H), 7.42 (d, J = 1.9 Hz, 1H), 4.77 (d, J = 5.4 Hz, 2H), 4.04 (s, 3H). |
| 54 | 4.34 | 545.2 | 1 | ** | * | * | DMSO δ 10.73 (s, 1H), 9.88 (t, J = 5.5 Hz, 1H), 9.24 (d, J = 2.1 Hz, 1H), 8.88 (m, 1H), 8.84 (d, J = 1.9 Hz, 1H), 8.63 (d, J = 2.2 Hz, 1H), 8.46 (t, J = 2.0 Hz, 1H), 8.28 (d, J = 8.0 Hz, 1H), 8.21 (d, J = 8.4 Hz, 1H), 8.11 (s, 1H), 7.83 (t, J = 7.8 Hz, 1H), 7.42 (d, J = 2.2 Hz, 1H), 4.73 (d, J = 5.7 Hz, 2H), 4.02 (s, 3H), 2.79 (s, 3H). |
| 55 | 4.65 | 536.0 | 1 | ** | * | *** (12) | DMSO δ 10.82 (s, 1H), 9.88 (t, J = 5.8 Hz, 1H), 9.11 (s, 1H), 8.67 (m, 2H), 8.23 (m, 2H), 8.10 (s, 1H), 7.87 (m, 2H), 7.44 (d, J = 2.2 Hz, 1H), 7.26 (d, J = 3.7 Hz, 1H), 4.85 (d, J = 5.7 Hz, 2H), 4.05 (s, 3H). |
| 56 | 4.46 | 545.1 | 1 | *** (13) | ** | *** (56) | DMSO δ 10.69 (broad s, 1H), 9.83 (t, J = 5.3 Hz, 1H), 9.36 (s, 1H), 9.28 (d, J = 2.1 Hz, 1H), 8.85 (d, J = 1.7 Hz, 1H), 8.80 (s, 1H), 8.54 (t, J = 2.0 Hz, 1H), 8.20 (m, 3H), 7.79 |

TABLE 3-continued

Analytical data and PI3K alpha, PIM-1 and mTOR activities

| Cpd. Nr. | $R_t$ | $[M + 1]^+$ | Meth. | PI3K | mTOR | PIM1 | $^1$H NMR (300 MHz; δ in ppm, J in Hz) |
|---|---|---|---|---|---|---|---|
| | | | | | | | (t, J = 7.8 Hz, 1H), 7.53 (s, 1H), 4.71 (d, J = 5.4 Hz, 2H), 4.01 (s, 3H), 2.58 (s, 3H). |
| 57 | 4.44 | 548.1 | 1 | *** (0.8) | ** | ** | DMSO δ 10.68 (broad s, 1H), 9.21 (t, J = 5.1 Hz, 1H), 9.13 (s, 1H), 8.80 (s, 1H), 8.41 (s, 1H), 8.32 (s, 1H), 8.20 (m, 2H), 8.11 (d, J = 8.1 Hz, 1H), 7.75 (t, J = 7.8 Hz, 1H), 7.33 (d, J = 2.1 Hz, 1H), 4.59 (d, J = 5.0 Hz, 2H), 4.03 (s, 3H), 3.71 (m, 2H), 2.54 (s, 3H). |
| 58 | 4.20 | 535.0 | 1 | *** (3.6) | * | ** | DMSO δ 11.12 (broad s, 1H), 9.90 (t, J = 4.9 Hz, 1H), 9.34 (s, 1H), 9.27 (s, 1H), 8.91 (m, 3H), 8.49 (s, 1H), 8.42 (s, 1H), 8.28 (m, 2H), 7.85 (t, J = 7.7 Hz, 1H), 7.53 (s, 1H), 4.74 (d, J = 4.7 Hz, 2H). |
| 59 | 4.89 | 562.1 | 1 | * | * | * | DMSO δ 10.58 (s, 1H), 9.19 (t, J = 5.4 Hz, 1H), 9.05 (s, 1H), 8.90 (t, J = 1.7 Hz, 1H), 8.63 (d, J = 2.3 Hz, 1H), 8.51 (s, 1H), 8.15 (m, 3H), 8.07 (s, 1H), 7.75 (t, J = 7.8 Hz, 1H), 7.24 (d, J = 2.2 Hz, 1H), 5.37 (hept, J = 6.2 Hz, 1H), 4.61 (m, 2H), 3.71 (m, 2H), 1.41 (d, J = 6.2 Hz, 6H). |
| 60 | 5.32 | 573.1 | 1 | * | * | * | DMSO δ 10.70 (broad s, 1H), 9.87 (t, J = 5.9 Hz, 1H), 9.29 (d, J = 2.1 Hz, 1H), 8.87 (m, 1H), 8.84 (d, J = 1.7 Hz, 1H), 8.59 (s, 1H), 8.46 (m, 1H), 8.25 (d, J = 7.6 Hz, 1H), 8.18 (d, J = 8.1 Hz, 1H), 8.14 (s, 1H), 7.81 (t, J = 7.8 Hz, 1H), 7.40 (d, J = 2.0 Hz, 1H), 4.72 (d, J = 5.5 Hz, 2H), 4.00 (s, 3H), 3.32 (m, 1H), 1.40 (d, J = 6.9 Hz, 6H). |
| 61 | 5.17 | 576.1 | 1 | * | * | * | DMSO δ 10.74 (s, 1H), 9.19 (t, J = 5.1 Hz, 1H), 8.89 (m, 1H), 8.64 (d, J = 2.1 Hz, 1H), 8.47 (s, 1H), 8.15 (m, 3H), 8.05 (s, 1H), 7.75 (t, J = 7.9 Hz, 1H), 7.25 (d, J = 2.1 Hz, 1H), 4.61 (m, 2H), 4.04 (s, 3H), 3.71 (m, 2H), 3.22 (m, 1H), 1.34 (d, J = 6.9 Hz, 3H). |
| 62 | 4.14 | 530.0 | 1 | ** | * | *** (31) | DMSO δ 10.62 (broad s, 1H), 9.84 (t, J = 5.8 Hz, 1H), 8.89 (d, J = 2.3 Hz, 1H), 8.81 (m, 1H), 8.78 (m, 2H), 8.58 (d, J = 2.3 Hz, 1H), 8.39 (t, J = 2.2 Hz, 1H), 8.22 (m, 2H), 8.12 (s, 1H), 7.80 (t, J = 7.8 Hz, 1H), 7.69 (d, J = 4.9 Hz, 1H), 7.37 (d, J = 2.2 Hz, 1H), 4.68 (d, J = 5.7 Hz, 2H), 4.00 (s, 3H). |
| 63 | 4.19 | 548.0 | 1 | *** (15) | * | *** (47) | DMSO δ 10.64 (s, 1H), 9.52 (t, J = 5.9 Hz, 1H), 8.86 (d, J = 2.2 Hz, 1H), 8.78 (m, 2H), 8.61 (d, J = 2.2 Hz, 1H), 8.44 (dd, J = 6.5, 2.4 Hz, 1H), 8.37 (t, J = 2.2 Hz, 1H), 8.21 (m, 1H), 8.16 (s, 1H), 7.72 (t, J = 9.4 Hz, 1H), 7.66 (d, J = 4.8 Hz, 1H), 7.40 (d, J = 2.2 Hz, 1H), 4.65 (d, J = 5.8 Hz, 2H), 4.00 (s, 3H). |
| 64 | 3.37 | 539.2 | 1 | * | * | ** | DMSO δ 10.61 (s, 1H), 9.37 (m, 1H), 8.85 (s, 1H), 8.52 (s, 1H), 8.21 (m, 2H), 7.89 (s, |

TABLE 3-continued

Analytical data and PI3K alpha, PIM-1 and mTOR activities

| Cpd. Nr. | $R_t$ | $[M + 1]^+$ | Meth. | PI3K | mTOR | PIM1 | ¹H NMR (300 MHz; δ in ppm, J in Hz) |
|---|---|---|---|---|---|---|---|
| | | | | | | | 1H), 7.80 (t, J = 7.8 Hz, 2H), 7.46 (s, 1H), 4.80 (d, J = 14.0 Hz, 1H), 4.61 (d, J = 12.3 Hz, 1H), 4.01 (m, 4H), 3.64 (m, 2H), 3.42 (m, 2H), 3.25 (m, 1H), 3.12 (m, 1H). |
| 65 | 5.24 | 548.1 | 1 | ** | * | * | DMSO δ 10.71 (s, 1H), 9.89 (m, 1H), 9.23 (s, 1H), 8.94 (s, 1H), 8.66 (s, 1H), 8.23 (m, 5H), 7.82 (m, 1H), 7.54 (m, 1H), 7.43 (s, 1H), 4.70 (d, J = 4.5 Hz, 2H), 4.02 (s, 3H). |
| 66 | 3.39 | 539.2 | 1 | ** | * | *** (88) | DMSO δ 10.62 (broad s, 1H), 9.37 (t, J = 5.4 Hz, 1H), 8.84 (s, 1H), 8.51 (s, 1H), 8.48 (s, 1H), 8.20 (d, J = 7.4 Hz, 2H), 7.88 (s, 1H), 7.80 (t, J = 7.9 Hz, 1H), 7.46 (s, 1H), 4.80 (d, J = 13.4 Hz, 1H), 4.61 (d, J = 13.7 Hz, 1H), 4.02 (m, 4H), 3.65 (m, 2H), 3.42 (m, 2H), 3.24 (m, 1H), 3.11 (m, 1H). |
| 67 | 5.02 | 549.1 | 1 | *** (0.5) | *** (12) | * | DMSO δ 10.56 (s, 1H), 9.44 (t, J = 6.0 Hz, 1H), 9.19 (d, J = 7.3 Hz, 1H), 8.54 (m, 2H), 8.24 (t, J = 7.7 Hz, 1H), 8.14 (d, J = 2.1 Hz, 1H), 7.80 (m, 1H), 7.69 (t, J = 10.0 Hz, 1H), 7.62 (m, 1H), 7.52 (d, J = 7.5 Hz, 1H), 7.44 (t, J = 7.6 Hz, 1H), 7.28 (d, J = 7.5 Hz, 1H), 4.49 (d, J = 5.8 Hz, 2H), 3.97 (s, 3H). |
| 68 | 4.99 | 550.1 | 1 | *** (2.5) | *** (90) | *** (28) | DMSO δ 10.79 (broad s, 1H), 9.89 (t, J = 5.5 Hz, 1H), 9.17 (s, 1H), 8.60 (s, 1H), 8.36 (m, 1H), 8.26 (d, J = 7.8 Hz, 1H), 8.19 (d, J = 7.8 Hz, 1H), 7.91 (d, J = 3.7 Hz, 1H), 7.85 (t, J = 7.6 Hz, 1H), 7.61 (s, 1H), 7.25 (d, J = 3.6 Hz, 1H), 4.83 (d, J = 4.8 Hz, 2H), 4.05 (s, 3H), 2.60 (s, 3H). |
| 69 | 4.53 | 520.0 | 1 | ** | * | ** | DMSO δ 10.60 (s, 1H), 9.83 (t, J = 5.7 Hz, 1H), 9.05 (s, 1H), 8.99 (m, 1H), 8.64 (d, J = 2.1 Hz, 1H), 8.26 (d, J = 7.8 Hz, 1H), 8.17 (d, J = 8.0 Hz, 1H), 8.07 (s, 1H), 7.80 (t, J = 7.8 Hz, 1H), 7.54 (d, J = 3.5 Hz, 1H), 7.43 (d, J = 2.1 Hz, 1H), 6.74 (d, J = 3.5 Hz, 1H), 4.79 (d, J = 5.5 Hz, 3H), 4.02 (s, 3H). |
| 70 | 2.73 | 497.1 | 1 | * | * | ** | DMSO δ 10.49 (broad s, 1H), 9.26 (t, J = 5.8 Hz, 1H), 8.84 (s, 1H), 8.48 (d, J = 1.6 Hz, 1H), 8.30 (s, 1H), 8.18 (m, 2H), 7.91 (t, J = 7.0 Hz, 1H), 7.79 (m, 2H), 7.51 (d, J = 2.2 Hz, 1H), 3.98 (s, 3H), 3.66 (m, 2H), 3.45 (m, 2H), 1.85 (m, 2H). |
| 71 | 3.85 | 561.2 | 1 | *** (0.15) | *** (25) | * | DMSO-d6 δ 10.44 (s, 1H), 9.14 (t, J = 6.2 Hz, 1H), 9.09 (d, J = 4.4 Hz, 1H), 8.82 (d, J = 2.2 Hz, 1H), 8.66 (d, J = 2.2 Hz, 1H), 8.60 (d, J = 8.7 Hz, 1H), 8.28 (d, J = 8.8 Hz, 1H), 8.09 (m, 3H), 7.90 (d, J = 4.5 Hz, 1H), 7.68 (t, J = 10.1 Hz, 1H), 7.33 (t, J = 7.2 Hz, 1H), 4.50 (d, J = 6.1 Hz, 2H), 3.64 (m, 3H). |

TABLE 3-continued

Analytical data and PI3K alpha, PIM-1 and mTOR activities

| Cpd. Nr. | $R_t$ | $[M + 1]^+$ | Meth. | PI3K | mTOR | PIM1 | $^1$H NMR (300 MHz; δ in ppm, J in Hz) |
|---|---|---|---|---|---|---|---|
| 72 | 5.28 | 548.1 | 1 | * | * | ** | DMSO-d6 δ 10.71 (s, 1H), 9.92 (t, J = 5.8 Hz, 1H), 9.26 (s, 1H), 8.94 (s, 1H), 8.66 (d, J = 2.2 Hz, 1H), 8.28 (d, J = 7.8 Hz, 1H), 8.21 (m, 2H), 8.05 (s, 1H), 7.91 (m, 1H), 7.82 (t, J = 7.8 Hz, 1H), 7.58 (m, 1H), 7.46 (d, J = 2.2 Hz, 1H), 4.70 (d, J = 5.8 Hz, 2H), 4.03 (s, 3H). |
| 73 | 5.13 | 560.0 | 1 | * | * | *** (45) | DMSO-d6 δ 9.86 (t, J = 5.6 Hz, 1H), 9.04 (s, 1H), 8.66 (d, J = 1.9 Hz, 1H), 8.63 (m, 1H), 8.22 (m, 1H), 8.20 (m, 2H), 7.85 (m, 2H), 7.69 (d, J = 3.7 Hz, 1H), 7.32 (m, 2H), 4.78 (d, J = 5.7 Hz, 2H), 4.03 (s, 3H). |
| 74 | 4.74 | 536.0 | 1 | * | | ** | DMSO-d6 δ 10.76 (s, 1H), 9.86 (t, J = 5.7 Hz, 1H), 9.13 (s, 1H), 8.80 (m, 1H), 8.67 (d, J = 2.1 Hz, 1H), 8.43 (d, J = 1.5 Hz, 1H), 8.28 (d, J = 7.8 Hz, 1H), 8.23 (d, J = 7.8 Hz, 1H), 8.14 (s, 1H), 7.87 (t, J = 7.8 Hz, 1H), 7.76 (d, J = 1.4 Hz, 1H), 7.42 (d, J = 2.1 Hz, 1H), 4.77 (d, J = 5.4 Hz, 2H), 4.04 (s, 3H). |
| 75 | 3.40 | 523.1 | 1 | * | | * | DMSO-d6 δ 10.16 (bs, 1H), 9.08 (d, J = 7.8 Hz, 1H), 8.55 (m, 3H), 8.29 (d, J = 7.6 Hz, 1H), 8.01 (d, J = 8.5 Hz, 1H), 7.79 (t, J = 7.8 Hz, 1H), 7.71 (s, 1H), 6.83 (d, J = 2.2 Hz, 1H), 4.47 (m, 1H), 4.35 (m, 1H), 4.23 (m, 1H), 3.98 (s, 3H), 3.43 (m, 1H), 3.03 (m, 1H), 2.03 (m, 3H), 1.70 (m, 1H). |
| 76 | 3.41 | 523.1 | 1 | * | | ** | DMSO-d6 δ 10.16 (bs, 1H), 9.08 (d, J = 7.8 Hz, 1H), 8.56 (m, 3H), 8.31 (d, J = 7.6 Hz, 1H), 8.02 (d, J = 8.1 Hz, 1H), 7.80 (t, J = 7.8 Hz, 1H), 7.71 (s, 1H), 6.84 (d, J = 2.0 Hz, 1H), 4.46 (m, 1H), 4.35 (m, 1H), 4.24 (m, 1H), 3.99 (s, 3H), 3.42 (m, 1H), 3.02 (m, 1H), 2.01 (m, 3H), 1.70 (m, 1H). |
| 77 | 4.82 | 536.1 | 1 | ** | * | *** (17) | DMSO-d6 δ 10.76 (broad s, 1H), 9.77 (t, J = 5.5 Hz, 1H), 9.09 (s, 1H), 8.83 (s, 1H), 8.68 (s, 1H), 8.29 (d, J = 7.7 Hz, 1H), 8.22 (d, J = 7.6 Hz, 1H), 8.15 (s, 1H), 7.92 (s, 1H), 7.87 (t, J = 7.9 Hz, 2H), 7.82 (s, 1H), 7.39 (d, J = 1.8 Hz, 1H), 4.63 (d, J = 5.5 Hz, 2H), 4.04 (s, 3H). |
| 78 | 4.15 | 518.0 | 1 | ** | * | ** | DMSO-d6 δ 12.41 (s, 1H), 10.61 (s, 1H), 9.83 (t, J = 5.9 Hz, 1H), 8.66 (s, 1H), 8.42 (s, 1H), 8.22 (m, 3H), 7.86 (t, J = 7.7 Hz, 1H), 7.58 (d, J = 3.6 Hz, 1H), 7.50 (s, 1H), 7.39 (d, J = 5.1 Hz, 1H), 7.13 (d, J = 3.5 Hz, 1H), 6.86 (s, 1H), 4.80 (d, J = 5.6 Hz, 2H), 4.01 (s, 3H). |
| 79 | 4.66 | 537.0 | 1 | ** | * | * | DMSO-d6 δ 10.65 (broad s, 1H), 9.96 (t, J = 5.7 Hz, 1H), 9.14 (s, 1H), 9.01 (s, 1H), 8.77 (s, 1H), 8.61 (s, 1H), |

TABLE 3-continued

Analytical data and PI3K alpha, PIM-1 and mTOR activities

| Cpd. Nr. | R$_t$ | [M + 1]$^+$ | Meth. | PI3K | mTOR | PIM1 | $^1$H NMR (300 MHz; δ in ppm, J in Hz) |
|---|---|---|---|---|---|---|---|
| 80 | 4.26 | 535.0 | 1 | ** | * | *** (15) | 8.22 (m, 2H), 8.07 (s, 1H), 7.81 (t, J = 7.8 Hz, 1H), 7.54 (d, J = 1.9 Hz, 1H), 5.02 (d, J = 5.5 Hz, 2H), 4.02 (s, 3H). DMSO-d6 δ 10.72 (broad s, 1H), 9.83 (t, J = 5.9 Hz, 1H), 8.64 (m, 3H), 8.22 (m, 2H), 8.05 (s, 1H), 7.86 (t, J = 7.8 Hz, 1H), 7.64 (m, 2H), 7.39 (d, J = 2.2 Hz, 1H), 7.20 (d, J = 3.6 Hz, 1H), 4.80 (d, J = 5.3 Hz, 2H), 4.03 (s, 3H). |
| 81 | 3.74 | 513.1 | 1 | ** | * | ** | DMSO-d6 δ 12.44 (s, 1H), 10.41 (s, 1H), 9.77 (t, J = 5.4 Hz, 1H), 9.02 (s, 1H), 8.87 (s, 1H), 8.71 (s, 1H), 8.42 (m, 1H), 8.32 (d, J = 4.9 Hz, 1H), 8.22 (m, 3H), 7.78 (t, J = 7.6 Hz, 1H), 7.57 (s, 1H), 7.38 (d, J = 5.0 Hz, 1H), 6.68 (s, 1H), 4.70 (d, J = 5.0 Hz, 2H), 3.97 (s, 3H). |
| 82 | 4.84 | 554.0 | 1 | *** (57) | * | *** (13) | DMSO-d6 δ 10.83 (broad s, 1H), 9.51 (m, 1H), 9.12 (s, 1H), 8.67 (d, J = 2.2 Hz, 1H), 8.56 (dd, J = 6.4, 2.5 Hz, 1H), 8.27 (m, 1H), 8.11 (s, 1H), 7.87 (d, J = 3.7 Hz, 1H), 7.79 (t, J = 9.5 Hz, 1H), 7.57 (d, J = 2.2 Hz, 1H), 7.24 (d, J = 3.7 Hz, 1H), 4.86 (s, 2H), 4.05 (s, 3H). |
| 83 | 3.40 | 537.1 | 1 | * | * | ** | DMSO-d6 δ 10.61 (s, 1H), 9.40 (m, 1H), 8.91 (s, 1H), 8.60 (s, 1H), 8.51 (s, 1H), 8.19 (t, J = 7.0 Hz, 3H), 7.83 (s, 1H), 7.78 (t, J = 7.8 Hz, 1H), 7.51 (s, 1H), 5.14 (d, J = 12.7 Hz, 1H), 4.69 (d, J = 13.0 Hz, 1H), 3.99 (s, 3H), 3.42 (m, 1H), 3.23 (m, 2H), 2.98 (m, 1H), 1.97 (m, 1H), 1.88 (m, 2H), 1.46 (m, 2H). |
| 84 | 3.40 | 537.1 | 1 | * | * | ** | DMSO-d6 δ 10.62 (broad s, 1H), 9.41 (t, J = 5.7 Hz, 1H), 8.91 (s, 1H), 8.63 (s, 1H), 8.51 (d, J = 2.1 Hz, 1H), 8.19 (t, J = 7.5 Hz, 2H), 7.83 (s, 1H), 7.78 (t, J = 7.8 Hz, 1H), 7.51 (d, J = 2.2 Hz, 1H), 5.15 (d, J = 13.3 Hz, 1H), 4.69 (d, J = 13.2 Hz, 1H), 3.99 (s, 3H), 3.42 (m, 1H), 3.21 (m, 2H), 2.99 (m, 1H), 1.98 (m, 1H), 1.88 (m, 2H), 1.48 (m, 2H). |
| 85 | 4.22 | 499.1 | 1 | ** | * | * | Methanol-d4 δ 8.84 (d, J = 7.3 Hz, 1H), 8.47 (m, 1H), 8.38 (s, 1H), 8.18 (d, J = 7.7 Hz, 1H), 8.10 (m, 2H), 7.97 (s, 1H), 7.74 (m, 2H), 7.64 (d, J = 8.0 Hz, 1H), 7.46 (t, J = 7.6 Hz, 1H), 7.30 (m, 1H), 7.22 (d, J = 7.3 Hz, 1H), 4.61 (s, 2H). |
| 86 | 2.82 | 523.1 | 1 | * | * | ** | DMSO-d6 δ 10.61 (broad s, 1H), 9.07 (d, J = 7.1 Hz, 1H), 8.69 (s, 1H), 8.55 (d, J = 2.1 Hz, 1H), 8.35 (s, 1H), 8.22 (d, J = 7.7 Hz, 1H), 8.15 (m, 1H), 7.84 (t, J = 7.8 Hz, 1H), 7.79 (s, 1H), 7.31 (d, J = 2.1 Hz, 1H), 4.06 (m, 1H), 4.00 |

TABLE 3-continued

Analytical data and PI3K alpha, PIM-1 and mTOR activities

| Cpd. Nr. | $R_t$ | $[M + 1]^+$ | Meth. | PI3K | mTOR | PIM1 | $^1$H NMR (300 MHz; δ in ppm, J in Hz) |
|---|---|---|---|---|---|---|---|
| | | | | | | | (s, 3H), 3.88 (m, 3H), 3.54 (m, 1H), 3.33 (m, 1H), 2.78 (m, 1H), 2.18 (m, 1H), 1.74 (m, 1H). |
| 87 | 2.82 | 523.1 | 1 | * | * | ** | DMSO-d6 δ 10.61 (broad s, 1H), 9.07 (d, J = 7.2 Hz, 1H), 8.69 (s, 1H), 8.55 (d, J = 2.0 Hz, 1H), 8.35 (s, 1H), 8.22 (d, J = 7.7 Hz, 1H), 8.15 (m, 1H), 7.84 (t, J = 7.8 Hz, 1H), 7.78 (s, 1H), 7.31 (d, J = 2.1 Hz, 1H), 4.06 (m, 1H), 4.00 (s, 3H), 3.87 (m, 3H), 3.56 (m, 1H), 3.33 (m, 1H), 2.79 (m, 1H), 2.18 (m, 1H), 1.74 (m, 1H). |
| 88 | 4.82 | 550.0 | 1 | ** | * | *** (69) | $^1$H NMR (300 MHz, DMSO-d6) δ 10.82 (s, 1H), 9.84 (t, J = 5.7 Hz, 1H), 9.09 (s, 1H), 8.68 (m, 1H), 8.65 (m, 1H), 8.25 (m, 2H), 8.09 (s, 1H), 7.89 (t, J = 7.8 Hz, 1H), 7.76 (s, 1H), 7.45 (d, J = 2.1 Hz, 1H), 4.75 (d, J = 5.4 Hz, 2H), 4.05 (s, 3H), 2.30 (s, 3H). |
| 89 | 3.95 | 531.1 | 1 | * | * | * | $^1$H NMR (300 MHz, DMSO-d6) δ 10.45 (broad s, 1H), 9.43 (t, J = 3.5 Hz, 1H), 9.30 (s, 1H), 8.85 (d, J = 5.2 Hz, 1H), 8.78 (m, 1H), 8.70 (s, 1H), 8.56 (d, J = 1.9 Hz, 1H), 8.14 (s, 1H), 8.04 (m, 2H), 7.80 (m, 2H), 7.70 (t, J = 7.8 Hz, 1H), 4.47 (dd, J = 13.6, 2.4 Hz, 1H), 3.93 (s, 3H), 3.89 (dd, J = 13.6, 4.3 Hz, 1H). |
| 90 | 5.21 | 568.1 | 1 | *** (1.8) | *** (56) | *** (27) | $^1$H NMR (300 MHz, DMSO) δ 10.80 (broad s, 1H), 9.58 (t, J = 5.2 Hz, 1H), 9.18 (s, 1H), 8.48 (dd, J = 6.4, 2.5 Hz, 1H), 8.37 (s, 1H), 8.32 (m, 1H), 7.93 (d, J = 3.7 Hz, 1H), 7.78 (d, J = 9.5 Hz, 1H), 7.73 (d, J = 2.0 Hz, 1H), 7.24 (d, J = 3.7 Hz, 1H), 4.85 (d, J = 4.8 Hz, 2H), 4.05 (s, 3H), 2.61 (s, 3H). |
| 91 | 3.78 | 553.2 | 1 | *** (10) | ** | *** (47) | DMSO-d6 δ 10.55 (s, 1H), 9.29 (s, 1H), 8.71 (s, 1H), 8.55 (s, 1H), 8.17 (m, 2H), 7.79 (m, 1H), 7.56 (s, 1H), 4.77 (d, J = 13.6 Hz, 1H), 4.57 (d, J = 12.6 Hz, 1H), 4.04 (s, 1H), 3.98 (s, 3H), 3.73 (broad s, 1H), 3.61 (m, 1H), 3.46 (s, 2H), 3.16 (m, 3H), 2.43 (s, 3H). |
| 92 | 5.46 | 562.1 | 1 | *** (15) | * | * | DMSO-d6 δ 10.64 (s, 1H), 9.85 (t, J = 5.9 Hz, 1H), 9.34 (s, 1H), 8.84 (s, 1H), 8.24 (m, 2H), 8.09 (s, 1H), 7.93 (d, J = 9.6 Hz, 1H), 7.81 (t, J = 7.8 Hz, 1H), 7.56 (m, 2H), 4.67 (d, J = 5.6 Hz, 2H), 4.02 (s, 3H), 2.57 (s, 3H). |
| 93 | 4.91 | 610.1 | 1 | ** | *** (32) | * | DMSO-d6 δ 10.64 (s, 1H), 9.16 (t, J = 6.1 Hz, 1H), 9.11 (s, 1H), 8.66 (d, J = 2.2 Hz, 2H), 8.16 (d, J = 8.8 Hz, 1H), 8.10 (s, 1H), 7.85 (d, J = 3.7 Hz, 1H), 7.58 (d, J = 8.9 Hz, 1H), 7.46 (d, J = 2.1 Hz, 1H), 7.23 (d, J = 3.7 Hz, 1H), 4.89 |

TABLE 3-continued

Analytical data and PI3K alpha, PIM-1 and mTOR activities

| Cpd. Nr. | $R_t$ | $[M + 1]^+$ | Meth. | PI3K | mTOR | PIM1 | $^1$H NMR (300 MHz; δ in ppm, J in Hz) |
|---|---|---|---|---|---|---|---|
| | | | | | | | (s, 2H), 4.44 (m, 2H), 4.04 (s, 3H), 3.79 (m, 2H), 3.29 (s, 3H). |
| 94 | 2.98 | 537.2 | 1 | *** (26) | * | *** (65) | DMSO-d6 δ 10.57 (s, 1H), 9.06 (d, J = 7.2 Hz, 1H), 8.64 (s, 1H), 8.42 (s, 1H), 8.20 (m, 3H), 7.83 (t, J = 7.8 Hz, 1H), 7.40 (d, J = 1.9 Hz, 1H), 4.01 (s, 3H), 3.91 (d, J = 6.9 Hz, 3H), 3.77 (dd, J = 21.3, 12.6 Hz, 1H), 3.59 (m, 1H), 3.23 (m, 1H), 2.80 (s, 1H), 2.43 (s, 3H), 2.16 (s, 1H), 1.75 (dd, J = 12.3, 8.1 Hz, 1H). |
| 95 | 5.26 | 624.3 | 1 | *** (20) | * | ** | DMSO-d6 δ 10.64 (s, 1H), 9.16 (s, 2H), 8.56 (d, J = 2.5 Hz, 1H), 8.30 (s, 1H), 8.17 (d, J = 9.1 Hz, 1H), 7.90 (d, J = 3.7 Hz, 1H), 7.59 (s, 1H), 7.53 (d, J = 9.0 Hz, 1H), 7.22 (d, J = 3.7 Hz, 1H), 4.86 (s, 2H), 4.42 (s, 2H), 4.04 (s, 3H), 3.79 (m, 2H), 3.29 (s, 3H), 2.60 (s, 3H). |
| 96 | 7.40 | 520.0 | 3 | *** (8.8) | ** | | DMSO-d6 δ 9.75 (t, J = 6.2 Hz, 1H), 8.81 (s, 1H), 8.57 (d, J = 5.4 Hz, 1H), 8.13 (m, 5H), 7.98 (s, 1H), 7.80 (s, 1H), 7.74 (d, J = 4.4 Hz, 2H), 4.67 (d, J = 5.7 Hz, 2H), 3.97 (s, 3H). |
| 97 | 5.37 | 566.1 | 1 | ** | * | *** (62) | DMSO-d6 δ 10.61 (s, 1H), 9.26 (t, J = 6.0 Hz, 1H), 9.11 (s, 1H), 8.66 (m, 2H), 8.17 (d, J = 9.2 Hz, 1H), 8.10 (s, 1H), 7.84 (d, J = 3.7 Hz, 1H), 7.54 (d, J = 8.9 Hz, 1H), 7.47 (d, J = 2.1 Hz, 1H), 7.21 (d, J = 3.7 Hz, 1H), 4.85 (s, 2H), 4.04 (s, 3H), 4.03 (s, 3H). |
| 98 | 5.05 | 570.1 | 1 | *** (37) | * | *** (13) | DMSO-d6 δ 10.90 (s, 1H), 9.73 (t, J = 5.9 Hz, 1H), 9.14 (s, 1H), 8.67 (d, J = 2.0 Hz, 1H), 8.35 (d, J = 2.2 Hz, 1H), 8.18 (dd, J = 8.6, 2.2 Hz, 1H), 8.10 (s, 1H), 7.98 (d, J = 8.6 Hz, 1H), 7.89 (d, J = 3.7 Hz, 1H), 7.82 (d, J = 2.1 Hz, 1H), 7.26 (d, J = 3.7 Hz, 1H), 4.86 (s, 2H), 4.05 (s, 3H). |
| 99 | 3.17 | 537.2 | 1 | *** (43) | * | *** (53) | DMSO-d6 δ 10.57 (s, 1H), 9.06 (d, J = 7.1 Hz, 1H), 8.64 (s, 1H), 8.43 (s, 1H), 8.21 (m, 3H), 7.83 (t, J = 7.8 Hz, 1H), 7.40 (d, J = 2.1 Hz, 1H), 4.01 (s, 3H), 3.91 (d, J = 7.0 Hz, 3H), 3.77 (dd, J = 21.4, 12.3 Hz, 1H), 3.60 (m, 1H), 3.27 (s, 1H), 2.81 (d, J = 6.3 Hz, 1H), 2.43 (s, 3H), 2.16 (s, 1H), 1.76 (m, 1H). |
| 100 | 5.11 | 580.0 | 1 | *** (3.3) | * | *** (31) | DMSO-d6 δ 10.61 (m, 1H), 9.25 (t, J = 5.7 Hz, 1H), 9.16 (s, 1H), 8.56 (d, J = 2.2 Hz, 1H), 8.31 (s, 1H), 8.20 (d, J = 8.7 Hz, 1H), 7.90 (d, J = 3.6 Hz, 1H), 7.61 (s, 1H), 7.50 (d, J = 8.9 Hz, 1H), 7.21 (d, J = 3.5 Hz, 1H), 4.84 (s, 2H), 4.04 (s, 3H), 4.02 (s, 3H), 2.60 (s, 3H). |
| 101 | 4.80 | 549.1 | 1 | *** (26) | * | *** (21) | DMSO-d6 δ 10.69 (s, 1H), 9.83 (t, J = 6.0 Hz, 1H), 8.71 (d, J = 5.0 Hz, 1H), 8.59 (d, J = 1.6 Hz, 1H), 8.29 (dd, J = |

TABLE 3-continued

Analytical data and PI3K alpha, PIM-1 and mTOR activities

| Cpd. Nr. | $R_t$ | $[M + 1]^+$ | Meth. | PI3K | mTOR | PIM1 | $^1$H NMR (300 MHz; δ in ppm, J in Hz) |
|---|---|---|---|---|---|---|---|
| | | | | | | | 10.1, 5.0 Hz, 2H), 8.16 (d, J = 7.9 Hz, 1H), 7.84 (t, J = 7.8 Hz, 1H), 7.73 (d, J = 5.0 Hz, 1H), 7.67 (d, J = 3.7 Hz, 1H), 7.60 (d, J = 2.1 Hz, 1H), 7.20 (d, J = 3.7 Hz, 1H), 4.78 (d, J = 5.6 Hz, 2H), 4.04 (s, 3H), 2.62 (s, 3H). |
| 102 | 5.31 | 584.1 | 1 | *** (0.1) | *** (28) | *** (9.5) | DMSO-d6 δ 10.84 (s, 1H), 9.79 (t, J = 5.8 Hz, 1H), 9.19 (s, 1H), 8.41 (d, J = 2.0 Hz, 1H), 8.29 (d, J = 2.2 Hz, 1H), 8.25 (dd, J = 8.6, 2.3 Hz, 1H), 8.02 (d, J = 2.1 Hz, 1H), 7.97 (d, J = 8.5 Hz, 1H), 7.93 (d, J = 3.7 Hz, 1H), 7.25 (d, J = 3.7 Hz, 1H), 4.83 (s, 2H), 4.05 (s, 3H), 2.62 (s, 3H). |

$R_t$ means retention time (in minutes), $[M + H]^+$ means the protonated mass of the compound, method refers to the method used for (LC)MS.
Biological activity in PI3K alpha, PIM-1 and mTOR for certain examples is represented in Table 3 by semi-quantative results: IC50 >1 μM (*), IC50 <100 nM (*), 100 nM < IC50 < 1 μM ().
Quantitative data is also presented, in parentheses, depicting the actual $IC_{50}$ values (nM) for representative examples.

TABLE 4

Pharmacokinetic parameters for some selected compounds.

| | Administration | | | | | | | | | |
|---|---|---|---|---|---|---|---|---|---|---|
| | I.V | | | | | | P.O | | | |
| | Parameter | | | | | | | | | |
| Example | Dose (mg/Kg) | AUC inf (h*ng/ml) | T½ last | Cl (L/h/Kg) | Vd (L/Kg) | MRT (h) | Dose (mg/Kg) | F % | C max (ng/ml) | Tmax (h) | AUC inf (h*ng/ml) |
| 3 | 5.00 | 23709.33 | 1.41 | 0.36 | 0.46 | 1.27 | 10.00 | 101.00 | 12403.41 | 0.25 | 48082.44 |
| 10 | 5.00 | 9467.60 | 0.57 | 0.53 | 0.28 | 0.53 | 10.00 | 39.94 | 3389.29 | 0.25 | 7563.83 |
| 16 | 5.00 | 23568.46 | 2.23 | 0.27 | 0.99 | 3.33 | 10.00 | 123.00 | 4820.00 | 0.50 | 29157.84 |
| 22 | 5.00 | 66912.04 | 3.42 | 0.07 | 0.37 | 4.94 | 10.00 | 33.50 | 14950.90 | 0.16 | 44830.22 |
| 33 | 5.00 | 9159.37 | 2.91 | 0.60 | 1.12 | 1.87 | 10.00 | 48.08 | 1266.30 | 0.16 | 8808.30 |
| 31 | 5.00 | 8930.77 | 0.39 | 0.69 | 0.56 | 0.81 | 10.00 | 34.00 | 1635.18 | 0.25 | 6083.27 |
| 39 | 1.00 | 4455.10 | 1.66 | 0.25 | 0.59 | 2.39 | 3.00 | 26.79 | 962.27 | 0.50 | 3580.16 |
| 68 | 5.00 | 16596.24 | 3.15 | 0.04 | 0.49 | 10.89 | 10.00 | 34.51 | 2929.00 | 0.25 | 57280.69 |

The parameters estimated are:
area under the curve (AUC);
plasmatic half life of the product (t½);
plasmatic clearance (Cl);
volume of distribution (Vd);
MRT (Mean residence time);
bioavailability (F %);
maximum plasma concentration after oral administration (Cmax); and
time at which the Cmax occurs (Tmax).

ABBREVIATIONS

DCM dichloromethane
MeOH methanol
THF tetrahydrofuran
dba dibenzylideneacetone
DMF dimethylformamide
DME 1,2-dimethoxyethane
DMSO dimethylsulfoxide
dppf diphenylphosphinoferrocene
EtOAc ethyl acetate
BOP (Benzotriazol-1-yloxy)tris(dimethylamino)phosphonium hexafluorophosphate
HOAt 1-hydroxy-7-azabenzotriazole
PyBOP (benzotriazol-1-yloxy)tripyrrolidinophosphonium hexafluorophosphate
PyBroP bromotripyrrolidinophosphonium hexafluorophosphate
DMAP 4-dimethylaminopyridine
HATU O-(7-azabenzotriazole-1-yl)-1,1,3,3-tetramethyluronium hexafluorophosphate
Pd(PPh$_3$)$_4$ tetrakis(triphenylphosphine)palladium
PdCl$_2$(dppf).DCM 1,1'-bis(diphenylphosphino)ferrocenepalladium(II) dichloride, dichloromethane
DIPEA diisopropylethylamine
TFA trifluoroacetic acid
min minutes
h hours
RT room temperature
eq equivalents
nBuOH n-butanol
mw microwave

The invention claimed is:

1. A method of treatment of a cancer, by administering to a patient suffering from, or susceptible to the cancer, wherein the cancer is selected from the group consisting of bladder cancer, breast cancer, colon cancer, liver cancer, lung cancer, ovary cancer, pancreatic cancer, stomach cancer, cervical cancer, prostate cancer, squamous cell carcinoma, glioblastoma, melanoma, colon-rectum cancer, oral cancer, B-cell lymphoma, T-cell-lymphoma, Hodgkin's lymphoma, non-Hodgkin's lymphoma, Burkett's lymphoma; hematopoietic tumors of myeloid lineage, and tumors of the central and peripheral nervous system, which method comprises administration of a therapeutically effective amount of a compound of formula I:

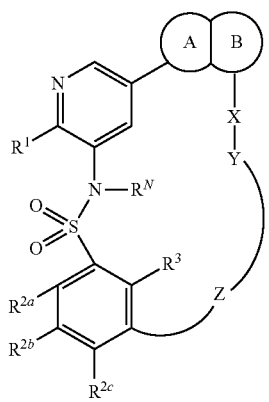

I wherein:

ring A and ring B represent a fused bicyclic group of any one of the following formulae:

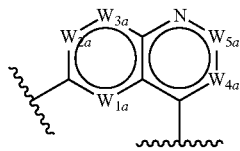

IA

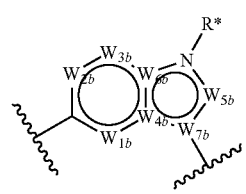

IB

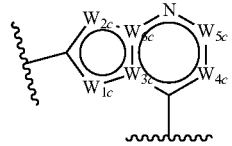

IC

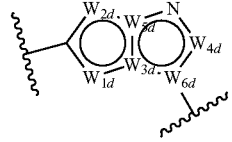

ID wherein in formula IA: $W^{1a}$ is CH, CF or N; $W^{2a}$ is CH, CF or N; $W^{3a}$ is $CR^{4a}$ or N; $W^{4a}$ is $CR^{5a}$ or N; $W^{5a}$ is $CR^{6a}$ or N;

in formula IB: $W^{1b}$ is CH, CF or N; $W^{2b}$ is CH, CF or N; $W^{3b}$ is $CR^{4b}$ or N; $W^{4b}$ is C or N; $W^{5b}$ is $CR^{6b}$ or N; $W^{6b}$ is C or N; $W^{7b}$ is C or N, and wherein when $W^{3b}$ represents N, $W^{4b}$ and $W^{6b}$ represent C and $W^{5b}$ represents C or N, then R* is hydrogen (in all other cases R* is absent);

in formula IC: $W^{1c}$ is CH, $CR^{t1}$, N, $NR^{q1}$, O or S; $W^{2c}$ is CH, $CR^{t2}$, N, $NR^{q2}$, O or S; $W^{3c}$ is C or N; $W^{4c}$ is $CR^{5c}$ or N; $W^{5c}$ is $CR^{6c}$ or N; $W^{6c}$ is C or N;

in formula ID: $W^{1d}$ is CH, $CR^{t3}$, N, $NR^{q3}$, O or S; $W^{2d}$ is CH, $CR^{t4}$, N, $NR^{q4}$, O or S; $W^{3d}$ is C or N; $W^{4d}$ is $CR^{5d}$ or N; $W^{5d}$ is C or N; $W^{6d}$ is C or N;

each $R^{t1}$, $R^{t2}$, $R^{t3}$, and $R^{t4}$ is independently selected from halo, $C_{1-3}$ alkyl or $C_3$ cycloalkyl, a 3- to 5-membered heterocycloalkyl group, $-OR^{s1}$, $-CN$, $-N(R^{s2})R^{s3}$, $-S(O)_{w1}CH_3$ or $-C(O)CH_3$;

w1 represents 0, 1 or 2;

each $R^{s1}$, $R^{s2}$ and $R^{3s}$ independently represent hydrogen or $C_{1-2}$ alkyl;

each $R^{q1}$, $R^{q2}$, $R^{q3}$ and $R^{q4}$ is independently selected from $C_{1-3}$ alkyl or $C_3$ cycloalkyl, a 3- to 5-membered heterocycloalkyl group or $-C(O)CH_3$;

each $R^1$, $R^{2a}$, $R^{2b}$, $R^{2c}$, $R^3$, $R^{4a}$, $R^{5a}$, $R^{6a}$, $R^{4b}$, $R^{6b}$, $R^{5c}$, $R^{6c}$, and $R^{5d}$ are independently selected from hydrogen or a substituent selected from halo, $-CN$, $-C(O)N$ $(R^{f1})R^{f2}$, —C(O)$R^{f3}$, —N($R^{f4}$)$R^{f5}$, —C(O)O$R^{f6}$, —O$R^{f7}$, —OC(O)—$R^{f8}$, —S(O)$_{w2}$CH$^3$, C$_{1-8}$ alkyl, C$_{3-8}$ cycloalkyl and a 3- to 8-membered heterocycloalkyl groups, which latter three groups are optionally substituted by one or more substituents selected from =O and E$^1$;

w2 represents 0, 1 or 2;

$R^{f1}$, $R^{f2}$, $R^{f4}$, $R^{f5}$ and $R^{f7}$ independently represent hydrogen, C$_{1-6}$ alkyl or C$_{3-6}$ cycloalkyl optionally substituted by one or more substituents selected from =O and E$^2$; or $R^{f1}$ and $R^{f2}$ and/or $R^{f4}$ and $R^{f5}$ may be linked together to form a 4- to 8- membered ring optionally substituted by one or more substituents selected from C$_{1-3}$ alkyl, C$_3$ cycloalkyl and halo;

$R^{f3}$, $R^{f6}$ and $R^{f8}$ independently represent C$_{1-6}$ alkyl or C$_{3-6}$ cycloalkyl optionally substituted by one or more substituents selected from =O and E$^2$;

X represents a direct bond, —C($R^a$)($R^b$)—, —O—, —S—, —N($R^c$)—, —N($R^d$)C(O)—, —C(O)N($R^e$)— or —N($R^f$)—C(O)—N($R^g$)—;

Y represents -arylene-, -heteroarylene- (which latter two groups are optionally substituted by one or more substituents selected from E$^3$), -heterocycloalkylene- or —C$_{1-12}$alkylene- (which latter two groups are optionally substituted by one or more substituents selected from =O and E$^4$);

$R^N$ represents hydrogen or C$_{1-6}$ alkyl optionally substituted by one or more substituents selected from =O and E$^5$;

Z represents -(A$^x$)$_{1-7}$-, wherein each A$^x$ independently represents —C($R^{x1}$)($R^{x2}$)—, —N($R^{x3}$)—, —C(O)—, —O—, —S—, —S(O)— or —S(O)$_2$—;

$R^{x1}$, $R^{x2}$ and $R^{x3}$ each independently represent hydrogen or a substituent selected from E$_x$;

each E$_x$ independently represents halo, —C(O)$R^{y1}$, —N($R^{y2}$)—C(O)—N($R^{y3}$)($R^{y4}$), C$_{1-6}$ alkyl or heterocycloalkyl (both of which latter two groups are optionally substituted by one or more halo atoms);

$R^{y1}$, $R^{y2}$, $R^{y3}$ and $R^{y4}$ each independently represent hydrogen or C$_{1-3}$ alkyl optionally substituted by one or more halo atoms;

each $R^a$, $R^b$, $R^c$, $R^d$, $R^e$, $R^f$ and $R^g$ independently represent hydrogen, C$_{1-6}$ alkyl or C$_{3-6}$ cycloalkyl optionally substituted by one or more halo atoms;

each E$^1$, E$^2$, E$^3$, E$^4$ and E$^5$ independently represents, on each occasion when used herein:

(i) Q$^4$;

(ii) C$_{1-12}$ alkyl or C$_{3-12}$ cycloalkyl or heterocycloalkyl, each of which is optionally substituted by one or more substituents selected from =O and Q$^5$;

any two E$^1$, E$^2$, E$^3$, E$^4$ and/or E$^5$ groups, may be linked together to form a 3- to 12-membered ring, optionally containing one or more unsaturations, and which ring is optionally substituted by one or more substituents selected from =O and J$^1$;

each Q$^4$ and Q$^5$ independently represent, on each occasion when used herein:

halo, —CN, —N($R^{20}$)$R^{21}$, —O$R^{20}$, —C(=Y$^1$)—$R^{20}$, —C(=Y$^1$)—O$R^{20}$, —C(=Y$^1$)N($R^{20}$)$R^{21}$, —C(=Y$^1$)N($R^{20}$)—O—$R^{21a}$, —OC(=Y$^1$)—$R^{20}$, —OC(=Y$^1$)—O$R^{20}$, —OC(=Y$^1$)N($R^{20}$)$R^{21}$, —OS(O)$_2$O$R^{20}$, —OP(=Y$^1$)(O$R^{20}$)(O$R^{21}$), —OP(O$R^{20}$)(O$R^{21}$), —N($R^{22}$)C(=Y$^1$)$R^{21}$, —N($R^{22}$)C(=Y$^1$)O$R^{21}$, —N($R^{22}$)C(=Y$^1$)N($R^{20}$)$R^{21}$, —NR$^{22}$S(O)$_2$R$^{20}$, —NR$^{22}$S(O)$_2$N($R^{20}$)$R^{21}$, —S(O)$_2$N($R^{20}$)$R^{21}$, —SC(=Y$^1$)$R^{20}$, —SC(=Y$^1$)O$R^{20}$, —SC(=Y$^1$)N($R^{20}$)$R^{21}$, —S(O)$_2$R$^{20}$, —SR$^{20}$, —S(O)R$^{20}$, —S(O)$_2$OR$^{20}$, C$_{1-6}$ alkyl, C$_{3-6}$ cycloalkyl or heterocloalkyl (which latter three groups are optionally substituted by one or more substituents selected from =O and J$^2$);

each Y$^1$ independently represents, on each occasion when used herein, =O, =S, =NR$^{23}$ or =N—CN;

each $R^{21a}$ represents C$_{1-6}$ alkyl, C$_{3-6}$ cycloalkyl or heterocycloalkyl (which latter three groups are optionally substituted by one or more substituents selected from J$^4$ and =O);

each $R^{20}$, $R^{21}$, $R^{22}$ and $R^{23}$ independently represent, on each occasion when used herein, hydrogen, C$_{1-6}$ alkyl, C$_{3-6}$ cycloalkyl or heterocycloalkyl (which latter three groups are optionally substituted by one or more substituents selected from J$^4$ and =O); or any relevant pair of $R^{20}$, $R^{21}$ and $R^{22}$, may be linked together to form a 4- to 20- membered ring, optionally containing one or more heteroatoms, optionally containing one or more unsaturations, and which ring is optionally substituted by one or more substituents selected from J$^6$ and =O;

each J$^1$, J$^2$, J$^4$ and J$^6$ independently represents, on each occasion when used herein:

(i) Q$^7$;

(ii) C$_{1-6}$ alkyl, C$_{3-6}$ cycloalkyl or heterocycloalkyl, each of which is optionally substituted by one or more substituents selected from =O and Q$^8$;

each Q$^7$ and Q$^8$ independently represents, on each occasion when used herein:

halo, —CN, —N($R^{50}$)$R^{51}$, —O$R^{50}$, —C(=Y$^a$)—$R^{50}$, —C(=Y$^a$)—O$R^{50}$, —C(=Y$^a$)N($R^{50}$)$R^{51}$, —N($R^{52}$)C(=Y$^a$)$R^{51}$, —NR$^{52}$S(O)$_2$R$^{50}$, —S(O)$_2$N($R^{50}$)$R^{51}$, —N($R^{52}$)—C(=Y$^a$)—N($R^{50}$)$R^{51}$, —S(O)$_2$R$^{50}$, —SR$^{50}$, —S(O)R$^{50}$, C$_{1-6}$ alkyl or C$_{3-6}$ cycloalkyl (optionally substituted by one or more fluoro atoms) or heterocycloalkyl (optionally substituted by one or more substituents selected from halo, —OR$^{60}$ and —N($R^{61}$)$R^{62}$);

each Y$^a$ independently represents, on each occasion when used herein, =O, =S, =NR$^{53}$ or =N—CN;

each $R^{50}$, $R^{51}$, $R^{52}$ and $R^{53}$ independently represents, on each occasion when used herein, hydrogen, C$_{1-6}$ alkyl, or C$_{3-6}$ cycloalkyl optionally substituted by one or more substituents selected from fluoro, —OR$^{60}$ and —N($R^{61}$)$R^{62}$; or any relevant pair of $R^{50}$, $R^{51}$ and $R^{52}$ may be linked together to form, a 3- to 8-membered ring, optionally containing one or more heteroatoms, optionally containing one or more unsaturations, and which ring is optionally substituted by one or more substituents selected from =O and C$_{1-3}$ alkyl;

$R^{60}$, $R^{61}$ and $R^{62}$ independently represent hydrogen, C$_{1-6}$ alkyl, or C$_{3-6}$ cycloalkyl optionally substituted by one or more fluoro atoms;

wherein any heterocycloalkyl group may be selected from non-aromatic monocyclic and bicyclic heterocycloalkyl groups in which one to four of the atoms in the ring system is a heteroatom selected from N, O or S, and in which the total number of atoms in the ring system is from five to ten, wherein the heterocycloalkyl group may be bridged, and wherein the heterocycloalkyl group may be saturated or unsaturated containing one or more double and/or triple bonds, wherein any heteroaryl group may be selected from an aromatic group containing one to four heteroatom(s) selected from N, O or S, wherein the heteroaryl group comprises five to ten atoms in the ring system, and wherein the heteroaryl group is monocyclic, bicyclic or tricyclic, provided that at least one of the rings is aromatic, and that when the heteroaryl group is bicyclic or tricyclic it is linked to the rest of the molecule via an aromatic ring, or a pharmaceutically acceptable salt thereof.

2. A method as claimed in claim 1, wherein the cancer is astrocytoma.

3. A method as claimed in claim 1, wherein the cancer is acute myelogenous leukemias.

4. A method as claimed in claim 1, wherein the cancer is non-small cell lung cancer.

5. A method as claimed in claim 1, wherein the cancer is non-Hodgkin's lymphoma.

6. A method as claimed in claim 1, wherein ring A and ring B represents a fused bicyclic group of the following structure (optional substituents are not shown):

Formula IA

Formula IB

Formula IC

Formula ID

7. A method as claimed in claim 1, wherein

Y represents arylene, heteroarylene, heterocycloalkylene or $C_{1-6}$alkylene, all of which groups are optionally substituted by one of the following groups:

($E^3$ = halo)

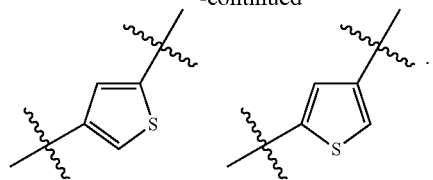
8. A method as claimed in claim 1, wherein
X represents —N(R$^c$)— or a direct bond; and/or
Z represents —C(O)-[T$^1$]- or —C(O)N(R$^{x3}$)-[T$^1$]-, in which T$^1$ represents —(CH$_2$)$_{0-4}$-T$^2$- and T$^2$ represents a direct bond or —C(O)—N(H)—CH$_2$—.
9. A method as claimed in claim 1, wherein the compound is selected from the following:
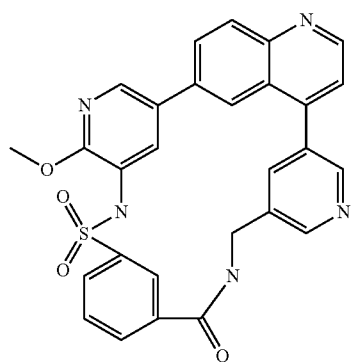
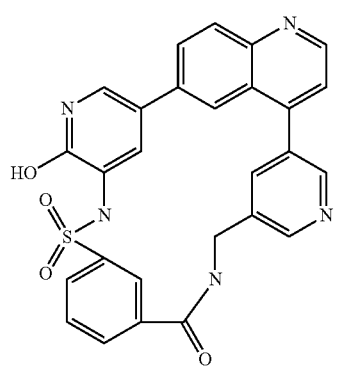
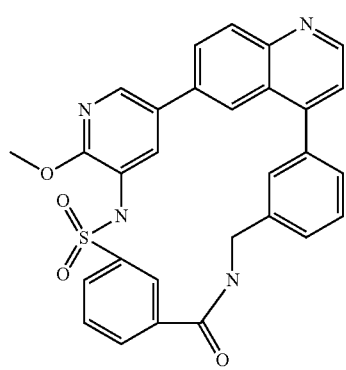
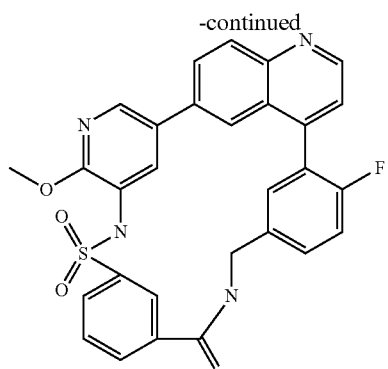
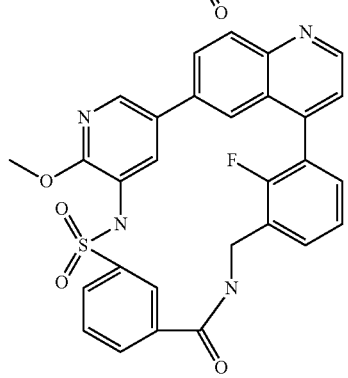
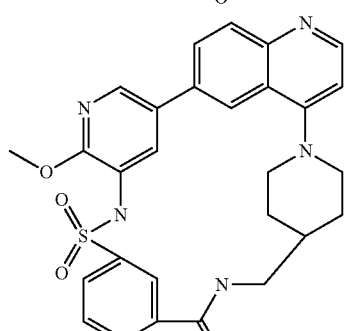
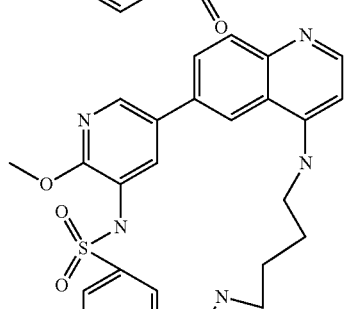
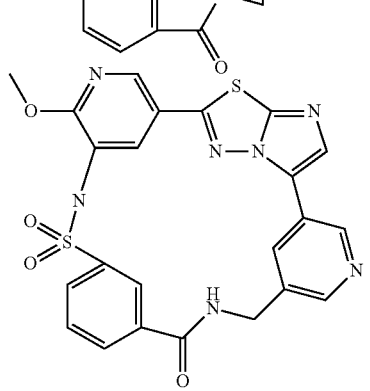

287
-continued
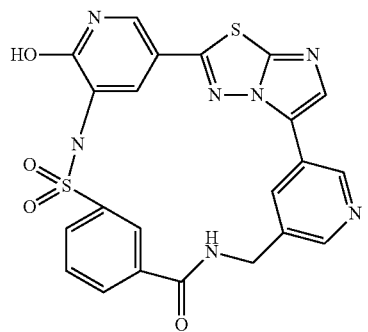
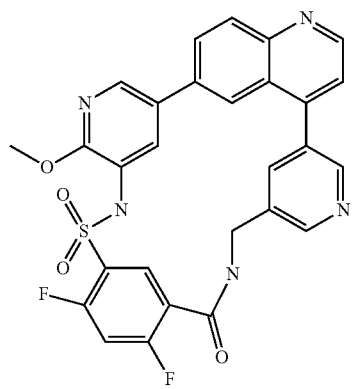
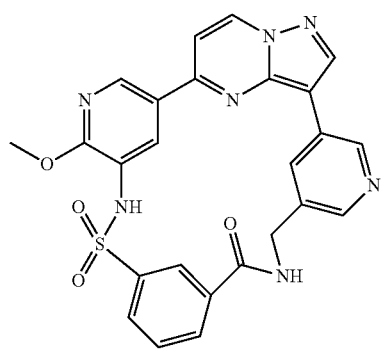
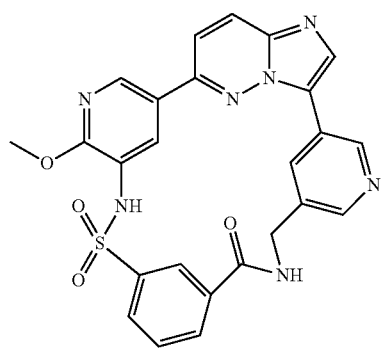
288
-continued
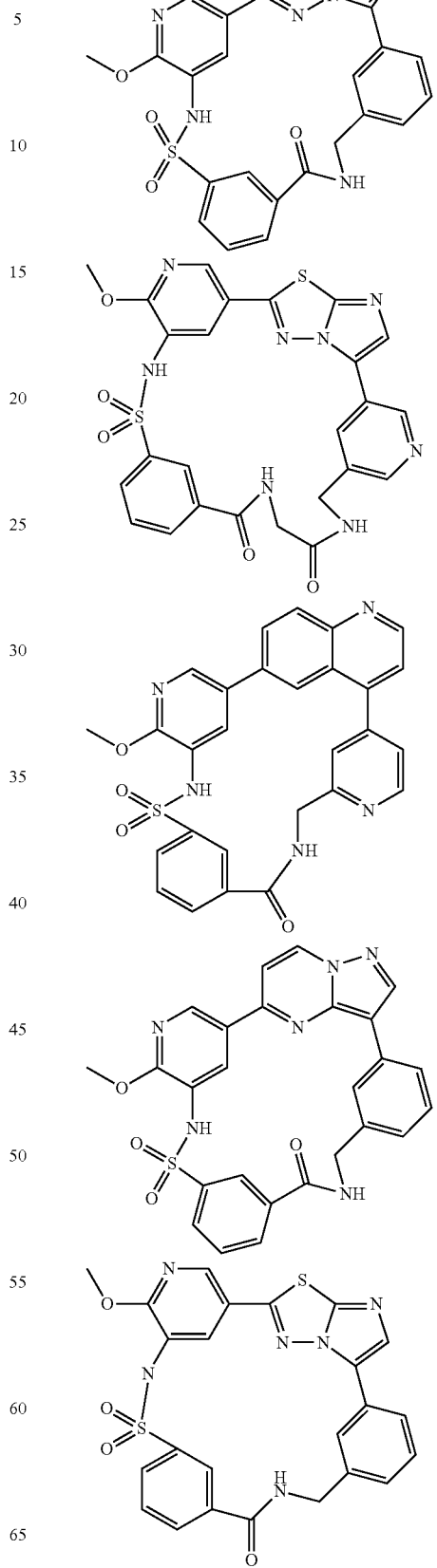

289
-continued
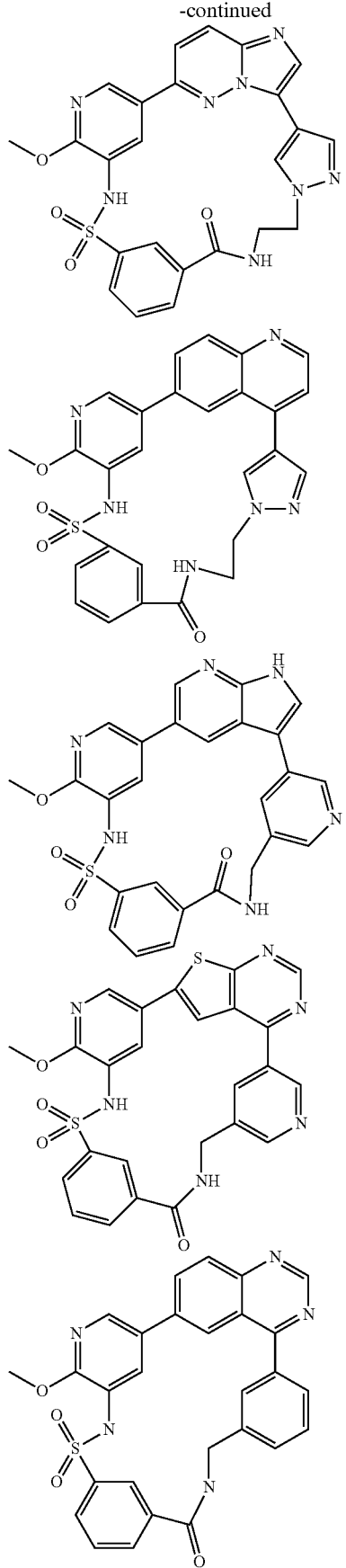
290
-continued
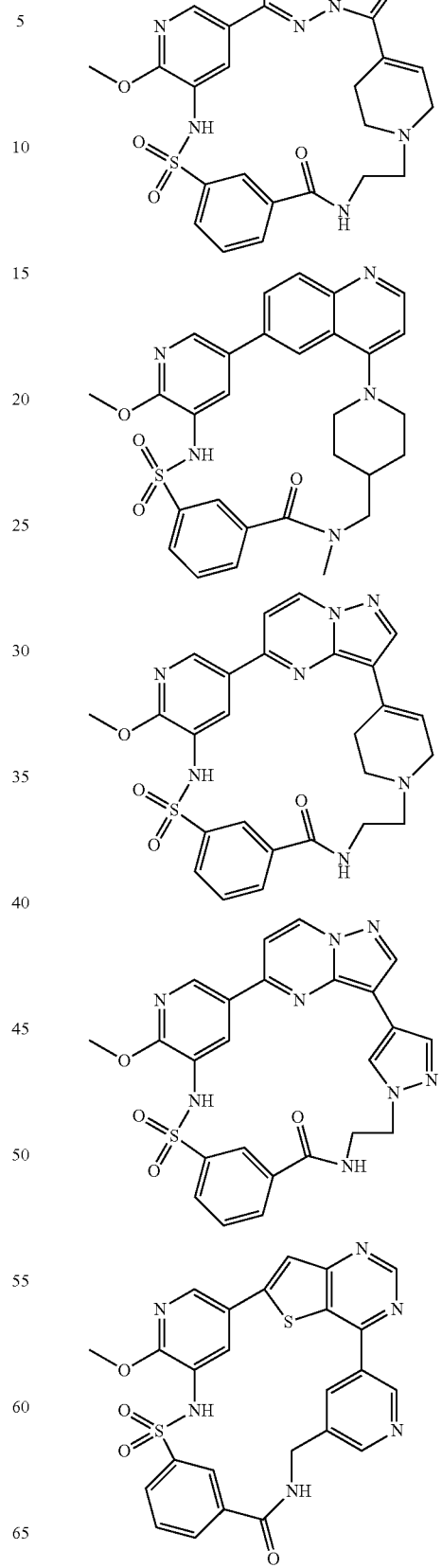

291
-continued
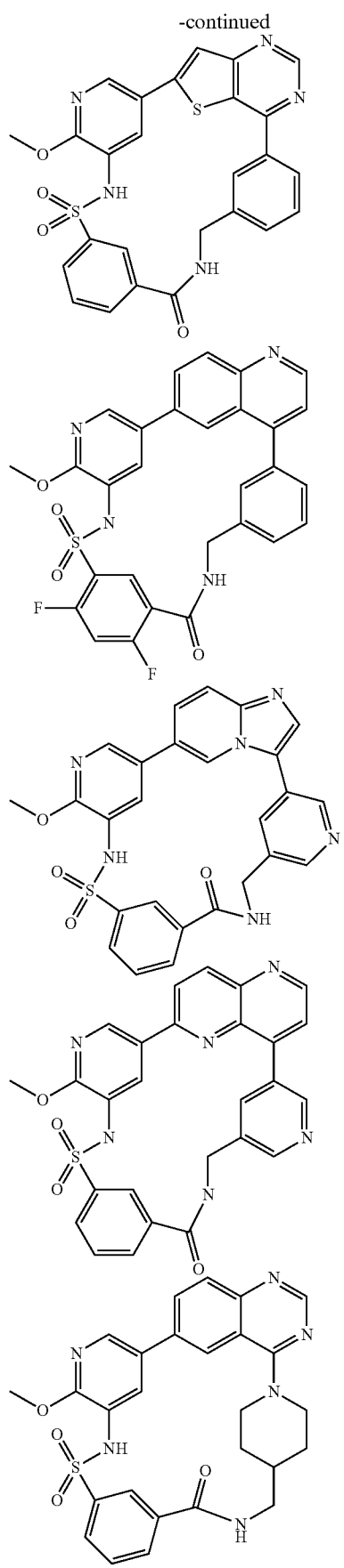
292
-continued
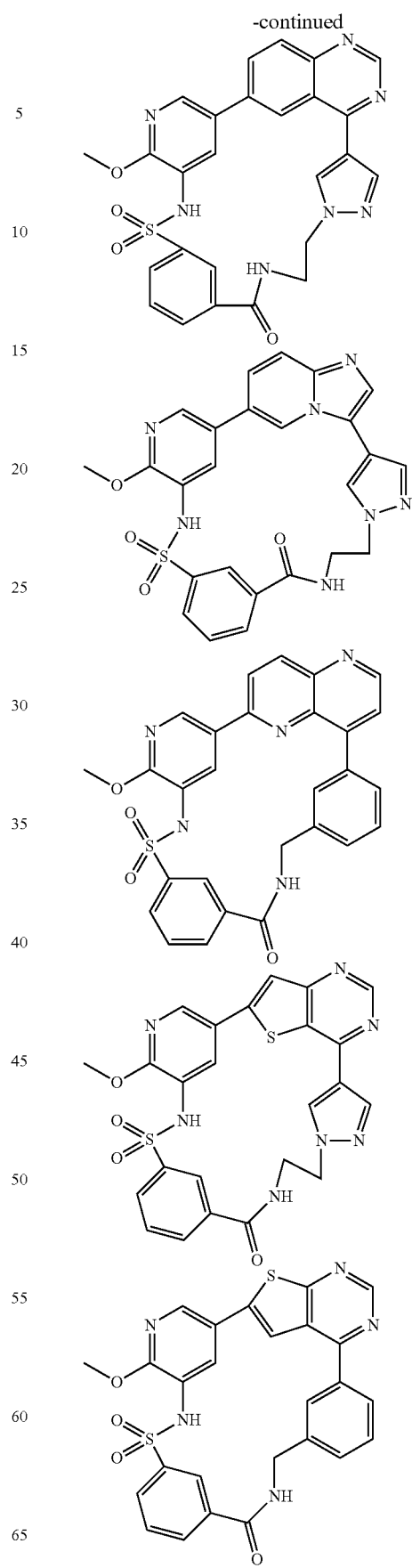

293
-continued
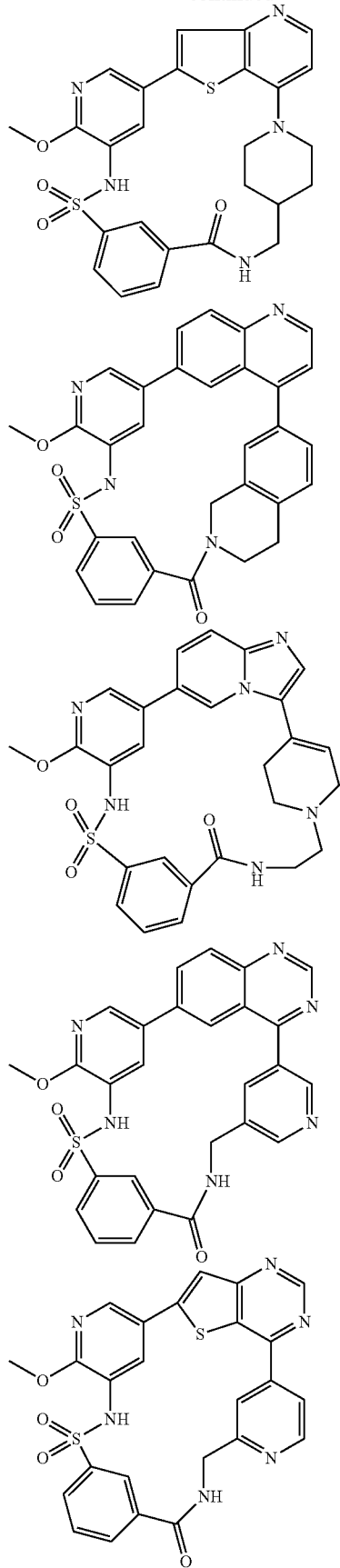
294
-continued
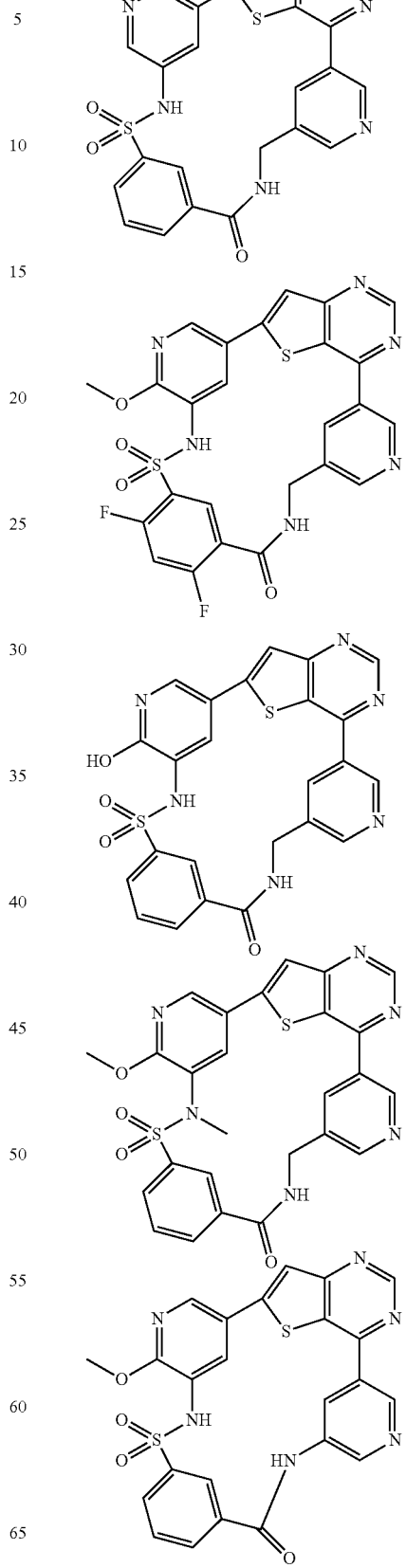

295
-continued
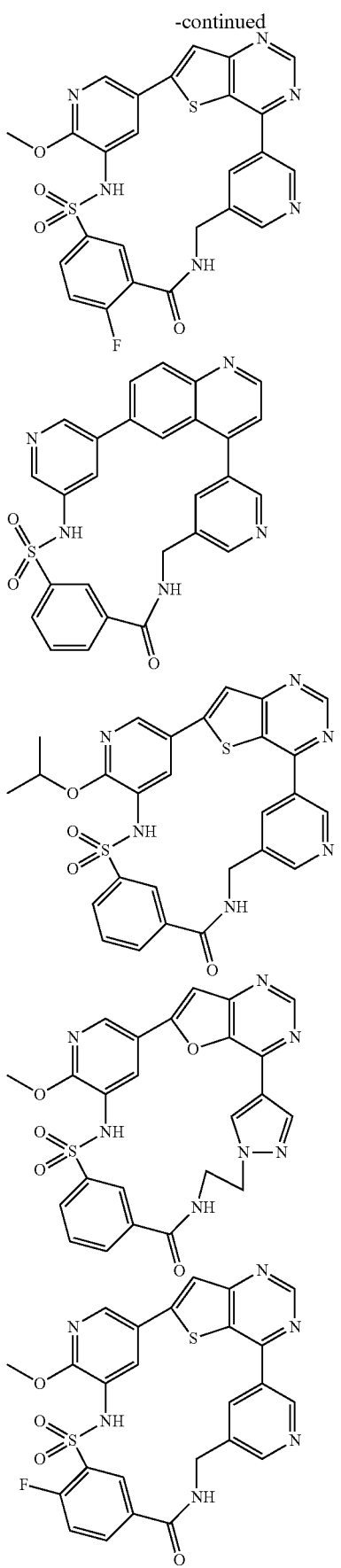
296
-continued
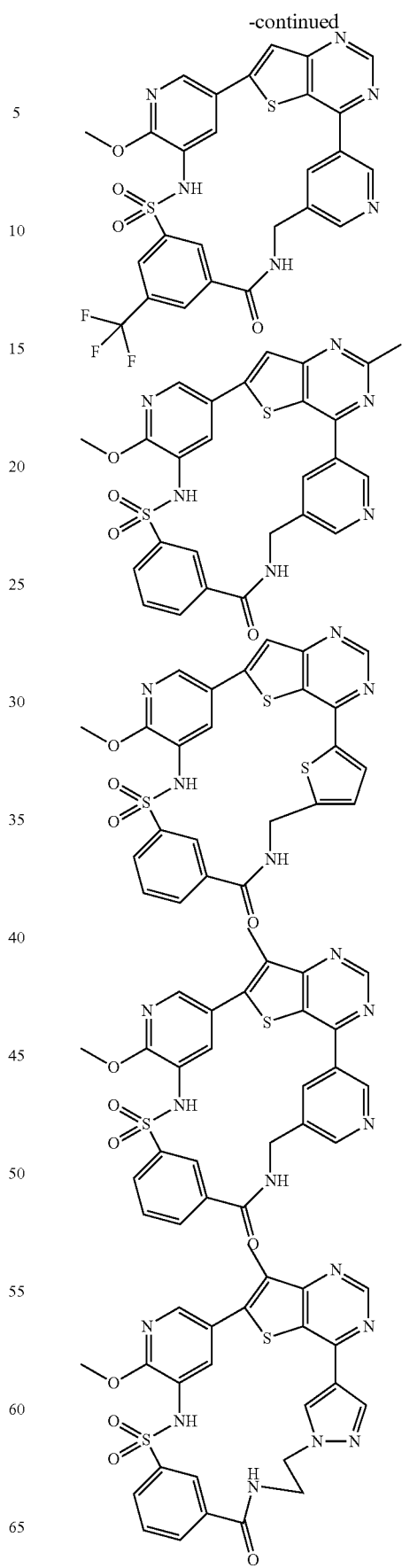

297
-continued
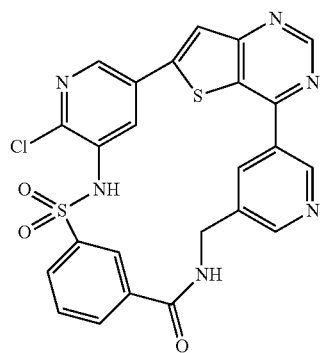
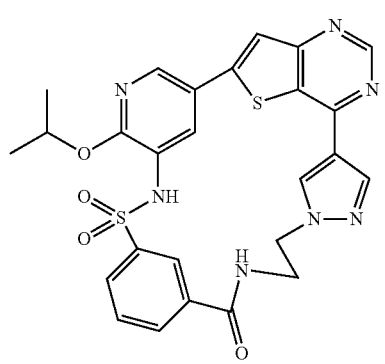
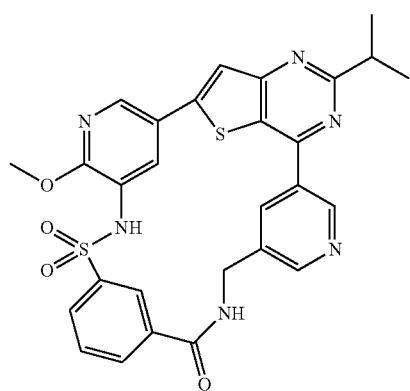
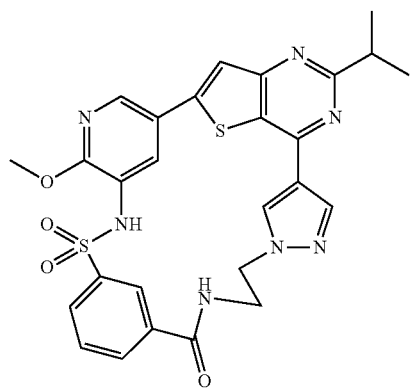
298
-continued
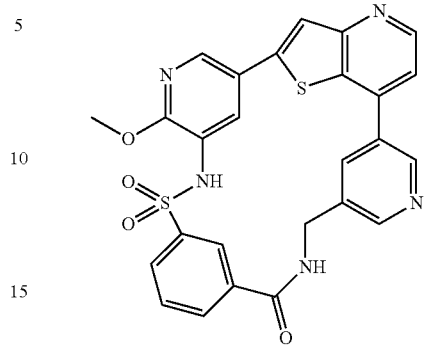
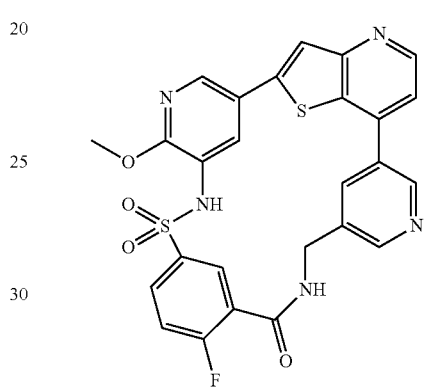
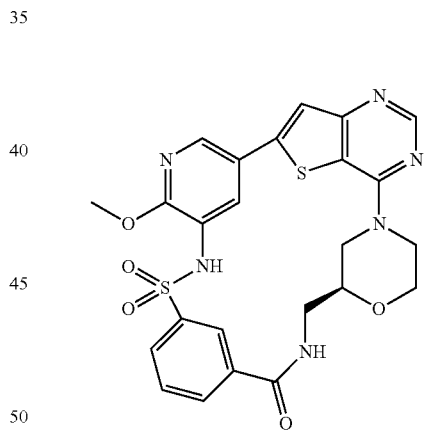
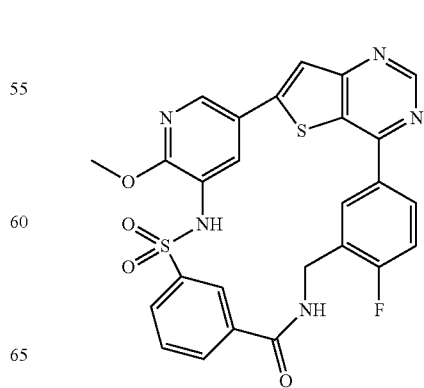

299
-continued
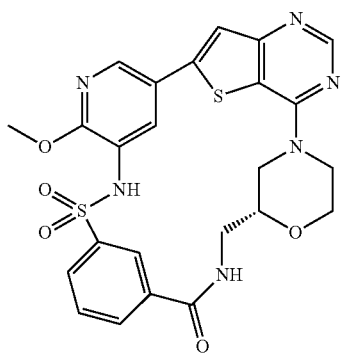
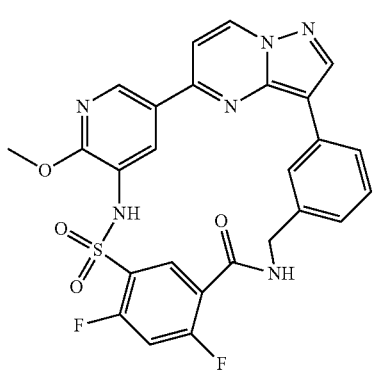
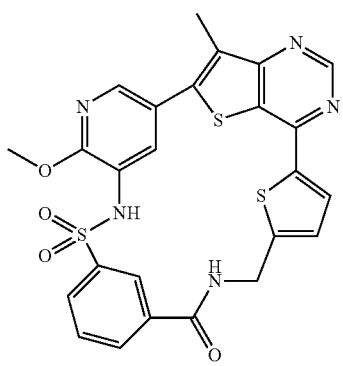
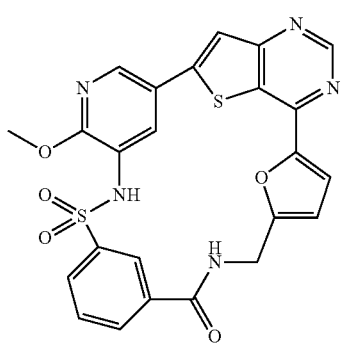
300
-continued
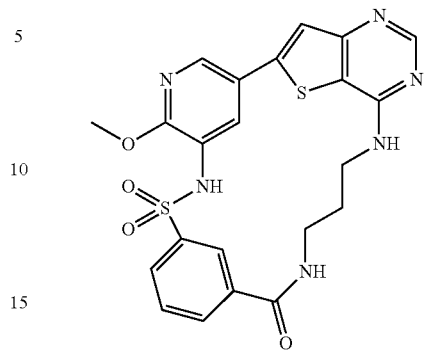
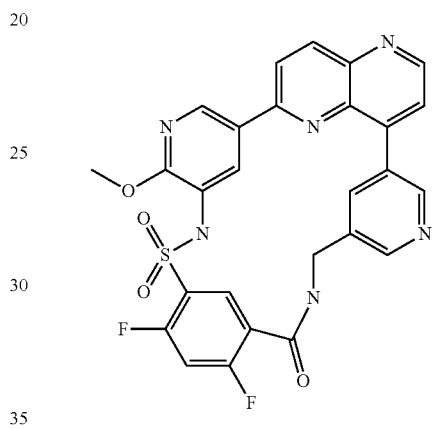
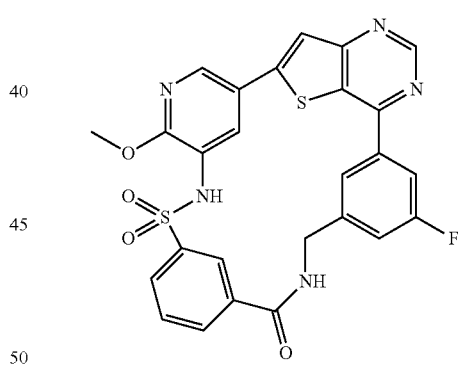
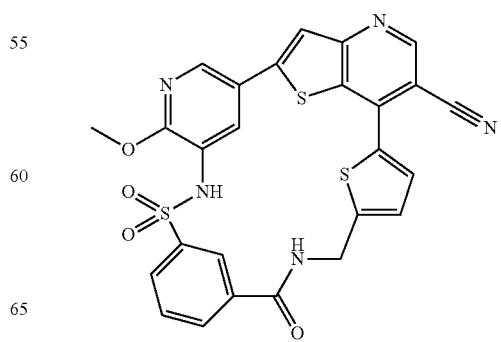

301
-continued
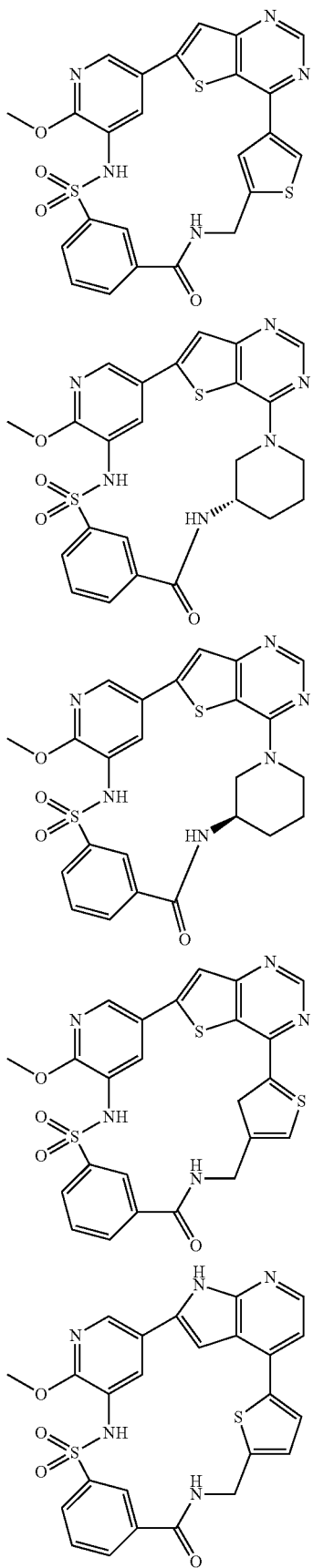
302
-continued
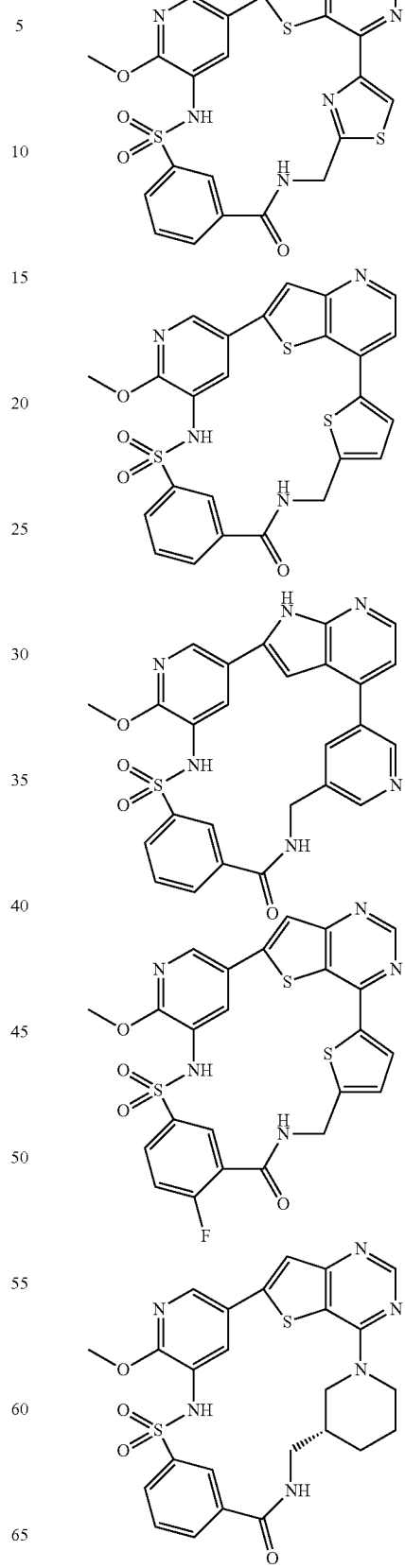

303
-continued
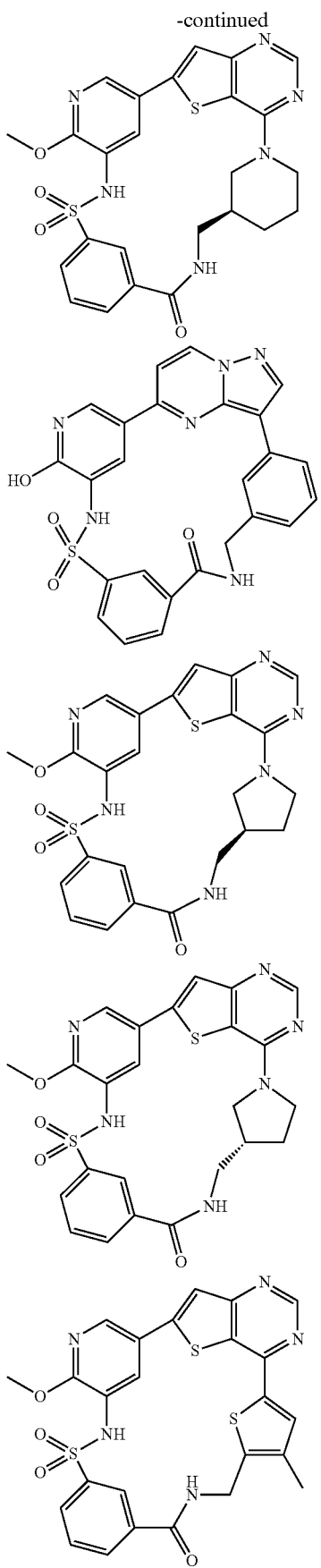
304
-continued
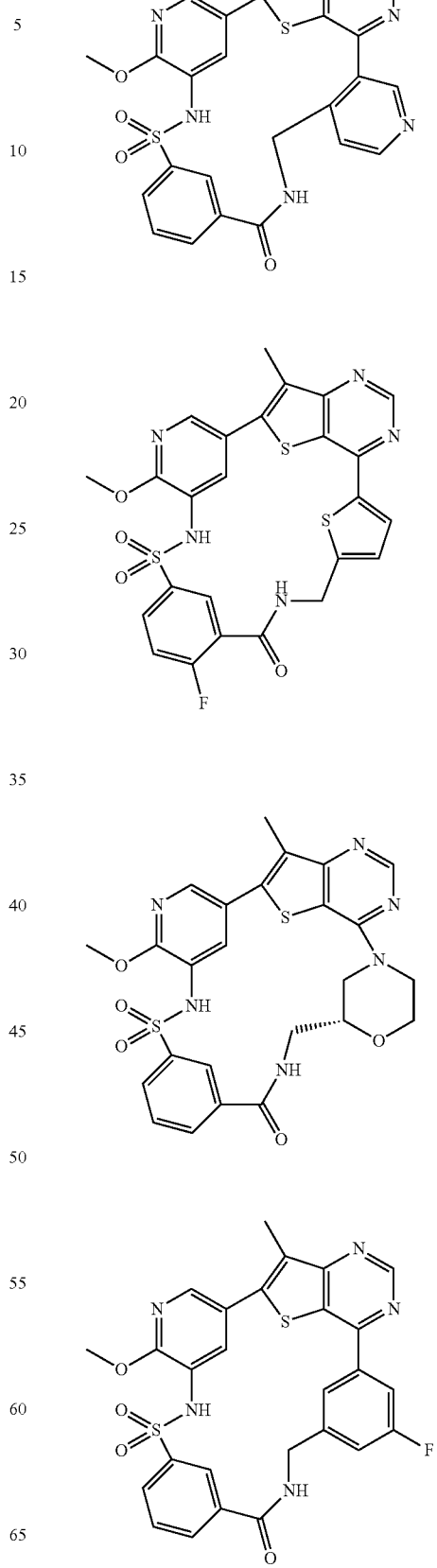

305
-continued
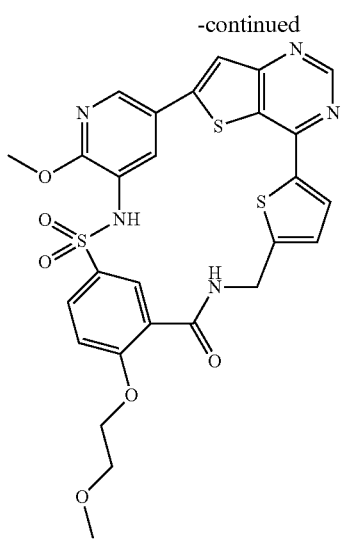
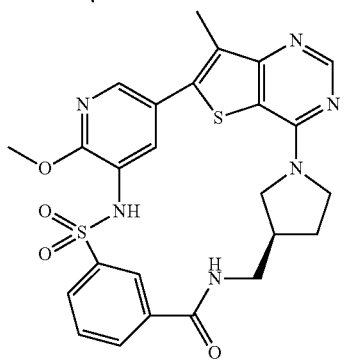
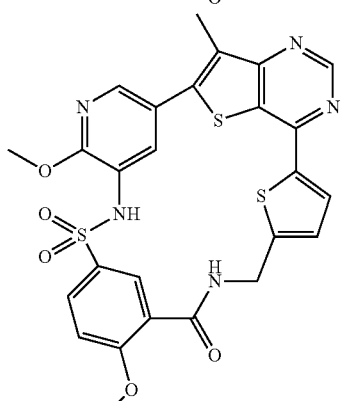
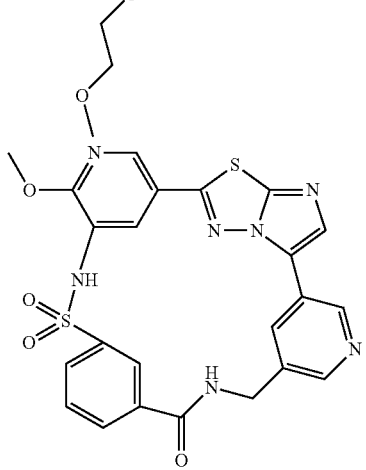
306
-continued
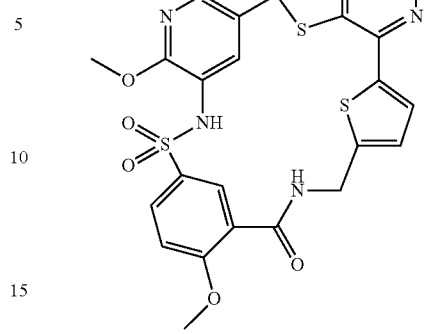
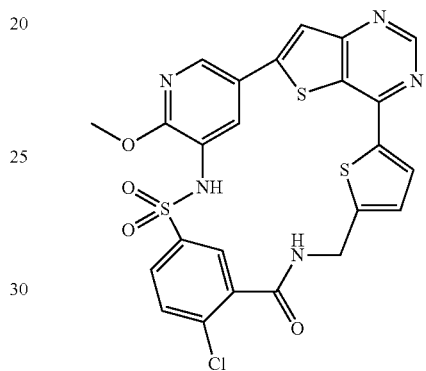
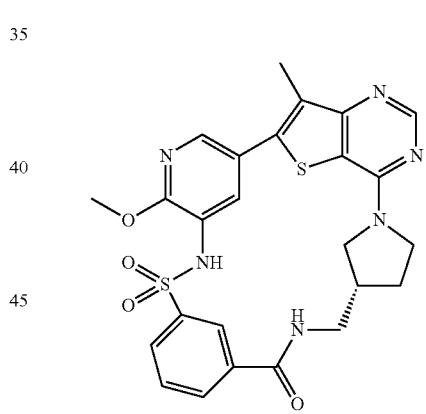
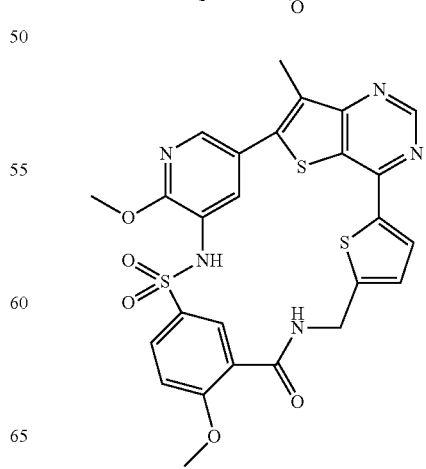

307
-continued
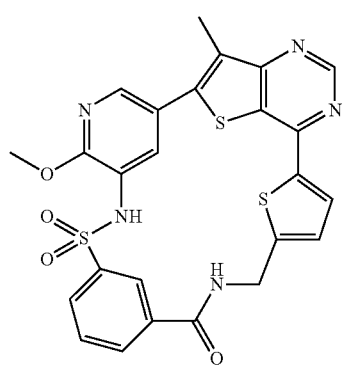
308
-continued
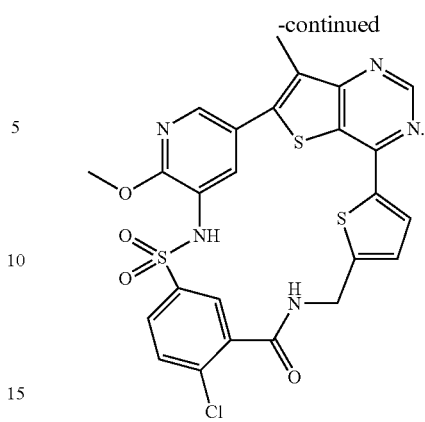
* * * * *

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: PIM-1 substrate peptide: PIMtide

<400> SEQUENCE: 1

Ala Arg Lys Arg Arg Arg His Pro Ser Gly Pro Pro Thr Ala
1               5                  10
```